US012766120B2

(12) United States Patent
Burzynski

(10) Patent No.: US 12,766,120 B2
(45) Date of Patent: Oct. 20, 2026

(54) COMPOSITIONS FOR AND METHODS OF PRECISION CANCER TREATMENT

(71) Applicant: Stanislaw R. Burzynski, Houston, TX (US)

(72) Inventor: Stanislaw R. Burzynski, Houston, TX (US)

( * ) Notice: Subject to any disclaimer, the term of this patent is extended or adjusted under 35 U.S.C. 154(b) by 0 days.

(21) Appl. No.: 18/073,944

(22) Filed: Dec. 2, 2022

(65) Prior Publication Data

US 2023/0190694 A1 Jun. 22, 2023

Related U.S. Application Data

(60) Provisional application No. 63/275,417, filed on Nov. 3, 2021.

(51) Int. Cl.

*A61K 31/216* (2006.01)
*A61K 31/165* (2006.01)
*A61K 45/06* (2006.01)
*A61P 35/00* (2006.01)

(52) U.S. Cl.

CPC .......... *A61K 31/216* (2013.01); *A61K 31/165* (2013.01); *A61K 45/06* (2013.01); *A61P 35/00* (2018.01)

(58) Field of Classification Search

CPC .. A61K 31/192; A61K 31/197; A61K 31/198; A61K 31/165; A61K 31/216; A61K 45/06; A61P 35/00

See application file for complete search history.

(56) References Cited

U.S. PATENT DOCUMENTS

| | | | | |
|---|---|---|---|---|
| 4,558,057 | A * | 12/1985 | Burzynski | C07K 4/12 546/220 |
| 6,258,849 | B1 | 7/2001 | Burzynski | |
| 6,943,192 | B2 * | 9/2005 | Burzynski | A61K 31/198 514/561 |
| 10,624,869 | B2 * | 4/2020 | Burzynski | A61K 31/197 |
| 11,234,951 | B2 * | 2/2022 | Burzynski | A61K 39/3955 |
| 11,334,521 | B2 | 5/2022 | Danilov et al. | |
| 11,607,397 | B2 | 3/2023 | Burzynski | |
| 2002/0103141 | A1 | 8/2002 | McKearn et al. | |
| 2008/0274909 | A1 | 11/2008 | Brothman | |
| 2016/0158186 | A1 | 6/2016 | Brown et al. | |
| 2018/0318421 | A1 * | 11/2018 | Burzynski | A61P 35/00 |
| 2022/0151958 | A1 | 5/2022 | Burzynski, Sr. | |

FOREIGN PATENT DOCUMENTS

| | | | |
|---|---|---|---|
| JP | 2002503209 | 5/2022 | |
| WO | 97/42939 | 11/1997 | |
| WO | WO-2015116868 A2 * | 8/2015 | C12Q 1/6886 |
| WO | 2016128146 | 8/2016 | |
| WO | 2018208697 | 11/2018 | |
| WO | 2018231733 | 12/2018 | |

OTHER PUBLICATIONS

Burzynski (Cancer and Clinical Oncology vol. 4 pp. 41-52. Published 2015) (Year: 2015).*

Burzynski (J. of Cancer Therapy vol. 5 pp. 1072-1091. Published 2014). (Year: 2014).*

Luo (Semin. Oncol. vol. 48 pp. 10-18. Published Feb. 2021). (Year: 2021).*

Reagan-Shaw et al (FASEBJ vol. 22 pp. 659-661. Published 2007) (Year: 2007).*

Luo (Semin. Oncology vol. 48 pp. 10-18. Published online Feb. 2021), (Year: 2021).*

Reagan-Shaw (FASEBJ vol. 22 pp. 659-661 Published 2007) (Year: 2007).*

Burzynski (Journal of Cancer Therapy vol. 5 pp. 1072-1091 published 2014) (Year: 2014).*

Harrison (Surgery vol. 124 pp. 541-550 published 1998). (Year: 1998).*

Gradiz (Scientific Reports vol. 6 e21648 published Feb. 2017) (Year: 2017).*

Burzynski S, et al. (2022) Recurrent and progressive ganglioglioma in an 11-year-old male treated with antineoplastons: Partial response with more than nine years and nine months survival and complete resolution of clinical symptoms/signs. Biomed Res. 37:1-3.

Burzynski B, et al. (2023) Persistent pineoblastoma: Complete response and >26 years overall survival in a ten-month-old female treated with antineoplastons. Biomed Res Clin Practice. 7:1-5.

Burzynski SR, et al. (2021) Resolution of clinical signs, a complete response, and long-term survival (>23 Years) in a 3 and ½ month female with a newly diagnosed diffuse intrinsic pontine glioma treated with antineoplastons. Biomed Res. 6:1-6.

Burzynski S, et al. (2022) Recurrent/Persistent Glioblastoma Complete Response and 24 Years Disease-Free-Survival in a 45-Year-Old Female Treated with Antineoplastons. Cancer Stud Ther J. 7(3):1-6.

Burzynski B, et al. (2023) Inoperable Optic Pathway Glioma: A Seven-Year-Old Male with >35 Years Overall Survival Following Treatment with Antineoplastons. European J Clin Med. ISSN:2736-5476.

Burzynski SR, et al. (2021) Long-term survival (23 years) in a 26-year-old male after Antineoplaston therapy for a progressive, diffuse intrinsic pontine glioma: A case report. Int J Brain Disord Treat. 6:038-044.

Burzynski SR, et al. (2022) A 25-year-female with Diffuse Intrinsic Pontine Glioma Surviving for More than Nine Years Following Treatment with Antineoplastons. Cancer Res. 7(1):1-7.

Burzynski S, et al. (2022) Newly-Diagnosed Multicentric Pilocytic Astrocytoma: Complete Response and> 22 Years Survival in a Six Year and Nine-month-old Female Treated with Antineoplastons. Internat J Clin Oncol Cancer Res. 7:76-82.

(Continued)

*Primary Examiner* — George W Kosturko

(74) *Attorney, Agent, or Firm* — POLSINELLI PC

(57) ABSTRACT

Disclosed herein are compositions comprising one or more antineoplastons and using those compositions in methods of treating and/or preventing cancer, prolonging the survival of a subject, and preventing and/or decreasing metastasis of cancer.

14 Claims, 19 Drawing Sheets

(56) References Cited

OTHER PUBLICATIONS

Burzynski SR, et al. (2021) Long-term survival (27.7 years) following IV Antineoplaston Therapy (ANP) in a 36-year-old-female with a progressive diffuse intrinsic pontine glioma (DIPG). Int J Radiol Imaging Technol. 7:073-078.
Burzynski SR, et al. (2014) A case of sustained objective response of recurrent/progressive diffuse intrinsic pontine glioma with phenylbutyrate and targeted agents. J Cancer Ther. 6(1):40-44.
Burzynski SR, et al. (2011) Successful Treatment of Recurrent Triple-Negative Breast Cancer with Combination of Targeted Therapies. J Cancer Ther. 2:372-376.
Burzynski SR, et al. (2015) Long-term survival (over 20 years), complete response and normal childhood development in medulloblastoma treated with Antineoplastons A10 and AS2-1. J Neurol Stroke. 2(3):00054.
Burzynski SR, et al. (2015 Long-term survival over 21 years and pathologically confirmed complete response in pediatric anaplastic astrocytoma: a case report. J Neurol Stroke. 2(6):00072.
Burzynski SR, et al. (2014) Long-term survival (> 13 years) in a child with recurrent diffuse pontine gliosarcoma: a case report. J Pediatric Hematol Oncol. 36(7):e433.
Burzynski S, et al. (2023) Newly Diagnosed Anaplastic Astrocytoma:> 23 Year Survival in a 31-Year and 11-Month-Old Female Treated with Antineoplastons. Neurol Neurosci. 4(2):1-6.
Burzynski B, et al. (2022) Twenty-two Year Survival in 15-Year-Old Female with a Recurrent Posterior Fossa Ependymoma Treated with Antineoplastons. Oncol Clin Res. 3(1):99-105.
Burzynski SR, et al. (2015) Complete response and Long-term survival (> 20 years) of a child with tectal glioma: A case report. Pediatric Neurosurgery. 50(2):99-103.
Burzynski S, et al. (2021) Diffuse Intrinsic Pontine Glioma in an 11-Year-Old Female Treated with Antineoplastons: Complete Response and > 25 Years Survival. Pediatrics Neonatal Med. 1(2):1-5.
Burzynski S, et al. (2022) Newly Diagnosed Glioblastoma: Partial Response and >27 Years Overall Survival in 37-Year-Old Male Treated with Antineoplastons (Treatment of Glioblastoma with Antineoplastons). Recent Adv Clin Trials. 2(2):1-7.
Burzynski S, et al. (2015) A Phase II Study of Antineoplastons A10 and AS2-1 in Adult Patients with Primary Brain Tumors—Final Report (Protocol BT-09). J Cancer Therapy. 6:1063-1074.
Burzynski SR, et al. (1987). Initial clinical study with antineoplaston A2 injections in cancer patients with five years' follow-up. Drugs Exp Clin Res. 13:1-11.
Burzynski SR, et al. (2014) A phase II study of antineoplastons A10 and AS2-1 in children with high-grade glioma. Final Report (Protocol BT-06), and review of recent trials. J Cancer Therapy. 5:565-577.
Burzynski SR, et al. (2014) A Phase II Study of Antineoplastons A10 and AS2-1 in Adult Patients with Recurrent Glioblastoma Multiforme: Final Report (Protocol BT-21). J Cancer Therapy. 5:946-956.
Burzynski SR, et al. (2014) The response and survival of children with recurrent diffuse intrinsic pontine glioma based on phase II study of antineoplastons A10 and AS2-1 in patients with brainstem glioma. Child's Nervous System. 30:2051-2061.
Burzynski SR, et al. (2014). A phase II study of antineoplastons A10 and AS2-1 in children with recurrent, refractory or progressive primary brain tumors—Final report (Protocol BT-22). J Cancer Therapy. 5:977-988.
Burzynski SR, et al. (2014). Preliminary findings on the use of targeted therapy with pazopanib and other agents in combination with sodium phenylbutyrate in the treatment of glioblastoma multiforme. J Cancer Therapy. 5 (14):1423-1437.
Burzynski SR, et al. (2015) A phase II study of antineoplastons A10 and AS2-1 in patients with brainstem gliomas. The report on non-diffuse intrinsic pontine glioma (Protocol BT-11). J Cancer Therapy. 6(4):334-344.
Burzynski SR, et al. (2015) A phase II study of antineoplastons A10 and AS2-1 in adult patients with newly-diagnosed anaplastic astrocytoma. Final report (Protocol BT-08). Cancer Clinical Oncology. 4:28-38.
Burzynski SR, et al. (2015) A Phase II Study of Antineoplastons A10 and AS2-1 in Adult Patients with Primary Brain Tumors—Final Report (Protocol BT-09). J Cancer Therapy. 6:1063-1074.
Ceja ME, et al. (2013). Dosing considerations in pediatric oncology. US Pharm. 38:8-11.
Burzynski SR, et al. (2015). A Phase II Study of Antineoplastons A10 and AS2-1 Injections in Adult Patients with Recurrent Anaplastic Astrocytoma—Final Report (Protocol BT-15). Cancer Clinical Oncology. 4:13-23.
Burzynski SR, et al. (2016) Primary CNS tumors and leptomeningeal, disseminated and/or multicentric disease in children treated in Phase II studies with Antineoplastons A10 and AS2-1. Cancer Clin Oncol. 5.2:38-48.
Burzynski SR, et al. (2016). A Phase II Study of Antineoplastons A10 and AS2-1 in Children with Low-Grade Astrocytomas—Final Report (Protocol BT-13). J Cancer Therapy. 7(12):837-850.
Burzynski SR, et al. (2017). A Phase II study of Antineoplastons A10 and AS2-1 in children with brain tumors. Final Report (Protocol BT-10). J Cancer Therapy. 8(02):173-187.
Burzynski SR, et al. (2017). Antineoplastons A10 and AS2-1 in the treatment of children with optic pathway glioma: Final report for protocol BT-23. Cancer Clin Oncol. 6(1):25-35.
Burzynski SR, et al. (2004) Phase II Study of Antineoplaston A10 and AS2-1 in Children with Recurrent and Progressive Multicentric Glioma: A Preliminary Report. Drugs in R&D. 5(6):315-326.
Johnson Ji, et al. (2001). Relationships between drug activity in NCI preclinical in vitro and in vivo models and early clinical trials. British J Cancer. 84(10):1424-1431.
Verhaak RG, et al. (2010). Integrated genomic analysis identifies clinically relevant subtypes of glioblastoma characterized by abnormalities in PDGFRA, IDH1, EGFR, and NF1. Cancer Cell. 17(1):98-110.
Moon JH, et al. (2012) Leptomeningeal Dissemination of a Low-Grade Brainstem Glioma without Local Recurrence. J Korean Neurosurg Soc. 51(2):109-112.
Reinert T, et al. (2019) Analysis of Plasma Cell-Free DNA by Ultradeep Sequencing in Patients With Stages I to III Colorectal Cancer. JAMA Oncol. 5(8):1124-1131.
Siegelin MD, et al. (2010) Sorafenib exerts anti-glioma activity in vitro and in vivo. Neurosci Lett. 478(3):165-170.
Valeriote F, et al. (1975) Synergistic interaction of anticancer agents: a cellular perspective. Cancer Chemother. Rep. 59(5):895-900.
Extended European Search Report mailed Feb. 24, 2021 for EP Application No. 18797766.5 (7 pages).
Extended European Search Report mailed Jan. 25, 2021 for EP Application No. 18818116.8 (6 pages).
International Search Report and Written Opinion mailed Jul. 18, 2018 for Int'l. Application No. PCT/US18/31456 (8 pages).
International Search Report and Written Opinion mailed Sep. 7, 2018 for Int'l. Application No. PCT/US18/036972 (7 pages).
Ma DJ, et al. (2015) A phase II trial of everolimus, temozolomide, and radiotherapy in patients with newly diagnosed glioblastoma: NCCTG N057K. Neuro Oncol. 17(9):1261-1269.
Burzynski SR, et al. (2015) Comprehensive Genomic Profiling of Recurrent Classic Glioblastoma in a Patient Surviving Eleven Years Following Antineoplaston Therapy. Can Clin Oncol. 4(2):.

* cited by examiner

| Alteration | % cfDNA or Amp | Alteration Trend |
|---|---|---|
| *TP53* V73fs | 0.7% |  |
| *ERBB2* (HER2) Amplification<br>Amplifications not graphed above | Medium (++) |  |
| *TP53* R175G | ND |  |
| *SMAD4* Splice Site SNV | ND |  |
| *SMAD4* Splice Site SNV | ND |  |

FIG. 7 (cont'd.)

| Alteration | % cfDNA or Amp | Alteration Trend | |
|---|---|---|---|
| *TP53* R196* | 17.3% | 10% 11.2% 17.3% | |
| *PIK3CA* E545K | 16.5% | 11.9% 12.6% 16.5% | |
| *MAPK3* E13K | 1.2% | ND ND 1.2% | Variant of Uncertain Significance § |
| *ERBB2* (HER2) D1218H | 1.0% | 0.1% 0.2% 1% | Variant of Uncertain Significance § |
| *PIK3CA* E453K | 0.2% | ND ND 0.2% | |
| *GNAS* E209Q | 0.1% | ND ND 0.1% | Variant of Uncertain Significance § |
| *ALK* Q1177H | 0.1% | ND ND 0.1% | Variant of Uncertain Significance § |

FIG. 7 (cont'd.)

| Alteration | % cfDNA or Amp | Alteration Trend |
|---|---|---|
| *ERBB2* (HER2) Amplification<br>Amplifications not graphed above | High (+++) | 5.7 4.2 5.2<br>Plasma copy number |
| *CCND1* Amplification<br>Amplifications not graphed above | Medium (++) | ND ND 2.5<br>Plasma copy number |
| *PIK3CA* Amplification<br>Amplifications not graphed above | Low (+) | ND ND 2.4<br>Plasma copy number |
| *MYC* Amplification<br>Amplifications not graphed above | ND | 2.2 ND ND<br>Plasma copy number |
| *BRCA2* D237N | ND | 0.3% 0.4% ND |
| *PIK3CA* E726K | ND | ND 0.3% ND |
| *APC* G29G | ND | ND 0.2% ND |
| *BRCA1* H862Q | ND | ND 0.1% ND |
| *FGFR3* H791H | ND | ND 0.2% ND |
| *RAF1* P63P | ND | 0.3% 0.3% ND |
| *ERBB2* (HER2) V219V | ND | ND 0.3% ND |
| *ARAF* Y495Y | ND | ND 0.2% ND |

| Alteration | % cfDNA or Amp | Alteration Trend |
|---|---|---|
| *CCNE1* P268P | 0.2% |  |
| *EGFR* Amplification<br>Amplifications not graphed above | ND | <br>Plasma copy number |
| *ERBB2* (HER2) Amplification<br>Amplifications not graphed above | ND | <br>Plasma copy number |
| *PIK3CA* Amplification<br>Amplifications not graphed above | ND | <br>Plasma copy number |

FIG. 9 (cont'd.)

| Alteration | % cfDNA or Amp | Alteration Trend | |
|---|---|---|---|
| *BRAF* V765fs | 0.02% | ND 0.02% | Variant of Uncertain Significance § |
| *CCND1* Amplification<br>Amplifications not graphed above | ND | 5 ND<br>Plasma copy number | |
| *CDK6* Amplification<br>Amplifications not graphed above | ND | 2.5 ND<br>Plasma copy number | |
| *ERBB2* (HER2) Amplification<br>Amplifications not graphed above | ND | 12.4 ND<br>Plasma copy number | |
| *FGFR1* Amplification<br>Amplifications not graphed above | ND | 2.4 ND<br>Plasma copy number | |
| *PIK3CA* Amplification<br>Amplifications not graphed above | ND | 2.8 ND<br>Plasma copy number | |
| *PTEN* D252Y | ND | 0.1% ND | |

FIG. 9 (cont'd.)

| Alteration | % cfDNA or Amp | Alteration Trend |
|---|---|---|
| *PIK3CA* E542K | ND | 0.7% ND |
| *PIK3CA* E545K | ND | 0.9% ND |
| *PIK3CA* E726K | ND | 0.1% ND |
| *APC* K455K | ND | 0.4% ND |
| *PIK3CA* R4_P18del | ND | 0.9% ND |
| *ARID1A* S1798L | ND | 0.9% ND |
| *FGFR1* S762F | ND | 0.1% ND |
| *PDGFRA* V299G | ND | 0.1% ND |

| Alteration | % cfDNA or Amp | Alteration Trend | |
|---|---|---|---|
| *TERT* Promoter SNV | 2.8% |   | |
| *TP53* T253A | 2.7% |   | |
| *EGFR* R252L | 0.3% |   | Variant of Uncertain Significance § |
| *ERBB2* (HER2) Amplification<br>Amplifications not graphed above | Medium (++) |   | |
| *BRAF* Amplification<br>Amplifications not graphed above | ND |   | |

COMPOSITIONS FOR AND METHODS OF PRECISION CANCER TREATMENT

I. CROSS-REFERENCE TO RELATED APPLICATION

This application claims priority to U.S. Provisional Application No. 63/275,417 filed 3 Nov. 2021, which is incorporated by reference herein in its entirety.

II. BACKGROUND

Cancer is daunting in the breadth and scope of its diversity, spanning genetics, cell and tissue biology, pathology, and response to therapy. Ever more powerful experimental and computational tools and technologies are providing an avalanche of "big data" about the myriad manifestations of the diseases that cancer encompasses. The integrative concept embodied in the hallmarks of cancer is helping to distill this complexity into an increasingly logical science, and the provisional new dimensions presented in this perspective may add value to that endeavor, to more fully understand mechanisms of cancer development and malignant progression, and apply that knowledge to cancer medicine.

Cancer is among the leading causes of death worldwide. In 2018, there were 18.1 million new cases and 9.5 million cancer-related deaths worldwide. By 2040, the number of new cancer cases per year is expected to rise to 29.5 million and the number of cancer-related deaths to 16.4 million. Generally, cancer rates are highest in countries whose populations have the highest life expectancy, education level, and standard of living. But for some cancer types, such as cervical cancer, the reverse is true, and the incidence rate is highest in countries in which the population ranks low on these measures.

Despite advances in care, there remains an unmet medical need for developing methods of effecting precision cancer treatment for subjects having cancer (e.g., terminal cancer).

III. BRIEF DESCRIPTION OF THE FIGURES

Figure 5:
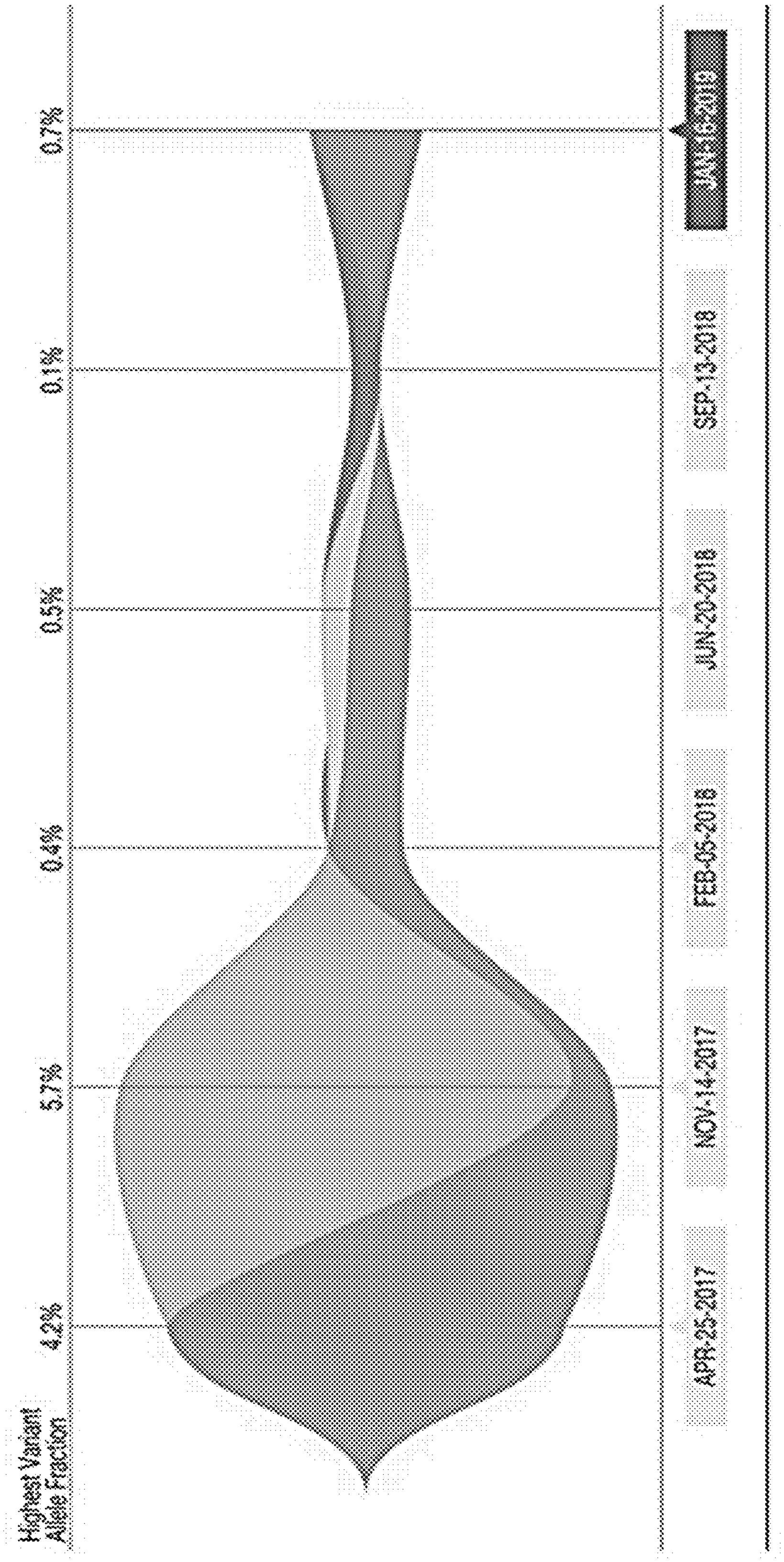
Figure 5:
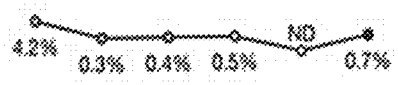
Figure 5:
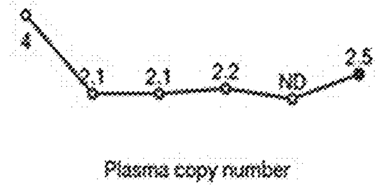
Figure 5:
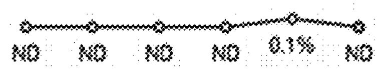
Figure 5:
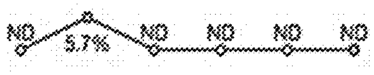
Figure 5:
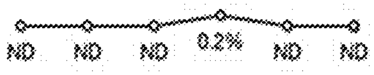

FIG. 5 shows a variant allele frequency map of ctDNA-detected mutations in an individual patient diagnosed with invasive ductal carcinoma with extensive DCIS, $ER^-$, $PR^-$, HER-$2^+$ with metastases to the lymph nodes and skin, (stage IV) in response to AS therapy. Mutated genes TP53, ERBB2, and SMAD4 were no longer seen on the Guardant test results of Sep. 13, 2018 and Jan. 16, 2019 due to successful treatment.

Figure 6:
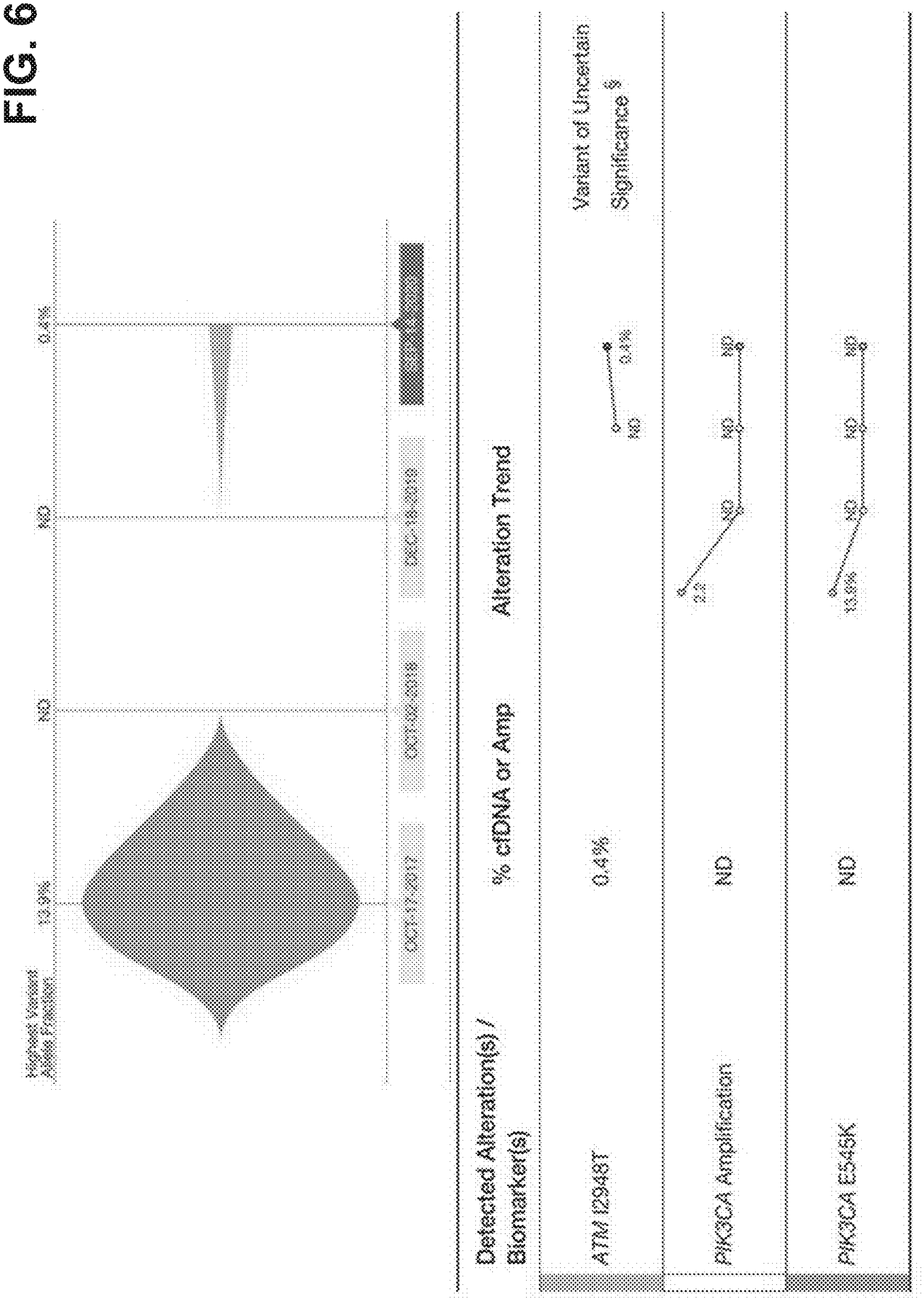

FIG. 6 shows a variant allele frequency map of ctDNA-detected mutations in an individual patient diagnosed with invasive ductal carcinoma $ER^+$, $PR^+$ HER-$2^-$ with extensive bone metastases (stage IV) in response to AS therapy. Mutated genes PIK3CA was no longer present on Oct. 2, 2018 due to successful treatment.

Figure 7:
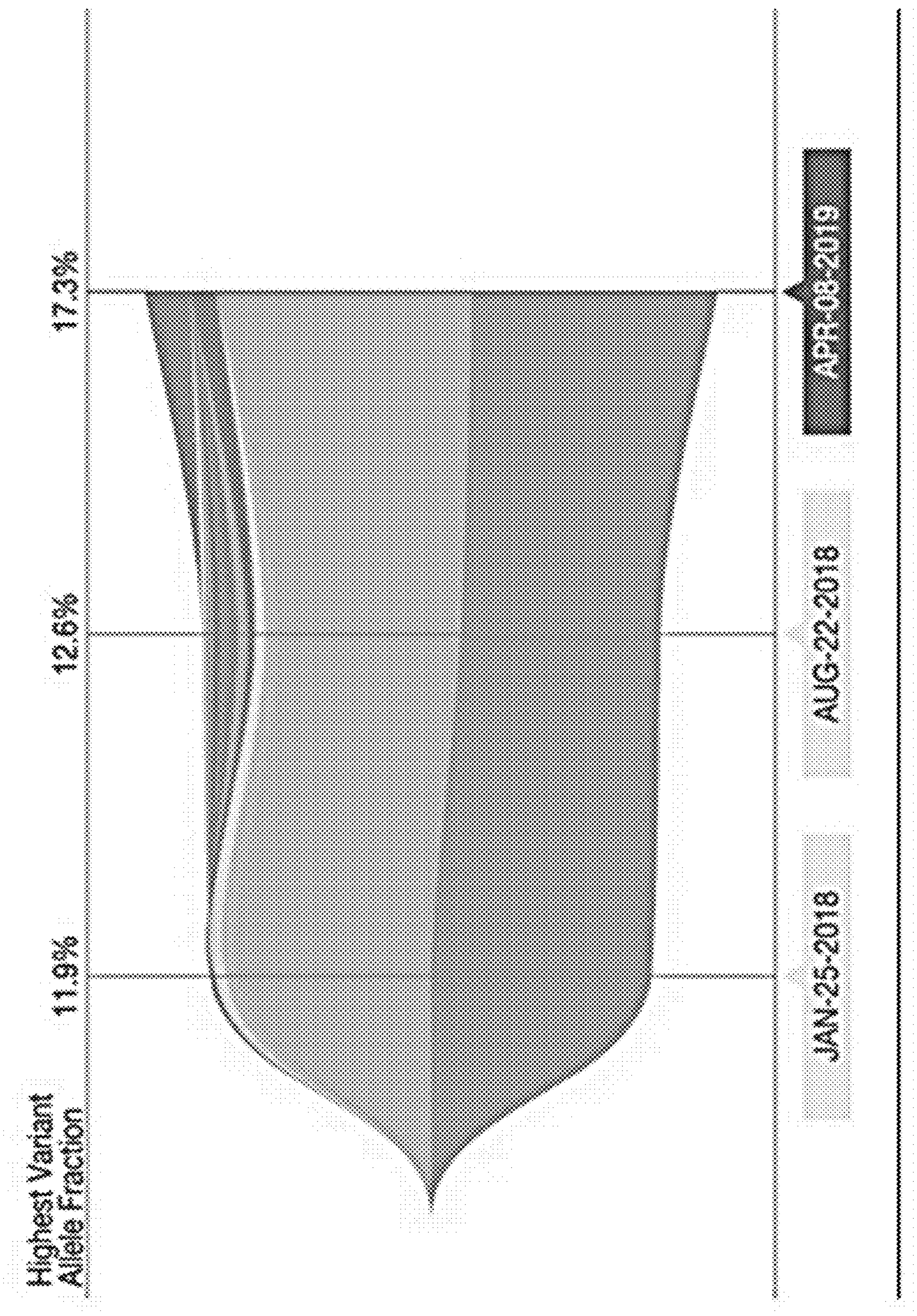

FIG. 7 shows a variant allele frequency map of ctDNA-detected mutations in an individual patient diagnosed with invasive ductal carcinoma, $ER^+$, $PR^+$, HER-$2^-$, with multiple metastases to the lymph nodes, bones and brain, (stage IV) in response to AS therapy. Mutated genes MYC, BRCA2, PIK3CA, APC, BRCA1, FGFR3, RAF1, and ARAF were no longer present on Apr. 8, 2019 due to successful treatment.

Figure 8:
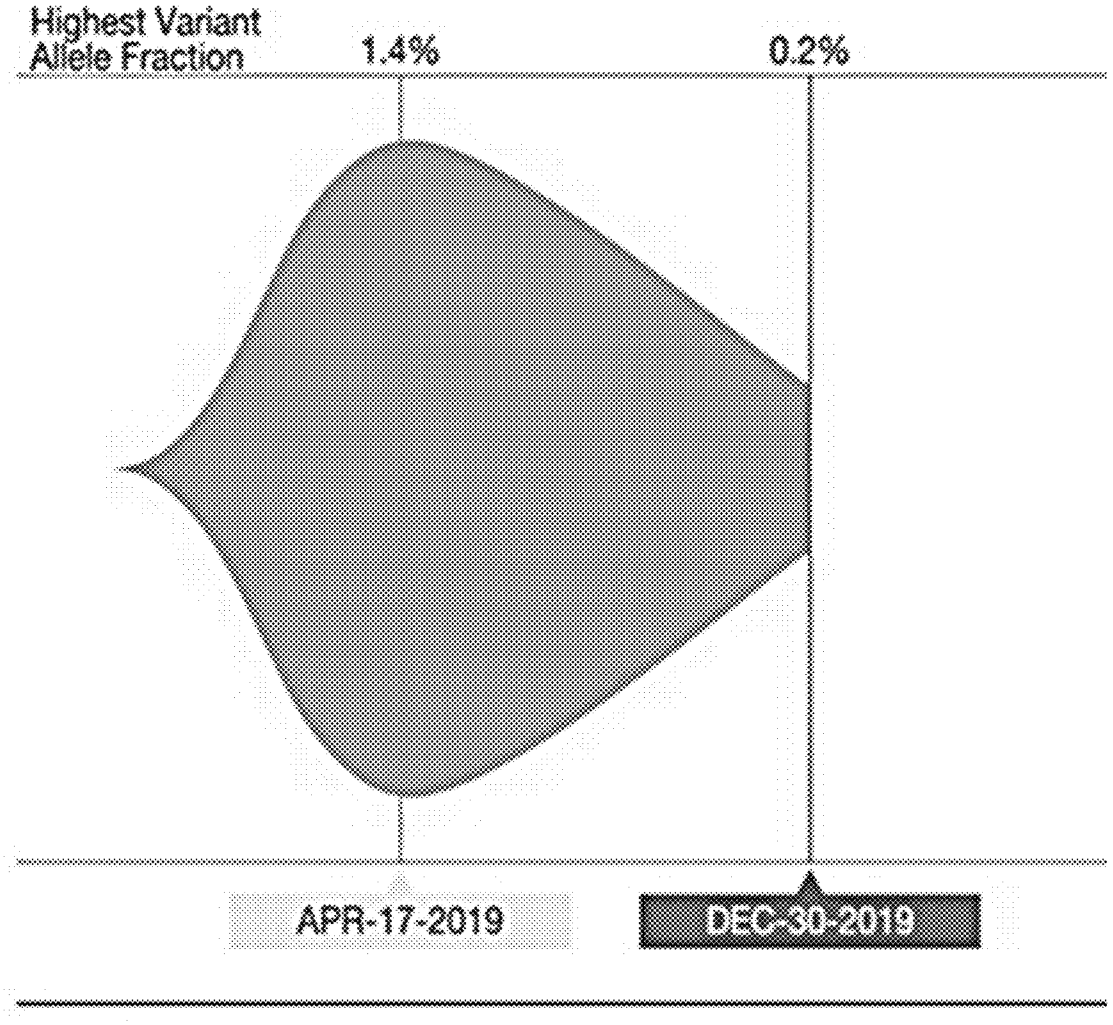
Figure 8:
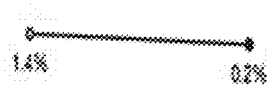
Figure 8:
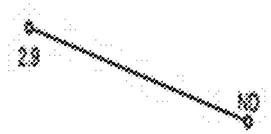
Figure 8:
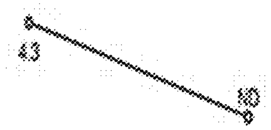
Figure 8:
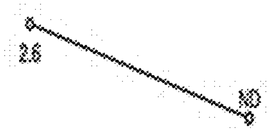

FIG. 8 shows a variant allele frequency map of ctDNA-detected mutations in an individual patient diagnosed with infiltrating ductal carcinoma of the left breast, $ER^+$, PR–, HER-$2^+$, with extensive metastases to the brain, bones, liver, lungs, and epidural involvement at T6-T12 (stage IV) in response to AS therapy. Mutated genes EGFR, ERBB2, and PIK3CA were no longer present on Dec. 30, 2019 due to successful treatment.

Figure 9:
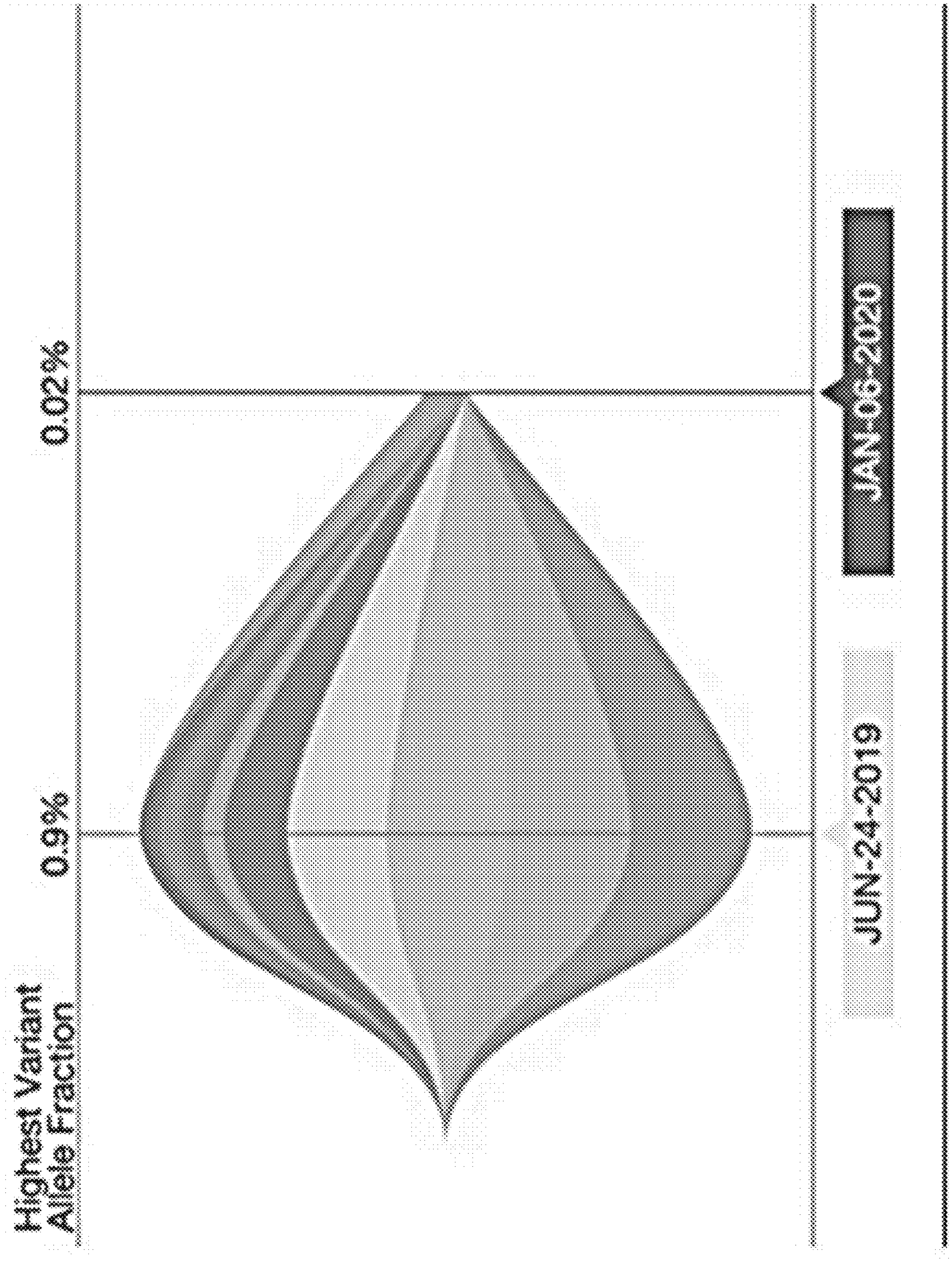

FIG. 9 shows a variant allele frequency map of ctDNA-detected mutations in an individual patient diagnosed with adenocarcinoma of the breast, $ER^+$, $PR^-$, HER-$2^+$ with metastases to the lymph nodes, brain, lungs, pleura, bones, peritoneum, and ovaries in response to AS therapy. Mutated genes CCND1, CDK6, ERBB2, FGFR1, PIK3CA, PTEN, ARID1A, and PDGFRA were no longer present on Jan. 6, 2020 due to successful treatment.

Figure 10:
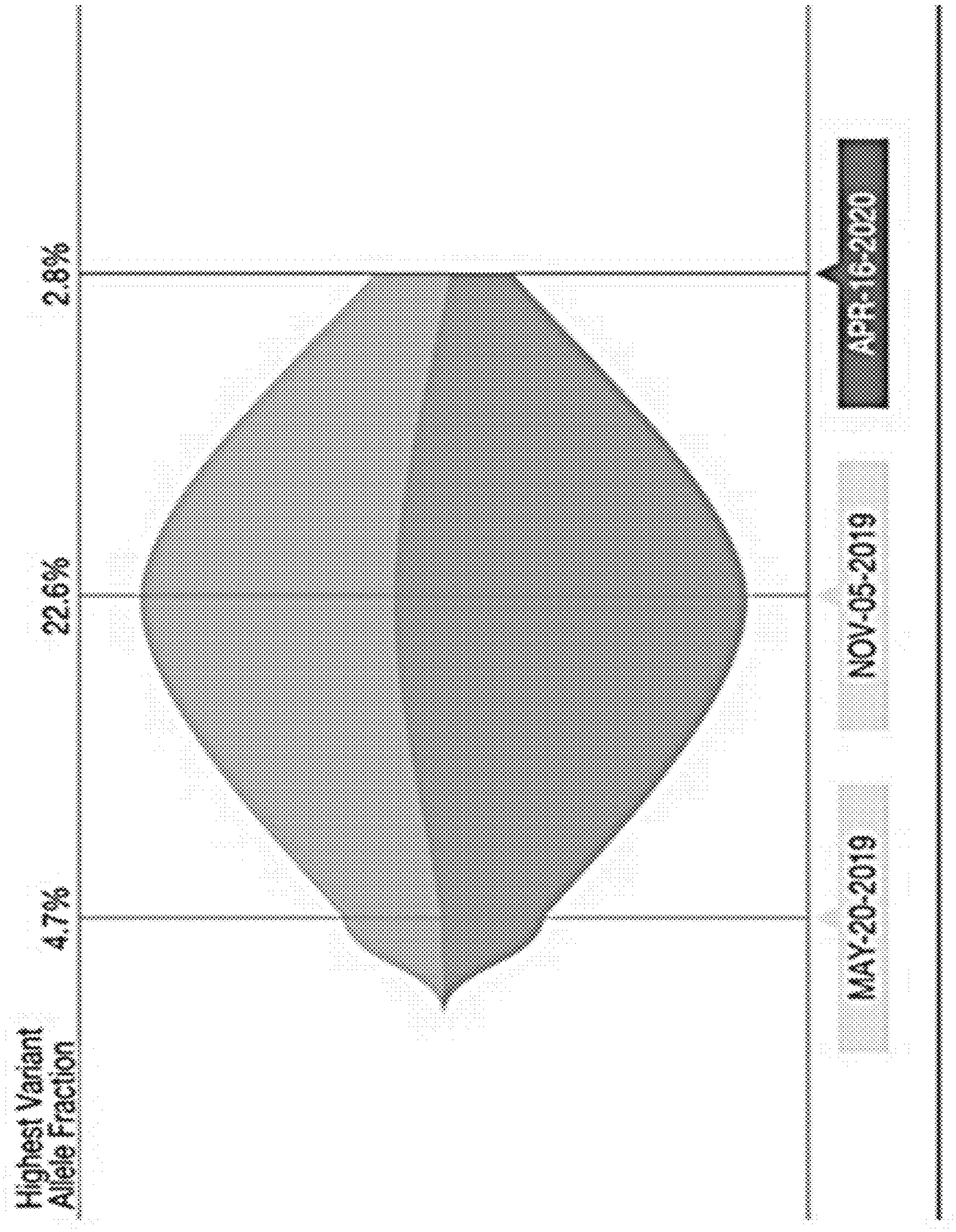
Figure 10:
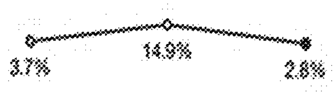
Figure 10:
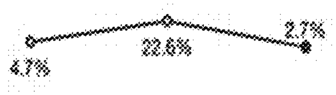
Figure 10:
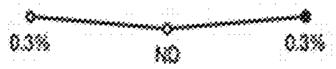
Figure 10:
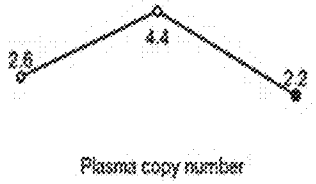
Figure 10:
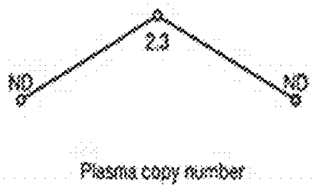

FIG. 10 shows a variant allele frequency map of ctDNA-detected mutations in an individual patient diagnosed with high grade invasive urothelial carcinoma of the bladder with metastases to the lymph nodes, lungs, bones, and brain (stage IV) in response to AS. Mutated gene EGFR was no longer present on Nov. 5, 2019 and BRAF no longer present on Apr. 16, 2020 and the concentration of mutated TERT, TP53, and ERBB2 decreased on Apr. 16, 2020.

Figure 11:
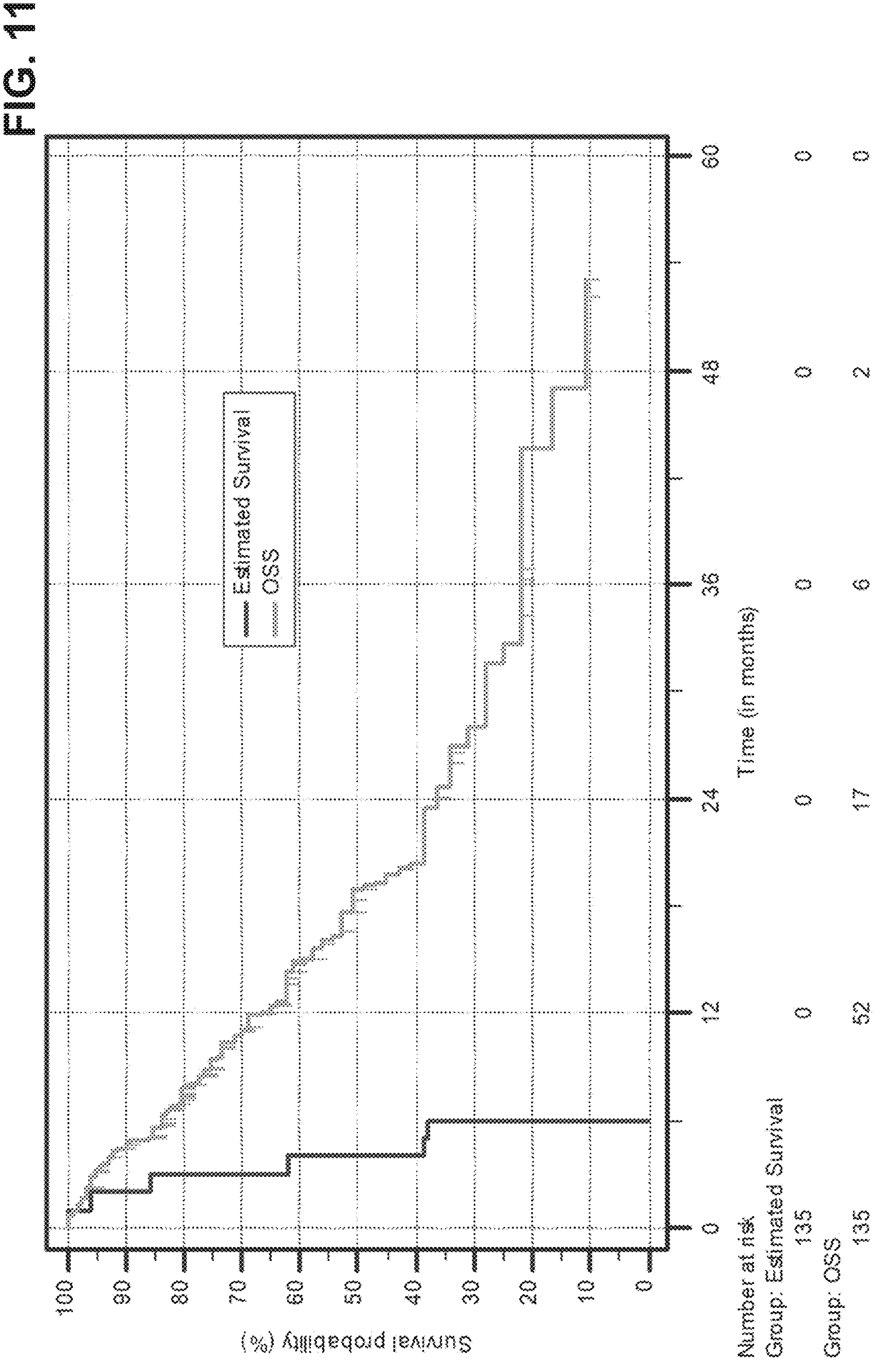

FIG. 11 shows a survival analysis of patients with common cancers treated with AS and A10 (ANP).

Figure 12:
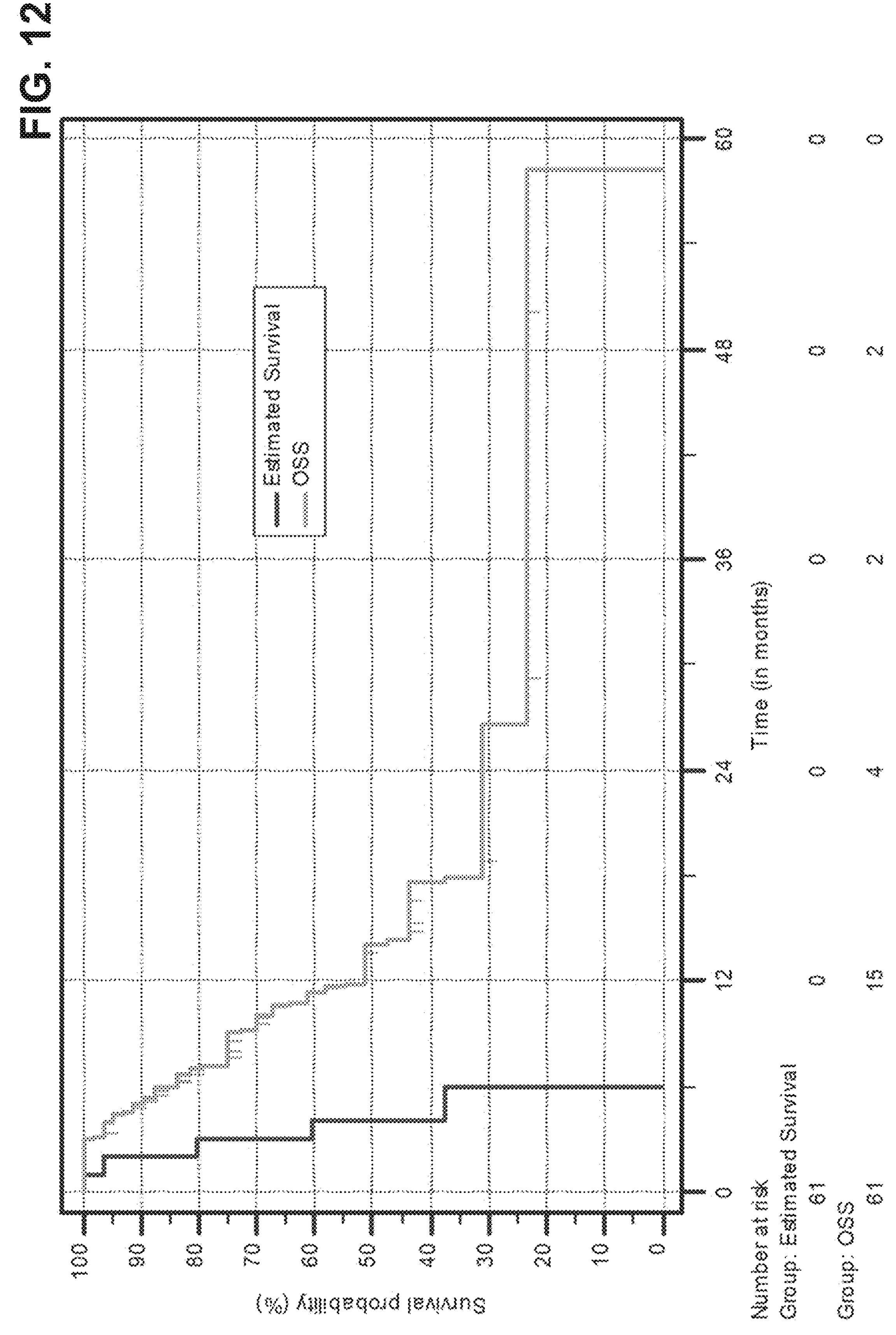

FIG. 12 shows a survival analysis of patients with uncommon cancers treated with AS and A10 (ANP).

IV. BRIEF SUMMARY

Disclosed herein are compositions comprising one or more antineoplastons.

Disclosed herein is a pharmaceutical formulation comprising one or more antineoplastons and one or more pharmaceutically acceptable carriers.

Disclosed herein is a method of treating and/or preventing cancer, the method comprising administering to a subject in need thereof a precision cancer treatment, wherein the subject demonstrates a tumor response and/or molecular response to the precision cancer treatment.

Disclosed herein is a method of treating cancer, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment.

Disclosed herein is a method of treating cancer, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and measuring the subject's tumor response and/or the subject's molecular response.

Disclosed herein is a method of treating cancer, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment.

Disclosed herein is a method of prolonging the survival of a subject, the method comprising administering to a subject in need thereof a precision cancer treatment, wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment, and wherein the subject's life expectancy is extended.

Disclosed herein is a method of preventing and/or decreasing metastases, the method comprising administering to a subject in need thereof a precision cancer treatment, wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof, subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment, and wherein metastases are prevented and/or decreased.

V. DETAILED DESCRIPTION

The present disclosure describes formulations, compounded compositions, kits, capsules, containers, and/or methods thereof. It is to be understood that the inventive aspects of which are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

This disclosure describes inventive concepts with reference to specific examples. However, the intent is to cover all modifications, equivalents, and alternatives of the inventive concepts that are consistent with this disclosure.

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein, when referring to any numerical value, the term "about" means a value falling within a range that is ±10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex, and thus, adult and child subjects, as well as fetuses, whether male or female, are intended to be covered. In an aspect, a subject can be a human patient. In an aspect, a subject can have cancer, be suspected of having cancer, or be at risk of developing cancer.

As used herein, the term "diagnosed" means having been subjected to an examination by a person of skill, for example, a physician, and found to have a condition that can be diagnosed or treated by one or more of the disclosed antineoplastons, disclosed pharmaceutical formulations, or any combination thereof, or by one or more of the disclosed methods. For example, "diagnosed with a disease or disorder" means having been subjected to an examination by a person of skill, for example, a physician, and found to have a condition (such as cancer) that can be treated by one or more of the disclosed antineoplastons, disclosed pharmaceutical formulations, or any combination thereof, or by one or more of the disclosed methods. For example, "suspected of having a disease or disorder" can mean having been subjected to an examination by a person of skill, for example, a physician, and found to have a condition (such as cancer) that can likely be treated by one or more of the disclosed antineoplastons, disclosed pharmaceutical formulations, or any combination thereof, or by one or more of the disclosed methods. In an aspect, an examination can be physical, can involve various tests (e.g., blood tests, genotyping, biopsies, etc.), scans (e.g., CT scans, PET scans, etc.), and assays (e.g., enzymatic assay), or a combination thereof.

A "patient" refers to a subject afflicted with a disease or disorder (e.g., cancer, a terminal cancer, a metastatic cancer). In an aspect, a patient can refer to a subject that has been diagnosed with or is suspected of having a disease or disorder such as cancer. In an aspect, a patient can refer to a subject that has been diagnosed with or is suspected of having a disease or disorder and is seeking treatment or receiving treatment for a disease or disorder (such as cancer).

As used herein, the phrase "identified to be in need of treatment for a disease or disorder," or the like, refers to selection of a subject based upon need for treatment of the disease or disorder. For example, a subject can be identified as having a need for treatment of a disease or disorder (e.g., cancer) based upon an earlier diagnosis by a person of skill and thereafter subjected to treatment for the cancer. In an aspect, the identification can be performed by a person different from the person making the diagnosis. In an aspect, the administration can be performed by one who performed the diagnosis.

As used herein, "inhibit," "inhibiting", and "inhibition" mean to diminish or decrease an activity, level, response, condition, severity, disease, or other biological parameter. This can include, but is not limited to, the complete ablation of the activity, level, response, condition, severity, disease, or other biological parameter (such as, for example, one or more genomic aberrations). This can also include, for example, a 10% inhibition or reduction in the activity, level, response, condition, severity, disease, or other biological parameter (such as, for example, one or more genomic aberrations) as compared to the native or control level (e.g., a subject not receiving a disclosed antineoplaston, a disclosed pharmaceutical formulation, or any combination thereof). Thus, in an aspect, the inhibition or reduction can be a 10%, 20%, 30%, 40%, 50%, 60%, 70%, 80%, 90%, 100%, or any amount of reduction in between as compared to native or control levels. In an aspect, the inhibition or reduction can be 10-20%, 20-30%, 30-40%, 40-50%, 50-60%, 60-70%, 70-80%, 80-90%, or 90-100% as compared to a native or control level (e.g., a subject not receiving a disclosed antineoplaston, a disclosed pharmaceutical formulation, or any combination thereof). In an aspect, the inhibition or reduction can be 0-25%, 25-50%, 50-75%, or 75-100% as compared to native or control levels. In an aspect, a native or control level can be a pre-disease or pre-disorder level (such as a pre-cancer state).

The words "treat" or "treating" or "treatment" include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In an aspect, the terms cover any treatment of a subject, including a mammal (e.g., a human), and includes: (i) preventing the undesired physiological change, disease, pathological condition, or disorder from occurring in a subject that can be predisposed to the disease but has not yet been diagnosed as having it; (ii) inhibiting the physiological change, disease, pathological condition, or disorder, i.e., arresting its development; or (iii) relieving the physiological change, disease, pathological condition, or disorder, i.e., causing regression of the disease. For example, in an aspect, treating a disease or disorder can reduce the severity of an established a disease or disorder in a subject by 1%-100% as compared to a control (such as, for example, an individual not having cancer). In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of a disease or disorder (such as cancer). For example, treating a disease or disorder can reduce one or more symptoms of a disease or disorder in a subject by 1%-100% as compared to a control (such as, for example, an individual not having cancer). In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms of an established a disease or disorder. It is understood that treatment does not necessarily refer to a cure or complete ablation or eradication of a disease or disorder. However, in an aspect, treatment can refer to a cure or complete ablation or eradication of a disease or disorder (such as cancer).

As used herein, the term "prevent" or "preventing" or "prevention" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a disease or disorder having chromatin deregulation and/or chromatin dysregulation is intended. The words "prevent", "preventing", and "prevention" also refer to prophylactic or preventative measures for protecting or precluding a subject (e.g., an individual) not having a given a disease or disorder (such as cancer) or related complication from progressing to that complication. In an aspect, preventing metastasis is intended.

As used herein, the terms "administering" and "administration" refer to any method of providing one or more of the disclosed antineoplastons, disclosed pharmaceutical formulations, or any combination thereof to a subject. Such methods are well known to those skilled in the art and include, but are not limited to, the following: oral administration, transdermal administration, administration by inhalation, nasal administration, topical administration, in utero administration, intratumoral administration, intrahepatic administration, intravaginal administration, ophthalmic administration, intraaural administration, otic administration, intracerebral administration, rectal administration, sublingual administration, buccal administration, and parenteral administration, including injectable such as intravenous administration, intra-CSF administration, intra-arterial administration, intramuscular administration, and subcutaneous administration. Administration can also include hepatic intra-arterial administration or administration through the hepatic portal vein (HPV). Administration of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof can comprise administration directly into the CNS or the PNS. Administration can be continuous or intermittent. Administration can comprise a combination of one or more routes. In an aspect, administering can comprise titrating a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects.

As known to the art, a disclosed small molecule can include any organic or inorganic material that is not a polymer. As known to the art, a disclosed small molecule can exclude large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weight of over 2,000, 3,000, 4,000, 5,000, 6,000, 7,000, 8,000, 9,000, or 10,000). In an aspect, a "small molecule", for example, can be a drug that can enter cells easily because it has a low molecular weight. In an aspect, a small molecule can be used in conjunction with a disclosed composition or a disclosed formulation in a disclosed method.

In an aspect, the skilled person can determine an efficacious dose, an efficacious schedule, and an efficacious route of administration for the disclosed antineoplastons, disclosed pharmaceutical formulations, or any combination thereof to treat or prevent a disease or disorder (such as cancer). In an aspect, the skilled person can also alter, change, or modify an aspect of an administering step to improve efficacy of the disclosed antineoplastons, the disclosed pharmaceutical formulations, or any combination thereof.

By "determining the amount" is meant both an absolute quantification of a particular analyte (e.g., biomarker for cancer, for example) or a determination of the relative abundance of a particular analyte (e.g., a cancer biomarker). The phrase includes both direct or indirect measurements of abundance or both.

As used herein, "modifying the method" can comprise modifying or changing one or more features or aspects of one or more steps of a disclosed method of treating and/or preventing cancer. In an aspect, a method can be altered by changing the amount of a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof administered to a subject, or by changing the frequency of administration of a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof to a subject, by changing the duration of time that a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof is administered to a subject, or by substituting for one or more of the disclosed components and/or reagents with a similar or equivalent component and/or reagent. The same applies to all disclosed precision cancer treatments, disclosed antineoplastons, disclosed pharmaceutical formulations, disclosed anti-chemokines, disclosed anti-cancer agents, disclosed chemotherapeutics, or combinations thereof.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. In an aspect, a pharmaceutical carrier employed can be a solid, liquid, or gas. In an aspect, examples of solid carriers can include lactose, terra alba, sucrose, talc, gelatin, agar, pectin, acacia, magnesium stearate, and stearic acid. In an aspect, examples of liquid carriers can include sugar syrup, peanut oil, olive oil, and water. In an aspect, examples of gaseous carriers can include carbon dioxide and nitrogen. In preparing a disclosed composition for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "excipient" refers to an inert substance that is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See also, for reference, Remington's Pharmaceutical Sciences, (1990) Mack Publishing Co., Easton, Pa., which is hereby incorporated by reference in its entirety. In an aspect, acceptable carriers, excipients, or stabilizers are nontoxic to recipients at the dosages and concentrations used herein, and can include buffers such as, but not limited to phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, Pluronics, or polyethylene glycol (PEG).

As used herein, “concurrently” means (1) simultaneously in time, or (2) at different times during the course of a common treatment schedule.

The term “contacting” as used herein refers to bringing one or more of a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof together with a target area or intended target area in such a manner that a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof can exert an effect on the intended target or targeted area either directly or indirectly. A target area or intended target area can be one or more of a subject’s organs (e.g., lungs, heart, liver, kidney, brain, etc.) hosting cancerous cells. In an aspect, a target area or intended target area can be any cell or any organ infected by a disease or disorder (such as cancer). In an aspect, a target area or intended target area can be any organ, tissue, or cells that are affected by a disease or disorder (such as cancer).

As used herein, “determining” can refer to measuring or ascertaining the presence and severity of a disease or disorder, such as, for example, cancer. Methods and techniques used to determine the presence and/or severity of a disease or disorder are typically known to the medical arts. For example, the art is familiar with the ways to identify and/or diagnose the presence, severity, or both of a disease or disorder (such as, for example, cancer).

As used herein, “effective amount” and “amount effective” can refer to an amount that is sufficient to achieve the desired result such as, for example, the treatment and/or prevention of a disease or disorder (e.g., a cancer) or a suspected disease or disorder. As used herein, the terms “effective amount” and “amount effective” can refer to an amount that is sufficient to achieve the desired an effect on an undesired condition (e.g., a cancer). For example, a “therapeutically effective amount” refers to an amount that is sufficient to achieve the desired therapeutic result or to have an effect on undesired symptoms, but is generally insufficient to cause adverse side effects. In an aspect, “therapeutically effective amount” means an amount of a disclosed precision cancer treatment, a disclosed antineoplaston, a disclosed pharmaceutical formulations, a disclosed anti-chemokine, a disclosed anti-cancer agents, a disclosed chemotherapeutic, or a combination thereof that (i) treats the particular disease, condition, or disorder (e.g., a cancer), (ii) attenuates, ameliorates, or eliminates one or more symptoms of the particular disease, condition, or disorder e.g., cancer), or (iii) delays the onset of one or more symptoms of the particular disease, condition, or disorder described herein (e.g., cancer). The specific therapeutically effective dose level for any particular patient will depend upon a variety of factors including the disorder being treated and the severity of the disorder; the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof employed; the disclosed methods employed; the age, body weight, general health, sex and diet of the patient; the time of administration; the route of administration; the rate of excretion of the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof employed; the duration of the treatment; drugs used in combination or coincidental with the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof employed, and other like factors well known in the medical arts. For example, it is well within the skill of the art to start doses of the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof at levels lower than those required to achieve the desired therapeutic effect and to gradually increase the dosage until the desired effect is achieved. If desired, then the effective daily dose can be divided into multiple doses for purposes of administration. Consequently, a single dose the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a “prophylactically effective amount”; that is, an amount effective for prevention of a disease or condition, such as, for example, a disease or disorder due to a missing, deficient, and/or mutant protein or enzyme.

A “monoclonal antibody” as used herein refers to homogenous antibody population involved in the highly specific recognition and binding of a single antigenic determinant, or epitope. This is in contrast to polyclonal antibodies that typically include different antibodies directed against different antigenic determinants. The term “monoclonal antibody” encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, “monoclonal antibody” refers to such antibodies made in any number of manners including, but not limited to, by hybridoma, phage selection, recombinant expression, and transgenic animals.

As used herein, the term “humanized antibody” refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues from the complementary determining region (CDR) are replaced by residues from the CDR of a non-human species (e.g., mouse, rat, rabbit, hamster, etc.) that have the desired specificity, affinity, and capability. In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin.

That an antibody "selectively binds" or "specifically binds" to an epitope or receptor means that the antibody reacts or associates more frequently, more rapidly, with greater duration, with greater affinity, or with some combination of the above to the epitope or receptor than with alternative substances, including unrelated proteins. "Selectively binds" or "specifically binds" means, for instance, that an antibody binds to a protein with a KD of about 0.1 mM or less, more usually about 1 μM or less. "Selectively binds" or "specifically binds" means at times that an antibody binds to a protein with a KD of about 0.1 mM or less, at times about 1 μM or less, at times about 0.1 μM or less, at times about 0.01 μM or less, and at times about 1 nM or less. It is understood that, in certain aspects, an antibody or binding moiety that specifically binds to a first target may or may not specifically bind to a second target. As such, "specific binding" does not necessarily require (although it can include) exclusive binding, e.g., binding to a single target.

Polyclonal antibodies can be prepared by any known method. Polyclonal antibodies are raised by immunizing an animal (e.g., a rabbit, rat, mouse, donkey, goat, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

As used herein, "precision medicine" methods and "precision cancer treatment" can be used interchangeably and refer to methods of administering a cancer treatment (e.g., a ANP therapy) to a subject after measuring the subject's molecular markers to assess the likelihood of response or lack of response of a particular cancer therapy. In an aspect, for example, precision cancer treatment can comprise ANP and one or more other therapeutic agents (which can be determined using a disclosed genomic analysis). For cancer treatment, precision medicine means measuring a subject's molecular markers to select treatments that are most likely to help the subject, while at the same time sparing the subject from getting treatments that are not likely to help. In an aspect, molecular markers disclosed herein can be used for identification of one or more precision cancer treatments to be administered to a subject herein and/or can be determined by assessing the genetic expression of one or more cancer related genes. In an aspect, molecular markers disclosed herein can be used for identification of one or more precision cancer treatments to be administered to a subject herein, and can be an increase in expression of one or more cancer related genes compared to that of a healthy subject not having or suspected of having a cancer. In an aspect, molecular markers disclosed herein can be used for identification of one or more precision cancer treatments to be administered to a subject herein, and can decrease in expression of one or more cancer related genes compared to that of a healthy subject not having or suspected of having a cancer. In an aspect, molecular markers disclosed herein can be used for identification of one or more precision cancer treatments to be administered to a subject herein, and can be a base mutation and/or variant in the sequence of one or more cancer related genes compared to that of a healthy subject not having or suspected of having a cancer.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, various types of brain tumors, or any combination thereof.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions. "Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" or "tumor stem cell" or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells" or "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

The terms "cancer cell" or "tumor cell" and grammatical equivalents refer to the total population of cells derived from a tumor including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the "tumorigenicity" of a tumor refers to the ability of a random sample of cells from the tumor to form palpable tumors upon serial transplantation into immunocompromised mice.

As used herein, "immune-modulating" refers to the ability of a disclosed isolated nucleic acid molecules, a disclosed precision cancer treatment, a disclosed pharmaceutical formulation, or a disclosed agent to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

As used herein, "immune modulator" refers to an agent that is capable of adjusting a given immune response to a desired level (e.g., as in immunopotentiation, immunosuppression, or induction of immunologic tolerance). Examples of immune modulators include but are not limited to, a disclosed immune modulator can comprise aspirin, azathioprine, belimumab, betamethasone dipropionate, betamethasone valerate, bortezomib, bredinin, cyazathioprine, cyclophosphamide, cyclosporine, deoxyspergualin, didemnin B, fluocinolone acetonide, folinic acid, ibuprofen, IL6 inhibitors (such as sarilumab) indomethacin, inebilizumab, intravenous gamma globulin (WIG), methotrexate, methylprednisolone, mycophenolate mofetil, naproxen, prednisolone, prednisone, prednisolone indomethacin, rapamycin, rituximab, sirolimus, sulindac, synthetic vaccine particles containing rapamycin (SVP-Rapamycin or ImmTOR), thalidomide, tocilizumab, tolmetin, triamcinolone acetonide, anti-CD3 antibodies, anti-CD4 antibodies, anti-CD19 antibodies, anti-CD20 antibodies, anti-CD22 antibodies, anti-CD40 antibodies, anti-FcRN antibodies, anti-IL6 antibodies, anti-IGF1R antibodies, an IL2 mutein, a BTK inhibitor, or a combination thereof. In an aspect, a disclosed immune modulator can comprise one or more Treg (regulatory T cells) infusions (e.g., antigen specific Treg cells to AAV). In an aspect, a disclosed immune modulator can be bortezomib or SVP-Rapamycin. In an aspect, an immune modulator can be administered by any suitable route of administration including, but not limited to, in utero, intra-CSF, intrathecally, intravenously, subcutaneously, transdermally, intradermally, intramuscularly, orally, transcutaneously, intraperitoneally (IP), or intravaginally. In an aspect, a disclosed immune modulator can be administered using a combination of routes. Administration can also include hepatic intra-arterial administration or administration through the hepatic portal vein (HPV). Administration of an immune modulator can be continuous or intermittent, and administration can comprise a combination of one or more routes.

As used herein, the term "package insert" is used to refer to instructions customarily included in commercial packages of therapeutic products, that contain information about the indications, usage, dosage, administration, contraindications and/or warnings concerning the use of such therapeutic products.

As used herein, the term "in combination" in the context of the administration of other therapies (e.g., other agents) includes the use of more than one therapy (e.g., drug therapy). Administration "in combination with" one or more further therapeutic agents includes simultaneous (e.g., concurrent) and consecutive administration in any order. The use of the term "in combination" does not restrict the order in which therapies are administered to a subject. By way of non-limiting example, a first therapy (e.g., the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof) may be administered prior to (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks or longer) the administration of a second therapy (e.g., the disclosed precision cancer treatment, the disclosed antineoplaston, the disclosed pharmaceutical formulations, the disclosed anti-chemokine, the disclosed anti-cancer agents, the disclosed chemotherapeutic, or a combination thereof) to a subject having or diagnosed with cancer.

Disclosed are the components to be used to prepare the disclosed isolated nucleic acid molecules, disclosed precision cancer treatments, or disclosed pharmaceutical formulations as well as the disclosed isolated nucleic acid molecules, disclosed precision cancer treatments, or disclosed pharmaceutical formulations used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific disclosed method or disclosed aspect or combination of disclosed methods or disclosed aspects.

B. Compositions for Use in the Disclosed Methods

1. Antineoplastons

Disclosed herein are compositions comprising one or more antineoplastons. Antineoplastons (ANP) are peptides, amino acid derivatives and carboxylic acids that were initially isolated from the blood and urine of healthy subjects.

Atengenal (A10) can comprise a 4:1 ratio of synthetic phenylacetylglutaminate sodium (PG) and phenylacetylisoglutaminate sodium (iso-PG). PG has a molecular weight of 286.26 and an empirical formula of $C_{13}H_{15}N_2NaO_4$. PG can be synthesized by the reaction of phenylacetyl chloride with L-glutamine in an aqueous solution containing sodium bicarbonate. PG is a hygroscopic white powder having a melting point of approximately 102° C. and is very soluble in water. The structural formula of PG is:

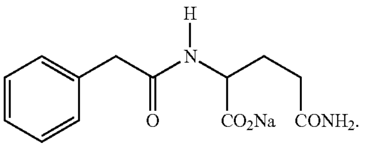

Iso-PG has a molecular weight of 286.26 and an empirical formula of $C_{13}H_{15}N_2NaO_4$. Iso-PG can be synthesized by the reaction of phenylacetyl chloride with L-glutamine in an aqueous solution containing sodium bicarbonate to afford PG, which in turn can be heated under vacuum at 160° C. to yield A10C (3-phenylacetylamino-2,6-piperidinedione). When A10C is treated with sodium hydroxide, it can produce a mixture of PG and iso-PG in a 4:1 ratio. Iso-PG is a white powder having a melting point of approximately 175-176° C. and is soluble in water. The structural formula of iso-PG is:

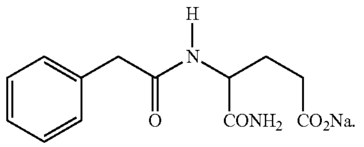

Astugenal (AS2-1) can comprise phenylacetate (PN) and PG in a 4:1 ratio. PN is characterized by a molecular weight of 158.63 and an empirical formula of $C_8H_8NaO_2$. PN can be synthesized by refluxing benzyl cyanide with dilute sulfuric acid or hydrochloric acid. In solid form, PN has a melting point of approximately 76.5° C. The structural formula of PN is:

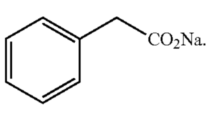

As used herein, "antineoplaston (ANP) therapy" can refer to administration to a subject or patient, by any administration route, of an "ANP therapeutic composition" or a disclosed composition or pharmaceutical formulation comprising one or more antineoplastons (e.g., a therapeutically effective amount of Atengenal (A10), Astugenal (AS2-1), or any combination thereof).

In an aspect, a disclosed ANP therapy can be used as a pan-tumor therapy.

2. Formulations

Disclosed herein is a pharmaceutical formulation comprising one or more antineoplastons and one or more pharmaceutically acceptable carriers.

In an aspect of a disclosed pharmaceutical formulation, disclosed antineoplastons can comprise phenylacetate, phenylacetylglutaminate, phenylacetylglutaminate sodium, phenylacetylisoglutaminate sodium, or any combination thereof.

In an aspect of a disclosed pharmaceutical formulation, the disclosed one or more antineoplastons can comprise phenylacetylglutaminate sodium (PG) and phenylacetylisoglutaminate sodium (iso-PG). In an aspect of a disclosed pharmaceutical formulation, a disclosed ratio of phenylacetylglutaminate sodium (PG) and phenylacetylisoglutaminate sodium (iso-PG) can be about 10:1, about 9:1, about 8:1, about 7:1, about 6:1, about 5:1, about 4:1, about 3:1, about 2:1, or about 1:1. In an aspect of a disclosed pharmaceutical formulation, a disclosed ratio of phenylacetylglutaminate sodium (PG) and phenylacetylisoglutaminate sodium (iso-PG) can range from about 10:1 to about 1:10. In an aspect of a disclosed pharmaceutical formulation, a disclosed ratio of phenylacetylglutaminate sodium (PG) and phenylacetylisoglutaminate sodium (iso-PG) can be about 4:1. In an aspect, a therapeutically effective amount of a disclosed pharmaceutical formulation can comprise about 0.1 g/kg/day to about 20 g/kg/day.

In an aspect of a disclosed pharmaceutical formulation, the disclosed one or more antineoplastons can comprise phenylacetate (PN) and phenylacetylglutaminate (PG). In an aspect of a disclosed pharmaceutical formulation, a disclosed ratio of phenylacetate (PN) and phenylacetylglutaminate (PG) can be about 10:1, about 9:1, about 8:1, about 7:1, about 6:1, about 5:1, about 4:1, about 3:1, about 2:1, or about 1:1. In an aspect of a disclosed pharmaceutical formulation, a disclosed ratio of phenylacetate (PN) and phenylacetylglutaminate (PG) can range from about 10:1 to about 1:10. In an aspect of a disclosed pharmaceutical formulation, a disclosed ratio of phenylacetate (PN) and phenylacetylglutaminate (PG) can be about 4:1. In an aspect, a therapeutically effective amount of a disclosed pharmaceutical formulation can comprise about 0.08 g/kg/day to about 0.6 g/kg/day.

In an aspect, a disclosed pharmaceutical formulation comprising one or more antineoplastons can comprise bevacizumab, pazopanib, sorafenib, dasatinib, everolimus, or any combination thereof. For example, in an aspect, pazopanib and/or sorafenib can be orally administered to a subject at a dose of from about 1 mg/kg/day to about 12 mg/kg/day or from 2 mg/kg/day to about 6 mg/kg/day. In an aspect, a disclosed optimal dose of pazopanib and/or sorafenib can be about 3 mg/kg/day. In an aspect, dasatinib can be orally administered to a subject at a dose of from about 0.3 mg/kg/day to about 2.0 mg/kg/day or from about 0.7 mg/kg/day to about 1.4 mg/kg/day. In an aspect, a disclosed optimal dose of dasatinib can be about 0.7 mg/kg/day. In an aspect, everolimus can be orally administered to a subject at a dose of from about 0.03 mg/kg/day to about 0.15 mg/kg/day or from about 0.03 mg/kg/day to about 0.10 mg/kg/day. In an aspect, a disclosed optimal dose of everolimus can be about 0.07 mg/kg/day.

In an aspect, a disclosed pharmaceutical formulation comprising one or more antineoplastons can reduce and/or eliminate the number and/or type of genomic aberrations. For example, in an aspect, if a subject initially had X number of genomic aberrations, then following administration of a disclosed pharmaceutical formulation, the subject has some number of genomic aberrations less than X. In an aspect, a disclosed pharmaceutical formulation comprising one or more antineoplastons can prevent and/or decreases metastases. In an aspect, a disclosed pharmaceutical formulation comprising one or more antineoplastons can prolong the survival of a subject. In an aspect, a disclosed pharmaceutical formulation comprising one or more antineoplastons can improve the survivability of the subject. In an aspect, a disclosed pharmaceutical formulation comprising one or more antineoplastons can increase the subject's survivability, can increase the length of time before metastasis, can reduce the likelihood of surgical intervention, can reduce the need for administration of one or more additional therapeutic agents or regiments, can reduce the size of one or more tumors in the subject, eliminating one or more tumors in the subject, can reduce and/or eliminate the prevalence of one or more genomic aberrations, can restore the normal metabolism of one or more organ systems in the subject, can restore one or more aspect of cellular homeostasis and/or cellular functionality, and/or metabolic dysregulation; or any combination thereof.

In an aspect, disclosed pharmaceutical formulation comprising one or more antineoplastons can protect the subject from metastasis. In an aspect, disclosed pharmaceutical formulation comprising one or more antineoplastons can reduce the risk of developing metastasis.

In an aspect, restoring one or more aspects of cellular homeostasis and/or cellular functionality can comprise one or more of the following: (i) correcting cell starvation in one or more cell types (such as, for example, liver cells and muscle cells); (ii) normalizing aspects of the autophagy pathway (such as, for example, correcting, preventing, reducing, and/or ameliorating autophagy); (iii) improving, enhancing, restoring, and/or preserving mitochondrial functionality and/or structural integrity; (iv) improving, enhancing, restoring, and/or preserving organelle functionality and/or structural integrity; (v) preventing, slowing, and/or eliminating hypoglycemia, ketosis, and/or other liver abnormalities; (vi) correcting liver enzyme dysregulation; (vii) reversing, inhibiting, preventing, stabilizing, and/or slowing the rate of progression of tumor metastasis; (viii) reversing, inhibiting, preventing, stabilizing, and/or slowing the rate of progression of tumor growth and/or cancer spread, or (ix) any combination thereof. In an aspect, restoring one or more aspects of cellular homeostasis can comprise improving, enhancing, restoring, and/or preserving one or more aspects of cellular structural and/or functional integrity in, for example, an organ or system that has been affected by cancer.

In an aspect, a disclosed pharmaceutical formulation comprising one or more antineoplastons can comprise one or more chemotherapeutic agents. In an aspect, a disclosed chemotherapeutic agent can comprise an anthracycline, a vinca alkaloid, an alkylating agent, an immune cell antibody, an antimetabolite, a TNFR glucocorticoid induced TNFR related protein (GITR) agonist, a proteasome inhibitor, an immunomodulator, or any combination thereof. In an aspect, a disclosed chemotherapeutic agent can comprise 5-fluorouracil (Adrucil, Efudex), 6-mercaptopurine (Purinethol), 6-thioguanine, aclarubicin or aclacinomycin A, alemtuzamab (Lemtrada), anastrozole (Arimidex), bicalutamide (Casodex), bleomycin sulfate (Blenoxane), bortezomib (Velcade), busulfan (Myleran), busulfan injection (Busulfex), capecitabine (Xeloda), carboplatin (Paraplatin), carmustine (BiCNU), chlorambucil (Leukeran), cisplatin (Platinol), cladribine (Leustatin), Cosmegan, cyclophosphamide (Cytoxan or Neosar), cyclophosphamide, cytarabine liposome injection (DepoCyt), cytarabine, cytosine arabinoside (Cytosar-U), dacarbazine (DTIC-Dome), dactinomycin (Cosmegen), daunorubicin citrate liposome injection (DaunoXome), daunorubicin hydrochloride (Cerubidine), dexamethasone, docetaxel (Taxotere), doxorubicin hydrochloride (Adriamycin, Rubex), etoposide (Vepesid), fludarabine phosphate (Fludara), flutamide (Eulexin), folic acid antagonists, gemcitabine (difluorodeoxycitidine), gemtuzumab, gliotoxin, hydroxyurea (Hydrea), Idarubicin (Idamycin), ifosfamide (IFEX), ifosfamide, irinotecan (Camptosar), L-asparaginase (ELSPAR), lenalidomide), leucovorin calcium, melphalan (Alkeran), melphalan, methotrexate (Folex), mitoxantrone (Novantrone), mylotarg, N4-pentoxycarbonyl-5 deoxy-5-fluorocytidine, nab-paclitaxel (Abraxane), paclitaxel (Taxol), pentostatin, phoenix (Yttrium90/MX-DTPA), polifeprosan 20 with carmustine implant (Gliadel), purine analogs and adenosine deaminase inhibitors (fludarabine), pyrimidine analogs, rituximab, tamoxifen citrate (Nolvadex), temozolomide), teniposide (Vumon), tezacitibine, thalidomide or a thalidomide derivative, thiotepa, tirapazamine (Tirazone), topotecan hydrochloride for injection (Hycamptin), tositumomab), vinblastine (Velban), vinblastine, vincristine (Oncovin), vindesine, vinorelbine (Navelbine), or any combination thereof.

In an aspect, a disclosed pharmaceutical formulation comprising one or more antineoplastons can comprise an anti-chemokine therapy that enhances the resident memory T cell formations in tumor-free tissues. In an aspect, a disclosed anti-chemokine therapy can comprise one or more antibodies against CCL1, CCL2, CCL4, CCL17, CCL19, CCL21, CCL22, CCL25, CXCL9, CXCL10, CXCL11, CXCL12, CXCL13, CCR2, CCR5, CCR7, CCR8, CCR9, CXCR3, CXCR4, CXCR5, CX3CL1, CX3CR1, or any combination thereof.

In an aspect, a disclosed pharmaceutical formulation comprising one or more antineoplastons can be prepared for systemic or direct administration. In an aspect, a disclosed pharmaceutical formulation can be prepared for oral administration, intravenous administration, intratumoral administration, intraperitoneal administration, or any combination thereof. In an aspect, a disclosed pharmaceutical formulation can be prepared for any method of administration disclosed herein. In an aspect, a disclosed pharmaceutical formulation can be prepared for administration via multiple routes either concurrently or sequentially. For example, in an aspect, a disclosed pharmaceutical formulation can be first administered intratumorally and then be administered intravenously. In an aspect, a disclosed pharmaceutical formulation can be first administered intratumorally and then be administered orally. A skilled clinical can determine the best route of administration for a subject at a given time.

In an aspect, a disclosed pharmaceutical formulation comprising one or more disclosed antineoplastons can comprise (i) one or more active agents, (ii) biologically active agents, (iii) one or more pharmaceutically active agents, (iv) one or more immune-based therapeutic agents, (v) one or more clinically approved agents, or (vi) a combination thereof. In an aspect, a disclosed pharmaceutical formulation can comprise one or more immune modulators. In an aspect, a disclosed pharmaceutical formulation can comprise one or more proteasome inhibitors. In an aspect, a disclosed pharmaceutical formulation can comprise one or more immunosuppressives or immunosuppressive agents. In an aspect, an immunosuppressive agent can be anti-thymocyte globulin (ATG), cyclosporine (CSP), mycophenolate mofetil (MMF), or a combination thereof.

In an aspect, a disclosed pharmaceutical formulation can comprise an anaplerotic agent (such as, for example, C7 compounds like triheptanoin or MCT).

In an aspect, a disclosed pharmaceutically acceptable carrier can comprise any disclosed carrier. In an aspect, a disclosed pharmaceutically acceptable carrier can comprise any disclosed excipient.

In an aspect, a disclosed pharmaceutical formulation can be packaged in unit dosage forms such as tablets, pills, capsules, powders, granules, solutions or suspensions, or suppositories, for oral, parenteral or rectal administration, or administration by inhalation or insufflation.

In an aspect, a disclosed pharmaceutical formulation can be used as a pan-tumor therapy.

C. Methods of Treating and/or Preventing Cancer

Disclosed herein is a method of treating and/or preventing cancer, the method comprising administering to a subject in need thereof a precision cancer treatment, wherein the subject demonstrates a tumor response and/or molecular response to the precision cancer treatment.

Disclosed herein is a method of treating cancer, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment.

Disclosed herein is a method of treating cancer, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and measuring the subject's tumor response and/or the subject's molecular response.

Disclosed herein is a method of treating cancer, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment.

In an aspect, a disclosed precision cancer treatment can comprise one or more antineoplastons or can comprise a composition comprising one or more antineoplastons. In an aspect, disclosed antineoplastons can comprise phenylacetate, phenylacetylglutaminate, phenylacetylglutaminate sodium, phenylacetylisoglutaminate sodium, or any combination thereof. In an aspect, a disclosed composition comprising one or more antineoplastons can comprise phenylacetate, phenylacetylglutaminate, phenylacetylglutaminate sodium, phenylacetylisoglutaminate sodium, or any combination thereof.

In an aspect, a disclosed composition comprising one or more antineoplastons can comprise a pharmaceutically acceptable carrier. In an aspect, the disclosed one or more antineoplastons can comprise phenylacetylglutaminate sodium (PG) and phenylacetylisoglutaminate sodium (iso-PG). In an aspect, a disclosed ratio of phenylacetylglutaminate sodium (PG) and phenylacetylisoglutaminate sodium (iso-PG) can be about 10:1, about 9:1, about 8:1, about 7:1, about 6:1, about 5:1, about 4:1, about 3:1, about 2:1, or about 1:1. In an aspect, a disclosed ratio of phenylacetylglutaminate sodium (PG) and phenylacetylisoglutaminate sodium (iso-PG) can range from about 10:1 to about 1:10. In an aspect, a disclosed ratio of phenylacetylglutaminate sodium (PG) and phenylacetylisoglutaminate sodium (iso-PG) can be about 4:1. In an aspect, a dose of the disclosed one or more antineoplastons can comprise about 0.1 g/kg/day to about 20 g/kg/day. In an aspect, a therapeutically effective dose of the disclosed one or more antineoplastons can comprise about 0.1 g/kg/day to about 20 g/kg/day. In an aspect, a disclosed dose of phenylacetylglutaminate sodium (PG) can comprise about 0.4 g/kg/day to about 16 g/kg/day, and a disclosed dose of phenylacetylisoglutaminate sodium (iso-PG) can comprise about 0.1 g/kg/day to about 4 g/kg/day.

In an aspect, a disclosed therapeutically effective amount of phenylacetylglutaminate sodium (PG) can comprise about 0.4 g/kg/day to about 16 g/kg/day. In an aspect, a disclosed therapeutically effective amount of phenylacetylisoglutaminate sodium (iso-PG) can comprise about 0.1 g/kg/day to about 4 g/kg/day.

In an aspect, the disclosed one or more antineoplastons can comprise phenylacetate (PN) and phenylacetylglutaminate (PG). In an aspect, a disclosed ratio of phenylacetate (PN) and phenylacetylglutaminate (PG) can be about 10:1, about 9:1, about 8:1, about 7:1, about 6:1, about 5:1, about 4:1, about 3:1, about 2:1, or about 1:1. In an aspect, a disclosed ratio of phenylacetate (PN) and phenylacetylglutaminate (PG) can range from about 10:1 to about 1:10. In an aspect, a disclosed ratio of phenylacetate (PN) and phenylacetylglutaminate (PG) can be about 4:1. In an aspect, a dose of the disclosed one or more antineoplastons can comprise about 0.08 g/kg/day to about 0.6 g/kg/day. In an aspect, a therapeutically effective dose of the disclosed one or more antineoplastons can comprise about 0.08 g/kg/day to about 0.6 g/kg/day. In an aspect, a disclosed dose of phenylacetate (PN) can comprise about 0.064 g/kg/day to about 0.48 g/kg/day, and a disclosed dose of phenylacetylglutaminate (PG) can comprise about 0.016 g/kg/day to about 0.12 g/kg/day. In an aspect, a therapeutically effective dose of phenylacetate (PN) can comprise about 0.064 g/kg/day to about 0.48 g/kg/day, and a therapeutically effective phenylacetylglutaminate (PG) can comprise about 0.016 g/kg/day to about 0.12 g/kg/day.

In an aspect of a disclosed method of treating and/or preventing cancer, administering a disclosed precision cancer treatment can comprise intravenous administration. In an aspect, a disclosed precision cancer treatment can be administered to a subject intravenously using, for example, a dual-channel infusion pump or two single channel pumps and central venous catheter. In an aspect, a disclosed IV administration of a disclosed precision cancer treatment can occur once every four hours at the infusion rate of from about 50 mL/hr to about 250 mL/hr (e.g., about 50, 75, 100, 125, 150, 175, 200, 225, 250 mL/hr) depending on the subject's age and condition/tolerance.

In an aspect, a disclosed method of treating and/or preventing cancer can comprise titrating the dose of a disclosed precision cancer treatment. In an aspect, a disclosed method of treating and/or preventing cancer can comprise titrating the dose of A10, AS2-1, or a combination thereof. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects.

In an aspect, a disclosed method of treating and/or preventing cancer can comprise titrating the dose of a disclosed precision cancer treatment in a specific or disclosed subject. In an aspect, a disclosed method of treating and/or preventing cancer can comprise titrating the dose of A10, AS2-1, or a combination thereof in a specific or disclosed subject. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects for a specific or disclosed subject.

In an aspect, administering comprises administering to the subject the maximum tolerated dose of A10, AS2-1, or both. In an aspect, administering comprises administering to the subject less than the maximum tolerated dose of A10, AS2-1, or both.

In an aspect, IV administration of a disclosed precision cancer treatment can comprise an outpatient setting. In an aspect, A10 can be administering prior to, concurrent with, or after administering of AS2-1. In an aspect, AS2-1 can be administering prior to, concurrently with, or after administering of A10. In an aspect, the order of administering one or more antineoplastons can change during a treatment regimen.

In an aspect, a disclosed method of treating and/or preventing cancer can further comprise obtaining a biological sample from the subject prior to administering a disclosed precision cancer treatment. In an aspect, a disclosed method of treating and/or preventing cancer can further comprise obtaining a biological sample from the subject after administering a disclosed precision cancer treatment. In an aspect, a disclosed method of treating and/or preventing cancer can further comprise subjecting the biological sample to a cell-free DNA (cfDNA) analysis. cfDNA analyses are known to the skilled person in the art. In an aspect, a disclosed cfDNA analysis can be repeated one or more times. In an aspect, a disclosed obtaining step can be repeated one or more times.

In an aspect of a disclosed method of treating and/or preventing cancer, a disclosed cfDNA analysis can comprise next generation sequencing. In an aspect, next generation sequencing (NGS) can comprise using one or more commercially available platforms. Commercially available NGS sequencing platforms can comprise, for example, Guardant360 CDx (Guardant Health, Inc.), FoundationOne CDx (F1CDx) (Foundation Medicine, Inc.), or Tempus xT (Tempus).

In an aspect of a disclosed method of treating and/or preventing cancer, a disclosed cancer-related gene can comprise ABL1, ABL2, ACO2, ACTB, ACVR1B, AKT, AKT1, AKT2, AKT3, ALK, AMER11, APC, AR, ARAF, ARFRP1, ARID1A, ARID1B, ARID2, ASK, ASPM, ASXL1, ATF1, ATF3, ATM, ATR, ATRX, AURKA, AURKB, AXIN1, AXL, BAD, BAGE, BAGE2, BAP1, BARD1, BAX, BCL2, BCL2L1, BCL2L2, BCL6, BCMA, BCOR, BCORL1, BDNF, BLM, BMPR1A, BRAF, BRCA1, BRCA2, BRD4, BRIP1, BTG1, BTK, BUB1, C10ORF54, CAGE1, CARD11, CASP5, CBFB, CBL, CCL1, CCL11, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL7, CCL8, CCNA 2, CCNB 1, CCNB 2, CCND, CCND1, CCND2, CCND3, CCNE1, CCNE2, CCR1, CCR10, CCR2, CCR3, CCR4, CCR5, CCR6, CCR7, CCR8, CCR9, CD123, CD19, CD20, CD25, CD274, CD276, CD30, CD33, CD4, CD79A, CD79B, CD8, CD80, CD86, CDC, CDC2, CDC20, CDC25A, CDC25B, CDC25C, CDC42, CDC6, CDC6; CDC7, CDC73, CDCA8, CDH1, CDK12, CDK2, CDK3, CDK4, CDK6, CDK8, CDKN1A, CDKN1B, CDKN2A, CDKN2B, CDKN2C, CEA, CEBPA, CFS1, CHD2, CHD4, CHEK1, CHEK2, CHK-1, CIC, CLDND1, CNE2, CREBBP, CRKL, CRLF2, CSF1, CSF1R, CSF3, CTAG1, CTAG1B, CTAG2, CTAG4, CTAG5, CTAG6, CTAG9, CTCF, CTLA4, CTNNA1, CTNNB1, CUL3, CXCL1, CXCL10, CXCL11, CXCL12, CXCL13, CXCL14, CXCL16, CXCL17, CXCL2, CXCL3, CXCL5, CXCL6, CXCL9, CXCR1, CXCR2, CXCR3, CXCR5, CXCR6, CYLD, DAXX DCC, DDR2, DEPTOR, DICER1, DLD, DLST, DNMT3A, DOT1L, DUSP1, DUSP6, E2F1, EBNA1, EBNA2, EGFR, EMSY, ENOX2, EP300, EPCAM, EPHA3, EPHA5, EPHA7, EPHB1, ERBB2, ERBB3, ERBB4, ERCC1, EREG, ERG, ERK, ERRF11, ESR1, EWSR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR, FGFR1, FGFR2, FGFR3, FGFR4, FH, FLCN, FLI1, FLT1, FLT3, FLT4, FOLH1, FOLR1, FOXL2, FOXP1, FRS2, FUBP1, GABRA6, GADD45A, GAGE1, GAGE10, GAGE12D, GAGE12F, GAGE12J, GAGE13, GAGE2A, GAGE2B, GAGE2C, GAGE2D, GAGE2E, GAGE4, GART, GATA1, GATA2, GATA3, GATA4, GATA6, GID4, GLI1, GNA, GNA11, GNA13, GNAQ, GNAS, GPNMB, GPR124, GRIN2A, GRM3, GSK3B, H3F3A, HAVCR2, HDAC, HDAC1, HDAC5, HGF, HHLA2, HIF1, HIF1A, HIST1H1D, HNF1A, HRAS, HSD3B1, HSP90AA1, ICOSLG, IDH1, IDH2, IDH3A, IDH3B, IDO, IGF1R, IGF2, IKBKE, IKZF1, IL1, IL15, IL1A, IL1B, IL6, IL7R, IL8, INHBA, INPP4B, IRF2, IRF4, IRS2, JAK1, JAK2, JAK3, JUN, KDM5A, KDM5C, KDM6A, KDR, KEAP, KEL, KIT, KLHL6, KLK3, KRAS, LAG1, LAG3, LMO1, LMP1, LRP1B, LYN, LZTR1, MAD2L1, MAGEA1, MAGEA10, MAGEA12, MAGEA2, MAGEA3, MAGEA4, MAGEA5, MAGEA6, MAGEA7, MAGEA8, MAGEA9, MAGEB1, MAGEB10, MAGEB16, MAGEB18, MAGEB2, MAGEB3, MAGEB4, MAGEB6, MAGEC1, MAGEC2, MAGEC3, MAGED1, MAGED2, MAGED4, MAGED4B, MAGEE1, MAGEE2, MAGEB1, MAGEH1, MAGEL2, MAGI2, MAP2K1, MAP2K2, MAP2K4, MAP3K1, MAP3K6, MAPK, MCL1, MCM, MCM2, MCM3, MCM4, MCM5, MCM6, MCM7, MDH1, MDM2, MDM4, MED12, MEF26, MEF2B, MEN1, MET, MITF, MLH1, MLL, MLL2, MLL3, MPL, MRE11A, MSH2, MSH6, MTOR, MUC1, MUTYH, MYC, MYCL, MYCN, MYD88, MYH, MYST3, NCR3LG1, Netrin, NF1, NF2, NFE2L2, NFKB, NFKB1A, NGF, NKX2-1, NOTCH1, NOTCH2, NOTCH3, NPM1, NRAS, NSD1, NTRK1, NTRK2, NTRK3, NUP93, OGDH, ORC, ORC1, ORC1L, ORC1L, ORC6L, ORCL, ORCLPCNA, PAK3, PALB2, PAPPA, PARK2, PAX, PAX3, PBRM1, PCNA, PDCD1, PDCD1LG2, PDGFRA, PDGFRB, PDHA1, PDK1, PGR, PIK3C2B, PIK3CA, PIK3CB, PIK3CG, PIK3R1, PIK3R2, PIK3R1, PKMYT, PKMYT1, PLCG2, PLK1, PMS2, POLD1, POLE, PPM1A, PPP2R1A, PREX2, PRKAR1A, PRKC1, PRKDC, PRSS8, PTCH1, PTEN, PTPN1, PTPN11, PTPRR, PTTG, PTTG1, PTTG2, PTTG3, QK1, RAC1, RAD50, RAD51, RAF1, RANBP1, RARA, RAS, RB1, RBL1, RBM10, RET, RICTOR, RIT1, RNF43, ROS1, RPTOR, RUNX1, RUNX1T1, SDHA, SDHB, SDHC, SDHD, SETD2, SF3B1, SKP2, SLAMF7, SLIT2, SMAD2, SMAD3, SMAD4, SMARCA4, SMARCB1, SMC1A, SMC1L1, SMO, SNCAIP, SOCS1, SOX10, SOX2, SOX9, SPAG1, SPAG11A, SPAG11B, SPAG16, SPAG17, SPAG4, SPAG5, SPAG6, SPAG7, SPAG8, SPAG9, SPEN, SPOP, SPTA1, SRC, SRSF2, STAG2, STAT3, STAT4, STAT5, STAT5B, STK11, SUCLG1, SUCLG2, SUFU, SYK, T(BRACHYURY), TAF1, TBC1D8, TBX3, TERC, TERT, TERT promoter, TET2, TFDP1, TGFRB2, TNFAIP3, TNFRSF14, TOP1, TOP2A, TOP2B, TP53, TRIB3, TSC1, TSC2, TSHR, TUBB3, TYMP, TYMS, U2AF1, UNC5A, UNC5B, VEGFA, VHL, VTCN1, WEE1, WISP3, WT1, XAGE1D, XAGE2, XAGE3, XAGE5, XCL1, XCL2, XCR1, XPO1, ZBTB2, ZNF217, ZNF703, or any combination thereof.

In an aspect, a disclosed cancer-related gene can comprise one or more genomic aberrations. In an aspect, a subject can have one or more genomic aberrations in a disclosed cancer-related gene.

In an aspect, a disclosed ALK gene can encode a ALK protein having an I1461L or N1544K mutation. In an aspect, a disclosed ARID2 gene can encode an ARID2 protein having a N127fs18 mutation. In an aspect, a disclosed AKT1 gene can encode a AKT1 protein having a E17K or R346H mutation. In an aspect, a disclosed APC gene can encode an APC protein having a G29G, K445K, V2716L, E918E, Q1378*, S457*, I1304fs, E888fs, R230C, Q1090Q, S1360P. In an aspect, a disclosed gene can encode an AR protein having a A356E M887V or S510R mutation. In an aspect, a disclosed ARAF gene can encode a ARAF protein having a Y495Y mutation. In an aspect, a disclosed ARID1A gene can encode an ARID1A protein having a S1798L, S1167F, G246V, R1889W, or Q802fs mutation. In an aspect, a disclosed ARID2 gene can encode an ARID2 protein having a N127fs18 mutation. In an aspect, a disclosed ARTX gene has a S850fs*2, or s N179fs*26 mutation. In an aspect, a disclosed ASXL1 gene has a R1273f*s mutation. In an aspect, a disclosed BRAF gene can encode a BRAF protein having a E264 or V600E mutation. In an aspect, a disclosed BRCA1 gene can encode a BRAC1 protein having a H662Q or a R1443* mutation. In an aspect, a disclosed BRCA2 gene can encode a BRCA2 protein having a D237N or 12040V mutation. In an aspect, a disclosed CCND1 gene can encode a CCND1 protein having a R291W mutation. In an aspect, a disclosed CCNE1 gene can encode a CCNE1 protein having a P268P or R95Q mutation. In an aspect, a disclosed CDKN1B gene can encode a CDKN1B protein having a K59fs* mutation. In an aspect, a disclosed CDKN2A gene can encode a CDKN2A protein having a D74N mutation. In an aspect, a disclosed CTNNB1 gene can encode a CTNNB1 protein having a T41A mutation. In an aspect, a disclosed DDR2 gene can encode a DDR2 protein having a L749L mutation. In an aspect, a disclosed EGFR gene can encode an EGFR protein having a P753L, V524I, D321D, or V7421 mutation. In an aspect, a disclosed ERBB2 gene can encode a ERBB2 protein having a C584G or V797del (Exon 20 deletion) mutation. In an aspect, a disclosed EWSR1 gene can encode a EWSR1 protein having a FLI1 fusion. In an aspect, a disclosed FBXW7 gene can encode a FBXW7 protein having a Y545C or R658* mutation. In an aspect, a disclosed FGFR gene can encode a FGFR protein having a T320T, S726F, H791H, P47P, S430fs, or R179H mutation. In an aspect, a disclosed FGFR1 gene can encode a FGFR1 protein having a S726F mutation. In an aspect, a disclosed FGFR2 gene can encode a FGFR2 protein having a KCNH7 fusion. In an aspect, a disclosed FGFR3 gene can encode a FGFR3 protein having a H290Y mutation. In an aspect, a disclosed GATA3 gene can encode a GATA3 protein having a P433fs43, P409fs, PS405fs, D336fs, S430fs, or c.1213_1214del mutation. In an aspect, a disclosed GNA11 gene can encode a GNA11 protein having a N244S mutation. In an aspect, a disclosed GNAS gene can encode a GNAS protein having a R201H* mutation. In an aspect, a disclosed HIST1H1D gene can encode a HIST1H1D protein having a K185-A186>T mutation. In an aspect, a disclosed H3F3A gene can encode a H3F3A protein having a K28N or K27 mutation. In an aspect, a disclosed IDH1 gene can encode an IDH1 protein having a R132H mutation. In an aspect, a disclosed JAK2 gene can encode a JAK2 protein having a V617 mutation. In an aspect, a disclosed KIT gene has a Q 775 fs (Exon 16 deletion). In an aspect, a disclosed ARID1A gene can encode an ARID1A protein having a S1798L, S1167F, G246V, R1889W, or Q802fs mutation. In an aspect, a disclosed KRAS gene can encode a KRAS protein having a G12V, G12D, G12S, G13D, or p.AG11GD mutation. In an aspect, a disclosed MAP2K1 gene can encode a MAP2K1 protein having a K57E mutation. In an aspect, a disclosed MAP2K4 gene has a loss of exon 2. In an aspect, a disclosed MAP3K1 gene can encode a MAP3K1 protein having a S398 mutation. In an aspect, a disclosed MAP3K6 gene can encode a MAP3K6 protein having a P646L mutation. a disclosed MET gene can encode a MET protein having a C385Y, T895M, T7591, or M391 mutation. In an aspect, a disclosed MPL gene can encode a MPL protein having a Y591D mutation. In an aspect, a disclosed MYC gene can encode a MYC protein having a S244S mutation. In an aspect, a disclosed NF1 gene has a Splice cite 480-11_4801del11, Splice cite SNV, c.6655>T, p.D2219Y, V2378fs*8, or can encode a A2617A, F710C, I1719T, or K583R mutation. In an aspect, a disclosed NOTCH1 gene can encode a NOTCH protein having a A465V, V220M, D1681H, or S223N mutation. In an aspect, a disclosed NOTCH2 gene can encode a NOTCH2 protein having a S2379F mutation. In an aspect, a disclosed NTRK1 gene can encode a NTRK1 protein having a P387L or R766Q mutation. In an aspect, a disclosed PDGFRA gene can encode a PDGFRA protein having a E86A or V299G mutation. In an aspect, a disclosed PIK3CA gene can encode a PIK3CA protein having a Q546H, Q546K, Q546R, Q597H, E542K, E545K, E726K, E39K, E453K, R4-P18del, H1047L, H104R, K567E, I15431, p.E545K, or G1049R mutation. In an aspect, a disclosed PIK3R1 gene can encode a PIK3R1 protein having a S399Y408del splice site 917-1G>A mutation. In an aspect, a disclosed PTCH1 has a p.M17 Start loss-LOF. In an aspect, a disclosed PTEN gene can encode a PTEN protein having a H196_1203DEL, R55fs, N323fs*23, Y27C, R130*, C136Y, D252Y, or loss of exons 4-7 mutation. In an aspect, a disclosed RAFT gene can encode a RAF protein having a P63P mutation. In an aspect, a disclosed RB1 gene can encode a RB1 protein having a Q217*, Y173fs*, or H673fs mutation. In an aspect, a disclosed RUNX1 gene can encode a RUNX1 protein having a R107C mutation. In an aspect, a disclosed SMAD4 gene can encode a SMAD4 protein having a P511 L, D537V, Q450H, L495R, A451P, or A406T mutation. In an aspect, a disclosed SPEN gene can encode a SPEN protein having a A2510V mutation. In an aspect, a disclosed SRSF2 gene can encode a SRSF2 protein having a P95H mutation. In an aspect, a disclosed STAT5B gene can encode a STAT5B protein having a R110H mutation. In an aspect, a disclosed TET2 gene can encode a TET2 protein having a C1875G mutation. In an aspect, a disclosed TP53 gene can encode a TP53 protein having a V73fs, R175G, R196, R249T, C176F, G187D, R282W, E287*, E285K, S241del, c.97-28_99del, Y126D, R273H, C176W, K320*, T253A, Splice site 37G-1G>A, Q104, P151H, H179Y, R273C, R248W, R176H, R209fs cer, N235-Y236del, R248Q er, R306*, C176Y, S241F, L252-1254del, L145P, R158H, R213*, Y220C, R110P, V274G, or c.376-4_384del mutation.

With respect to the Guardant360 platform, a genomic aberration in a disclosed cancer-related gene can comprise a single nucleotide variant. For example, in an aspect, a disclosed single nucleotide variant can be identified in the following genes—AKT1, ALK, APC, AR, ARAF, ATM, BRAF, BRCA1, BRCA2, CCND1, CDH1, CDK4, CDK6, CDK12, CDKN2A, CTNNB1, EGFR, ERBB2, ESR1, FGFR1, FGFR2, FGFR3, GATA3, GNA11, GNAQ, HRAS, IDH1, IDH2, KIT, KRAS, MAP2K1, MAP2K2, MET, MLH1, MTOR, MYC, NF1, NFE2L2, NRAS, NTRK1, NTRK3, PDGFRA, PIK3CA, PTEN, RAF1, RET, RHEB, ROS1, SMAD4, SMO, STK11, TERT, TSC1, VHL, or any combination thereof. With respect to the Guardant360 platform, a genomic aberration in a disclosed cancer-related gene can comprise an insertion and/or deletion. For example, in an aspect, a disclosed Indel can be identified in the following genes—AKT1, ALK, APC, ATM, BRAF, BRCA1, BRCA2, CDH1, CDK12, CDKN2A, EGFR, ERBB2, ESR1, FGFR2, GATA3, HNF1A, HRAS, KIT, KRAS, MET, MLH1, NF1, PDGFRA, PIK3CA, PTEN, RET, ROS1, STK11, TSC1, VHL, or any combination thereof. With respect to the Guardant360 platform, in an aspect, a genomic aberration in a disclosed cancer-related gene can comprise a copy number amplification (CNA). For example, in an aspect, a disclosed CNA can be identified in the following genes—ERBB2 and/or MET. With respect to the Guardant360 platform, in an aspect, a disclosed fusion can comprise ALK, NTRK1, RET, ROS1, or any combination thereof.

With respect to the Foundation platform, in an aspect, a genomic aberration in a disclosed cancer-related gene can comprise a substitution, an Indel, or a copy number amplification. For example, in an aspect, a disclosed substitution, a disclosed Indel, or a disclosed CNA can be identified in the following genes—ABL1, ACVR1B, AKT1, AKT2, AKT3, ALK, ALOX12B, AMER1 (FAM723B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR, BCORL1, BRAF, BRCA1, BRCA2, BRD4, BRIP1, BTG1, BTG2, BTK, C11ORF30 (EMSY), CALR, CARD11, CASP8, CBFB, CBL, CCND1, CCND2, CCND3, CCNE1, CD22, CD274 (PD-L7), CD70, CD79A, CD79B, CDC73, CDH1, CDK12, CDK4, CDK6, CDK8, CDKN1A, CDKN1B, CDKN2A, CDKN2B, CDKN2C, CEBPA, CHEK7, CHEK2, CIC, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRF11, ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GID4 (C17ORF39), GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A (MLL), KMT2D (MLL2), KRAS, LTK, LYN, MAF, MAP2K1 (MEK1), MAP2K2 (MEK2), MAP2K4, MAP3K1, MAP3K13, MAPK1, MCL1, MDM2, MDM4, MEDJ2, MEF2B, MEN1, MERTK, MET, MITF, MKNK1, MLH1, MPL, MRE11A, MSH2, MSH3, MSH6, MST1R, MTAP, MTOR, MUTYH, MYC, MYCL (MYCL1), MYCN, MYD88, NBN, NF1, NF2, NFE2L2, NFKB1A, NKX2-1, NOTCH1, NOTCH2, NOTCH3, NPM1, NRAS, NT5C2, NTRK1, NTRK2, NTRK3, P2RY8, PALB2, PARK2, PARP1, PARP2, PARP3, PAX5, PBRM1, PDCD1 (PD-1), PDCD1LG2 (PD-L2), PDGFRA, PDGFRB, PDK1, PIK3C2B, PIK3C2G, PIK3CA, PIK3CB, PIK3R1, PIM1, PMS2, POLD1, POLE, PPARG, PP2R1A, PPP2R2A, PRDM1, PRKAR1A, PRKCL, PTCH1, PTEN, PTPN11, PTPRO, OK1, RAC1, RAD21, RAD51, RAD51B, RAD51C, RAD51D, RAD52, RAD54L, RAF1, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCAIP, SOCS1, SOX2, SOX9, SPEN, SPOP, SRC, STAG2, STAT3, STK11, SUFU, SYK, TBX3, TEK, TET2, TGFBR2, TIPARP, TNFAIP3, TNFRSF14, TP53, TSC1, TSC2, TYRO3, U2AF1, VEGFA, VHL, WHSC1 (MMSET), WHSC1L1, WT1, XPO1, XRCC2, ZNF217, ZNF703, or any combination thereof. With respect to the Foundation platform, a genomic aberration in a disclosed cancer-related gene can comprise a rearrangement. For example, in an aspect, a disclosed rearrangement can be identified in the following genes—ALK, BCL2, BCR, BRAF, BRCA1, BRCA2, CD74, EGFR, ETV4, ETVS, ETV6, EWSR1, EZR, FGFR1, FGFR2, FGFR3, KIT, KMT2A (MLL), MSH2, MYB, MYC, NOTCH2, NTRK1 NTRK2 NUTML, PDGFRA, RAFT, RARA, RET, ROS1, RSPO2 SDC4, SLC34A2 TERC (a ncRNA), TERT (promoter only), TMPRSS2, or any combination thereof.

With respect to the Tempus platform, in an aspect, a genomic aberration in a disclosed cancer-related gene can comprise a rearrangement. For example, in an aspect, a disclosed rearrangement can be identified in the following genes—ABL1, ALK, BCR, BRAF, EGFR, ETV6, EWSR1, FGFR2, FGFR3, MYB, NRG1, NTRK1, NTRK2, NTRK3, PAX8, PDGFRA, PML, RARA, RET, ROS1, TFE3, TMPRSS2, or any combination thereof. With respect to the Tempus platform, in an aspect, a genomic aberration in a disclosed cancer-related gene can comprise a single nucleotide variant, an Indel, or a copy number amplification. For example, in an aspect, a disclosed single nucleotide variant, a disclosed Indel, or a disclosed CNA can be identified in the following genes—ABCB1, ABCC3, ABL1, ABL2, ABRAXAS1, ACTA2, ACVR1, (ALK2), ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf4, CALR, CARD11, CARM1, CASP8, CASR, CBFB, CBL, CBLB, CBLC, CBR3, CCDC6, CCND1, CCND2, CCND3, CCNE1, CD19, CD22, CD274, (PD-L1), CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYN, C2H1, EBF1, ECT2L, EGF, EGFR, EGLN1, EIF1AX, ELF3, ELOC, (TCEB1), EMSY, ENG, EP300, EPCAM, EPHA2, EPHA7, EPHB1, EPHB2, EPOR, ERBB2, (HER2), ERBB3, ERBB4, ERCC1, ERCC2, ERCC3, ERCC4, ERCC5, ERCC6, ERG, ERRF11, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANCL, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOX, P1, FOXQ1, FRS2, FUBP1, FUSG6PD, GABRA6, GALNT12, GATA1, GATA2, GATA3, GATA4, GATA6, GENT, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDOL, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEFT, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MK167, MLH1, MLH3, MLLT3, MN1, MPL, MRE11, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKB1A, NHP2, NKX2-1, NOP10, NOTCH1, NOTCH2, NOTCH3, NOTCH4, NPM1, NQO1, NRAS, NRG1, NSD1, NSD2, NT5C2, NTH, L1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDGFRB, PDK1, PHF6, PHGDH, PHLPP1, PHLPP2, PHOX2B, PIAS4, PIK3C2B, P1, K3, CA, PIK3CB, P1, K3, CD, PIK3CG, P1, K3, R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PRKN, PRSS1, PTC, H, 1, PTCH2, PTEN, PTPN11, PTPN13, PTPN22, PTPRD, PTPRT, QK1, RAC, RAD21, RAD50, RAD51, RAD51B, RAD51C RAD51D, RAD54L, RAFT, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SM, AD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STAT6, STK11, SUFU, SUZ12, SYK, SYNE1, TAFT, TANC1, TAP, TAP2, TARBP2, TBCID12, TBL1XR1, TBX3, TCF3, TCF7L2, TCL1A, TERT (promoter), TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, VSIR, WEE, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, ZRSR2, or any combination thereof.

With respect to the Tempus platform, the following applies: APC (APC-associated conditions), ATM (Ataxia-Telangiectasia, Breast cancer susceptibility, Pancreatic cancer susceptibility), AXIN2 (Oligodontia-colorectal cancer syndrome), BAP1 (BAP1tumor predisposition syndrome), BARD1 (Breast cancer susceptibility), BLM (Bloom syndrome), BMPR1A (Juvenile polyposis), BRCA1 (Hereditary breast and ovarian cancer), BRCA2 (Hereditary breast and ovarian cancer, Fanconi anemia), BRIP1 (Ovarian cancer susceptibility, Fanconi anemia), CDH1 (Hereditary diffuse gastric cancer, Breast cancer susceptibility), CDK4 (Melanoma susceptibility), CDKN2A (Melanoma-pancreatic cancer syndrome), CEBPA (Acute myeloid leukemia susceptibility), CHEK2 (Breast cancer susceptibility, Colon cancer susceptibility), DICER1 (DICER1 tumor predisposition syndrome), EGFR (Lung cancer susceptibility, TKI resistance), EPCAM (Lynch syndrome), ETV6 (Leukemia susceptibility, thrombocytopenia susceptibility), FH (Hereditary leiomyomatosis and renal cell cancer), FLCN (Birt-Hogg-Dube syndrome), GATA2 (GATA2 deficiency with susceptibility to myeloid malignancies), KIT (Familial gastrointestinal stromal tumor), MAX (Hereditary paraganglioma-pheochromocytoma syndrome), MEN1 (Multiple endocrine neoplasia type 1), MET (Hereditary papillary renal cell carcinoma), MLH1 (Lynch syndrome, Constitutional mismatch repair deficiency), MSH2 (Lynch syndrome, Constitutional mismatch repair deficiency), MSH3 (MSH3-associated polyposis), MSH6 (Lynch syndrome, Constitutional mismatch repair deficiency), MUTYH (MUTYH-associated polyposis), NBN (Nijmegen breakage syndrome, Breast cancer susceptibility), NF1 (Neurofibromatosis type 1), NF2 (Neurofibromatosis type 2), NTHL1 (NTHL1 tumor syndrome, NTHL1-associated polyposis), PALB2 (Breast cancer susceptibility, Pancreatic cancer susceptibility, Ovarian cancer susceptibility, Fanconi anemia), PDGFRA (Familial gastrointestinal stromal tumor, GIST-plus syndrome), PHOX2B (Neuroblastoma susceptibility), PMS2 (Lynch syndrome, Constitutional mismatch repair deficiency), POLD1 (Polymerase proofreading-associated polyposis), POLE (Polymerase proofreading-associated polyposis), PRKAR1A (Carney complex), PTCH1 (Gorlin syndrome, Basal cell nevus syndrome), PTEN (PTEN hamartoma tumor syndrome), RAD51C (Ovarian cancer susceptibility, Breast cancer susceptibility, Fanconi anemia), RAD51D (Ovarian cancer susceptibility, Breast cancer susceptibility), RB1 (Retinoblastoma), RET (Multiple endocrine neoplasia type 2, Familial medullary thyroid cancer), RUNX1 (Acute myeloid leukemia susceptibility), SDHA (Hereditary paraganglioma-pheochromocytoma syndrome), SDHAF2 (Hereditary paraganglioma-pheochromocytoma syndrome), SDHB (Hereditary paraganglioma-pheochromocytoma syndrome), SDHC (Hereditary paraganglioma-pheochromocytoma syndrome), SDHD (Hereditary paraganglioma-pheochromocytoma syndrome), SMAD4 Juvenile polyposis, Hereditary hemorrhagic telangiectasia), SMARCA4 (Rhabdoid tumor predisposition syndrome), SMARCB1 (Rhabdoid tumor predisposition syndrome, Schwannomatosis), STK11 (Peutz-Jeghers syndrome), SUFU (Gorlin syndrome, Basal cell nevus syndrome), TMEM127 (Hereditary paraganglioma-pheochromocytoma syndrome), TP53 (L1-Fraumeni syndrome), TSC1 (Tuberous sclerosis complex), TSC2 (Tuberous sclerosis complex), VHL (Von Hippel-Lindau syndrome), and WT1 (WT1-related Wilms tumor).

In an aspect of a disclosed method of treating and/or preventing cancer, next generation sequencing can comprise sequencing one or more cancer related genes. In an aspect of a disclosed method of treating and/or preventing cancer, sequencing one or more cancer related genes can comprise identifying one or more genomic aberrations. In an aspect, one or more genomic aberrations can comprise somatic genomic aberrations. In an aspect, the disclosed one or more somatic genomic aberrations can comprise mutations, insertions, deletions, chromosomal rearrangements, copy number aberrations, or any combination thereof.

In an aspect of a disclosed method of treating and/or preventing cancer, a disclosed cfDNA analysis can comprises quantification of one or more cancer related genes. In an aspect, if the expression and/or amount and/or presence of the disclosed one or more genomic aberrations in the pre-treatment biological sample is higher than the expression and/or amount and/or presence of the same one or more genomic aberrations in a control sample, then a disclosed method of treating and/or preventing cancer can comprise diagnosing the subject as being in need of precision cancer treatment. In an aspect, a disclosed control sample can be a sample obtained from a subject not having cancer. In an aspect, a disclosed control sample can be a pooled sample obtained from more than one subject not having cancer.

In an aspect, if the expression and/or amount and/or presence of the disclosed one or more genomic aberrations in the post-treatment biological sample is lower than the expression and/or amount and/or presence of the same one or more genomic aberrations in a pre-treatment sample, then a disclosed method of treating and/or preventing cancer can comprise continuing to administer to the subject a disclosed precision cancer treatment. In an aspect, if the expression and/or amount and/or presence of the disclosed one or more genomic aberrations in the post treatment biological sample is lower than the expression and/or amount and/or presence of the same one or more genomic aberrations in a prior post-treatment sample, then a disclosed method of treating and/or preventing cancer of treating and/or preventing cancer can comprise continuing to administer to the subject a disclosed precision cancer treatment.

In an aspect, a disclosed method of treating and/or preventing cancer can further comprise measuring the subject's tumor response to the precision cancer treatment. In an aspect, a subject's tumor response can comprise a partial response or a complete response. In an aspect, a disclosed partial response can comprise a decrease in the size of a tumor or a decrease in one or more tumors by 25% or more when compared to the size of the same tumor or the same one or more tumors prior to treatment. In an aspect, a disclosed partial response can comprise a decrease in the size of a tumor or a decrease in one or more tumors by 50% or more when compared to the size of the same tumor or the same one or more tumors prior to treatment. In an aspect, a disclosed partial response can comprise a decrease in the size of a tumor or a decrease in one more tumors by about 100% or more when compared to the size of the same tumor or the same one or more tumors prior to treatment.

In an aspect, a disclosed method of treating and/or preventing cancer can further comprise measuring the subject's molecular response to a disclosed precision cancer treatment. In an aspect, a disclosed molecular response can comprise a decrease in the number of somatic genomic aberrations in a disclosed biological sample obtained from the subject. In an aspect, disclosed somatic genomic aberrations can comprise mutations, insertions, deletions, chromosomal rearrangements, copy number aberrations, fusions, or any combination thereof. In an aspect, a disclosed method of treating and/or preventing cancer can further comprise administering to the subject one or more additional therapeutic agents.

In an aspect, disclosed additional therapeutic agents can comprise chemotherapeutic agents, monoclonal antibodies, cell cycle inhibitors, small molecules, or any combination thereof.

Monoclonal antibodies are known to the skilled person in the arts. Monoclonal antibodies can comprise—but are not limited to—adotrastuzumab, alemtuzumab, atezolizumab, avelumab, bevacizumab, blinatumomab, brentuximab, cemiplimab, cetuximab, daratumumab, denosumab, dinutuximab, durvalumab, elotuzumab, gemtuzumab, ibritumomab, inotuzumab, ipilimumab, necitumumab, nivolumab, obinutuzumab, ofatumumab, olaratumab, panitumumab, pembrolizumab, pertuzumab, ramucirumab, rituximab, tositumomab, trastuzumab, or any combination thereof.

Small molecules are known to the skilled person in the arts. Small molecules can include—but are not limited to—abemaciclib, afatinib, alectinib, alpelisib, axitinib, binimetinib, bosutinib, brigatinib, cabozantinib, carfilzomib, ceritinib, cgilteritinib, cobimetinib, copanlisib, crizotinib, dabrafenib, dacomitinib, dasatinib, duvelisib, encorafenib, entrectinib, erdafitinib, erlotinib, gefitinib, ibrutinib, imatinib, ivosidenib, lapatinib, larotrectinib, lenvatinib, lorlatinib, marizomib, neratinib, nilotinib, niraparib, olaparib, osimertinib, palbociclib, pazopanib, ponatinib, regorafenib, ribociclib, rucaparib, sorafenib, sunitinib, talazoparib, trametinib, vandetanib, vemurafenib, or any combination thereof. In an aspect, an additional therapeutic agent can comprise bevacizumab, pazopanib, sorafenib, dasatinib, everolimus, or any combination thereof.

For example, in an aspect, pazopanib and/or sorafenib can be orally administered to a subject at a dose of from about 1 mg/kg/day to about 12 mg/kg/day or from 2 mg/kg/day to about 6 mg/kg/day. In an aspect, a disclosed optimal dose of pazopanib and/or sorafenib can be about 3 mg/kg/day. In an aspect, dasatinib can be orally administered to a subject at a dose of from about 0.3 mg/kg/day to about 2.0 mg/kg/day or from about 0.7 mg/kg/day to about 1.4 mg/kg/day. In an aspect, a disclosed optimal dose of dasatinib can be about 0.7 mg/kg/day. In an aspect, everolimus can be orally administered to a subject at a dose of from about 0.03 mg/kg/day to about 0.15 mg/kg/day or from about 0.03 mg/kg/day to about 0.10 mg/kg/day. In an aspect, a disclosed optimal dose of everolimus can be about 0.07 mg/kg/day. In an aspect, bevacizumab can be administered intravenously to a subject every 1 to 3 weeks at a dose of from about 2 mg/kg/day to about 15 mg/kg/day or can be administered to a patient every 1 to 3 weeks at a dose of from about 5 mg/kg/day to about 12 mg/kg/day. In an aspect, a disclosed optimal dose of bevacizumab can be administered intravenously to a subject every 2 weeks and with an optimal dose of about 10 mg/kg/day.

In an aspect, a disclosed molecular marker that can determine one or more suitable precision cancer treatments in one or more disclosed methods can be measured from a sample by high-density expression array, DNA microarray, polymerase chain reaction (PCR), reverse transcriptase PCR (RT-PCR), real-time quantitative reverse transcription PCR (qRT-PCR), serial analysis of gene expression (SAGE), spotted cDNA arrays, GeneChip, spotted oligo arrays, bead arrays, RNA Seq, tiling array, northern blotting, hybridization microarray, in situ hybridization, whole-exome sequencing, whole-genome sequencing, liquid biopsy, next-generation sequencing, or any combination thereof.

In an aspect, a disclosed molecular marker can determine one or more suitable precision cancer treatments for use in a disclosed method of treating and/or preventing cancer can determined from the nucleic acid sequence of the at least one of circulating DNA and/or RNA. In an aspect, a disclosed molecular marker can be assessed from circulating tumor DNA and/or RNA (ctDNA and/or ctRNA); circulating cell-free DNA and/or RNA (cfDNA, cfRNA); or any combination thereof. ctDNA/ctRNA refers to tumor-derived fragmented DNA in the bloodstream that is not associated with cells. cfDNA/cfRNA refers to DNA that is freely circulating in the bloodstream, but is not necessarily of tumor origin. In an aspect, cfDNA/ctDNA can include any whole or fragmented genomic DNA, or mitochondrial DNA, and/or cfRNA/ctRNA can include mRNA, tRNA, microRNA, small interfering RNA, long non-coding RNA (1 ncRNA). In an aspect, cfDNA and/or ctDNA can be a fragmented DNA with a length of at least about 50 base pair (bp), about 100 bp, about 200 bp, about 500 bp, or about 1 kbp. In an aspect, cfRNA and/or ctRNA can be a full length or a fragment of mRNA (e.g., at least 70% of full-length, at least 50% of full length, at least 30% of full length, etc.). In an aspect, a disclosed molecular marker can be directed against any cancer-related gene disclosed herein.

In an aspect, a disclosed method can further comprise surgically resecting one or more tumors from the subject. In an aspect, a disclosed method can further comprise repeating one or more disclosed steps of a disclosed method.

For example, in an aspect, repeating one or more disclosed steps of a disclosed method can comprise repeating the administering to the subject the precision cancer treatment, repeating the measuring of the subject's tumor response, repeating the obtaining of a biological sample from the subject, repeating the subjecting the biological sample to cfDNA analysis, repeating the administering of one or more additional therapeutic agents, or any combination thereof.

In an aspect, a disclosed molecular marker can be detected, quantified, and/or analyzed over time (at different time points) to determine the effectiveness of a disclosed precision cancer treatment (e.g., AS therapy) to the subject and/or to determine the response of a subject or subject's tumor to the precision cancer treatment (e.g., developing resistance, susceptibility, etc.). In an aspect, a disclosed method can comprise obtaining multiple measurements over time from the same subject and same sample may be quantified at a single time point or over time. In an aspect, a disclosed treatment regimen treatment (e.g., a disclosed precision cancer treatment comprising one or more antineoplastons) can be designed and/or determined based on the cancer status and/or the changes/types of one or more molecular markers. In an aspect, the likelihood of success of a disclosed precision cancer treatment can be determined based on the cancer status and the type/quantity of one or more molecular markers.

In an aspect, a disclosed molecular marker can be derived from a gene expressed in one or more cells of a tumor or in a immune cell and can indicate immune suppressive tumor microenvironment, the development of cancer sternness, the onset of metastasis, cancer status, or any combination thereof. In an aspect, a disclosed molecular marker can be the protein or peptide encoded by the gene from which the molecular marker is derived and can be targeted by an antagonist or any other type of binding molecule to inhibit the function of the peptide.

Thus, in an aspect, increased expression (e.g., above a predetermined threshold) of a disclosed molecular marker derived from a disclosed gene related to immune suppressive tumor microenvironment can implicate the presence of immune suppressive tumor microenvironment, and can also implicate that an antagonist to the peptide encoded by the gene related to immune suppressive tumor microenvironment can have a high likelihood of success to inhibit the progress of the cancer by inhibiting immune suppressive tumor microenvironment and further promoting immune cell activity against tumor cells in such microenvironment. In an aspect, once the molecular marker has been identified, any suitable antagonist to a target gene or protein product can be used. For example, in an aspect, a specific kinase can be targeted by a kinase inhibitor, or a specific signaling receptor can be targeted by synthetic ligand, or a specific checkpoint receptor targeted by synthetic antagonist or antibody, etc. In an aspect, a disclosed antagonists to a target molecule herein can be administered before, after, or in combination with AS therapy.

In an aspect, a subject can be a human patient. In an aspect a subject can be any age (e.g., geriatric, adult, young adult, teenager, tween, adolescent, child, toddler, baby, or infant), can be male or female, can be any nationality, can be of any ethnicity, and/or can be of any race. In an aspect, a subject can have a terminal cancer.

In an aspect, a disclosed subject has not received treatment prior to the administering of a disclosed precision cancer treatment. In an aspect, a disclosed subject has received treatment prior to the administering of a disclosed precision cancer treatment. In an aspect of a disclosed method, prior to the administering of a disclosed precision cancer treatment, the subject has received surgical treatment, antibody treatment, chemotherapy treatment, radiation treatment, immunotherapy treatment, or any combination thereof. In an aspect of a disclosed method, a subject in need thereof has been diagnosed as having cancer, or wherein the subject in need thereof is suspected of having a cancer.

In an aspect, a disclosed cancer can be a refractory cancer or refractory disease. In an aspect, "refractory" refers to cancer and/or tumor that does not respond to and/or becomes resistant to a treatment. In an aspect, a subject can have a relapsed disease. In an aspect, "relapsed" or "relapses" refers to a tumor that returns or progresses following a period of improvement (e.g., a partial or complete response) with treatment. In an aspect, a disclosed cancer can comprise a solid tumor. In an aspect, a disclosed cancer can comprise metastatic cancer. In an aspect, a disclosed cancer can comprise a terminal cancer.

In an aspect, a disclosed cancer can comprise adenocarcinoma (including of the appendix and cervix), adenoid cystic carcinoma, adult t-cell leukemia, anaplastic astrocytoma, anaplastic ependymoma, anaplastic oligodendroglioma, astrocytoma, basal cell carcinoma, B-cell cancers, benign and malignant lymphomas, biliary tract—cholangiocarcinoma, bowel, brain cancer (including anaplastic astrocytoma, anaplastic ependymoma, anaplastic oligodendroglioma, brainstem anaplastic astrocytoma, brainstem glioma, diffuse astrocytoma, DIPG h3k27 mutation, ganglioglioma, glioblastoma multiforme, medulloblastoma, pilocytic astrocytoma, brainstem glioma), breast cancer, breast carcinoma, Burkitt's lymphoma, bladder cancer and carcinoma, carcinoma of unknown primary, carcinosarcoma, cervical cancer, cholangiocarcinoma, chronic atypical myelogenous leukemia, chronic atypical myelogenous leukemia, colon cancer, colorectal carcinoma, diffuse astrocytoma, diffuse intrinsic pontine glioma (DIPG), endometrial cancer, endometrial carcinoma, ependymomas, esophageal cancer and carcinoma, esophagus, Ewing's sarcoma, ganglioglioma, ganglioneuromas, gastrointestinal stromal tumor (gist), gliobastomas, gliomas, head and neck cancer and carcinoma, hemangiosarcoma, hepatocellular carcinomas, renal cell carcinomas, Hodgkin's disease, Kaposi's sarcoma, kidney cancer and carcinoma, large b-cell lymphoma, leptomeningeal carcinomatosis, leukemias, liposarcoma, liver cancer, lung carcinoma (non-small cell and small cell carcinoma), medulloblastoma, melanoma, meningeal sarcomas, meningiomas, multiple myeloma, myelodysplastic syndrome, myeloproliferative diseases, myosarcomas, neuroblastomas, neuroendocrine carcinoma, neurofibromas, non-Hodgkin's lymphoma, oligodendrogliomas, osteosarcoma, ovarian cancer and carcinoma, pancreatic cancer and carcinoma, peripheral neuroepithelioma, peripheral t-cell lymphoma, Philadelphia chromosome positive all and positive CML, pilocytic astrocytoma, pineal cell tumors, pleomorphic sarcoma, pre-b lymphomas, primitive neuroectodermal tumor (PNET), prostate cancer and carcinoma, refractory anemia, salivary gland carcinoma, sarcoma, schwannomas, skin cancer and carcinoma, squamous-cell carcinoma, stomach cancer and carcinoma, synovial sarcoma, testicular cancer, thyroid cancer and carcinoma, T-lineage acute lymphoblastic leukemia (T-all), T-lineage lymphoblastic lymphoma (T-LL), urothelial cancer and urothelial high-grade carcinoma, uterine, cervix, vulvar, and/or endometrium carcinoma, Wilms' tumor or teratocarcinomas, or any combination thereof.

In an aspect, a disclosed cancer can comprise breast cancer, colorectal cancer, head and neck cancer, kidney cancer, lung cancer, ovarian cancer, pancreatic cancer, prostate cancer, brain cancer, adenoid cystic carcinoma, anaplastic astrocytoma, anaplastic ependymoma, anaplastic oligodendroglioma, brainstem glioma, diffuse astrocytoma, diffuse intrinsic pontine glioma (DIPG), ganglioglioma, medulloblastoma, pilocytic astrocytoma, cholangiocarcinoma, chronic atypical myelogenous leukemia, endometrial carcinoma, esophageal cancer, Ewing's sarcoma, gastrointestinal stromal tumor (GIST), leptomeningeal carcinomatosis, multiple myeloma, myelodysplastic syndrome, neuroendocrine carcinoma, Non-Hodgkin's lymphoma, pleomorphic sarcoma, primitive neuroectodermal tumor (PNET), refractory anemia, salivary gland carcinoma, skin cancer, stomach cancer, thyroid cancer, urothelial cancer, or any combination thereof.

In an aspect, a disclosed method can further comprise comprising monitoring the subject for adverse effects (such as, e.g., hepatic impairment, hematologic toxicity, neurologic toxicity, cutaneous toxicity, gastrointestinal toxicity, or any combination thereof). In an aspect, in the absence of adverse effects, a disclosed method can further comprise continuing to administering to the subject a disclosed precision cancer treatment. In an aspect, in the presence of adverse effects, a disclosed method can further comprise modifying one or more disclosed steps of a disclosed method. In an aspect, a disclosed method can further comprise treating the one or more adverse effects.

In an aspect, a disclosed method can comprise modifying a disclosed administering step. In an aspect, modifying a disclosed administering step can comprise changing the amount of the one or more antineoplastons or composition comprising one or more antineoplastons administered to the subject, changing the frequency that the one or more antineoplastons or composition comprising one or more antineoplastons are administered to the subject, changing the duration of administration of the one or more antineoplastons or composition comprising one or more antineoplastons, changing the route of administration of the one or more antineoplastons or composition comprising one or more antineoplastons administered to the subject, or any combination thereof.

In an aspect, a disclosed method can further comprise obtaining a tissue biopsy from the subject. In an aspect, a disclosed tissue biopsy can be subjected to next generation sequencing. In an aspect, a disclosed method can comprise subjecting the subject to one or more invasive or non-invasive diagnostic assessments. Diagnostic assessments are known to the art. In an aspect, a disclosed non-invasive diagnostic assessment can comprise x-rays, computerized tomography (CT) scans, magnetic resonance imaging (MRI) scans, ultrasounds, positron emission tomography (PET) scans, or any combination thereof. In an aspect, a disclosed invasive diagnostic assessment can comprise a tissue biopsy or exploratory surgery.

In an aspect, a disclosed subject can improve the life expectancy of the subject. In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of prolonging the survival of a subject, the subject's cancer is treated.

In an aspect, a disclosed method can improve life expectancy compared to the cancer life expectancy of an untreated subject with the identical or near identical disease condition and the identical or near identical predicted outcome. As used herein, "life expectancy" is defined as the time at which 50 percent of subjects are alive and 50 percent have passed away. In an aspect, patient life expectancy can be indefinite following treatment with a disclosed method. In an aspect, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with the identical or near identical disease condition and the identical or near identical predicted outcome.

In an aspect, life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and the identical or near identical predicted outcome. In an aspect, life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with the identical or near identical disease condition and the identical or near identical predicted outcome.

In an aspect, a disclosed method can comprise protecting the subject from metastasis. In an aspect, a disclosed method can comprise reducing the risk of developing metastasis. In an aspect of a disclosed method, treating the cancer can comprise increasing the subject's survivability, increasing the length of time before metastasis, reducing the likelihood of surgical intervention, reducing the need for administration of one or more additional therapeutic agents or regiments, reducing the size of one or more tumors in the subject, eliminating one or more tumors in the subject, reducing or eliminating the prevalence of one or more genomic aberrations, restoring the normal metabolism of one or more organ systems in the subject, restoring one or more aspect of cellular homeostasis and/or cellular functionality, and/or metabolic dysregulation; or any combination thereof.

In an aspect of a disclosed method, restoring one or more aspects of cellular homeostasis and/or cellular functionality can comprise one or more of the following: (i) correcting cell starvation in one or more cell types (such as, for example, liver cells and muscle cells); (ii) normalizing aspects of the autophagy pathway (such as, for example, correcting, preventing, reducing, and/or ameliorating autophagy); (iii) improving, enhancing, restoring, and/or preserving mitochondrial functionality and/or structural integrity; (iv) improving, enhancing, restoring, and/or preserving organelle functionality and/or structural integrity; (v) preventing, slowing, and/or eliminating hypoglycemia, ketosis, and/or other liver abnormalities; (vi) correcting liver enzyme dysregulation; (vii) reversing, inhibiting, preventing, stabilizing, and/or slowing the rate of progression of tumor metastasis; (viii) reversing, inhibiting, preventing, stabilizing, and/or slowing the rate of progression of tumor growth and/or cancer spread, or (ix) any combination thereof. In an aspect, restoring one or more aspects of cellular homeostasis can comprise improving, enhancing, restoring, and/or preserving one or more aspects of cellular structural and/or functional integrity in, for example, an organ or system that has been affected by cancer.

For example, in an aspect, tumor growth can be impaired at least about 5% or greater to at least about 100%, at least about 10% or greater to at least about 95% or greater, at least about 20% or greater to at least about 80% or greater, at least about 40% or greater to at least about 60% or greater compared to an untreated subject having the identical or near identical disease condition and the identical or near identical predicted outcome. In an aspect, one or more tumors in a subject treated using a disclosed method can grow at least 5% less (or more as described above) when compared to an untreated subject with the identical or near identical disease condition and identical or near identical predicted outcome.

In an aspect, tumor growth can be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and identical or near identical predicted outcome.

In an aspect, tumor growth can be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with the identical or near identical disease condition and identical or near identical predicted outcome.

In an aspect, treatment of tumors according to the methods disclosed herein (e.g., AS therapy) can result in a shrinking of a tumor in comparison to the starting size of the tumor. In an aspect, tumor shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In an aspect, a disclosed subject can present with one or more cancerous solid tumors, metastatic nodes, or any combination thereof. In any aspect, a subject herein can have a cancerous tumor cell source that can be less than about 0.2 $cm^3$ to at least about 20 $cm^3$ or greater, at least about 2 $cm^3$ to at least about 18 $cm^3$ or greater, at least about 3 $cm^3$ to at least about 15 $cm^3$ or greater, at least about 4 $cm^3$ to at least about 12 $cm^3$ or greater, at least about 5 $cm^3$ to at least about 10 $cm^3$ or greater, or at least about 6 $cm^3$ to at least about 8 $cm^3$ or greater.

In an aspect, a disclosed method of treating and/or prevent cancer can comprise a pan-tumor approach such as, for example, administering a disclosed ANP therapy.

D. Methods of Prolonging the Survival

Disclosed herein is a method of prolonging the survival of a subject, the method comprising administering to a subject in need thereof a precision cancer treatment, wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and wherein the subject demonstrates a tumor response and/or molecular response to the precision cancer treatment, and wherein the subject's life expectancy is extended.

Disclosed herein is a method of prolonging the survival of a subject, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment, and wherein the subject's life expectancy is extended.

In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of prolonging the survival of a subject, the subject's cancer is treated.

In an aspect, a disclosed precision cancer treatment can comprise one or more antineoplastons or can comprise a composition comprising one or more antineoplastons. In an aspect, disclosed antineoplastons can comprise phenylacetate, phenylacetylglutaminate, phenylacetylglutaminate sodium, phenylacetylisoglutaminate sodium, or any combination thereof. In an aspect, a disclosed composition comprising one or more antineoplastons can comprise phenylacetate, phenylacetylglutaminate, phenylacetylglutaminate sodium, phenylacetylisoglutaminate sodium, or any combination thereof.

In an aspect, a disclosed composition comprising one or more antineoplastons can comprise a pharmaceutically acceptable carrier. In an aspect, the disclosed one or more antineoplastons can comprise phenylacetylglutaminate sodium (PG) and phenylacetylisoglutaminate sodium (iso-PG). In an aspect, a disclosed ratio of phenylacetylglutaminate sodium (PG) and phenylacetylisoglutaminate sodium (iso-PG) can be about 10:1, about 9:1, about 8:1, about 7:1, about 6:1, about 5:1, about 4:1, about 3:1, about 2:1, or about 1:1. In an aspect, a disclosed ratio of phenylacetylglutaminate sodium (PG) and phenylacetylisoglutaminate sodium (iso-PG) can range from about 10:1 to about 1:10. In an aspect, a disclosed ratio of phenylacetylglutaminate sodium (PG) and phenylacetylisoglutaminate sodium (iso-PG) can be about 4:1. In an aspect, a dose of the disclosed one or more antineoplastons can comprise about 0.1 g/kg/day to about 20 g/kg/day. In an aspect, a disclosed therapeutically effective dose of the disclosed one or more antineoplastons can comprise about 0.1 g/kg/day to about 20 g/kg/day. In an aspect, a disclosed dose of phenylacetylglutaminate sodium (PG) can comprise about 0.4 g/kg/day to about 16 g/kg/day, and a disclosed dose of phenylacetylisoglutaminate sodium (iso-PG) can comprise about 0.1 g/kg/day to about 4 g/kg/day. In an aspect, a disclosed therapeutically effective amount of phenylacetylglutaminate sodium (PG) can comprise about 0.4 g/kg/day to about 16 g/kg/day, and a disclosed therapeutically effective amount of phenylacetylisoglutaminate sodium (iso-PG) can comprise about 0.1 g/kg/day to about 4 g/kg/day.

In an aspect, the disclosed one or more antineoplastons can comprise phenylacetate (PN) and phenylacetylglutaminate (PG). In an aspect, a disclosed ratio of phenylacetate (PN) and phenylacetylglutaminate (PG) can be about 10:1, about 9:1, about 8:1, about 7:1, about 6:1, about 5:1, about 4:1, about 3:1, about 2:1, or about 1:1. In an aspect, a disclosed ratio of phenylacetate (PN) and phenylacetylglutaminate (PG) can range from about 10:1 to about 1:10. In an aspect, a disclosed ratio of phenylacetate (PN) and phenylacetylglutaminate (PG) can be about 4:1. In an aspect, a dose of the disclosed one or more antineoplastons can comprise about 0.08 g/kg/day to about 0.6 g/kg/day. In an aspect, a therapeutically effective dose of the disclosed one or more antineoplastons can comprise about 0.08 g/kg/day to about 0.6 g/kg/day. In an aspect, a disclosed dose of phenylacetate (PN) can comprise about 0.064 g/kg/day to about 0.48 g/kg/day, and a disclosed dose of phenylacetylglutaminate (PG) can comprise about 0.016 g/kg/day to about 0.12 g/kg/day. In an aspect, a disclosed therapeutically effective dose of phenylacetate (PN) can comprise about 0.064 g/kg/day to about 0.48 g/kg/day, and a disclosed therapeutically effective dose of phenylacetylglutaminate (PG) can comprise about 0.016 g/kg/day to about 0.12 g/kg/day.

In an aspect of a disclosed method of prolonging the survival of a subject, administering a disclosed precision cancer treatment can comprise intravenous administration. In an aspect, a disclosed precision cancer treatment can be administered to a subject intravenously using, for example, a dual-channel infusion pump or two single channel pumps and central venous catheter. In an aspect, a disclosed IV administration of a disclosed precision cancer treatment can occur once every four hours at the infusion rate of from about 50 mL/hr to about 250 mL/hr (e.g., about 50, 75, 100, 125, 150, 175, 200, 225, 250 mL/hr) depending on the subject's age and condition/tolerance.

In an aspect, a disclosed method of prolonging the survival of a subject can comprise titrating the dose of a disclosed precision cancer treatment. In an aspect, a disclosed method of treating and/or preventing cancer can comprise titrating the dose of A10, AS2-1, or a combination thereof. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects.

In an aspect, a disclosed method of treating and/or preventing cancer can comprise titrating the dose of a disclosed precision cancer treatment in a specific or disclosed subject. In an aspect, a disclosed method of treating and/or preventing cancer can comprise titrating the dose of A10, AS2-1, or a combination thereof in a specific or disclosed subject. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects for a specific or disclosed subject.

In an aspect, administering comprises administering to the subject the maximum tolerated dose of A10, AS2-1, or both. In an aspect, administering comprises administering to the subject less than the maximum tolerated dose of A10, AS2-1, or both.

In an aspect, IV administration of a disclosed precision cancer treatment can comprise an outpatient setting. In an aspect, A10 can be administering prior to, concurrent with, or after administering of AS2-1. In an aspect, AS2-1 can be administering prior to, concurrently with, or after administering of A10. In an aspect, the order of administering one or more antineoplastons can change during a treatment regimen.

In an aspect, a disclosed method of prolonging the survival of a subject can further comprise obtaining a biological sample from the subject prior to administering a disclosed precision cancer treatment. In an aspect, a disclosed method of prolonging the survival of a subject can further comprise obtaining a biological sample from the subject after administering a disclosed precision cancer treatment. In an aspect, a disclosed method of prolonging the survival of a subject can further comprise subjecting the biological sample to a cell-free DNA (cfDNA) analysis. cfDNA analyses are known to the skilled person in the art. In an aspect, a disclosed cfDNA analysis can be repeated one or more times. In an aspect, a disclosed obtaining step can be repeated one or more times.

In an aspect of a disclosed method of prolonging the survival of a subject, a disclosed cfDNA analysis can comprise next generation sequencing. In an aspect, next generation sequencing (NGS) can comprise using one or more commercially available platforms. Commercially available NGS sequencing platforms can comprise, for example, Guardant360 CDx (Guardant Health, Inc.), FoundationOne CDx (F1CDx) (Foundation Medicine, Inc.), or Tempus xT (Tempus).

In an aspect of a disclosed method of prolonging the survival of a subject, a disclosed cancer-related gene can comprise ABL1, ABL2, ACO2, ACTB, ACVR1B, AKT, AKT1, AKT2, AKT3, ALK, AMER11, APC, AR, ARAF, ARFRP1, ARID1A, ARID1B, ARID2, ASK, ASPM, ASXL1, ATF1, ATF3, ATM, ATR, ATRX, AURKA, AURKB, AXIN1, AXL, BAD, BAGE, BAGE2, BAP1, BARD1, BAX, BCL2, BCL2L1, BCL2L2, BCL6, BCMA, BCOR, BCORL1, BDNF, BLM, BMPR1A, BRAF, BRCA1, BRCA2, BRD4, BRIP1, BTG1, BTK, BUB1, C10ORF54, CAGE1, CARD11, CASP5, CBFB, CBL, CCL1, CCL11, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL7, CCL8, CCNA 2, CCNB 1, CCNB 2, CCND, CCND1, CCND2, CCND3, CCNE1, CCNE2, CCR1, CCR10, CCR2, CCR3, CCR4, CCR5, CCR6, CCR7, CCR8, CCR9, CD123, CD19, CD20, CD25, CD274, CD276, CD30, CD33, CD4, CD79A, CD79B, CD8, CD80, CD86, CDC, CDC2, CDC20, CDC25A, CDC25B, CDC25C, CDC42, CDC6, CDC6; CDC7, CDC73, CDCA8, CDH1, CDK12, CDK2, CDK3, CDK4, CDK6, CDK8, CDKN1A, CDKN1B, CDKN2A, CDKN2B, CDKN2C, CEA, CEBPA, CFS1, CHD2, CHD4, CHEK1, CHEK2, CHK-1, CIC, CLDND1, CNE2, CREBBP, CRKL, CRLF2, CSF1, CSF1R, CSF3, CTAG1, CTAG1B, CTAG2, CTAG4, CTAG5, CTAG6, CTAG9, CTCF, CTLA4, CTNNA1, CTNNB1, CUL3, CXCL1, CXCL10, CXCL11, CXCL12, CXCL13, CXCL14, CXCL16, CXCL17, CXCL2, CXCL3, CXCL5, CXCL6, CXCL9, CXCR1, CXCR2, CXCR3, CXCR5, CXCR6, CYLD, DAXX, DCC, DDR2, DEPTOR, DICER1, DLD, DLST, DNMT3A, DOT1L, DUSP1, DUSP6, E2F1, EBNA1, EBNA2, EGFR, EMSY, ENOX2, EP300, EPCAM, EPHA3, EPHA5, EPHA7, EPHB1, ERBB2, ERBB3, ERBB4, ERCC1, EREG, ERG, ERK, ERRF11, ESR1, EWSR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR, FGFR1, FGFR2, FGFR3, FGFR4, FH, FLCN, FLI1, FLT1, FLT3, FLT4, FOLH1, FOLR1, FOXL2, FOXP1, FRS2, FUBP1, GABRA6, GADD45A, GAGE1, GAGE10, GAGE12D, GAGE12F, GAGE12J, GAGE13, GAGE2A, GAGE2B, GAGE2C, GAGE2D, GAGE2E, GAGE4, GART, GATA1, GATA2, GATA3, GATA4, GATA6, GID4, GLI1, GNA, GNA11, GNA13, GNAQ, GNAS, GPNMB, GPR124, GRIN2A, GRM3, GSK3B, H3F3A, HAVCR2, HDAC, HDAC1, HDAC5, HGF, HHLA2, HIF1, HIF1A, HIST1H1D, HNF1A, HRAS, HSD3B1, HSP90AA1, ICOSLG, IDH1, IDH2, IDH3A, IDH3B, IDO, IGF1R, IGF2, IKBKE, IKZF1, IL1, IL15, IL1A, IL1B, IL6, IL7R, IL8, INHBA, INPP4B, IRF2, IRF4, IRS2, JAK1, JAK2, JAK3, JUN, KDM5A, KDM5C, KDM6A, KDR, KEAP, KEL, KIT, KLHL6, KLK3, KRAS, LAG1, LAG3, LMO1, LMP1, LRP1B, LYN, LZTR1, MAD2L1, MAGEA1, MAGEA10, MAGEA12, MAGEA2, MAGEA3, MAGEA4, MAGEA5, MAGEA6, MAGEA7, MAGEA8, MAGEA9, MAGEB1, MAGEB10, MAGEB16, MAGEB18, MAGEB2, MAGEB3, MAGEB4, MAGEB6, MAGEC1, MAGEC2, MAGEC3, MAGED1, MAGED2, MAGED4, MAGED4B, MAGEE1, MAGEE2, MAGEB1, MAGEH1, MAGEL2, MAGI2, MAP2K1, MAP2K2, MAP2K4, MAP3K1, MAP3K6, MAPK, MCL1, MCM, MCM2, MCM3, MCM4, MCM5, MCM6, MCM7, MDH1, MDM2, MDM4, MED12, MEF26, MEF2B, MEN1, MET, MITF, MLH1, MLL, MLL2, MLL3, MPL, MRE11A, MSH2, MSH6, MTOR, MUC1, MUTYH, MYC, MYCL, MYCN, MYD88, MYH, MYST3, NCR3LG1, Netrin, NF1, NF2, NFE2L2, NFKB, NFKB1A, NGF, NKX2-1, NOTCH1, NOTCH2, NOTCH3, NPM1, NRAS, NSD1, NTRK1, NTRK2, NTRK3, NUP93, OGDH, ORC, ORC1, ORC1L, ORC1L, ORC6L, ORCL, ORCLPCNA, PAK3, PALB2, PAPPA, PARK2, PAX, PAX3, PBRM1, PCNA, PDCD1, PDCD1LG2, PDGFRA, PDG-FRB, PDHA1, PDK1, PGR, PIK3C2B, PIK3CA, PIK3CB, PIK3CG, PIK3R1, PIK3R2, PIK3R1, PKMYT, PKMYT1, PLCG2, PLK1, PMS2, POLD1, POLE, PPM1A, PPP2R1A, PREX2, PRKAR1A, PRKC1, PRKDC, PRSS8, PTCH1, PTEN, PTPN1, PTPN11, PTPRR, PTTG, PTTG1, PTTG2, PTTG3, QK1, RAC1, RAD50, RAD51, RAF1, RANBP1, RARA, RAS, RB1, RBL1, RBM10, RET, RICTOR, RID, RNF43, ROS1, RPTOR, RUNX1, RUNX1 T1, SDHA, SDHB, SDHC, SDHD, SETD2, SF3B1, SKP2, SLAMF7, SLIT2, SMAD2, SMAD3, SMAD4, SMARCA4, SMARCB1, SMC1A, SMC1L1, SMO, SNCAIP, SOCS1, SOX10, SOX2, SOX9, SPAG1, SPAG11A, SPAG11B, SPAG16, SPAG17, SPAG4, SPAG5, SPAG6, SPAG7, SPA G8, SPAG9, SPEN, SPOP, SPTA1, SRC, SRSF2, STAG2, STAT3, STAT4, STAT5, STAT5B, STK11, SUCLG1, SUCLG2, SUFU, SYK, T(BRACHYURY), TAF1, TBC1D8, TBX3, TERC, TERT, TERT promoter, TET2, TFDP1, TGFRB2, TNFAIP3, TNFRSF14, TOP1, TOP2A, TOP2B, TP53, TRIB3, TSC1, TSC2, TSHR, TUBB3, TYMP, TYMS, U2AF1, UNC5A, UNC5B, VEGFA, VHL, VTCN1, WEE1, WISP3, WT1, XAGE1D, XAGE2, XAGE3, XAGE5, XCL1, XCL2, XCR1, XPO1, ZBTB2, ZNF217, ZNF703, or any combination thereof.

In an aspect, a disclosed cancer-related gene can comprise one or more genomic aberrations. In an aspect, a subject can have one or more genomic aberrations in a disclosed cancer-related gene.

In an aspect, a disclosed ALK gene can encode a ALK protein having an I1461L or N1544K mutation. In an aspect, a disclosed ARID2 gene can encode an ARID2 protein having a N127fs18 mutation. In an aspect, a disclosed AKT1 gene can encode a AKT1 protein having a E17K or R346H mutation. In an aspect, a disclosed APC gene can encode an APC protein having a G29G, K445K, V2716L, E918E, Q1378*, S457*, I1304fs, E888fs, R230C, Q1090Q, S1360P. In an aspect, a disclosed gene can encode an AR protein having a A356E M887V or S510R mutation. In an aspect, a disclosed ARAF gene can encode a ARAF protein having a Y495Y mutation. In an aspect, a disclosed ARID1A gene can encode an ARID1A protein having a S1798L, S1167F, G246V, R1889W, or Q802fs mutation. In an aspect, a disclosed ARID2 gene can encode an ARID2 protein having a N127fs18 mutation. In an aspect, a disclosed ARTX gene has a S850fs*2, or s N179fs*26 mutation. In an aspect, a disclosed ASXL1 gene has a R1273f*s mutation. In an aspect, a disclosed BRAF gene can encode a BRAF protein having a E264 or V600E mutation. In an aspect, a disclosed BRCA1 gene can encode a BRAC1 protein having a H662Q or a R1443* mutation. In an aspect, a disclosed BRCA2 gene can encode a BRCA2 protein having a D237N or 12040V mutation. In an aspect, a disclosed CCND1 gene can encode a CCND1 protein having a R291 W mutation. In an aspect, a disclosed CCNE1 gene can encode a CCNE1 protein having a P268P or R95Q mutation. In an aspect, a disclosed CDKN1B gene can encode a CDKN1B protein having a K59fs* mutation. In an aspect, a disclosed CDKN2A gene can encode a CDKN2A protein having a D74N mutation. In an aspect, a disclosed CTNNB1 gene can encode a CTNNB1 protein having a T41A mutation. In an aspect, a disclosed DDR2 gene can encode a DDR2 protein having a L749L mutation. In an aspect, a disclosed EGFR gene can encode an EGFR protein having a P753L, V524I, D321D, or V7421 mutation. In an aspect, a disclosed ERBB2 gene can encode a ERBB2 protein having a C584G or V797del (Exon 20 deletion) mutation. In an aspect, a disclosed EWSR1 gene can encode a EWSR1 protein having a FLI1 fusion. In an aspect, a disclosed FBXW7 gene can encode a FBXW7 protein having a Y545C or R658* mutation. In an aspect, a disclosed FGFR gene can encode a FGFR protein having a T320T, S726F, H791H, P47P, S430fs, or R179H mutation. In an aspect, a disclosed FGFR1 gene can encode a FGFR1 protein having a S726F mutation. In an aspect, a disclosed FGFR2 gene can encode a FGFR2 protein having a KCNH7 fusion. In an aspect, a disclosed FGFR3 gene can encode a FGFR3 protein having a H290Y mutation. In an aspect, a disclosed GATA3 gene can encode a GATA3 protein having a P433fs43, P409fs, PS405fs, D336fs, S430fs, or c.1213_1214del mutation. In an aspect, a disclosed GNA11 gene can encode a GNA11 protein having a N244S mutation. In an aspect, a disclosed GNAS gene can encode a GNAS protein having a R201H* mutation. In an aspect, a disclosed HIST1H1D gene can encode a HIST1H1D protein having a K185-A186>T mutation. In an aspect, a disclosed H3F3A gene can encode a H3F3A protein having a K28N or K27 mutation. In an aspect, a disclosed IDH1 gene can encode an IDH1 protein having a R132H mutation. In an aspect, a disclosed JAK2 gene can encode a JAK2 protein having a V617 mutation. In an aspect, a disclosed KIT gene has a Q 775 fs (Exon 16 deletion). In an aspect, a disclosed ARID1A gene can encode an ARID1A protein having a S1798L, S1167F, G246V, R1889W, or Q802fs mutation. In an aspect, a disclosed KRAS gene can encode a KRAS protein having a G12V, G12D, G12S, G13D, or p.AG11GD mutation. In an aspect, a disclosed MAP2K1 gene can encode a MAP2K1 protein having a K57E mutation. In an aspect, a disclosed MAP2K4 gene has a loss of exon 2. In an aspect, a disclosed MAP3KJ gene can encode a MAP3K1 protein having a S398 mutation. In an aspect, a disclosed MAP3K6 gene can encode a MAP3K6 protein having a P646L mutation. a disclosed MET gene can encode a MET protein having a C385Y, T895M, T7591, or M391 mutation. In an aspect, a disclosed MPL gene can encode a MPL protein having a Y591D mutation. In an aspect, a disclosed MYC gene can encode a MYC protein having a S244S mutation. In an aspect, a disclosed NF1 gene has a Splice cite 480-11_4801 del11, Splice cite SNV, c.6655>T, p.D2219Y, V2378fs*8, or can encode a A2617A, F710C, I1719T, or K583R mutation. In an aspect, a disclosed NOTCH1 gene can encode a NOTCH1 protein having a A465V, V220M, D1681H, or S223N mutation. In an aspect, a disclosed NOTCH2 gene can encode a NOTCH2 protein having a S2379F mutation. In an aspect, a disclosed NTRK1 gene can encode a NTRK1 protein having a P387L or R766Q mutation. In an aspect, a disclosed PDGFRA gene can encode a PDGFRA protein having a E86A or V299G mutation. In an aspect, a disclosed PIK3CA gene can encode a PIK3CA protein having a Q546H, Q546K, Q546R, Q597H, E542K, E545K, E726K, E39K, E453K, R4-P18del, H1047L, H104R, K567E, 115431, p.E545K, or G1049R mutation. In an aspect, a disclosed PIK3R1 gene can encode a PIK3R1 protein having a S399Y408del splice site 917-1G>A mutation. In an aspect, a disclosed PTCH1 has a p.M17 Start loss-LOF. In an aspect, a disclosed PTEN gene can encode a PTEN protein having a H196_1203DEL, R55fs, N323fs*23, Y27C, R130*, C136Y, D252Y, or loss of exons 4-7 mutation. In an aspect, a disclosed RAF1 gene can encode a RAF1 protein having a P63P mutation. In an aspect, a disclosed RB1 gene can encode a RB1 protein having a Q217*, Y173fs*, or H673fs mutation. In an aspect, a disclosed RUNX1 gene can encode a RUNX1 protein having a R107C mutation. In an aspect, a disclosed SMAD4 gene can encode a SMAD4 protein having a P511 L, D537V, Q450H, L495R, A451P, or A406T mutation. In an aspect, a disclosed SPEN gene can encode a SPEN protein having a A2510V mutation. In an aspect, a disclosed SRSF2 gene can encode a SRSF2 protein having a P95H mutation. In an aspect, a disclosed STAT5B gene can encode a STAT5B protein having a R110H mutation. In an aspect, a disclosed TET2 gene can encode a TET2 protein having a C1875G mutation. In an aspect, a disclosed TP53 gene can encode a TP53 protein having a V73fs, R175G, R196, R249T, C176F, G187D, R282W, E287*, E285K, S241del, c.97-28_99del, Y126D, R273H, C176W, K320*, T253A, Splice site 37G-1G>A, Q104, P151H, H179Y, R273C, R248W, R176H, R209fs cer, N235-Y236del, R248Q er, R306*, C176Y, S241F, L252-1254del, L145P, R158H, R213*, Y220C, R110P, V274G, or c.376-4_384del mutation.

With respect to the Guardant360 platform, a genomic aberration in a disclosed cancer-related gene can comprise a single nucleotide variant. For example, in an aspect, a disclosed single nucleotide variant can be identified in the following genes—AKT1, ALK, APC, AR, ARAF, ATM, BRAF, BRCA1, BRCA2, CCND1, CDH1, CDK4, CDK6, CDK12, CDKN2A, CTNNB1, EGFR, ERBB2, ESR1, FGFR1, FGFR2, FGFR3, GATA3, GNA11, GNAQ, HRAS, IDH1, IDH2, KIT, KRAS, MAP2K1, MAP2K2, MET, MLH1, MTOR, MYC, NF1, NFE2L2, NRAS, NTRK1, NTRK3, PDGFRA, PIK3CA, PTEN, RAF1, RET, RHEB, ROS1, SMAD4, SMO, STK11, TERT, TSC1, VHL, or any combination thereof. With respect to the Guardant360 platform, a genomic aberration in a disclosed cancer-related gene can comprise an insertion and/or deletion. For example, in an aspect, a disclosed Indel can be identified in the following genes—AKT1, ALK, APC, ATM, BRAF, BRCA1, BRCA2, CDH1, CDK12, CDKN2A, EGFR, ERBB2, ESR1, FGFR2, GATA3, HNF1A, HRAS, KIT, KRAS, MET, MLH1, NF1, PDGFRA, PIK3CA, PTEN, RET, ROS1, STK11, TSC1, VHL, or any combination thereof. With respect to the Guardant360 platform, in an aspect, a genomic aberration in a disclosed cancer-related gene can comprise a copy number amplifications (CNA). For example, in an aspect, a disclosed CNA can be identified in the following genes—ERBB2 and/or MET. With respect to the Guardant360 platform, in an aspect, a disclosed fusion can comprise ALK, NTRK1, RET, ROS1, or any combination thereof.

With respect to the Foundation platform, in an aspect, a genomic aberration in a disclosed cancer-related gene can comprise a substitution, an Indel, or a copy number amplification. For example, in an aspect, a disclosed substitution, a disclosed Indel, or a disclosed CNA can be identified in the following genes—ABL1, ACVR1B, AKT1, AKT2, AKT3, ALK, ALOX12B, AMER1 (FAM723B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR, BCORL1, BRAF, BRCA1, BRCA2, BRD4, BRIP1, BTG1, BTG2, BTK, C11ORF30 (EMSY), CALR, CARD11, CASF8, CBFB, CBL, CCND1, CCND2, CCND3, CCNE1, CD22, CD274 (PD-L7), CD70, CD79A, CD79B, CDC73, CDH1, CDK12, CDK4, CDK6, CDK8, CDKN1A, CDKN1B, CDKN2A, CDKN2B, CDKN2C, CEBPA, CHEK7, CHEK2, CIC, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRF11, ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GID4 (C17ORF39), GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A (MLL), KMT2D (MLL2), KRAS, LTK, LYN, MAF, MAP2K1 (MEK1), MAP2K2 (MEK2), MAP2K4, MAP3K1, MAP3K13, MAPK1, MCL1, MDM2, MDM4, MED12, MEF2B, MEN1, MERTK, MET, MITF, MKNK1, MLH1, MPL, MRE11A, MSH2, MSH3, MSH6, MST1R, MTAP, MTOR, MUTYH, MYC, MYCL (MYCL1), MYCN, MYD88, NBN, NF1, NF2, NFE2L2, NFKB1A, NKX2-1, NOTCH1, NOTCH2, NOTCH3, NPM1, NRAS, NT5C2, NTRK1, NTRK2, NTRK3, P2RY8, PALB2, PARK2, PARP1, PARP2, PARP3, PAX5, PBRM1, PDCD1 (PD-1), PDCD1LG2 (PD-L2), PDGFRA, PDGFRB, PDK1, PIK3C2B, PIK3C2G, PIK3CA, PIK3CB, PIK3R1, PIM1, PMS2, POLD1, POLE, PPARG, PP2R1A, PPP2R2A, PRDM1, PRKAR1A, PRKC1, PTCH1, PTEN, PTPN11, PTPRO, OK1, RAC1, RAD21, RAD51, RAD51B, RAD51C, RAD51D, RAD52, RAD54L, RAF1, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCAIP, SOCS1, SOX2, SOX9, SPEN, SPOP, SRC, STAG2, STAT3, STK11, SUFU, SYK, TBX3, TEK, TET2, TGFBR2, TIPARP, TNFAIP3, TNFRSF14, TP53, TSC1, TSC2, TYRO3, U2AF1, VEGFA, VHL, WHSC1 (MMSET), WHSC1L1, WT1, XPO1, XRCC2, ZNF217, ZNF703, or any combination thereof. With respect to the Foundation platform, a genomic aberration in a disclosed cancer-related gene can comprise a rearrangement. For example, in an aspect, a disclosed rearrangement can be identified in the following genes—ALK, BCL2, BCR, BRAF, BRCA1, BRCA2, CD74, EGFR, ETV4, ETVS, ETV6, EWSR1, EZR, FGFR1, FGFR2, FGFR3, KIT, KMT2A (MLL), MSH2, MYB, MYC, NOTCH2, NTRK1 NTRK2 NUTM1, PDGFRA, RAFT, RARA, RET, ROS1, RSPO2 SDC4, SLC34A2 TERC (a ncRNA), TERT (promoter only), TMPRSS2, or any combination thereof.

With respect to the Tempus platform, in an aspect, a genomic aberration in a disclosed cancer-related gene can comprise a rearrangement. For example, in an aspect, a disclosed rearrangement can be identified in the following genes—ABL1, ALK, BCR, BRAF, EGFR, ETV6, EWSR1, FGFR2, FGFR3, MYB, NRG1, NTRK1, NTRK2, NTRK3, PAX8, PDGFRA, PML, RARA, RET, ROS1, TFE3, TMPRSS2, or any combination thereof. With respect to the Tempus platform, in an aspect, a genomic aberration in a disclosed cancer-related gene can comprise a single nucleotide variant, an Indel, or a copy number amplification. For example, in an aspect, a disclosed single nucleotide variant, a disclosed Indel, or a disclosed CNA can be identified in the following genes—ABCB1, ABCC3, ABL1, ABL2, ABRAXAS1, ACTA2, ACVR1, (ALK2), ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, (PD-L1), CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYN, C2H1, EBF1, ECT2L, EGF, EGFR, EGLN1, EIF1AX, ELF3, ELOC, (TCEB1), EMSY, ENG, EP300, EPCAM, EPHA2, EPHA7, EPHB1, EPHB2, EPOR, ERBB2, (HER2), ERBB3, ERBB4, ERCC1, ERCC2, ERCC3, ERCC4, ERCC5, ERCC6, ERG, ERRF11, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANC1, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOX, P1, FOXQ1, FRS2, FUBP1, FUSG6PD, GABRA6, GALNT12, GATA1, GATA2, GATA3, GATA4, GATA6, GENT, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDOL, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITF, MK167, MLH1, MLH3, MLLT3, MN1, MPL, MRE11, MS4A1, MSH2, MSH3, MSH6, MTAP, MTHFD2, MTHFR, MTOR, MTRR, MUTYH, MYB, MYC, MYCL, MYCN, MYD88, MYH1, NBN, NCOR1, NCOR2, NF1, NF2, NFE2L2, NFKB1A, NHP2, NKX2-1, NOP10, NOTCH1, NOTCH2, NOTCH3, NOTCH4, NPM1, NQO1, NRAS, NRG1, NSD1, NSD2, NT5C2, NTH, L1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDGFRB, PDK1, PHF6, PHGDH, PHLPP1, PHLPP2, PHOX2B, PIAS4, PIK3C2B, P1, K3, CA, PIK3CB, P1, K3, CD, PIK3CG, P1, K3, R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PRKN, PRSS1, PTC, H, 1, PTCH2, PTEN, PTPN11, PTPN13, PTPN22, PTPRD, PTPRT, QK1, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SM, AD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STAT6, STK11, SUFU, SUZ12, SYK, SYNE1, TAF1, TANC1, TAP1, TAP2, TARBP2, TBCID12, TBL1XR1, TBX3, TCF3, TCF7L2, TCL1A, TERT (promoter), TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, VSIR, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, ZRSR2, or any combination thereof.

With respect to the Tempus platform, the following applies: APC (APC-associated conditions), ATM (Ataxia-Telangiectasia, Breast cancer susceptibility, Pancreatic cancer susceptibility), AXIN2 (Oligodontia-colorectal cancer syndrome), BAP1 (BAP1tumor predisposition syndrome), BARD1 (Breast cancer susceptibility), BLM (Bloom syndrome), BMPR1A (Juvenile polyposis), BRCA1 (Hereditary breast and ovarian cancer), BRCA2 (Hereditary breast and ovarian cancer, Fanconi anemia), BRIP1 (Ovarian cancer susceptibility, Fanconi anemia), CDH1 (Hereditary diffuse gastric cancer, Breast cancer susceptibility), CDK4 (Melanoma susceptibility), CDKN2A (Melanoma-pancreatic cancer syndrome), CEBPA (Acute myeloid leukemia susceptibility), CHEK2 (Breast cancer susceptibility, Colon cancer susceptibility), DICER1 (DICER1 tumor predisposition syndrome), EGFR (Lung cancer susceptibility, TKI resistance), EPCAM (Lynch syndrome), ETV6 (Leukemia susceptibility, thrombocytopenia susceptibility), FH (Hereditary leiomyomatosis and renal cell cancer), FLCN (Birt-Hogg-Dube syndrome), GATA2 (GATA2 deficiency with susceptibility to myeloid malignancies), KIT (Familial gastrointestinal stromal tumor), MAX (Hereditary paraganglioma-pheochromocytoma syndrome), MEN1 (Multiple endocrine neoplasia type 1), MET (Hereditary papillary renal cell carcinoma), MLH1 (Lynch syndrome, Constitutional mismatch repair deficiency), MSH2 (Lynch syndrome, Constitutional mismatch repair deficiency), MSH3 (MSH3-associated polyposis), MSH6 (Lynch syndrome, Constitutional mismatch repair deficiency), MUTYH (MUTYH-associated polyposis), NBN (Nijmegen breakage syndrome, Breast cancer susceptibility), NF1 (Neurofibromatosis type 1), NF2 (Neurofibromatosis type 2), NTHL1 (NTHL1 tumor syndrome, NTHL1-associated polyposis), PALB2 (Breast cancer susceptibility, Pancreatic cancer susceptibility, Ovarian cancer susceptibility, Fanconi anemia), PDGFRA (Familial gastrointestinal stromal tumor, GIST-plus syndrome), PHOX2B (Neuroblastoma susceptibility), PMS2 (Lynch syndrome, Constitutional mismatch repair deficiency), POLD1 (Polymerase proofreading-associated polyposis), POLE (Polymerase proofreading-associated polyposis), PRKAR1A (Carney complex), PTCH1 (Gorlin syndrome, Basal cell nevus syndrome), PTEN (PTEN hamartoma tumor syndrome), RAD51C (Ovarian cancer susceptibility, Breast cancer susceptibility, Fanconi anemia), RAD51D (Ovarian cancer susceptibility, Breast cancer susceptibility), RB1 (Retinoblastoma), RET (Multiple endocrine neoplasia type 2, Familial medullary thyroid cancer), RUNX1 (Acute myeloid leukemia susceptibility), SDHA (Hereditary paraganglioma-pheochromocytoma syndrome), SDHAF2 (Hereditary paraganglioma-pheochromocytoma syndrome), SDHB (Hereditary paraganglioma-pheochromocytoma syndrome), SDHC (Hereditary paraganglioma-pheochromocytoma syndrome), SDHD (Hereditary paraganglioma-pheochromocytoma syndrome), SMAD4 Juvenile polyposis, Hereditary hemorrhagic telangiectasia), SMARCA4 (Rhabdoid tumor predisposition syndrome), SMARCB1 (Rhabdoid tumor predisposition syndrome, Schwannomatosis), STK11 (Peutz-Jeghers syndrome), SUFU (Gorlin syndrome, Basal cell nevus syndrome), TMEM127 (Hereditary paraganglioma-pheochromocytoma syndrome), TP53 (Li-Fraumeni syndrome), TSC1 (Tuberous sclerosis complex), TSC2 (Tuberous sclerosis complex), VHL (Von Hippel-Lindau syndrome), and WT1 (WT1-related Wilms tumor).

In an aspect of a disclosed method of prolonging the survival of a subject, next generation sequencing can comprise sequencing one or more cancer related genes. In an aspect of a disclosed method of prolonging the survival of a subject, sequencing one or more cancer related genes can comprise identifying one or more genomic aberrations. In an aspect, one or more genomic aberrations can comprise somatic genomic aberrations. In an aspect, the disclosed one or more somatic genomic aberrations can comprise mutations, insertions, deletions, chromosomal rearrangements, copy number aberrations, or any combination thereof.

In an aspect of a disclosed method of prolonging the survival of a subject, a disclosed cfDNA analysis can comprises quantification of one or more cancer related genes. In an aspect, if the expression and/or amount and/or presence of the disclosed one or more genomic aberrations in the pre-treatment biological sample is higher than the expression and/or amount and/or presence of the same one or more genomic aberrations in a control sample, then a disclosed method of prolonging the survival of a subject can comprise diagnosing the subject as being in need of precision cancer treatment. In an aspect, a disclosed control sample can be a sample obtained from a subject not having cancer. In an aspect, a disclosed control sample can be a pooled sample obtained from more than one subject not having cancer.

In an aspect, if the expression and/or amount and/or presence of the disclosed one or more genomic aberrations in the post-treatment biological sample is lower than the expression and/or amount and/or presence of the same one or more genomic aberrations in a pre-treatment sample, then a disclosed method of prolonging the survival of a subject can comprise continuing to administer to the subject a disclosed precision cancer treatment. In an aspect, if the expression and/or amount and/or presence of the disclosed one or more genomic aberrations in the post treatment biological sample is lower than the expression and/or amount and/or presence of the same one or more genomic aberrations in a prior post-treatment sample, then a disclosed method of prolonging the survival of a subject can comprise continuing to administer to the subject a disclosed precision cancer treatment.

In an aspect, a disclosed method of prolonging the survival of a subject can further comprise measuring the subject's tumor response to the precision cancer treatment. In an aspect, a subject's tumor response can comprise a partial response or a complete response. In an aspect, a disclosed partial response can comprise a decrease in the size of a tumor or a decrease in one or more tumors by 25% or more when compared to the size of the same tumor or the same one or more tumors prior to treatment. In an aspect, a disclosed partial response can comprise a decrease in the size of a tumor or a decrease in one more tumors by 50% or more when compared to the size of the same tumor or the same one or more tumors prior to treatment. In an aspect, a disclosed partial response can comprise a decrease in the size of a tumor or a decrease in one more tumors by about 100% or more when compared to the size of the same tumor or the same one or more tumors prior to treatment.

In an aspect, a disclosed method of prolonging the survival of a subject can further comprise measuring the subject's molecular response to a disclosed precision cancer treatment. In an aspect, a disclosed molecular response can comprise a decrease in the number of somatic genomic aberrations in a disclosed biological sample obtained from the subject. In an aspect, disclosed somatic genomic aberrations can comprise mutations, insertions, deletions, chromosomal rearrangements, copy number aberrations, fusions, or any combination thereof. In an aspect, a disclosed method of prolonging the survival of a subject can further comprise administering to the subject one or more additional therapeutic agents.

In an aspect, disclosed additional therapeutic agents can comprise chemotherapeutic agents, monoclonal antibodies, cell cycle inhibitors, small molecules, or any combination thereof.

Monoclonal antibodies are known to the skilled person in the arts. Monoclonal antibodies can comprise—but are not limited to—adotrastuzumab, alemtuzumab, atezolizumab, avelumab, bevacizumab, blinatumomab, brentuximab, cemiplimab, cetuximab, daratumumab, denosumab, dinutuximab, durvalumab, elotuzumab, gemtuzumab, ibritumomab, inotuzumab, ipilimumab, necitumumab, nivolumab, obinutuzumab, ofatumumab, olaratumab, panitumumab, pembrolizumab, pertuzumab, ramucirumab, rituximab, tositumomab, trastuzumab, or any combination thereof.

Small molecules are known to the skilled person in the arts. Small molecules can include—but are not limited to—abemaciclib, afatinib, alectinib, alpelisib, axitinib, binimetinib, bosutinib, brigatinib, cabozantinib, carfilzomib, ceritinib, cgilteritinib, cobimetinib, copanlisib, crizotinib, dabrafenib, dacomitinib, dasatinib, duvelisib, encorafenib, entrectinib, erdafitinib, erlotinib, gefitinib, ibrutinib, imatinib, ivosidenib, lapatinib, larotrectinib, lenvatinib, lorlatinib, marizomib, neratinib, nilotinib, niraparib, olaparib, osimertinib, palbociclib, pazopanib, ponatinib, regorafenib, ribociclib, rucaparib, sorafenib, sunitinib, talazoparib, trametinib, vandetanib, vemurafenib, or any combination thereof. In an aspect, an additional therapeutic agent can comprise bevacizumab, pazopanib, sorafenib, dasatinib, everolimus, or any combination thereof.

For example, in an aspect, pazopanib and/or sorafenib can be orally administered to a subject at a dose of from about 1 mg/kg/day to about 12 mg/kg/day or from 2 mg/kg/day to about 6 mg/kg/day. In an aspect, a disclosed optimal dose of pazopanib and/or sorafenib can be about 3 mg/kg/day. In an aspect, dasatinib can be orally administered to a subject at a dose of from about 0.3 mg/kg/day to about 2.0 mg/kg/day or from about 0.7 mg/kg/day to about 1.4 mg/kg/day. In an aspect, a disclosed optimal dose of dasatinib can be about 0.7 mg/kg/day. In an aspect, everolimus can be orally administered to a subject at a dose of from about 0.03 mg/kg/day to about 0.15 mg/kg/day or from about 0.03 mg/kg/day to about 0.10 mg/kg/day. In an aspect, a disclosed optimal dose of everolimus can be about 0.07 mg/kg/day. In an aspect, bevacizumab can be administered intravenously to a subject every 1 to 3 weeks at a dose of from about 2 mg/kg/day to about 15 mg/kg/day or can be administered to a patient every 1 to 3 weeks at a dose of from about 5 mg/kg/day to about 12 mg/kg/day. In an aspect, a disclosed optimal dose of bevacizumab can be administered intravenously to a subject every 2 weeks and with an optimal dose of about 10 mg/kg/day.

In an aspect, a disclosed molecular marker that can determine one or more suitable precision cancer treatments in one or more disclosed methods can be measured from a sample by high-density expression array, DNA microarray, polymerase chain reaction (PCR), reverse transcriptase PCR (RT-PCR), real-time quantitative reverse transcription PCR (qRT-PCR), serial analysis of gene expression (SAGE), spotted cDNA arrays, GeneChip, spotted oligo arrays, bead arrays, RNA Seq, tiling array, northern blotting, hybridization microarray, in situ hybridization, whole-exome sequencing, whole-genome sequencing, liquid biopsy, next-generation sequencing, or any combination thereof.

In an aspect, a disclosed molecular marker can determine one or more suitable precision cancer treatments for use in a disclosed method of prolonging the survival of a subject can determined from the nucleic acid sequence of the at least one of circulating DNA and/or RNA. In an aspect, a disclosed molecular marker can be assessed from circulating tumor DNA and/or RNA (ctDNA and/or ctRNA); circulating cell-free DNA and/or RNA (cfDNA, cfRNA); or any combination thereof ctDNA/ctRNA refers to tumor-derived fragmented DNA in the bloodstream that is not associated with cells. cfDNA/cfRNA refers to DNA that is freely circulating in the bloodstream, but is not necessarily of tumor origin. In an aspect, cfDNA/ctDNA can include any whole or fragmented genomic DNA, or mitochondrial DNA, and/or cfRNA/ctRNA can include mRNA, tRNA, microRNA, small interfering RNA, long non-coding RNA (1 ncRNA). In an aspect, cfDNA and/or ctDNA can be a fragmented DNA with a length of at least about 50 base pair (bp), about 100 bp, about 200 bp, about 500 bp, or about 1 kbp. In an aspect, cfRNA and/or ctRNA can be a full length or a fragment of mRNA (e.g., at least 70% of full-length, at least 50% of full length, at least 30% of full length, etc.). In an aspect, a disclosed molecular marker can be directed against any cancer-related gene disclosed herein.

In an aspect, a disclosed method of prolonging the survival of a subject can further comprise surgically resecting one or more tumors from the subject. In an aspect, a disclosed method of prolonging the survival of a subject can further comprise repeating one or more disclosed steps of a disclosed method.

For example, in an aspect, repeating one or more disclosed steps of a disclosed method of prolonging the survival of a subject can comprise repeating the administering to the subject the precision cancer treatment, repeating the measuring of the subject's tumor response, repeating the obtaining of a biological sample from the subject, repeating the subjecting the biological sample to cfDNA analysis, repeating the administering of one or more additional therapeutic agents, or any combination thereof.

In an aspect, a disclosed molecular marker can be detected, quantified, and/or analyzed over time (at different time points) to determine the effectiveness of a disclosed precision cancer treatment (e.g., AS therapy) to the subject and/or to determine the response of a subject or subject's tumor to the precision cancer treatment (e.g., developing resistance, susceptibility, etc.). In an aspect, a disclosed method of prolonging the survival of a subject can comprise obtaining multiple measurements over time from the same subject and same sample may be quantified at a single time point or over time. In an aspect, a disclosed treatment regimen treatment (e.g., a disclosed precision cancer treatment comprising one or more antineoplastons) can be designed and/or determined based on the cancer status and/or the changes/types of one or more molecular markers. In an aspect, the likelihood of success of a disclosed precision cancer treatment can be determined based on the cancer status and the type/quantity of one or more molecular markers.

In an aspect, a disclosed molecular marker can be derived from a gene expressed in one or more cells of a tumor or in a immune cell and can indicate immune suppressive tumor microenvironment, the development of cancer sternness, the onset of metastasis, cancer status, or any combination thereof. In an aspect, a disclosed molecular marker can be the protein or peptide encoded by the gene from which the molecular marker is derived and can be targeted by an antagonist or any other type of binding molecule to inhibit the function of the peptide.

Thus, in an aspect, increased expression (e.g., above a predetermined threshold) of a disclosed molecular marker derived from a disclosed gene related to immune suppressive tumor microenvironment can implicate the presence of immune suppressive tumor microenvironment, and can also implicate that an antagonist to the peptide encoded by the gene related to immune suppressive tumor microenvironment can have a high likelihood of success to inhibit the progress of the cancer by inhibiting immune suppressive tumor microenvironment and further promoting immune cell activity against tumor cells in such microenvironment. In an aspect, once the molecular marker has been identified, any suitable antagonist to a target gene or protein product can be used. For example, in an aspect, a specific kinase can be targeted by a kinase inhibitor, or a specific signaling receptor can be targeted by synthetic ligand, or a specific checkpoint receptor targeted by synthetic antagonist or antibody, etc. In an aspect, a disclosed antagonists to a target molecule herein can be administered before, after, or in combination with AS therapy.

In an aspect, a subject can be a human patient. In an aspect a subject can be any age (e.g., geriatric, adult, young adult, teenager, tween, adolescent, child, toddler, baby, or infant), can be male or female, can be any nationality, can be of any ethnicity, and/or can be of any race. In an aspect, a subject can have a terminal cancer.

In an aspect, a disclosed subject has not received treatment prior to the administering of a disclosed precision cancer treatment. In an aspect, a disclosed subject has received treatment prior to the administering of a disclosed precision cancer treatment. In an aspect of a disclosed method of prolonging the survival of a subject, prior to the administering of a disclosed precision cancer treatment, the subject has received surgical treatment, antibody treatment, chemotherapy treatment, radiation treatment, immunotherapy treatment, or any combination thereof. In an aspect of a disclosed method of prolonging the survival of a subject, a subject in need thereof has been diagnosed as having cancer, or wherein the subject in need thereof is suspected of having a cancer.

In an aspect, a disclosed cancer can be a refractory cancer or refractory disease. In an aspect, "refractory" refers to cancer and/or tumor that does not respond to and/or becomes resistant to a treatment. In an aspect, a subject can have a relapsed disease. In an aspect, "relapsed" or "relapses" refers to a tumor that returns or progresses following a period of improvement (e.g., a partial or complete response) with treatment. In an aspect, a disclosed cancer can comprise a solid tumor. In an aspect, a disclosed cancer can comprise metastatic cancer. In an aspect, a disclosed cancer can comprise a terminal cancer.

In an aspect, a disclosed cancer can comprise adenocarcinoma (including of the appendix and cervix), adenoid cystic carcinoma, adult t-cell leukemia, anaplastic astrocytoma, anaplastic ependymoma, anaplastic oligodendroglioma, astrocytoma, basal cell carcinoma, B-cell cancers, benign and malignant lymphomas, biliary tract—cholangiocarcinoma, bowel, brain cancer (including anaplastic astrocytoma, anaplastic ependymoma, anaplastic oligodendroglioma, brainstem anaplastic astrocytoma, brainstem glioma, diffuse astrocytoma, DIPG h3k27 mutation, ganglioglioma, glioblastoma multiforme, medulloblastoma, pilocytic astrocytoma, brainstem glioma), breast cancer, breast carcinoma, Burkitt's lymphoma, bladder cancer and carcinoma, carcinoma of unknown primary, carcinosarcoma, cervical cancer, cholangiocarcinoma, chronic atypical myelogenous leukemia, chronic atypical myelogenous leukemia, colon cancer, colorectal carcinoma, diffuse astrocytoma, diffuse intrinsic pontine glioma (DIPG), endometrial cancer, endometrial carcinoma, ependymomas, esophageal cancer and carcinoma, esophagus, Ewing's sarcoma, ganglioglioma, ganglioneuromas, gastrointestinal stromal tumor (gist), gliobastomas, gliomas, head and neck cancer and carcinoma, hemangiosarcoma, hepatocellular carcinomas, renal cell carcinomas, Hodgkin's disease, Kaposi's sarcoma, kidney cancer and carcinoma, large b-cell lymphoma, leptomeningeal carcinomatosis, leukemias, liposarcoma, liver cancer, lung carcinoma (non-small cell and small cell carcinoma), medulloblastoma, melanoma, meningeal sarcomas, meningiomas, multiple myeloma, myelodysplastic syndrome, myeloproliferative diseases, myosarcomas, neuroblastomas, neuroendocrine carcinoma, neurofibromas, non-Hodgkin's lymphoma, oligodendrogliomas, osteosarcoma, ovarian cancer and carcinoma, pancreatic cancer and carcinoma, peripheral neuroepithelioma, peripheral t-cell lymphoma, Philadelphia chromosome positive all and positive CML, pilocytic astrocytoma, pineal cell tumors, pleomorphic sarcoma, pre-b lymphomas, primitive neuroectodermal tumor (PNET), prostate cancer and carcinoma, refractory anemia, salivary gland carcinoma, sarcoma, schwannomas, skin cancer and carcinoma, squamous-cell carcinoma, stomach cancer and carcinoma, synovial sarcoma, testicular cancer, thyroid cancer and carcinoma, T-lineage acute lymphoblastic leukemia (T-all), T-lineage lymphoblastic lymphoma (T-LL), urothelial cancer and urothelial high-grade carcinoma, uterine, cervix, vulvar, and/or endometrium carcinoma, Wilms' tumor or teratocarcinomas, or any combination thereof.

In an aspect, a disclosed cancer can comprise breast cancer, colorectal cancer, head and neck cancer, kidney cancer, lung cancer, ovarian cancer, pancreatic cancer, prostate cancer, brain cancer, adenoid cystic carcinoma, anaplastic astrocytoma, anaplastic ependymoma, anaplastic oligodendroglioma, brainstem glioma, diffuse astrocytoma, diffuse intrinsic pontine glioma (DIPG), ganglioglioma, medulloblastoma, pilocytic astrocytoma, cholangiocarcinoma, chronic atypical myelogenous leukemia, endometrial carcinoma, esophageal cancer, Ewing's sarcoma, gastrointestinal stromal tumor (GIST), leptomeningeal carcinomatosis, multiple myeloma, myelodysplastic syndrome, neuroendocrine carcinoma, Non-Hodgkin's lymphoma, pleomorphic sarcoma, primitive neuroectodermal tumor (PNET), refractory anemia, salivary gland carcinoma, skin cancer, stomach cancer, thyroid cancer, urothelial cancer, or any combination thereof.

In an aspect, a disclosed method of prolonging the survival of a subject can further comprise comprising monitoring the subject for adverse effects (such as, e.g., hepatic impairment, hematologic toxicity, neurologic toxicity, cutaneous toxicity, gastrointestinal toxicity, or any combination thereof). In an aspect, in the absence of adverse effects, a disclosed method of prolonging the survival of a subject can further comprise continuing to administering to the subject a disclosed precision cancer treatment. In an aspect, in the presence of adverse effects, a disclosed method of prolonging the survival of a subject can further comprise modifying one or more disclosed steps of a disclosed method. In an aspect, a disclosed method of prolonging the survival of a subject can further comprise treating the one or more adverse effects.

In an aspect, a disclosed method of prolonging the survival of a subject can comprise modifying a disclosed administering step. In an aspect, modifying a disclosed administering step can comprise changing the amount of the one or more antineoplastons or composition comprising one or more antineoplastons administered to the subject, changing the frequency that the one or more antineoplastons or composition comprising one or more antineoplastons are administered to the subject, changing the duration of administration of the one or more antineoplastons or composition comprising one or more antineoplastons, changing the route of administration of the one or more antineoplastons or composition comprising one or more antineoplastons administered to the subject, or any combination thereof.

In an aspect, a disclosed method of prolonging the survival of a subject can further comprise obtaining a tissue biopsy from the subject. In an aspect, a disclosed tissue biopsy can be subjected to next generation sequencing. In an aspect, a disclosed method of prolonging the survival of a subject can comprise subjecting the subject to one or more invasive or non-invasive diagnostic assessments. Diagnostic assessments are known to the art. In an aspect, a disclosed non-invasive diagnostic assessment can comprise x-rays, computerized tomography (CT) scans, magnetic resonance imaging (MRI) scans, ultrasounds, positron emission tomography (PET) scans, or any combination thereof. In an aspect, a disclosed invasive diagnostic assessment can comprise a tissue biopsy or exploratory surgery.

In an aspect, a disclosed subject can improve the life expectancy of the subject. In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of prolonging the survival of a subject, the subject's cancer is treated.

In an aspect, a disclosed method can improve life expectancy compared to the cancer life expectancy of an untreated subject with the identical or near identical disease condition and the identical or near identical predicted outcome. As used herein, "life expectancy" is defined as the time at which 50 percent of subjects are alive and 50 percent have passed away. In an aspect, patient life expectancy can be indefinite following treatment with a disclosed method. In an aspect, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with the identical or near identical disease condition and the identical or near identical predicted outcome.

In an aspect, life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and the identical or near identical predicted outcome. In an aspect, life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with the identical or near identical disease condition and the identical or near identical predicted outcome.

In an aspect, a disclosed method of prolonging the survival of a subject can comprise protecting the subject from metastasis. In an aspect, a disclosed method of prolonging the survival of a subject can comprise reducing the risk of developing metastasis. In an aspect of a disclosed method of prolonging the survival of a subject, treating the cancer can comprise increasing the subject's survivability, increasing the length of time before metastasis, reducing the likelihood of surgical intervention, reducing the need for administration of one or more additional therapeutic agents or regiments, reducing the size of one or more tumors in the subject, eliminating one or more tumors in the subject, reducing or eliminating the prevalence of one or more genomic aberrations, restoring the normal metabolism of one or more organ systems in the subject, restoring one or more aspect of cellular homeostasis and/or cellular functionality, and/or metabolic dysregulation; or any combination thereof.

In an aspect of a disclosed method of prolonging the survival of a subject, restoring one or more aspects of cellular homeostasis and/or cellular functionality can comprise one or more of the following: (i) correcting cell starvation in one or more cell types (such as, for example, liver cells and muscle cells); (ii) normalizing aspects of the autophagy pathway (such as, for example, correcting, preventing, reducing, and/or ameliorating autophagy); (iii) improving, enhancing, restoring, and/or preserving mitochondrial functionality and/or structural integrity; (iv) improving, enhancing, restoring, and/or preserving organelle functionality and/or structural integrity; (v) preventing, slowing, and/or eliminating hypoglycemia, ketosis, and/or other liver abnormalities; (vi) correcting liver enzyme dysregulation; (vii) reversing, inhibiting, preventing, stabilizing, and/or slowing the rate of progression of tumor metastasis; (viii) reversing, inhibiting, preventing, stabilizing, and/or slowing the rate of progression of tumor growth and/or cancer spread, or (ix) any combination thereof. In an aspect, restoring one or more aspects of cellular homeostasis can comprise improving, enhancing, restoring, and/or preserving one or more aspects of cellular structural and/or functional integrity in, for example, an organ or system that has been affected by cancer.

For example, in an aspect, tumor growth can be impaired at least about 5% or greater to at least about 100%, at least about 10% or greater to at least about 95% or greater, at least about 20% or greater to at least about 80% or greater, at least about 40% or greater to at least about 60% or greater compared to an untreated subject having the identical or near identical disease condition and the identical or near identical predicted outcome. In an aspect, one or more tumors in a subject treated using a disclosed method of prolonging the survival of a subject can grow at least 5% less (or more as described above) when compared to an untreated subject with the identical or near identical disease condition and identical or near identical predicted outcome.

In an aspect, tumor growth can be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and identical or near identical predicted outcome.

In an aspect, tumor growth can be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with the identical or near identical disease condition and identical or near identical predicted outcome.

In an aspect, treatment of tumors according to the methods disclosed herein (e.g., AS therapy) can result in a shrinking of a tumor in comparison to the starting size of the tumor. In an aspect, tumor shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In an aspect, a disclosed subject can present with one or more cancerous solid tumors, metastatic nodes, or any combination thereof. In any aspect, a subject herein can have a cancerous tumor cell source that can be less than about 0.2 $cm^3$ to at least about 20 $cm^3$ or greater, at least about 2 $cm^3$ to at least about 18 $cm^3$ or greater, at least about 3 $cm^3$ to at least about 15 $cm^3$ or greater, at least about 4 $cm^3$ to at least about 12 $cm^3$ or greater, at least about 5 $cm^3$ to at least about 10 $cm^3$ or greater, or at least about 6 $cm^3$ to at least about 8 $cm^3$ or greater.

In an aspect, a disclosed method prolonging the survival can comprise a pan-tumor approach such as, for example, administering a disclosed ANP therapy.

E. Methods of Preventing and/or Decreasing Metastases

Disclosed herein is a method of preventing and/or decreasing metastases, the method comprising administering to a subject in need thereof a precision cancer treatment, wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; and administering to the subject a precision cancer treatment, wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof; subjecting the biological sample to a cell-free DNA (cfDNA) analysis; diagnosing the subject as being in need of precision cancer treatment when the expression and/or amount of one or more genomic aberrations in the biological sample is higher than the expression and/or amount of the same one or more genomic aberrations in a control sample; administering to the subject a precision cancer treatment; and wherein the subject demonstrates a tumor response and/or molecular response to the precision cancer treatment, and wherein metastases are prevented and/or decreased.

Disclosed herein is a method of preventing and/or decreasing metastases, the method comprising obtaining a biological sample from a subject in need thereof; subjecting the biological sample to a cell-free DNA (cfDNA) analysis; wherein if the expression and/or amount of one or more genomic aberrations in the biological sample is higher than the expression and/or amount of the same one or more genomic aberrations in a control sample, then diagnosing the subject as being in need of precision cancer treatment when; and administering to the subject a precision cancer treatment, wherein the subject demonstrates a tumor response and/or molecular response to the precision cancer treatment, and wherein metastases are prevented and/or decreased.

In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of preventing and/or decreasing metastases, the subject's cancer is treated.

In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of preventing and/or decreasing metastases, the subject's cancer is treated.

In an aspect, a disclosed precision cancer treatment can comprise one or more antineoplastons or can comprise a composition comprising one or more antineoplastons. In an aspect, disclosed antineoplastons can comprise phenylacetate, phenylacetylglutaminate, phenylacetylglutaminate sodium, phenylacetylisoglutaminate sodium, or any combination thereof. In an aspect, a disclosed composition comprising one or more antineoplastons can comprise phenylacetate, phenylacetylglutaminate, phenylacetylglutaminate sodium, phenylacetylisoglutaminate sodium, or any combination thereof.

In an aspect, a disclosed composition comprising one or more antineoplastons can comprise a pharmaceutically acceptable carrier. In an aspect, the disclosed one or more antineoplastons can comprise phenylacetylglutaminate sodium (PG) and phenylacetylisoglutaminate sodium (iso-PG). In an aspect, a disclosed ratio of phenylacetylglutaminate sodium (PG) and phenylacetylisoglutaminate sodium (iso-PG) can be about 10:1, about 9:1, about 8:1, about 7:1, about 6:1, about 5:1, about 4:1, about 3:1, about 2:1, or about 1:1. In an aspect, a disclosed ratio of phenylacetylglutaminate sodium (PG) and phenylacetylisoglutaminate sodium (iso-PG) can range from about 10:1 to about 1:10. In an aspect, a disclosed ratio of phenylacetylglutaminate sodium (PG) and phenylacetylisoglutaminate sodium (iso-PG) can be about 4:1. In an aspect, a dose of the disclosed one or more antineoplastons can comprise about 0.1 g/kg/day to about 20 g/kg/day. In an aspect, a therapeutically effective dose of the disclosed one or more antineoplastons can comprise about 0.1 g/kg/day to about 20 g/kg/day. In an aspect, a disclosed dose of phenylacetylglutaminate sodium (PG) can comprise about 0.4 g/kg/day to about 16 g/kg/day, and a disclosed dose of phenylacetylisoglutaminate sodium (iso-PG) can comprise about 0.1 g/kg/day to about 4 g/kg/day. In an aspect, a disclosed therapeutically effective amount of phenylacetylglutaminate sodium (PG) can comprise about 0.4 g/kg/day to about 16 g/kg/day, and a disclosed therapeutically effective amount of phenylacetylisoglutaminate sodium (iso-PG) can comprise about 0.1 g/kg/day to about 4 g/kg/day.

In an aspect, the disclosed one or more antineoplastons can comprise phenylacetate (PN) and phenylacetylglutaminate (PG). In an aspect, a disclosed ratio of phenylacetate (PN) and phenylacetylglutaminate (PG) can be about 10:1, about 9:1, about 8:1, about 7:1, about 6:1, about 5:1, about 4:1, about 3:1, about 2:1, or about 1:1. In an aspect, a disclosed ratio of phenylacetate (PN) and phenylacetylglutaminate (PG) can range from about 10:1 to about 1:10. In an aspect, a disclosed ratio of phenylacetate (PN) and phenylacetylglutaminate (PG) can be about 4:1. In an aspect, a dose of the disclosed one or more antineoplastons can comprise about 0.08 g/kg/day to about 0.6 g/kg/day. In an aspect, a therapeutically effective dose of the disclosed one or more antineoplastons can comprise about 0.08 g/kg/day to about 0.6 g/kg/day. In an aspect, a disclosed dose of phenylacetate (PN) can comprise about 0.064 g/kg/day to about 0.48 g/kg/day, and a disclosed dose of phenylacetylglutaminate (PG) can comprise about 0.016 g/kg/day to about 0.12 g/kg/day. In an aspect, a disclosed therapeutically effective dose of phenylacetate (PN) can comprise about 0.064 g/kg/day to about 0.48 g/kg/day, and a disclosed therapeutically effective dose of phenylacetylglutaminate (PG) can comprise about 0.016 g/kg/day to about 0.12 g/kg/day.

In an aspect of a disclosed method of preventing and/or decreasing metastases, administering a disclosed precision cancer treatment can comprise intravenous administration. In an aspect, a disclosed precision cancer treatment can be administered to a subject intravenously using, for example, a dual-channel infusion pump or two single channel pumps and central venous catheter. In an aspect, a disclosed IV administration of a disclosed precision cancer treatment can occur once every four hours at the infusion rate of from about 50 mL/hr to about 250 mL/hr (e.g., about 50, 75, 100, 125, 150, 175, 200, 225, 250 mL/hr) depending on the subject's age and condition/tolerance.

In an aspect, a disclosed method of preventing and/or decreasing metastases can comprise titrating the dose of a disclosed precision cancer treatment. In an aspect, a disclosed method of treating and/or preventing cancer can comprise titrating the dose of A10, AS2-1, or a combination thereof. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects.

In an aspect, a disclosed method of treating and/or preventing cancer can comprise titrating the dose of a disclosed precision cancer treatment in a specific or disclosed subject. In an aspect, a disclosed method of treating and/or preventing cancer can comprise titrating the dose of A10, AS2-1, or a combination thereof in a specific or disclosed subject. In an aspect, a disclosed method of treating and/or preventing cancer can comprise titrating the dose of a disclosed composition, a disclosed pharmaceutical composition, a disclosed therapeutic agent, a disclosed immune modulator, a disclosed proteasome inhibitor, a disclosed small molecule, a disclosed endonuclease, a disclosed oligonucleotide, a disclosed RNA therapeutic, or any combination thereof to identify an effective dose and/or to identify an effective dose eliciting only mild adverse and/or side effects for a specific or disclosed subject.

In an aspect, administering comprises administering to the subject the maximum tolerated dose of A10, AS2-1, or both. In an aspect, administering comprises administering to the subject less than the maximum tolerated dose of A10, AS2-1, or both.

In an aspect, IV administration of a disclosed precision cancer treatment can comprise an outpatient setting. In an aspect, A10 can be administering prior to, concurrent with, or after administering of AS2-1. In an aspect, AS2-1 can be administering prior to, concurrently with, or after administering of A10. In an aspect, the order of administering one or more antineoplastons can change during a treatment regimen.

In an aspect, a disclosed method of preventing and/or decreasing metastases can further comprise obtaining a biological sample from the subject prior to administering a disclosed precision cancer treatment. In an aspect, a disclosed method of preventing and/or decreasing metastases can further comprise obtaining a biological sample from the subject after administering a disclosed precision cancer treatment. In an aspect, a disclosed method of prolonging a disclosed method of preventing and/or decreasing metastases can further comprise subjecting the biological sample to a cell-free DNA (cfDNA) analysis. cfDNA analyses are known to the skilled person in the art. In an aspect, a disclosed cfDNA analysis can be repeated one or more times. In an aspect, a disclosed obtaining step can be repeated one or more times.

In an aspect of a disclosed method of preventing and/or decreasing metastases, a disclosed cfDNA analysis can comprise next generation sequencing. In an aspect, next generation sequencing (NGS) can comprise using one or more commercially available platforms. Commercially available NGS sequencing platforms can comprise, for example, Guardant360 CDx (Guardant Health, Inc.), FoundationOne CDx (F1CDx) (Foundation Medicine, Inc.), or Tempus xT (Tempus).

In an aspect of a disclosed method of preventing and/or decreasing metastases, a disclosed cancer-related gene can comprise ABL1, ABL2, ACO2, ACTB, ACVR1B, AKT, AKT1, AKT2, AKT3, ALK, AMER11, APC, AR, ARAF, ARFRP1, ARID1A, ARID1B, ARID2, ASK, ASPM, ASXL1, ATF1, ATF3, ATM, ATR, ATRX, AURKA, AURKB, AXIN1, AXL, BAD, BAGE, BAGE2, BAP1, BARD1, BAX, BCL2, BCL2L1, BCL2L2, BCL6, BCMA, BCOR, BCORL1, BDNF, BLM, BMPR1A, BRAF, BRCA1, BRCA2, BRD4, BRIP1, BTG1, BTK, BUB1, C10ORF54, CAGE1, CARD11, CASP5, CBFB, CBL, CCL1, CCL11, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL7, CCL8, CCNA 2, CCNB 1, CCNB 2, CCND, CCND1, CCND2, CCND3, CCNE1, CCNE2, CCR1, CCR10, CCR2, CCR3, CCR4, CCR5, CCR6, CCR7, CCR8, CCR9, CD123, CD19, CD20, CD25, CD274, CD276, CD30, CD33, CD4, CD79A, CD79B, CD8, CD80, CD86, CDC, CDC2, CDC20, CDC25A, CDC25B, CDC25C, CDC42, CDC6, CDC6; CDC7, CDC73, CDCA8, CDH1, CDK12, CDK2, CDK3, CDK4, CDK6, CDK8, CDKN1A, CDKN1B, CDKN2A, CDKN2B, CDKN2C, CEA, CEBPA, CFS1, CHD2, CHD4, CHEK1, CHEK2, CHK-1, CIC, CLDND1, CNE2, CREBBP, CRKL, CRLF2, CSF1, CSF1R, CSF3, CTAG1, CTAG1B, CTAG2, CTAG4, CTAG5, CTAG6, CTAG9, CTCF, CTLA4, CTNNA1, CTNNB1, CUL3, CXCL1, CXCL10, CXCL11, CXCL12, CXCL13, CXCL14, CXCL16, CXCL17, CXCL2, CXCL3, CXCL5, CXCL6, CXCL9, CXCR1, CXCR2, CXCR3, CXCR5, CXCR6, CYLD, DAXX, DCC, DDR2, DEPTOR, DICER1, DLD, DLST, DNMT3A, DOT1L, DUSP1, DUSP6, E2F1, EBNA1, EBNA2, EGFR, EMSY, ENOX2, EP300, EPCAM, EPHA3, EPHA5, EPHA7, EPHB1, ERBB2, ERBB3, ERBB4, ERCC1, EREG, ERG, ERK. ERRF11, ESR1, EWSR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR, FGFR1, FGFR2, FGFR3, FGFR4, FH, FLCN, FLI1, FLT1, FLT3, FLT4, FOLH1, FOLR1, FOXL2, FOXP1, FRS2, FUBP1, GABRA6, GADD45A, GAGE1, GAGE10, GAGE12D, GAGE12F, GAGE12J, GAGE13, GAGE2A, GAGE2B, GAGE2C, GAGE2D, GAGE2E, GAGE4, GART, GATA1, GATA2, GATA3, GATA4, GATA6, GID4, GLI1, GNA, GNA11, GNA13, GNAQ, GNAS, GPNMB, GPR124, GRIN2A, GRM3, GSK3B, H3F3A, HAVCR2, HDAC, HDAC1, HDAC5, HGF, HHLA2, HIF1, HIF1A, HIST1H1D, HNF1A, HRAS, HSD3B1, HSP90AA1, ICOSLG, IDH1, IDH2, IDH3A, IDH3B, IDO, IGF1R, IGF2, IKBKE, IKZF1, IL1, IL15, IL1A, IL1B, IL6, IL7R, IL8, INHBA, INPP4B, IRF2, IRF4, IRS2, JAK1, JAK2, JAK3, JUN, KDM5A, KDM5C, KDM6A, KDR, KEAP, KEL, KIT, KLHL6, KLK3, KRAS, LAG1, LAG3, LMO1, LMP1, LRP1B, LYN, LZTR1, MAD2L1, MAGEA1, MAGEA10, MAGEA12, MAGEA2, MAGEA3, MAGEA4, MAGEA5, MAGEA6, MAGEA7, MAGEA8, MAGEA9, MAGEB1, MAGEB10, MAGEB16, MAGEB18, MAGEB2, MAGEB3, MAGEB4, MAGEB6, MAGEC1, MAGEC2, MAGEC3, MAGED1, MAGED2, MAGED4, MAGED4B, MAGEE1, MAGEE2, MAGEB1, MAGEH1, MAGEL2, MAGI2, MAP2K1, MAP2K2, MAP2K4, MAP3K1, MAP3K6, MAPK, MCL1, MCM, MCM2, MCM3, MCM4, MCM5, MCM6, MCM7, MDH1, MDM2, MDM4, MED12, MEF26, MEF2B, MEN1, MET, MITF, MLH1, MLL, MLL2, MLL3, MPL, MRE11A, MSH2, MSH6, MTOR, MUC1, MUTYH, MYC, MYCL, MYCN, MYD88, MYH, MYST3, NCR3LG1, Netrin, NF1, NF2, NFE2L2, NFKB, NFKB1A, NGF, NKX2-1, NOTCH1, NOTCH2, NOTCH3, NPM1, NRAS, NSD1, NTRK1, NTRK2, NTRK3, NUP93, OGDH, ORC, ORC1, ORC1L, ORC1L, ORC6L, ORCL, ORCLPCNA, PAK3, PALB2, PAPPA, PARK2, PAX, PAX3, PBRM1, PCNA, PDCD1, PDCD1LG2, PDGFRA, PDGFRB, PDHA1, PDK1, PGR, PIK3C2B, PIK3CA, PIK3CB, PIK3CG, PIK3R1, PIK3R2, PIK3R1, PKMYT, PKMYT1, PLCG2, PLK1, PMS2, POLD1, POLE, PPM1A, PPP2R1A, PREX2, PRKAR1A, PRKC1, PRKDC, PRSS8, PTCH1, PTEN, PTPN1, PTPN11, PTPRR, PTTG, PTTG1, PTTG2, PTTG3, QK1, RAC1, RAD50, RAD51, RAF1, RANBP1, RARA, RAS, RB1, RBL1, RBM10, RET, RICTOR, RITZ, RNF43, ROS1, RPTOR, RUNX1, RUNX1T1, SDHA, SDHB, SDHC, SDHD, SETD2, SF3B1, SKP2, SLAMF7, SLIT2, SMAD2, SMAD3, SMAD4, SMARCA4, SMARCB1, SMC1A, SMC1L1, SMO, SNCAIP, SOCS1, SOX10, SOX2, SOX9, SPAG1, SPAG11A, SPAG11B, SPAG16, SPAG17, SPAG4, SPAG5, SPAG6, SPAG7, SPA G8, SPAG9, SPEN, SPOP, SPTA1, SRC, SRSF2, STAG2, STAT3, STAT4, STAT5, STAT5B, STK11, SUCLG1, SUCLG2, SUFU, SYK, T(BRACHYURY), TAF1, TBC1D8, TBX3, TERC, TERT, TERT promoter, TET2, TFDP1, TGFRB2, TNFAIP3, TNFRSF14, TOP1, TOP2A, TOP2B, TP53, TRIB3, TSC1, TSC2, TSHR, TUBB3, TYMP, TYMS, U2AF1, UNC5A, UNC5B, VEGFA, VHL, VTCN1, WEE1, WISP3, WT1, XAGE1D, XAGE2, XAGE3, XAGE5, XCL1, XCL2, XCR1, XPO1, ZBTB2, ZNF217, ZNF703, or any combination thereof.

In an aspect, a disclosed cancer-related gene can comprise one or more genomic aberrations. In an aspect, a subject can have one or more genomic aberrations in a disclosed cancer-related gene.

In an aspect, a disclosed ALK gene can encode a ALK protein having an 11461 L or N1544K mutation. In an aspect, a disclosed ARID2 gene can encode an ARID2 protein having a N127fs18 mutation. In an aspect, a disclosed AKT1 gene can encode a AKT1 protein having a E17K or R346H mutation. In an aspect, a disclosed APC gene can encode an APC protein having a G29G, K445K, V2716L, E918E, Q1378*, S457*, 11304fs, E888fs, R230C, Q1090Q, S1360P. In an aspect, a disclosed gene can encode an AR protein having a A356E M887V or S510R mutation. In an aspect, a disclosed ARAF gene can encode a ARAF protein having a Y495Y mutation. In an aspect, a disclosed ARID1A gene can encode an ARID1A protein having a S1798L, S1167F, G246V, R1889W, or Q802fs mutation. In an aspect, a disclosed ARID2 gene can encode an ARID2 protein having a N127fs18 mutation. In an aspect, a disclosed ARTX gene has a S850fs*2, or s N179fs*26 mutation. In an aspect, a disclosed ASXL1 gene has a R1273f*s mutation. In an aspect, a disclosed BRAF gene can encode a BRAF protein having a E264 or V600E mutation. In an aspect, a disclosed BRCA1 gene can encode a BRAC1 protein having a H662Q or a R1443* mutation. In an aspect, a disclosed BRCA2 gene can encode a BRCA2 protein having a D237N or 12040V mutation. In an aspect, a disclosed CCND1 gene can encode a CCND1 protein having a R291W mutation. In an aspect, a disclosed CCNE1 gene can encode a CCNE1 protein having a P268P or R95Q mutation. In an aspect, a disclosed CDKN1B gene can encode a CDKN1B protein having a K59fs* mutation. In an aspect, a disclosed CDKN2A gene can encode a CDKN2A protein having a D74N mutation. In an aspect, a disclosed CTNNB1 gene can encode a CTNNB1 protein having a T41A mutation. In an aspect, a disclosed DDR2 gene can encode a DDR2 protein having a L749L mutation. In an aspect, a disclosed EGFR gene can encode an EGFR protein having a P753L, V524I, D321D, or V7421 mutation. In an aspect, a disclosed ERBB2 gene can encode a ERBB2 protein having a C584G or V797del (Exon 20 deletion) mutation. In an aspect, a disclosed EWSR1 gene can encode a EWSR1 protein having a FLIT fusion. In an aspect, a disclosed FBXW7 gene can encode a FBXW7 protein having a Y545C or R658* mutation. In an aspect, a disclosed FGFR gene can encode a FGFR protein having a T320T, S726F, H791H, P47P, S430fs, or R179H mutation. In an aspect, a disclosed FGFR1 gene can encode a FGFR1 protein having a S726F mutation. In an aspect, a disclosed FGFR2 gene can encode a FGFR2 protein having a KCNH7 fusion. In an aspect, a disclosed FGFR3 gene can encode a FGFR3 protein having a H290Y mutation. In an aspect, a disclosed GATA3 gene can encode a GATA3 protein having a P433fs43, P409fs, PS405fs, D336fs, S430fs, or c.1213_1214del mutation. In an aspect, a disclosed GNA11 gene can encode a GNA11 protein having a N244S mutation. In an aspect, a disclosed GNAS gene can encode a GNAS protein having a R201H* mutation. In an aspect, a disclosed HIST1H1D gene can encode a HIST1H1D protein having a K185-A186>T mutation. In an aspect, a disclosed H3F3A gene can encode a H3F3A protein having a K28N or K27 mutation. In an aspect, a disclosed IDH1 gene can encode an IDH1 protein having a R132H mutation. In an aspect, a disclosed JAK2 gene can encode a JAK2 protein having a V617 mutation. In an aspect, a disclosed KIT gene has a Q 775 fs (Exon 16 deletion). In an aspect, a disclosed ARID1A gene can encode an ARID1A protein having a S1798L, S1167F, G246V, R1889W, or Q802fs mutation. In an aspect, a disclosed KRAS gene can encode a KRAS protein having a G12V, G12D, G12S, G13D, or p.AG11GD mutation. In an aspect, a disclosed MAP2K1 gene can encode a MAP2K1 protein having a K57E mutation. In an aspect, a disclosed MAP2K4 gene has a loss of exon 2. In an aspect, a disclosed MAP3KJ gene can encode a MAP3K1 protein having a S398 mutation. In an aspect, a disclosed MAP3K6 gene can encode a MAP3K6 protein having a P646L mutation. a disclosed MET gene can encode a MET protein having a C385Y, T895M, T7591, or M391 mutation. In an aspect, a disclosed MPL gene can encode a MPL protein having a Y591D mutation. In an aspect, a disclosed MYC gene can encode a MYC protein having a S244S mutation. In an aspect, a disclosed NF1 gene has a Splice cite 480-11_4801del11, Splice cite SNV, c.6655>T, p.D2219Y, V2378fs*8, or can encode a A2617A, F710C, I1719T, or K583R mutation. In an aspect, a disclosed NOTCH1 gene can encode a NOTCH protein having a A465V, V220M, D1681H, or S223N mutation. In an aspect, a disclosed NOTCH2 gene can encode a NOTCH2 protein having a S2379F mutation. In an aspect, a disclosed NTRK1 gene can encode a NTRK1 protein having a P387L or R766Q mutation. In an aspect, a disclosed PDGFRA gene can encode a PDGFRA protein having a E86A or V299G mutation. In an aspect, a disclosed PIK3CA gene can encode a PIK3CA protein having a Q546H, Q546K, Q546R, Q597H, E542K, E545K, E726K, E39K, E453K, R4-P18del, H1047L, H104R, K567E, I15431, p.E545K, or G1049R mutation. In an aspect, a disclosed PIK3R1 gene can encode a PIK3R1 protein having a S399Y408del splice site 917-1G>A mutation. In an aspect, a disclosed PTCH1 has a p.M17 Start loss-LOF. In an aspect, a disclosed PTEN gene can encode a PTEN protein having a H196_1203DEL, R55fs, N323fs*23, Y27C, R130*, C136Y, D252Y, or loss of exons 4-7 mutation. In an aspect, a disclosed RAFT gene can encode a RAF1 protein having a P63P mutation. In an aspect, a disclosed RB1 gene can encode a RB1 protein having a Q217*, Y173fs*, or H673fs mutation. In an aspect, a disclosed RUNX1 gene can encode a RUNX1 protein having a R107C mutation. In an aspect, a disclosed SMAD4 gene can encode a SMAD4 protein having a P511 L, D537V, Q450H, L495R, A451P, or A406T mutation. In an aspect, a disclosed SPEN gene can encode a SPEN protein having a A2510V mutation. In an aspect, a disclosed SRSF2 gene can encode a SRSF2 protein having a P95H mutation. In an aspect, a disclosed STAT5B gene can encode a STAT5B protein having a R110H mutation. In an aspect, a disclosed TET2 gene can encode a TET2 protein having a C1875G mutation. In an aspect, a disclosed TP53 gene can encode a TP53 protein having a V73fs, R175G, R196, R249T, C176F, G187D, R282W, E287*, E285K, S241del, c.97-28_99del, Y126D, R273H, C176W, K320*, T253A, Splice site 37G-1G>A, Q104, P151H, H179Y, R273C, R248W, R176H, R209fs cer, N235-Y236del, R248Q er, R306*, C176Y, S241F, L252-1254del, L145P, R158H, R213*, Y220C, R110P, V274G, or c.376-4_384del mutation.

With respect to the Guardant360 platform, a genomic aberration in a disclosed cancer-related gene can comprise a single nucleotide variant. For example, in an aspect, a disclosed single nucleotide variant can be identified in the following genes—AKT1, ALK, APC, AR, ARAF, ATM, BRAF, BRCA1, BRCA2, CCND1, CDH1, CDK4, CDK6, CDK12, CDKN2A, CTNNB1, EGFR, ERBB2, ESR1, FGFR1, FGFR2, FGFR3, GATA3, GNA11, GNAQ, HRAS, IDH1, IDH2, KIT, KRAS, MAP2K1, MAP2K2, MET, MLH1, MTOR, MYC, NF1, NFE2L2, NRAS, NTRK1, NTRK3, PDGFRA, PIK3CA, PTEN, RAF1, RET, RHEB, ROS1, SMAD4, SMO, STK11, TERT, TSC1, VHL, or any combination thereof. With respect to the Guardant360 platform, a genomic aberration in a disclosed cancer-related gene can comprise an insertion and/or deletion. For example, in an aspect, a disclosed Indel can be identified in the following genes—AKT1, ALK, APC, ATM, BRAF, BRCA1, BRCA2, CDH1, CDK12, CDKN2A, EGFR, ERBB2, ESR1, FGFR2, GATA3, HNF1A, HRAS, KIT, KRAS, MET, MLH1, NF1, PDGFRA, PIK3CA, PTEN, RET, ROS1, STK11, TSC1, VHL, or any combination thereof. With respect to the Guardant360 platform, in an aspect, a genomic aberration in a disclosed cancer-related gene can comprise a copy number amplifications (CNA). For example, in an aspect, a disclosed CNA can be identified in the following genes—ERBB2 and/or MET. With respect to the Guardant360 platform, in an aspect, a disclosed fusion can comprise ALK, NTRK1, RET, ROS1, or any combination thereof.

With respect to the Foundation platform, in an aspect, a genomic aberration in a disclosed cancer-related gene can comprise a substitution, an Indel, or a copy number amplification. For example, in an aspect, a disclosed substitution, a disclosed Indel, or a disclosed CNA can be identified in the following genes—ABL1, ACVR1B, AKT1, AKT2, AKT3, ALK, ALOX12B, AMER1 (FAM723B), APC, AR, ARAF, ARFRP1, ARID1A, ASXL1, ATM, ATR, ATRX, AURKA, AURKB, AXIN1, AXL, BAP1, BARD1, BCL2, BCL2L1, BCL2L2, BCL6, BCOR, BCORL1, BRAF, BRCA1, BRCA2, BRD4, BRIP1, BTG1, BTG2, BTK, C11ORF30 (EMSY), CALR, CARD11, CASP8, CBFB, CBL, CCND1, CCND2, CCND3, CCNE1, CD22, CD274 (PD-L7), CD70, CD79A, CD79B, CDC73, CDH1, CDK12, CDK4, CDK6, CDK8, CDKN1A, CDKN1B, CDKN2A, CDKN2B, CDKN2C, CEBPA, CHEK7, CHEK2, CIC, CREBBP, CRKL, CSF1R, CSF3R, CTCF, CTNNA1, CTNNB1, CUL3, CUL4A, CXCR4, CYP17A1, DAXX, DDR1, DDR2, DIS3, DNMT3A, DOT1L, EED, EGFR, EP300, EPHA3, EPHB1, EPHB4, ERBB2, ERBB3, ERBB4, ERCC4, ERG, ERRF11, ESR1, EZH2, FAM46C, FANCA, FANCC, FANCG, FANCL, FAS, FBXW7, FGF10, FGF12, FGF14, FGF19, FGF23, FGF3, FGF4, FGF6, FGFR1, FGFR2, FGFR3, FGFR4, FH, FLCN, FLT1, FLT3, FOXL2, FUBP1, GABRA6, GATA3, GATA4, GATA6, GID4 (C17ORF39), GNA11, GNA13, GNAQ, GNAS, GRM3, GSK3B, H3F3A, HDAC1, HGF, HNF1A, HRAS, HSD3B1, ID3, IDH1, IDH2, IGF1R, IKBKE, IKZF1, INPP4B, IRF2, IRF4, IRS2, JAK1, JAK2, JAK3, JUN, KDM5A, KDM5C, KDM6A, KDR, KEAP1, KEL, KIT, KLHL6, KMT2A (MLL), KMT2D (MLL2), KRAS, LTK, LYN, MAF, MAP2K1 (MEK1), MAP2K2 (MEK2), MAP2K4, MAP3K1, MAP3K13, MAPK1, MCL1, MDM2, MDM4, MED12, MEF2B, MEN1, MERTK, MET, MITF, MKNK1, MLH1, MPL, MRE11A, MSH2, MSH3, MSH6, MST1R, MTAP, MTOR, MUTYH, MYC, MYCL (MYCL1), MYCN, MYD88, NBN, NF1, NF2, NFE2L2, NFKB1A, NKX2-1, NOTCH1, NOTCH2, NOTCH3, NPM1, NRAS, NT5C2, NTRK1, NTRK2, NTRK3, P2RY8, PALB2, PARK2, PARP1, PARP2, PARP3, PAX5, PBRM1, PDCD1 (PD-1), PDCD1LG2 (PD-L2), PDGFRA, PDGFRB, PDK1, PIK3C2B, PIK3C2G, PIK3CA, PIK3CB, PIK3R1, PIM1, PMS2, POLD1, POLE, PPARG, PP2R1A, PPP2R2A, PRDM1, PRKAR1A, PRKC1, PTCH1, PTEN, PTPN11, PTPRO, OK1, RAC1, RAD21, RAD51, RAD51B, RAD51C, RAD5ID, RAD52, RAD54L, RAFT, RARA, RB1, RBM10, REL, RET, RICTOR, RNF43, ROS1, RPTOR, SDHA, SDHB, SDHC, SDHD, SETD2, SF3B1, SGK1, SMAD2, SMAD4, SMARCA4, SMARCB1, SMO, SNCAIP, SOCS1, SOX2, SOX9, SPEN, SPOP, SRC, STAG2, STAT3, STK11, SUFU, SYK, TBX3, TEK, TET2, TGFBR2, TIPARP, TNFAIP3, TNFRSF14, TP53, TSC1, TSC2, TYRO3, U2AF1, VEGFA, VHL, WHSC1 (MMSET), WHSC1L1, WT1, XPO1, XRCC2, ZNF217, ZNF703, or any combination thereof. With respect to the Foundation platform, a genomic aberration in a disclosed cancer-related gene can comprise a rearrangement. For example, in an aspect, a disclosed rearrangement can be identified in the following genes—ALK, BCL2, BCR, BRAF, BRCA1, BRCA2, CD74, EGFR, ETV4, ETVS, ETV6, EWSR1, EZR, FGFR1, FGFR2, FGFR3, KIT, KMT2A (MLL), MSH2, MYB, MYC, NOTCH2, NTRK1 NTRK2 NUTM1, PDGFRA, RAFT, RARA, RET, ROS1, RSPO2 SDC4, SLC34A2 TERC (a ncRNA), TERT (promoter only), TMPRSS2, or any combination thereof.

With respect to the Tempus platform, in an aspect, a genomic aberration in a disclosed cancer-related gene can comprise a rearrangement. For example, in an aspect, a disclosed rearrangement can be identified in the following genes—ABL1, ALK, BCR, BRAF, EGFR, ETV6, EWSR1, FGFR2, FGFR3, MYB, NRG1, NTRK1, NTRK2, NTRK3, PAX8, PDGFRA, PML, RARA, RET, ROS1, TFE3, TMPRSS2, or any combination thereof. With respect to the Tempus platform, in an aspect, a genomic aberration in a disclosed cancer-related gene can comprise a single nucleotide variant, an Indel, or a copy number amplification. For example, in an aspect, a disclosed single nucleotide variant, a disclosed Indel, or a disclosed CNA can be identified in the following genes—ABCB1, ABCC3, ABL1, ABL2, ABRAXAS1, ACTA2, ACVR1, (ALK2), ACVR1B, AGO1, AJUBA, AKT1, AKT2, AKT3, ALK, AMER1, APC, APLNR, APOB, AR, ARAF, ARHGAP26, ARHGAP35, ARID1A, ARID1B, ARID2, ARID5B, ASNS, ASPSCR1, ASXL1, ATIC, ATM, ATP7B, ATR, ATRX, AURKA, AURKB, AXIN1, AXIN2, AXL, B2M, BAP1, BARD1, BCL10, BCL11B, BCL2, BCL2L1, BCL2L11, BCL6, BCL7A, BCLAF1, BCOR, BCORL1, BCR, BIRC3, BLM, BMPR1A, BRAF, BRCA1, BRCA2, BRD4, BRIP1, BTG1, BTK, BUB1B, C11orf65, C3orf70, C8orf34, CALR, CARD11, CARM1, CASP8, CASR, CBFB, CBL, CBLB, CBLC, CBR3, CCDC6, CCND1, CCND2, CCND3, CCNE1, CD19, CD22, CD274, (PD-L1), CD40, CD70, CD79A, CD79B, CDC73, CDH1, CDK12, CDK4, CDK6, CDK8, CDKN1A, CDKN1B, CDKN1C, CDKN2A, CDKN2B, CDKN2C, CEBPA, CEP57, CFTR, CHD2, CHD4, CHD7, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUL1, CUL3, CUL4A, CUL4B, CUX1, CXCR4, CYLD, CYP1B1, CYP2D6, CYP3A5, CYSLTR2, DAXX, DDB2, DDR2, DDX3X, DICER1, DIRC2, DIS3, DIS3L2, DKC1, DNM2, DNMT3A, DOT1L, DPYD, DYN, C2H1, EBF1, ECT2L, EGF, EGFR, EGLN1, EIF1AX, ELF3, ELOC, (TCEB1), EMSY, ENG, EP300, EPCAM, EPHA2, EPHA7, EPHB1, EPHB2, EPOR, ERBB2, (HER2), ERBB3, ERBB4, ERCC1, ERCC2, ERCC3, ERCC4, ERCC5, ERCC6, ERG, ERRF11, ESR1, ETS1, ETS2, ETV1, ETV4, ETV5, ETV6, EWSR1, EZH2, FAM46C, FANCA, FANCB, FANCC, FANCD2, FANCE, FANCF, FANCG, FANC1, FANCL, FANCM, FAS, FAT1, FBXO11, FBXW7, FCGR2A, FCGR3A, FDPS, FGF1, FGF10, FGF14, FGF2, FGF23, FGF3, FGF4, FGF5, FGF6, FGF7, FGF8, FGF9, FGFR1, FGFR2, FGFR3, FGFR4, FH, FHIT, FLCN, FLT1, FLT3, FLT4, FNTB, FOXA1, FOXL2, FOXO1, FOXO3, FOX, P1, FOXQ1, FRS2, FUBP1, FUSG6PD, GABRA6, GALNT12, GATA1, GATA2, GATA3, GATA4, GATA6, GEN1, GLI1, GLI2, GNA11, GNA13, GNAQ, GNAS, GPC3, GPS2, GREM1, GRIN2A, GRM3, GSTP1, H19, H3F3A, HAS3, HAVCR2, HDAC1, HDAC2, HDAC4, HGF, HIF1A, HIST1H1E, HIST1H3B, HIST1H4E, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HLA-E, HLA-F, HLA-G, HNF1A, HNF1B, HOXA11, HOXB13, HRAS, HSD11B2, HSD3B1, HSD3B2, HSP90AA1, HSPH1, IDH1, IDH2, IDOL, IFIT1, IFIT2, IFIT3, IFNAR1, IFNAR2, IFNGR1, IFNGR2, IFNL3, IKBKE, IKZF1, IL10RA, IL15, IL2RA, IL6R, IL7R, ING1, INPP4B, IRF1, IRF2, IRF4, IRS2, ITPKB, JAK1, JAK2, JAK3, JUN, KAT6A, KDM5A, KDM5C, KDM5D, KDM6A, KDR, KEAP1, KEL, KIF1B, KIT, KLF4, KLHL6, KLLN, KMT2A, KMT2B, KMT2C, KMT2D, KRAS, L2HGDH, LAG3, LATS1, LCK, LDLR, LEF1, LMNA, LMO1, LRP1B, LYN, LZTR1, MAD2L2, MAF, MAFB, MAGI2, MALT1, MAP2K1, MAP2K2, MAP2K4, MAP3K1, MAP3K7, MAPK1, MAX, MC1R, MCL1, MDM2, MDM4, MED12, MEF2B, MEN1, MET, MGMT, MIB1, MITE, MK167, MLH1, MLH3, MLLT3, MN1, MPL, MRE11, MS4A1, MSH2, MSH3, MSH6, MTAP, MTHFD2, MTHFR, MTOR, MTRR, MUTYH, MYB, MYC, MYCL, MYCN, MYD88, MYH11, NBN, NCOR1, NCOR2, NF1, NF2, NFE2L2, NFKB1A, NHP2, NKX2-1, NOP10, NOTCH1, NOTCH2, NOTCH3, NOTCH4, NPM1, NQO1, NRAS, NRG1, NSD1, NSD2, NT5C2, NTH, L1, NTRK1, NTRK2, NTRK3, NUDT15, NUP98, OLIG2, P2RY8, PAK1, PALB2, PALLD, PAX3, PAX5, PAX7, PAX8, PBRM1, PCBP1, PDCD1, PDCD1LG2, PDGFRA, PDGFRB, PDK1, PHF6, PHGDH, PHLPP1, PHLPP2, PHOX2B, PIAS4, PIK3C2B, P1, K3, CA, PIK3CB, P1, K3, CD, PIK3CG, P1, K3, R1, PIK3R2, PIM1, PLCG1, PLCG2, PML, PMS1, PMS2, POLD1, POLE, POLH, POLQ, POT1, POU2F2, PPARA, PPARD, PPARG, PPM1D, PPP1R15A, PPP2R1A, PPP2R2A, PPP6C, PRCC, PRDM1, PREX2, PRKAR1A, PRKDC, PRKN, PRSS1, PTC, H, 1, PTCH2, PTEN, PTPN11, PTPN13, PTPN22, PTPRD, PTPRT, QK1, RAC1, RAD21, RAD50, RAD51, RAD51B, RAD51C, RAD51D, RAD54L, RAF1, RANBP2, RARA, RASA1, RB1, RBM10, RECQL4, RET, RHEB, RHOA, RICTOR, RINT1, RIT1, RNF139, RNF43, ROS1, RPL5, RPS15, RPS6KB1, RPTOR, RRM1, RSF1, RUNX1, RUNX1T1, RXRA, SCG5, SDHA, SDHAF2, SDHB, SDHC, SDHD, SEC23B, SEMA3C, SETBP1, SETD2, SF3B1, SGK1, SH2B3, SHH, SLC26A3, SLC47A2, SLC9A3R1, SLIT2, SLX4, SM, AD2, SMAD3, SMAD4, SMARCA1, SMARCA4, SMARCB1, SMARCE1, SMC1A, SMC3, SMO, SOCS1, SOD2, SOX10, SOX2, SOX9, SPEN, SPINK1, SPOP, SPRED1, SRC, SRSF2, STAG2, STAT3, STAT4, STAT5A, STAT5B, STAT6, STK11, SUFU, SUZ12, SYK, SYNE1, TAF1, TANC1, TAP1, TAP2, TARBP2, TBCID12, TBL1XR1, TBX3, TCF3, TCF7L2, TCL1A, TERT (promoter), TET2, TFE3, TFEB, TFEC, TGFBR1, TGFBR2, TIGIT, TMEM127, TMEM173, TMPRSS2, TNF, TNFAIP3, TNFRSF14, TNFRSF17, TNFRSF9, TOP1, TOP2A, TP53, TP63, TPM1, TPMT, TRAF3, TRAF7, TSC1, TSC2, TSHR, TUSC3, TYMS, U2AF1, UBE2T, UGT1A1, UGT1A9, UMPS, VEGFA, VEGFB, VHL, VSIR, WEE1, WNK1, WNK2, WRN, WT1, XPA, XPC, XPO1, XRCC1, XRCC2, XRCC3, YEATS4, ZFHX3, ZMYM3, ZNF217, ZNF471, ZNF620, ZNF750, ZNRF3, ZRSR2, or any combination thereof.

With respect to the Tempus platform, the following applies: APC (APC-associated conditions), ATM (Ataxia-Telangiectasia, Breast cancer susceptibility, Pancreatic cancer susceptibility), AXIN2 (Oligodontia-colorectal cancer syndrome), BAP1 (BAP1tumor predisposition syndrome), BARD1 (Breast cancer susceptibility), BLM (Bloom syndrome), BMPR1A (Juvenile polyposis), BRCA1 (Hereditary breast and ovarian cancer), BRCA2 (Hereditary breast and ovarian cancer, Fanconi anemia), BRIP1 (Ovarian cancer susceptibility, Fanconi anemia), CDH1 (Hereditary diffuse gastric cancer, Breast cancer susceptibility), CDK4 (Melanoma susceptibility), CDKN2A (Melanoma-pancreatic cancer syndrome), CEBPA (Acute myeloid leukemia susceptibility), CHEK2 (Breast cancer susceptibility, Colon cancer susceptibility), DICER1 (DICER1 tumor predisposition syndrome), EGFR (Lung cancer susceptibility, TKI resistance), EPCAM (Lynch syndrome), ETV6 (Leukemia susceptibility, thrombocytopenia susceptibility), FH (Hereditary leiomyomatosis and renal cell cancer), FLCN (Birt-Hogg-Dube syndrome), GATA2 (GATA2 deficiency with susceptibility to myeloid malignancies), KIT (Familial gastrointestinal stromal tumor), MAX (Hereditary paraganglioma-pheochromocytoma syndrome), MEN1 (Multiple endocrine neoplasia type 1), MET (Hereditary papillary renal cell carcinoma), MLH1 (Lynch syndrome, Constitutional mismatch repair deficiency), MSH2 (Lynch syndrome, Constitutional mismatch repair deficiency), MSH3 (MSH3-associated polyposis), MSH6 (Lynch syndrome, Constitutional mismatch repair deficiency), MUTYH (MUTYH-associated polyposis), NBN (Nijmegen breakage syndrome, Breast cancer susceptibility), NF1 (Neurofibromatosis type 1), NF2 (Neurofibromatosis type 2), NTHL1 (NTHL1 tumor syndrome, NTHL1-associated polyposis), PALB2 (Breast cancer susceptibility, Pancreatic cancer susceptibility, Ovarian cancer susceptibility, Fanconi anemia), PDGFRA (Familial gastrointestinal stromal tumor, GIST-plus syndrome), PHOX2B (Neuroblastoma susceptibility), PMS2 (Lynch syndrome, Constitutional mismatch repair deficiency), POLD1 (Polymerase proofreading-associated polyposis), POLE (Polymerase proofreading-associated polyposis), PRKAR1A (Carney complex), PTCH1 (Gorlin syndrome, Basal cell nevus syndrome), PTEN (PTEN hamartoma tumor syndrome), RAD51C (Ovarian cancer susceptibility, Breast cancer susceptibility, Fanconi anemia), RAD51 D (Ovarian cancer susceptibility, Breast cancer susceptibility), RB1 (Retinoblastoma), RET (Multiple endocrine neoplasia type 2, Familial medullary thyroid cancer), RUNX1 (Acute myeloid leukemia susceptibility), SDHA (Hereditary paraganglioma-pheochromocytoma syndrome), SDHAF2 (Hereditary paraganglioma-pheochromocytoma syndrome), SDHB (Hereditary paraganglioma-pheochromocytoma syndrome), SDHC (Hereditary paraganglioma-pheochromocytoma syndrome), SDHD (Hereditary paraganglioma-pheochromocytoma syndrome), SMAD4 Juvenile polyposis, Hereditary hemorrhagic telangiectasia), SMARCA4 (Rhabdoid tumor predisposition syndrome), SMARCB1 (Rhabdoid tumor predisposition syndrome, Schwannomatosis), STK11 (Peutz-Jeghers syndrome), SUFU (Gorlin syndrome, Basal cell nevus syndrome), TMEM127 (Hereditary paraganglioma-pheochromocytoma syndrome), TP53 (Li-Fraumeni syndrome), TSC1 (Tuberous sclerosis complex), TSC2 (Tuberous sclerosis complex), VHL (Von Hippel-Lindau syndrome), and WT1 (WT1-related Wilms tumor).

In an aspect of a disclosed method of preventing and/or decreasing metastases, next generation sequencing can comprise sequencing one or more cancer related genes. In an aspect of a disclosed method of preventing and/or decreasing metastases, sequencing one or more cancer related genes can comprise identifying one or more genomic aberrations. In an aspect, one or more genomic aberrations can comprise somatic genomic aberrations. In an aspect, the disclosed one or more somatic genomic aberrations can comprise mutations, insertions, deletions, chromosomal rearrangements, copy number aberrations, or any combination thereof.

In an aspect of a disclosed method of preventing and/or decreasing metastases, a disclosed cfDNA analysis can comprises quantification of one or more cancer related genes. In an aspect, if the expression and/or amount and/or presence of the disclosed one or more genomic aberrations in the pre-treatment biological sample is higher than the expression and/or amount and/or presence of the same one or more genomic aberrations in a control sample, then a disclosed method of preventing and/or decreasing metastases can comprise diagnosing the subject as being in need of precision cancer treatment. In an aspect, a disclosed control sample can be a sample obtained from a subject not having cancer. In an aspect, a disclosed control sample can be a pooled sample obtained from more than one subject not having cancer.

In an aspect, if the expression and/or amount and/or presence of the disclosed one or more genomic aberrations in the post-treatment biological sample is lower than the expression and/or amount and/or presence of the same one or more genomic aberrations in a pre-treatment sample, then a disclosed method of preventing and/or decreasing metastases can comprise continuing to administer to the subject a disclosed precision cancer treatment. In an aspect, if the expression and/or amount and/or presence of the disclosed one or more genomic aberrations in the post treatment biological sample is lower than the expression and/or amount and/or presence of the same one or more genomic aberrations in a prior post-treatment sample, then a disclosed method of preventing and/or decreasing metastases can comprise continuing to administer to the subject a disclosed precision cancer treatment.

In an aspect, a disclosed method of preventing and/or decreasing metastases can further comprise measuring the subject's tumor response to the precision cancer treatment. In an aspect, a subject's tumor response can comprise a partial response or a complete response. In an aspect, a disclosed partial response can comprise a decrease in the size of a tumor or a decrease in one or more tumors by 25% or more when compared to the size of the same tumor or the same one or more tumors prior to treatment. In an aspect, a disclosed partial response can comprise a decrease in the size of a tumor or a decrease in one more tumors by 50% or more when compared to the size of the same tumor or the same one or more tumors prior to treatment. In an aspect, a disclosed partial response can comprise a decrease in the size of a tumor or a decrease in one more tumors by about 100% or more when compared to the size of the same tumor or the same one or more tumors prior to treatment.

In an aspect, a disclosed method of preventing and/or decreasing metastases can further comprise measuring the subject's molecular response to a disclosed precision cancer treatment. In an aspect, a disclosed molecular response can comprise a decrease in the number of somatic genomic aberrations in a disclosed biological sample obtained from the subject. In an aspect, disclosed somatic genomic aberrations can comprise mutations, insertions, deletions, chromosomal rearrangements, copy number aberrations, fusions, or any combination thereof. In an aspect, a disclosed method of preventing and/or decreasing metastases can further comprise administering to the subject one or more additional therapeutic agents.

In an aspect, disclosed additional therapeutic agents can comprise chemotherapeutic agents, monoclonal antibodies, cell cycle inhibitors, small molecules, or any combination thereof.

Monoclonal antibodies are known to the skilled person in the arts. Monoclonal antibodies can comprise—but are not limited to—adotrastuzumab, alemtuzumab, atezolizumab, avelumab, bevacizumab, blinatumomab, brentuximab, cemiplimab, cetuximab, daratumumab, denosumab, dinutuximab, durvalumab, elotuzumab, gemtuzumab, ibritumomab, inotuzumab, ipilimumab, necitumumab, nivolumab, obinutuzumab, ofatumumab, olaratumab, panitumumab, pembrolizumab, pertuzumab, ramucirumab, rituximab, tositumomab, trastuzumab, or any combination thereof.

Small molecules are known to the skilled person in the arts. Small molecules can include—but are not limited to—abemaciclib, afatinib, alectinib, alpelisib, axitinib, binimetinib, bosutinib, brigatinib, cabozantinib, carfilzomib, ceritinib, cgilteritinib, cobimetinib, copanlisib, crizotinib, dabrafenib, dacomitinib, dasatinib, duvelisib, encorafenib, entrectinib, erdafitinib, erlotinib, gefitinib, ibrutinib, imatinib, ivosidenib, lapatinib, larotrectinib, lenvatinib, lorlatinib, marizomib, neratinib, nilotinib, niraparib, olaparib, osimertinib, palbociclib, pazopanib, ponatinib, regorafenib, ribociclib, rucaparib, sorafenib, sunitinib, talazoparib, trametinib, vandetanib, vemurafenib, or any combination thereof. In an aspect, an additional therapeutic agent can comprise bevacizumab, pazopanib, sorafenib, dasatinib, everolimus, or any combination thereof.

For example, in an aspect, pazopanib and/or sorafenib can be orally administered to a subject at a dose of from about 1 mg/kg/day to about 12 mg/kg/day or from 2 mg/kg/day to about 6 mg/kg/day. In an aspect, a disclosed optimal dose of pazopanib and/or sorafenib can be about 3 mg/kg/day. In an aspect, dasatinib can be orally administered to a subject at a dose of from about 0.3 mg/kg/day to about 2.0 mg/kg/day or from about 0.7 mg/kg/day to about 1.4 mg/kg/day. In an aspect, a disclosed optimal dose of dasatinib can be about 0.7 mg/kg/day. In an aspect, everolimus can be orally administered to a subject at a dose of from about 0.03 mg/kg/day to about 0.15 mg/kg/day or from about 0.03 mg/kg/day to about 0.10 mg/kg/day. In an aspect, a disclosed optimal dose of everolimus can be about 0.07 mg/kg/day. In an aspect, bevacizumab can be administered intravenously to a subject every 1 to 3 weeks at a dose of from about 2 mg/kg/day to about 15 mg/kg/day or can be administered to a patient every 1 to 3 weeks at a dose of from about 5 mg/kg/day to about 12 mg/kg/day. In an aspect, a disclosed optimal dose of bevacizumab can be administered intravenously to a subject every 2 weeks and with an optimal dose of about 10 mg/kg/day.

In an aspect, a disclosed molecular marker that can determine one or more suitable precision cancer treatments in one or more disclosed methods can be measured from a sample by high-density expression array, DNA microarray, polymerase chain reaction (PCR), reverse transcriptase PCR (RT-PCR), real-time quantitative reverse transcription PCR (qRT-PCR), serial analysis of gene expression (SAGE), spotted cDNA arrays, GeneChip, spotted oligo arrays, bead arrays, RNA Seq, tiling array, northern blotting, hybridization microarray, in situ hybridization, whole-exome sequencing, whole-genome sequencing, liquid biopsy, next-generation sequencing, or any combination thereof.

In an aspect, a disclosed molecular marker can determine one or more suitable precision cancer treatments for use in a disclosed method of preventing and/or decreasing metastases can determined from the nucleic acid sequence of the at least one of circulating DNA and/or RNA. In an aspect, a disclosed molecular marker can be assessed from circulating tumor DNA and/or RNA (ctDNA and/or ctRNA); circulating cell-free DNA and/or RNA (cfDNA, cfRNA); or any combination thereof ctDNA/ctRNA refers to tumor-derived fragmented DNA in the bloodstream that is not associated with cells. cfDNA/cfRNA refers to DNA that is freely circulating in the bloodstream, but is not necessarily of tumor origin. In an aspect, cfDNA/ctDNA can include any whole or fragmented genomic DNA, or mitochondrial DNA, and/or cfRNA/ctRNA can include mRNA, tRNA, microRNA, small interfering RNA, long non-coding RNA (1 ncRNA). In an aspect, cfDNA and/or ctDNA can be a fragmented DNA with a length of at least about 50 base pair (bp), about 100 bp, about 200 bp, about 500 bp, or about 1 kbp. In an aspect, cfRNA and/or ctRNA can be a full length or a fragment of mRNA (e.g., at least 70% of full-length, at least 50% of full length, at least 30% of full length, etc.). In an aspect, a disclosed molecular marker can be directed against any cancer-related gene disclosed herein.

In an aspect, a disclosed method of preventing and/or decreasing metastases can further comprise surgically resecting one or more tumors from the subject. In an aspect, a disclosed method of preventing and/or decreasing metastases can further comprise repeating one or more disclosed steps of a disclosed method.

For example, in an aspect, repeating one or more disclosed steps a disclosed method of preventing and/or decreasing metastases rise repeating the administering to the subject the precision cancer treatment, repeating the measuring of the subject's tumor response, repeating the obtaining of a biological sample from the subject, repeating the subjecting the biological sample to cfDNA analysis, repeating the administering of one or more additional therapeutic agents, or any combination thereof.

In an aspect, a disclosed molecular marker can be detected, quantified, and/or analyzed over time (at different time points) to determine the effectiveness of a disclosed precision cancer treatment (e.g., AS therapy) to the subject and/or to determine the response of a subject or subject's tumor to the precision cancer treatment (e.g., developing resistance, susceptibility, etc.). In an aspect, a disclosed method of preventing and/or decreasing metastases can comprise obtaining multiple measurements over time from the same subject and same sample may be quantified at a single time point or over time. In an aspect, a disclosed treatment regimen treatment (e.g., a disclosed precision cancer treatment comprising one or more antineoplastons) can be designed and/or determined based on the cancer status and/or the changes/types of one or more molecular markers. In an aspect, the likelihood of success of a disclosed precision cancer treatment can be determined based on the cancer status and the type/quantity of one or more molecular markers.

In an aspect, a disclosed molecular marker can be derived from a gene expressed in one or more cells of a tumor or in a immune cell and can indicate immune suppressive tumor microenvironment, the development of cancer sternness, the onset of metastasis, cancer status, or any combination thereof. In an aspect, a disclosed molecular marker can be the protein or peptide encoded by the gene from which the molecular marker is derived and can be targeted by an antagonist or any other type of binding molecule to inhibit the function of the peptide.

Thus, in an aspect, increased expression (e.g., above a predetermined threshold) of a disclosed molecular marker derived from a disclosed gene related to immune suppressive tumor microenvironment can implicate the presence of immune suppressive tumor microenvironment, and can also implicate that an antagonist to the peptide encoded by the gene related to immune suppressive tumor microenvironment can have a high likelihood of success to inhibit the progress of the cancer by inhibiting immune suppressive tumor microenvironment and further promoting immune cell activity against tumor cells in such microenvironment. In an aspect, once the molecular marker has been identified, any suitable antagonist to a target gene or protein product can be used. For example, in an aspect, a specific kinase can be targeted by a kinase inhibitor, or a specific signaling receptor can be targeted by synthetic ligand, or a specific checkpoint receptor targeted by synthetic antagonist or antibody, etc. In an aspect, a disclosed antagonists to a target molecule herein can be administered before, after, or in combination with AS therapy.

In an aspect, a subject can be a human patient. In an aspect a subject can be any age (e.g., geriatric, adult, young adult, teenager, tween, adolescent, child, toddler, baby, or infant), can be male or female, can be any nationality, can be of any ethnicity, and/or can be of any race. In an aspect, a subject can have a terminal cancer.

In an aspect, a disclosed subject has not received treatment prior to the administering of a disclosed precision cancer treatment. In an aspect, a disclosed subject has received treatment prior to the administering of a disclosed precision cancer treatment. In an aspect of a disclosed method of preventing and/or decreasing metastases, prior to the administering of a disclosed precision cancer treatment, the subject has received surgical treatment, antibody treatment, chemotherapy treatment, radiation treatment, immunotherapy treatment, or any combination thereof. In an aspect of a disclosed method of preventing and/or decreasing metastases, a subject in need thereof has been diagnosed as having cancer, or wherein the subject in need thereof is suspected of having a cancer.

In an aspect, a disclosed cancer can be a refractory cancer or refractory disease. In an aspect, "refractory" refers to cancer and/or tumor that does not respond to and/or becomes resistant to a treatment. In an aspect, a subject can have a relapsed disease. In an aspect, "relapsed" or "relapses" refers to a tumor that returns or progresses following a period of improvement (e.g., a partial or complete response) with treatment. In an aspect, a disclosed cancer can comprise a solid tumor. In an aspect, a disclosed cancer can comprise metastatic cancer. In an aspect, a disclosed cancer can comprise a terminal cancer.

In an aspect, a disclosed cancer can comprise adenocarcinoma (including of the appendix and cervix), adenoid cystic carcinoma, adult t-cell leukemia, anaplastic astrocytoma, anaplastic ependymoma, anaplastic oligodendroglioma, astrocytoma, basal cell carcinoma, B-cell cancers, benign and malignant lymphomas, biliary tract—cholangiocarcinoma, bowel, brain cancer (including anaplastic astrocytoma, anaplastic ependymoma, anaplastic oligodendroglioma, brainstem anaplastic astrocytoma, brainstem glioma, diffuse astrocytoma, DIPG h3k27 mutation, ganglioglioma, glioblastoma multiforme, medulloblastoma, pilocytic astrocytoma, brainstem glioma), breast cancer, breast carcinoma, Burkitt's lymphoma, bladder cancer and carcinoma, carcinoma of unknown primary, carcinosarcoma, cervical cancer, cholangiocarcinoma, chronic atypical myelogenous leukemia, chronic atypical myelogenous leukemia, colon cancer, colorectal carcinoma, diffuse astrocytoma, diffuse intrinsic pontine glioma (DIPG), endometrial cancer, endometrial carcinoma, ependymomas, esophageal cancer and carcinoma, esophagus, Ewing's sarcoma, ganglioglioma, ganglioneuromas, gastrointestinal stromal tumor (gist), gliobastomas, gliomas, head and neck cancer and carcinoma, hemangiosarcoma, hepatocellular carcinomas, renal cell carcinomas, Hodgkin's disease, Kaposi's sarcoma, kidney cancer and carcinoma, large b-cell lymphoma, leptomeningeal carcinomatosis, leukemias, liposarcoma, liver cancer, lung carcinoma (non-small cell and small cell carcinoma), medulloblastoma, melanoma, meningeal sarcomas, meningiomas, multiple myeloma, myelodysplastic syndrome, myeloproliferative diseases, myosarcomas, neuroblastomas, neuroendocrine carcinoma, neurofibromas, non-Hodgkin's lymphoma, oligodendrogliomas, osteosarcoma, ovarian cancer and carcinoma, pancreatic cancer and carcinoma, peripheral neuroepithelioma, peripheral t-cell lymphoma, Philadelphia chromosome positive all and positive CML, pilocytic astrocytoma, pineal cell tumors, pleomorphic sarcoma, pre-b lymphomas, primitive neuroectodermal tumor (PNET), prostate cancer and carcinoma, refractory anemia, salivary gland carcinoma, sarcoma, schwannomas, skin cancer and carcinoma, squamous-cell carcinoma, stomach cancer and carcinoma, synovial sarcoma, testicular cancer, thyroid cancer and carcinoma, T-lineage acute lymphoblastic leukemia (T-all), T-lineage lymphoblastic lymphoma (T-LL), urothelial cancer and urothelial high-grade carcinoma, uterine, cervix, vulvar, and/or endometrium carcinoma, Wilms' tumor or teratocarcinomas, or any combination thereof.

In an aspect, a disclosed cancer can comprise breast cancer, colorectal cancer, head and neck cancer, kidney cancer, lung cancer, ovarian cancer, pancreatic cancer, prostate cancer, brain cancer, adenoid cystic carcinoma, anaplastic astrocytoma, anaplastic ependymoma, anaplastic oligodendroglioma, brainstem glioma, diffuse astrocytoma, diffuse intrinsic pontine glioma (DIPG), ganglioglioma, medulloblastoma, pilocytic astrocytoma, cholangiocarcinoma, chronic atypical myelogenous leukemia, endometrial carcinoma, esophageal cancer, Ewing's sarcoma, gastrointestinal stromal tumor (GIST), leptomeningeal carcinomatosis, multiple myeloma, myelodysplastic syndrome, neuroendocrine carcinoma, Non-Hodgkin's lymphoma, pleomorphic sarcoma, primitive neuroectodermal tumor (PNET), refractory anemia, salivary gland carcinoma, skin cancer, stomach cancer, thyroid cancer, urothelial cancer, or any combination thereof.

In an aspect, a disclosed method of preventing and/or decreasing metastases can further comprise comprising monitoring the subject for adverse effects (such as, e.g., hepatic impairment, hematologic toxicity, neurologic toxicity, cutaneous toxicity, gastrointestinal toxicity, or any combination thereof). In an aspect, in the absence of adverse effects, a disclosed method of preventing and/or decreasing metastases can further comprise continuing to administering to the subject a disclosed precision cancer treatment. In an aspect, in the presence of adverse effects, a disclosed method of preventing and/or decreasing metastases can further comprise modifying one or more disclosed steps of a disclosed method. In an aspect, a disclosed method of preventing and/or decreasing metastases can further comprise treating the one or more adverse effects.

In an aspect, a disclosed method of preventing and/or decreasing metastases can comprise modifying a disclosed administering step. In an aspect, modifying a disclosed administering step can comprise changing the amount of the one or more antineoplastons or composition comprising one or more antineoplastons administered to the subject, changing the frequency that the one or more antineoplastons or composition comprising one or more antineoplastons are administered to the subject, changing the duration of administration of the one or more antineoplastons or composition comprising one or more antineoplastons, changing the route of administration of the one or more antineoplastons or composition comprising one or more antineoplastons administered to the subject, or any combination thereof.

In an aspect, a disclosed method of preventing and/or decreasing metastases can further comprise obtaining a tissue biopsy from the subject. In an aspect, a disclosed tissue biopsy can be subjected to next generation sequencing. In an aspect, a disclosed method of preventing and/or decreasing metastases can comprise subjecting the subject to one or more invasive or non-invasive diagnostic assessments. Diagnostic assessments are known to the art. In an aspect, a disclosed non-invasive diagnostic assessment can comprise x-rays, computerized tomography (CT) scans, magnetic resonance imaging (MRI) scans, ultrasounds, positron emission tomography (PET) scans, or any combination thereof. In an aspect, a disclosed invasive diagnostic assessment can comprise a tissue biopsy or exploratory surgery.

In an aspect, a disclosed subject can improve the life expectancy of the subject. In an aspect, the subject's life expectancy is compared to the life expectancy of a control. In an aspect, a control is a subject not receiving the precision cancer treatment. In an aspect, a control is a pooled number of subjects not receiving the precision cancer treatment. In an aspect, a control is one or more subjects having the same type of cancer and the same stage of cancer as the subject. In an aspect of a disclosed method of preventing and/or decreasing metastases et, the subject's cancer is treated.

In an aspect, a disclosed method of preventing and/or decreasing metastases can improve life expectancy compared to the cancer life expectancy of an untreated subject with the identical or near identical disease condition and the identical or near identical predicted outcome. As used herein, "life expectancy" is defined as the time at which 50 percent of subjects are alive and 50 percent have passed away. In an aspect, patient life expectancy can be indefinite following treatment with a disclosed method. In an aspect, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with the identical or near identical disease condition and the identical or near identical predicted outcome.

In an aspect, life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and the identical or near identical predicted outcome. In an aspect, life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with the identical or near identical disease condition and the identical or near identical predicted outcome.

In an aspect, a disclosed method of preventing and/or decreasing metastases can comprise protecting the subject from metastasis. In an aspect a disclosed method of preventing and/or decreasing metastases can comprise reducing the risk of developing metastasis. In an aspect of a disclosed method of preventing and/or decreasing metastases, treating the cancer can comprise increasing the subject's survivability, increasing the length of time before metastasis, reducing the likelihood of surgical intervention, reducing the need for administration of one or more additional therapeutic agents or regiments, reducing the size of one or more tumors in the subject, eliminating one or more tumors in the subject, reducing or eliminating the prevalence of one or more genomic aberrations, restoring the normal metabolism of one or more organ systems in the subject, restoring one or more aspect of cellular homeostasis and/or cellular functionality, and/or metabolic dysregulation; or any combination thereof.

In an aspect of a disclosed method of preventing and/or decreasing metastases, restoring one or more aspects of cellular homeostasis and/or cellular functionality can comprise one or more of the following: (i) correcting cell starvation in one or more cell types (such as, for example, liver cells and muscle cells); (ii) normalizing aspects of the autophagy pathway (such as, for example, correcting, preventing, reducing, and/or ameliorating autophagy); (iii) improving, enhancing, restoring, and/or preserving mitochondrial functionality and/or structural integrity; (iv) improving, enhancing, restoring, and/or preserving organelle functionality and/or structural integrity; (v) preventing, slowing, and/or eliminating hypoglycemia, ketosis, and/or other liver abnormalities; (vi) correcting liver enzyme dysregulation; (vii) reversing, inhibiting, preventing, stabilizing, and/or slowing the rate of progression of tumor metastasis; (viii) reversing, inhibiting, preventing, stabilizing, and/or slowing the rate of progression of tumor growth and/or cancer spread, or (ix) any combination thereof. In an aspect, restoring one or more aspects of cellular homeostasis can comprise improving, enhancing, restoring, and/or preserving one or more aspects of cellular structural and/or functional integrity in, for example, an organ or system that has been affected by cancer.

For example, in an aspect, tumor growth can be impaired at least about 5% or greater to at least about 100%, at least about 10% or greater to at least about 95% or greater, at least about 20% or greater to at least about 80% or greater, at least about 40% or greater to at least about 60% or greater compared to an untreated subject having the identical or near identical disease condition and the identical or near identical predicted outcome. In an aspect, one or more tumors in a subject treated using a disclosed method of preventing and/or decreasing metastases can grow at least 5% less (or more as described above) when compared to an untreated subject With the identical or near identical disease condition and identical or near identical predicted outcome.

In an aspect, tumor growth can be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with the identical or near identical disease condition and identical or near identical predicted outcome.

In an aspect, tumor growth can be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with the identical or near identical disease condition and identical or near identical predicted outcome.

In an aspect, treatment of tumors according to the methods disclosed herein (e.g., AS therapy) can result in a shrinking of a tumor in comparison to the starting size of the tumor. In an aspect, tumor shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In an aspect, a disclosed subject can present with one or more cancerous solid tumors, metastatic nodes, or any combination thereof. In any aspect, a subject herein can have a cancerous tumor cell source that can be less than about 0.2 $cm^3$ to at least about 20 $cm^3$ or greater, at least about 2 $cm^3$ to at least about 18 $cm^3$ or greater, at least about 3 $cm^3$ to at least about 15 $cm^3$ or greater, at least about 4 $cm^3$ to at least about 12 $cm^3$ or greater, at least about 5 $cm^3$ to at least about 10 $cm^3$ or greater, or at least about 6 $cm^3$ to at least about 8 $cm^3$ or greater.

In an aspect, a disclosed method of preventing and/or decreasing metastases can comprise a pan-tumor approach such as, for example, administering a disclosed ANP therapy.

F. Kits

Disclosed herein is a kit comprising one or more disclosed antineoplastons, disclosed pharmaceutical formulations, or any combination thereof. In an aspect, a kit can comprise a disclosed pharmaceutical formulation comprising one or more antineoplastons, one or more additional and/or therapeutic agents, or any combination thereof. “Agents” and “Therapeutic Agents” are known to the art and are described supra.

In an aspect, the one or more agents can treat, prevent, inhibit, and/or ameliorate one or more comorbidities in a subject. In an aspect, one or more active agents can treat, inhibit, prevent, and/or ameliorate cellular and/or metabolic complications related to cancer or cancer cells or cancerous cells.

In an aspect, a disclosed kit can comprise at least two components constituting the kit. Together, the components constitute a functional unit for a given purpose (such as, for example, treating a subject diagnosed with or suspected of having a disease or disorder such as cancer). Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation. In an aspect, a kit for use in a disclosed method can comprise one or more containers holding one or more disclosed antineoplastons, disclosed pharmaceutical formulations, one or more therapeutic and/or additional agents, or any combination thereof, and a label or package insert with instructions for use. In an aspect, suitable containers include, for example, bottles, vials, syringes, blister pack, etc. The containers can be formed from a variety of materials such as glass or plastic. The container can hold one or more disclosed antineoplastons, disclosed pharmaceutical formulations, or any combination thereof, and can have a sterile access port (for example the container may be an intravenous solution bag or a vial having a stopper pierceable by a hypodermic injection needle). The label or package insert can indicate one or more disclosed antineoplastons, disclosed pharmaceutical formulations, or any combination thereof can be used for treating, preventing, inhibiting, and/or ameliorating a disease or disorder or complications and/or symptoms associated with a disease or disorder such as cancer or metastatic cancer. A kit can comprise additional components necessary for administration such as, for example, other buffers, diluents, filters, needles, and syringes.

In an aspect, a disclosed kit can be used to treat and/or prevent cancer, prolong the survival, preventing and/or decreasing metastases, or any combination thereof.

VI. EXAMPLES

Example 1

Patients diagnosed with 34 types of terminal cancer were treated with Antineoplaston AS2-1 (AS) therapy to reduce and/or abolish tumors and other signs of cancer and reduce and/or abolish expression of cancer-causing genes. In brief, patients admitted for treatment herein were diagnosed with terminal, Stage IV, cancers of varying types with multiple metastases and had failed standard-of-care regimens, except for a small number of patients who were treatment naive, but were not candidates for standard treatment because of very advanced disease and less than 6 months life expectancy. The estimated survival for these patients was from less than one to less than 6 months. The patients had radiological evidence of advanced metastatic cancer performed within 4 weeks from treatment start and genomic analysis, usually ordered at admission, including Guardant 360 blood test and/or Foundation One and/or Tempus blood or tissue test and/or SEMA4 tissue test. They had histological conformation of diagnosis performed at medical institutions not associated with Burzynski Clinic (BC).

AS and A10 (ANP) and targeted, immunological, hormonal and/or chemotherapeutic agents were anti-cancer treatments administered to patients. In some cases, palliative radiation therapy (RT) and/or surgery were used in addition to anti-cancer drugs. ANPs were delivered via an ambulatory infusion pump and subclavian catheter every 4 hours. The dose of AS was gradually escalated from 0.1 g/kg/day to a maximum of 0.4 g/kg/day after 4 days and a flow rate from 50 mL/hr to 250 mL/hr. The dose of A10 was increased to the maximum of 12 g/kg/day. Most of the patients were continuing the treatment on the optimally tolerated dosage of AS of 0.2 to 0.4 g/kg/day and A10 of 5 g/kg/day and the flow rate of 200-250 mL/hr.

Medications that were considered necessary for the patient's welfare, and did not interfere with the treatment, were prescribed at the discretion of the treating physician. Patients received full supportive care and dietary instructions. The treatment was given outpatient in cooperation with the patient's local physicians.

At baseline, history taking, physical examination, necessary laboratory, genomic and radiological evaluations were performed. Two largest perpendicular diameters of the radiologically significant lesions were measured including MRI contrast-enhanced lesions in the brain and spinal cord. The follow-up scans, usually at 4 to 8-week intervals, were used to determine the response. Complete response (CR) required the disappearance of all enhancing lesions and stable or improved non-enhancing lesions, and disappearance of the lesions outside the target tissue by CT, or metabolically active lesions by PET. Partial response (PR) required a 50% or higher decrease of the sum of the products of the two largest perpendicular diameters of the lesions, and progressive disease (PD) was more than a 25% increase. Stable disease (SD) was the status between PR and PD, and minor response (MR) was more than a 25% decrease. Mixed response was determined when there was a CR or PR of some lesions and PD of the other lesions.

In clinical trials, the CR and PR should be sustained for at least 4 weeks, and SD for 7 weeks. In private practice some patients did not agree to have a follow-up radiological evaluation because of exposure to radiation or the additional cost. Such responses were marked as CR* or PR*. Some patients with metastases in many organs accomplished CR or PR in one organ, for instance the liver, but not in the other sites. They were marked accordingly, for instance, CR (HEP) and SD (OSS), meaning CR in the liver and SD in the bones.

Molecular response was determined by repeated Guardant 360 tests. In brief, Guardant 360 tests generally involve cell-free circulating tumor DNA (ctDNA) panel testing from a blood (e.g., plasma) sample as an alternative to tissue biopsy in the diagnosis of cancer and for clinical response to targeted agents of cancer treatment. Herein, blood samples were collected from patients and provided to Guardant for panel testing wherein a "panel" was defined as five or more ctDNA genes or gene mutation variants tested on the same day on the same member by the same rendering provider (i.e., Guardant).

A treatment plan was formulated based on the patient's history and evaluation including genomic data. All patients were treated with AS to cover 158 abnormal genes plus additional targeted drugs to act on genes not affected by AS. The genes affected by AS and A10 are listed in Table 1. In some cases, a mild form of chemotherapy was used at the beginning to accelerate the response and in some patients, A10 was added.

TABLE 1

Genes affected by AS and A10 in Example 1.

| | | | | | | |
|---|---|---|---|---|---|---|
| ACO2 | CCNE2 | CHK-1 | IL1A | ORC1 | RAS | TBC1D8 |
| AKT | CDC2 | CLDND1 | IL1B | ORCIL | RBL1 | TFDP1 |
| ASK | CDC42 | CSF1 | IL6 | ORC6L | SDHC | TP53 |
| ASPM | CDC6 | CSF3 | IL8 | ORCL | SKP2 | TRIB3 |
| ATF3 | CDC7 | CXCL2 | IL15 | PCNA | SMCIA | UNC5B |
| BAD | CDC20 | DLD | JUN | PDHA1 | SMC1L1 | WEE1 |
| BAX | CDC25A | DLST | MAD2L1 | PIK3CA | STAT5 | OGDH |
| BCL2 | CDC25B | DUSPI | MAPK | PKMYT1 | SUCLG1 | IL1 |
| BDNF | CDC25C | DUSP6 | MCM2 | PLK1 | SUCLG2 | CFSI |
| BLM | CDCA8 | E2F1 | MCM3 | MCM4 | ERK | GADD45A |
| BRAF | CDK2 | BUBI | CDK3 | MCM5 | FH | MDHI |
| HIF1A | PTTG3 | PTPRR | PPM1A | CDKN2B | MEF26 | HDAC1 |
| IDH2 | NGF | PTTG1 | PTEN | CDKN2C | NF1 | HDAC5 |
| 1DH3A | CCNE1 | PTTG2 | PTPN11 | NFKB | CDKN1B | MCM7 |
| CCL2 | CDK6 | CASP5 | CDK4 | MCM6 | CDKN2A | IDH3B |
| CCNA2 | CDKN1A | CCNB1 | CCND2 | CCND3 | CCNB2 | |

The goal of the treatment was to accomplish a CR and complete disappearance of abnormal genes from the patient's blood. At this point, the patient was advised to continue maintenance treatment for up to 8 months and monitor CR by radiological evaluations, preferably every 8 weeks, and blood genomic tests every 3 months. In this representative example, only evaluable patients who had the recommended radiology and genomic follow-up evaluations are included.

The results of this study are described herein in three parts: Part 1 describes the results in common cancers; Part 2 describes the results in uncommon cancers; and Part 3 summarizes the results in all evaluable patients.

The following abbreviations are used herein: am (amplification); AS (Antineoplaston AS2-1); BC (Burzynski Clinic, site of the study reported herein); BRA (brain metastases); CH (chemotherapy); CR (complete response); CR* (complete response not confirmed by the follow-up scan); DAMA (discontinued against medical advice); Dd (patient died from their malignancy while on treatment); De (patient died from something other than their malignancy while on treatment); Dx (patient died while on treatment, cause not documented); DEPB (dasatinib, everolimus, pazopanib, bevacizumab); DESB (dasatinib, everolimus, sorafenib, bevacizumab); ER+ (estrogen positive); GBM (glioblastoma, glioblastoma multiforme); H (hormonal treatment); $HER\text{-}2^-$ ($HER\text{-}2^-$ negative); $HER\text{-}2^+$ (HER-2 positive); IM (improvement); LMN (leptomeningeal metastases); LYM (lymph node metastases); MR (minor response); ND (non-detectable); OR (objective response); OS (overall survival from treatment start); OSS (bone metastases); PE (physical examination); PR (partial response); $PR^+$ (progesterone positive); PUL (pulmonary metastases); RT (radiation therapy); SKI (skin metastases); SU (surgery, the number before indicates how many); TN BC (triple negative breast cancer); and TT (targeted therapy, in parenthesis is target of TT).

Part I—Common Cancers.

Breast Cancer. There were 19 patients diagnosed with advanced terminal breast cancer who qualified for inclusion in this review as described above. All patients were females; 11 of them in the age range of 51-65 years and 8 in the range of 38-48 years. The patients were segregated into three groups. There were 11 of them in the HER-2 negative group, 2 in the triple negative group, 6 in the HER-2 positive group and 1 case was a heterogenous cell population with some cancer cells being HER-2 negative and some being HER-2 positive. There were 10 patients who had a long history of disease, 4 to 16 years, and 9 patients who had 1 to 3 years. All of them failed multiple treatment regimens including surgery, radiation, chemotherapy and hormonal and/or targeted therapy except for one patient who was treatment naive because she was close to death and not a candidate for standard of care therapy. The patients had widely spread metastatic disease including involvement of brain, meninges, bones, liver, lungs, lymph nodes, pleura, peritoneum, ovaries, skin, thyroid, and opposite breast. The estimated survival of eleven patients was from 1 to 3 months and for eight patients less than 6 months.

Five patients received prior treatment with surgery, radiation therapy, chemotherapy, and hormonal therapy, five patients with surgery, radiation, and chemotherapy and three with surgery, radiation and hormonal therapy and one with radiation, chemotherapy, hormonal therapy and targeted therapy. Eight patients were treated with targeted therapy and one with surgery and targeted therapy. Three patients underwent multiple surgeries and another two had multiple types of radiation therapy. Five patients were given multiple chemotherapy regimens and three patients multiple targeted therapy regimens. The details are provided in Table 2.

TABLE 2

Breast Cancer Patient Demographics.

| Characteristics | N = 19 |
|---|---|
| Age (Years) | N |
| Range 51-65 | 11 |
| Range 38-48 | 8 |
| HER-2 Status | |
| $HER\text{-}2^+$ | 6 |
| $HER\text{-}2^-$ | 10 |
| Triple Negative | 2 |
| Heterogenous | 1 |
| Duration of the Disease (Years) | |
| 4-16 | 10 |
| 1-3 | 9 |
| Metastatic Sites | |
| Brain | 7 |
| Meninges | 2 |
| Bones | 15 |
| Liver | 7 |
| Lungs | 8 |
| Lymph nodes | 10 |
| Pleura | 3 |
| Peritoneum | 2 |
| Ovaries | 1 |

TABLE 2-continued

Breast Cancer Patient Demographics.

| Characteristics | N = 19 |
|---|---|
| Skin | 5 |
| Opposite Breast | 1 |
| Thyroid | 1 |
| Estimated Survival (Months) | |
| 1-3 | 11 |
| Less than 6 | 8 |
| Prior Treatment | |
| SU, RT, CH, H, TT | 1 |
| SU, RT, CH, H | 5 |
| SU, RT, CH | 5 |
| SU, RT, H | 1 |
| RT, CH, H | 1 |
| SU, H, TT | 2 |
| SU | 1 |
| SU Embolization | 1 |
| SU, TT | 1 |
| T1 | 8 |

SU (surgery);
RT (radiation therapy);
CH (chemotherapy);
H (hormonal treatment);
TT (targeted therapy);
HER-$2^-$ (HER-2 negative);
HER-$2^+$ (HER-2 positive)

Patients were treated as described above. The details and results of treatment are provided in Tables 3, 4, 5, and 6. Five patients in the HER-2 negative group obtained CR. The remaining five patients in this group accomplished PR and one patient, MR. There was a possible contribution of radiation therapy of the brain to the response of two patients (Table 3). In four patients, the genomic abnormalities in blood, identified at baseline, were no longer found after the treatment. Two patients in the triple negative group, including one case with brain and leptomeningeal involvement, obtained CR. In one patient, multiple mutated genes in blood were no longer seen in the repeated Guardant360 test (Table 4). Five patients in the HER-$2^+$ group accomplished CR but in four of them, there was CR confirmed radiologically in one organ and a different response in other organs. One patient accomplished PR. Three patients failed to respond to prior targeted therapy with HER-2 inhibitors but responded to such targeted therapy in combination with AS (Table 5). All of the genomic abnormalities in the blood in the baseline Guardant 360 tests were no longer present after the treatment, except for gene CCNE1, which decreased by 85% in one case (Table 5).

TABLE 3

Evaluable Patients Treated with Antineoplaston AS-1 in Combination with Other Drugs
Breast Cancer, HER-2 Negative with Multiple Metastases, Stage IV.

| | | | | | Response | | | Survival from | |
|---|---|---|---|---|---|---|---|---|---|
| Patient | Diagnosis | Duration of Cancer (Years) | Prior Treatment | Treatment at BC (study) | RT and by PE | Genes Affected by AS | Estimated Survival (Months) | Treatment Start (Months) | Comments |
| 4 BE | $ER^+$, $PR^+$, $HER\text{-}2^-$ OSS | 3 | SU, RT, CH' 2H, TT (CDK4/6) | AS, CH, TT (VEGF, mTOR, PARP), H, RT (Spot = RT) | CR | PIK3CAam, PIK3CA, ND | <6 | >33 | TT at BC - bevacizumab, rucaparib, olaparib, rapamycin, everolimus, H at BC - exemestane, CH at BC - capecitabine, RT contributed to CR of one lesion among multiple lesions. |
| 5BE | $ER^+$, $PR^+$, $HER\text{-}2^-$ LYM, BRA, OSS Blood genomics Revealed HER-2 amplification and mutation | 5 | SU, RT, CH | AS, H, 2RT, TT (HER-2) | PR-BRA' MR-LYM, OSS | BRACA1, BRACA2, PIK3CA, APC, EGFR, RAF1, ARAF, MYCam, ND | <3 | >18 | H at BC - exemestane, goserelin. TT at BC - trastuzumab, pertuzumab, adotrastuzumab emtansine. Mixed tumor population. HER-2+ and - and numerous genomic abnormalities. RT contriibuted to PR-BRA. DAMA |
| 8BE | $ER^+$, $PR^+$, $HER\text{-}2^-$ OSS, PUL, SKI | 5 | SU, H, RT | AS, H, TT (CDK4/6) TT (BRAF) | CR | CTN NB1, GATA3 | <6 | >9 continues | H at BC - fulvestrant, TT at BC - abemaciclib, sorafenib. No genomic abnormalities at baseline by blood genomic analysis. |
| 9BE | $ER^+$, $PR^+$, $HER\text{-}2^-$ LYM, PUL, OSS, SKI | 3 | None | AS, H, TT (CDK4/6) | PR (PE) IM (LYM, PUL, OSS) | FGFR2, ND | <3 | >8 continues | H at BC - letrozole, TT at BC - palbociclib, Very extensive skin and chest wall involvement. |
| 10BE | $ER^+$, $PR^+$, $HER\text{-}2^-$ LYM, SKI | 1 | SU | AS, CH | CR | TP53 84% decrease, EDFRam, ND | <6 | <6 | CH at BC - capecitabine. Developed resistance after premature discontinuation and restarted the treatment. DAMA |
| 14BE | $ER^+$, $PR^+$, $HER\text{-}2^-$ OSS | 6 | SU, RT, CH | AS, H, TT | CR* | PIK3CA H1047L TP53 R282W | <6 | >4 | H at BC - letrozole. TT at BC - abemaciclib, DAMA |

TABLE 3-continued

Evaluable Patients Treated with Antineoplaston AS-1 in Combination with Other Drugs
Breast Cancer, HER-2 Negative with Multiple Metastases, Stage IV.

| Patient | Diagnosis | Duration of Cancer (Years) | Prior Treatment | Treatment at BC (study) | Response: RT and by PE | Response: Genes Affected by AS | Estimated Survival (Months) | Survival from Treatment Start (Months) | Comments |
|---|---|---|---|---|---|---|---|---|---|
| 15BE | $ER^+$, $PR^+$, HER-$2^-$ HEP, PUL, OSS, BRA | 3 | SU, RT, CH, 2H | AS, 2H, 2TT | PR - BRA, SD - HEP, PUL, OSS | PIK3CA E542K and 39K, AKT1 E17K, FGFR1 amplification, TP53 E287* and E285K | <3 | <7 | H at BC - letrozole, fulvestrant. TT at BC - palbociclib, abemaciclib DAMA |
| 16BE | $ER^+$, $PR^+$, HER-$2^-$, HEP, PUL, PLE, OSS, BRA | 2 | SU, RT, CH | AS, H | PR* - BRA PD - HEP | PIK3CA E542K and E453K, CDKN2A D74N, GATA3 D336fs | >2 | 6 | Hat BC - fulvestrant, Lupron DAMA |
| 17BE | $ER^+$, $PR^+$, HER-$2^-$ BRACA1, germline mutation, HEP, OSS, RRA | 15 | SU, H, 2TT | AS, H, TT | PR | PIK3CA amplification, RB1 Q217* | <3 | >6 continues | H at BA - fulvestrant TT at BC - talazoparib |
| 18BE | $ER^+$, $PR^+$, LYM, HEP, PUL, OSS, PFR; thyroid, opposite breast | 11 | SU, emoblization | AS, SU, CH | MR - HEP, OSS, PER, Thyroid | H, TT continues CCND1 amplification, GATA3 c.1213-1214del and p.S405fs | <3 | >9 | CH at BC - capecitabine H at BC - letrozole, goserelin TT at BC - abemaciclib |
| 19BE | $ER^+$, $PR^+$, HER-$2^-$ OSS | 16 | SU, TT | AS, A10 (1 month), H, TT | CR* | CCND1 Q264K | <6 | >12 | H at BC - letrozole, fulvestrant TT at BC - abemaciclib, palbociclib |

TABLE 4

Evaluable Patients Treated with Antineoplaston AS2-1 in Combination with Other Drugs Breast Cancer, Triple Negative with Multiple Metastases, Stage IV.

| Patient | Diagnosis | Duration of Cancer (Years) | Prior Treatment | Treatment at BC (study) | Response: RT and by PE | Response: Genes Affected By AS | Estimated Survival (Months) | Survival from Treatment Start (Months) | Comments |
|---|---|---|---|---|---|---|---|---|---|
| 1BE | TNBC BRA, LMN | 1BE6 CR* | SU, 2RT, CH, H | AS, CH, TT (VEGF) | CR* | PTEN, TP53, NF1, MAP3K1 | <1 | 15 | CH at BC - capecitabine. TT at BC - bevacizumab. DAMA |
| 12BE | TNBC LYM, OSS, SKI | 4 | SU CH, H | AS TT CH | CR* | TP53G187D, MAP2K1 K57E, PTEN R130*, METT895M, PTEN Y27C, ND | <6 | > 10 continues | TT at BC - atezolizumab. CH at BC - nab-paclitaxel. |

TABLE 5

Evaluable Patients Treated with Antineoplaston AS2-1 in Combination with Other Drugs Breast Cancer, HER-$2^+$ with Multiple Metastases, Stage IV.

| Patient | Diiagnosis | Duration of Cancer (Years) | Prior Treatment | Treatment at BC (study) | Response RT and by PE | Response Genes Affected By AS | Estimated Survival (Months) | Survival from Treatment Start (Months) | Comments |
|---|---|---|---|---|---|---|---|---|---|
| 2BE | $ER^+$, $PR^+$, HER-$2^+$ HEP | 15 | 15 RT, 3SU, H, 2TT (HER-2) | AS, CH, TT (HER-2) | CR | PIK3CA and FGFR ND | <3 | >30 | CH at BC - capecitabine, TT at BC - trastuzumab, pertuzumab. CR was accomplished on the same TT (HER-2) and AS, which was not effective before. DAMA |
| 3BE | $ER^-$, $PR^-$, HER-$2^+$ LYM, SKI | 2 | SU, 2CH, RT, TT (HER-2) | AS, PB, CH, 4TT (HER-2, PIK3CA, HDAC, RET) | CR* PR (SKI, PE) | TP53 ND | <6 | 29 | CH at BC - capecitabine, vinorelbine. TT at BC - lapatinib, neratinib, trastuzumab, ado-trastuzumab emtansine, sorafenib, vorinostat, alpelisisb. The patient had numerous genomic abnormalities and poor toleracne of drugs. She used sequentialy different TTs. She responded to TT (HER-2) which did not produce response before. CH at BC was capecitabine. |
| 6BE | $ER^+$, $PR^-$, BRA, HEP, PUL, OSS, epidural | | ISD 2RT, CH, H, AS, CH, TT (HER-2) | H, 4TT (HER-2) | PR (HEP) (BRA, PUL, OSS) | EGFRam ND, PIK3CAam ND, CCNE1 85% decrease | <2 | >10 | CH at BC - capecitabine, vinorelbine. H at BC - anastrozole. TT at BC - trastuzumab, pertuzumab. |
| 7BE | $ER^-$, $PR^-$, HER-$2^+$ LYM, BRA, PUL, PLE, OSS, PER, ovaries | 2 | RT, 3CH, TT (HER-2) | AS, 2H, TT (HER-2) | PR (BRA, LYM, PUL) CR* (HEP) | CCND1am, FGFR1am, PIK3CAam, PTEN, 3PIK3CA (mutation), ARID1A, FDFR1 (mutation) PDGFR ND | <2 | >7 | H at BC - letrozole, Lupron, fulvestrant. TT at BC - ado-trastuzumab emtansine. Very aggressive cancer with numerous genomic abnormailites which were gone during the treatment. RT contributed to response in BRA. DAMA |

TABLE 5-continued

Evaluable Patients Treated with Antineoplaston AS2-1 in Combination with Other Drugs Breast Cancer, $HER\text{-}2^+$ with Multiple Metastases, Stage IV.

| Patient | Diiagnosis | Duration of Cancer (Years) | Prior Treatment | Treatment at BC (study) | Response RT and by PE | Response Genes Affected By AS | Estimated Survival (Months) | Survival from Treatment Start (Months) | Comments |
|---|---|---|---|---|---|---|---|---|---|
| 11BE | $ER^+$, $PR^-$, $HER\text{-}2^+$ LYM OSS, SKI | 6 | SU, RT, 3CH, 3TT | AS, RT, 2CH, 6TT | CR - PUL SD - OSS | MYCS244S ND | <6 | 47 | CH at BC - docetaxel, carboplatin, vinorelbine. TT at BC - everolimus, dasatinib, pazopanib, ado-trastuzumab, pertuzumab, bevacizumab. RT at BC DAMA |
| 13BE | $ER^+$, $PR^+$, $HER\text{-}2^+$ LYM, PUL, PLE, HET, OSS, BRA | 2 | SU, CH, TT | AS, CH, H, 6TT | CR - LYM MR - PLE MR - Some HEP SD - OSS, PUL PD- BRA | CCND1, EGFR, MYC and PIK3CA amplifications - ND GATA3 P409FS and EGFR V5241 - ND | <3 | 5 | CH at BC - capecitabine H at BC - fulvestrant TT at BC - trastuzumab TT at BC - trastuzumab, pertuzumab, ado-trastuzumab, fam-deruxtecannxki, neratinib, vorinostat |

TABLE 6

Treatment of Breast Cancer with Antineoplaston AS2-1 and Targeted Drugs in Comparison with AS2-1 Alone and Prior Targeted Therapy.

| | Treatment Type (Number of Patients) | | | | | |
|---|---|---|---|---|---|---|
| Cancer Type | AS2-1+ Additional Drugs | Response | AS2-1+A10 Protocol BR-12 | Response | Prior TT | Response |
| HER-2 − | 11 | 5CR<br>5PR<br>1MR | | | | |
| Triple Negative | 2 | 2CR | | | | |
| HER-2 + | 6 | 5CR<br>1PR | | | 4PD | |
| All Patients | 19 | 12CR<br>6PR<br>1MR | 11 | 4SD<br>7PD | | |

Table 6 summarizes the responses in comparison to responses in the Phase 2 trial of AS and A10 in breast cancer and prior targeted therapy. As shown in Table 6, there was a very high objective response rate with 12 CRs, 6 PRs and 1 MRs and no PDs. There were no objective responses when AS and A10 were used in clinical trial and four cases of PD on prior targeted therapy. The overall survival at 2 years was 78.9% and at 3 years was 42.1%.

There was an additional group of 14 patients treated under the Right to Try law who were not evaluable for this report. Four of them died from cancer and can be classified as PD, but there were two cases of PR and one case of MR who are alive. The addition of these seven cases will increase the patient number to 26. In this expanded group there are the following responses: CR (12), 46.1%; PR (8), 30.7%; MR (2), 7.6%; PD (4), 15.3%; and objective response (OR) 84.7%.

Table 7 provides the genes and the site mutations thereof affected by antineoplaston AS2-1 based on clinical results in breast cancer.

TABLE 7

Genes Affected by Antineoplaston AS2-1 Based on Clinical Results in Breast Cancer.

| Gene | Mutation or Amplification |
|---|---|
| AKT1 | E17K |
| APC | G29G, K445K |
| AR1DIA | S1798L |
| ARAF | Y495Y |
| BRACA1 | H662Q |
| BRACA2 | D237N |
| CCND1 | amplification |
| CCNE1 | P268P |
| CDK4 | amplifications |
| CDK6 | amplifications |
| CDKN2A | D74N |
| CTNNB1 | S45-subclonal |
| EGFR | V524I - Amplification |
| FGFR | Amplificaiton - T320T, S726F, H791H, P47P, FGFRI S726F - |
| FGFR1 | |
| GATA 3 | P433fs43, P409fs, PS405fs, D336fs, c.1213_1214del |
| MAP2K1 | K57E |
| MAP2K4 | Loss exon 2 |
| MAP3K1 | 5398 |
| MET | T895M |
| MYC | Amplification - S244S |
| NF1 | Splice cite 480-11_4801delll |

TABLE 7-continued

Genes Affected by Antineoplaston AS2-1 Based on Clinical Results in Breast Cancer.

| Gene | Mutation or Amplification |
|---|---|
| P1K3CA | Mutation - Q546H<br>Amplification - E542K, E545K, E726K, E39K, E453K, R4-P18del, H1047L |
| PDGFRA | V299G |
| PTEN | Loss exons 4-7, D252Y, R130*, Y27C |
| RAF1 | P63P |
| RB1 | Q217 |
| TP53 | V73fs, R175G, R196, C176F, G187D, R282W, E287, E285K |

Colorectal Cancer. A total of 8 terminal patients were treated. There were 4 females and 4 males in this group with ages from 50 to 78 years. One patient was diagnosed with adenocarcinoma of the rectum and the remaining patients with adenocarcinoma of the colon. Four patients had 3 to 7-year histories of the disease and the remaining three, from less than a year to 2 years. The patients had widely spread metastatic disease: four of them had liver, lungs and lymph node metastases and four peritoneal metastases. The estimated survival was less than 4 months for one patient and less than 6 months for five patients. One patient received prior treatment with surgery, radiation, chemotherapy and targeted therapy; three patients had surgery, chemotherapy and targeted therapy; three additional patients has surgery only and one did not have prior treatment (Table 8).

TABLE 8

Colorectal Cancer Patient Demographics.

| Characteristics | N = 8 |
|---|---|
| Age (Years) | N |
| Range 50-78 | 8 |
| Duration of the Disease (Years) | |
| 3-7 | 4 |
| 0.5-2 | 4 |
| Metastatic Sites | |
| Bones | 1 |
| Liver | 4 |
| Lungs | 4 |
| Lymph nodes | 4 |
| Pleura | 1 |
| Peritoneum | 3 |
| Spleen | 1 |
| Brain | 1 |
| Pericardium | 1 |

TABLE 8-continued

| Colorectal Cancer Patient Demographics. | |
|---|---|
| Characteristics | N = 8 |
| Adrenal | 1 |
| Estimated Survival (Months) | |
| Less than 4 | 1 |
| Less than 6 | 7 |
| Prior Treatment | |
| SU RT CH Tr | 1 |
| SU CH TT | 3 |
| SU | 3 |
| None | 1 |

Patients were treated as described above. The details and results of treatment are provided in Tables 9, 10 and 11. Four patients accomplished CR, two MR and one SD. Both colonic and rectal cancer patients responded objectively. Table 10 summarizes the responses and compares them to responses in the Phase 2 trial of AS and A10 in colon cancer and prior targeted therapy. As shown in Table 10, there was very high response rate in current treatment group with 4 CR, 1 MR and 1 SD versus no objective responses in clinical trials and to prior targeted therapy.

TABLE 9

Evaluable Patients Treated with Antineoplaston AS2-1 in Combination with Other Drugs; Colorectal Cancer with Multiple Metastases, Stage IV.

| | | | | | Response | | | Survival from | |
|---|---|---|---|---|---|---|---|---|---|
| Patient | Diagnosis | Duration of Cancer (Years) | Prior Treatment | Treatment at BC (study) | RT and by PE | Genes Affected By AS | Estimated Survival (Months) | Treatment Start (Months) | Comments |
| 1 CL | Colon LYM, HEP, PER | 0.5 | SU | AS, CH, TT | CR | BRAF V600E | <4 | >36 | CH at BC - FOLFOX, XELOX TT at BC - pembrolizumab |
| 2 CL | Colon LYM, HEP, PUL | 1 | SU | AS, CH, TT | CR | EGFR D321D | <6 | >12 | CH at BC - FOLFOX, XELOX TT at BC - bevacizumab, cetuximab, encorafenib, binimetinib |
| 3 CL | Colon PUL, PLE | 7 | 3SU CH RT TT | AS CH TT RT | CR | TP53, R273H, PTEN R55fs, APC E888fs, APC R230C | <6 | >24 | CH at BC - FOLFIRI TT at BC - bevacizumab, atezolizumab, cobimetinib, nivolumab, regorafenib RT at BC DAMA |
| 4 CL | Colon LYM, PER | 3 | SU, 3CH | AS, CH, TT | CR* | TP53 S241F | <6 | >12 | CH at BC - capecitabine TT at BC - panitumumab DAMA |
| 5 CL | Rectum LYM, HEP, PUL | 2 | None | AS, CH, TT | MR - rectal tumor SD - metastatic tumors | KRAS G13D, TP53 R282W, SMAD4 D537V, PIK3CA E542K, PIK3CA 115431, ARID1A Q802fs, AR Splice Site SNV | <6 | >6 | CH at BC - XELOX TT at BC - bevacizumab DAMA |
| 6 CL | Colon PUL, HEP, OSS, PER, Spleen | 7 | SU, 2CH, TT | AS, A10, CH, TT | SD | TP53 CV76Y | <6 | >12 | CH at BC - FOLFIRI, FOLFOX TT at BC - regorafenib |
| 7 CL | Colon BRA, PUL, ADR | 3 | 2SU, 4CH, 2TT, RT | AS, TT, CH | MR | | <6 | >6 | CH at BC - capecitabine TT at BC - bevacizumab |
| 8 CL | Cecum PER, Pericardium | 1 | SU | AS, 2TT, CH | MR | | <6 | >17 | CH at BC - capecitabine TT at BC - nivolumab, regorafenib |

TABLE 10

| Treatment of Colorectal Cancer with Antineoplaston AS2-1 and Targeted Drugs in ComDarison with AS2-1 Alone and Prior Targeted Therapy. Treatment Type (Number of Patients) | | | | | |
|---|---|---|---|---|---|
| AS2-1+ | Response | AS2-1 + A10 Protocol CO-02 | Response | Prior Pharmacological Treatment | Response |
| 8 | 4 CR<br>3MR<br>1 SD | 9 | 2 SD<br>7 PD | 2 | 2 PD |

The patients had marked improvement and a decrease in the concentration of mutated genomic markers in the blood, which are compiled in Table 11. The estimated survival before the treatment was below 4 to 6 months. After the treatment, however, survival at 4 years was 77.8%.

TABLE 11

Genes Affected by Antineoplaston AS2-1 Based on Clinical Results in Colorectal Cancer.

| Mutations | Mutations | Mutations |
|---|---|---|
| BRAF (V600E) | APC (E888fs, R230C) | P1K3CA (E542K, 115431) |
| KRAS (G13D) | ARID1A (Q802fs) | PTEN (R55fs) |
| EGFR (D321D) | TP53 (R273H. R282W. S241F. C176Y) | SMAD4 (D537V) |

There was an additional group of 8 patients treated under the Right to Try law who were not evaluable for this report. Four of them died from cancer and were classified as PD, but 4 accomplished MR and 3 are alive and one died from other causes. In the expanded group, there are the following responses: CR (4), 25%; PR (0), 0%; MR (7), 43.7%; SD (1), 6.2%; PD (4) 25%; OR 12, 74.9%.

Head and Neck Cancer. A group of four patients diagnosed with terminal head and neck cancer qualified for inclusion in this review. There were three males and one female in this group. Their history of the disease was from 2 to 14 years and their life expectancy was from less than 1 month to 6 months. The patients had widely spread metastatic disease to lymph nodes, lungs, pleura, liver and bones. Their pathology diagnoses included squamous cell carcinoma, mucoepidermoid carcinoma of the submandibular gland and poorly differentiated acinic cell carcinoma of the parotid gland. Their prior treatment included surgery, radiation, three chemotherapy regimens and two targeted therapies; surgery, radiation and targeted therapy; surgery, radiation and two chemotherapy regimens; and radiation and targeted therapy (Table 12).

TABLE 12

Head and Neck Cancer Patient Demographics.

| Characteristics | N = 4 |
|---|---|
| Age - 45-77 Years | 4 |
| Duration of the Disease (Years) 2-14 | 4 |
| Metastatic Sites | |
| LYM, PUL, HEP | 1 |
| LYM, PUL, PLE | 1 |
| LYM, OSS | 1 |
| LYM, PUL | 1 |
| Estimated Survival (Months) | <1-<6 |
| Prior Treatment | |
| 1HK: | SU, RT, 3CH, 2TT |
| 2HK: | SU, RT, TT |
| 3HK: | SU, RT, 2CH |
| 4HK: | RT, TT |

Patients were treated as described above. The details and the results are provided in Tables 13, 14 and 15. Single patients accomplished PR, MR and SD and one developed PD. Genomic analysis showed activity against two mutated and one amplified gene (Table 15). Table 14 summarizes the responses in comparison with prior clinical trials with AS and A10 and targeted therapy indicating no OR.

TABLE 13

Evaluable Patients Treated with Antineoplaston AS2-1 in Combination with Other Drugs; Head and Neck Cancer, Stage IV.

| | | | | | Response | | | Survival from | |
|---|---|---|---|---|---|---|---|---|---|
| Patient | Diagnosis | Duration of Cancer (Years) | Prior Treatment | Treatment at BC (study) | RT and by PE | Genes Affected By AS | Estimated Survival (Months) | Treatment Start (Months) | Comments |
| 1HK | Mucoepidermoid Carcinoma of the Right Submandibular Gland, Stage IV LYM, PUL, HEP | 2 | SU, RT, 3CH, 2TT | AS, A10, TT, CH | PR | ARID1A, GNAQ | <2 | >12 | TT at BC: AS, A10, pembrolizumab, trastuzumab CH at BC: paclitaxel, carboplatin DAMA |

TABLE 13-continued

Evaluable Patients Treated with Antineoplaston AS2-1 in Combination with Other Drugs; Head and Neck Cancer, Stage IV.

| Patient | Diagnosis | Duration of Cancer (Years) | Prior Treatment | Treatment at BC (study) | Response: RT and by PE | Response: Genes Affected By AS | Estimated Survival (Months) | Survival from Treatment Start (Months) | Comments |
|---|---|---|---|---|---|---|---|---|---|
| 2HK | Acinic Cell Carcinoma, High-Grade, of Right Parotid Gland, Stage IV LYM, PUL, PLE | 14 | SU, RT, TT | AS, TT | PD | GATA3 multiplication | <3 | >4 | TT at BC: AS, pembrolizumab, vorinostat |
| 3HK | Moderately Differentiated Squamous Cell Carcinoma of the Hard Palate, Stage IVC LYM, OSS | 2 | SU RT, 2CH | AS, TT | MR | NA | <1 | >7 | TT at BC: AS, nivolumab, ipilimumab, cetuximab DAMA |
| 4HK | Invasive Squamous Cell Carcinoma of the Head and Neck, Stage IVC LYM, PUL | 3 | TT, RT | AS, TT | SD | TP53 R248Q and C242S | <6 | >8 | TT at BC: AS, pembrolizumab DAMA |

TABLE 14

Treatment of Head and Neck Cancer, Stage IV with Antineoplaston AS2-1 and Targeted Drugs in Comparison with AS2-1 Alone and Prior Targeted Therapy.

| | Treatment Type (Number of Patients) | | | | | |
|---|---|---|---|---|---|---|
| Cancer Type | AS2-1 + TT | Response S2-1 + A10 | A Protocol HN-02 | Response | Prior TT | Response |
| Mucoepidermoid Carcinoma of the Right Submandibular Gland, Stage IV LYM, PUL, HEP | 1 | PR | | | 1 | NE |
| Acinic Cell Carcinoma, High-Grade, of Right Parotid Gland, Stage IV LYM, PUL, PLE | 1 | PD | | | 1 | PD |
| Moderately Differentiated Squamous Cell Carcinoma of the Hard Palate, Stage IVC LYM, OSS | 1 | MR | | 3SD 1PD 6NE | None | |
| Squamous Cell Carcinoma of the Tongue with Metastases to the Lymph Nodes and Lungs, Stage IVC LYM, PUL | 1 | SD | | | | |

TABLE 15

Genes Possibly Affected by Antineoplaston AS2-1 Based on Clinical Results (Tissue Genomic Analysis) in Head and Neck Cancer, Stage IV

| Patient | Mutation |
|---|---|
| 1HK | ARID1A. GNAQ |
| 2HK | GATA3 multiplication |
| 3HK | NA |

The estimated survival before the treatment was less than 1 month to 6 months. As the result of the treatment, it has increased to over 4 to over 12 months and was associated with symptomatic improvement. There was an additional group of two patients treated under the Right to Try law who were not evaluable for this report. Both discontinued the treatment before the evaluation of response was possible. Both patients are alive at present.

Kidney Cancer. Two patients diagnosed with terminal kidney cancer qualified for inclusion in this review. Both patients were 39-year-old males. History of their disease was from 1 to 3 years and the estimated survival was from less than 2 months to less than 6 months. The patients had widespread metastatic disease to the lymph nodes, lungs, brain, bones and the opposite kidney. Their pathology diagnoses were renal cell carcinoma. The prior treatment included surgery, three types of radiation therapy and targeted therapy in one case, and two surgical procedures and targeted therapy in the second case (Table 16).

TABLE 16

Kidney Cancer Patient Demographics.

| Characteristics | N = 2 |
|---|---|
| Age (Years) 39 | 2 |
| Duration of the Disease (Years) 1-3 | 2 |
| Estimated Survival (Months) | <2-<6 |
| Metastatic Sites | |
| LYM, PUL, BRA, Opposite Kidney | 1 |
| LYM, PUL, BRA, OSS | 1 |

TABLE 16-continued

| Kidney Cancer Patient Demographics. | |
|---|---|
| Characteristics | N = 2 |
| Prior Treatment | |
| 1KI | SU, 3RT, TT |
| 2KI | 2SU, TT |

Patients were treated as described above. The details of the treatment and results are provided in Tables 17 and 18. One of the patients accomplished PR and another CR. Genomic analysis indicated effect on CDKN2A/B, SDKN2A, PTEN Y27C and AKT2 multiplication (Table 19). Table 18 summarizes the responses in comparison with prior clinical trials with AS and A10 and targeted therapy, which did not accomplish any objective responses.

Lung Cancer. A total of 7 terminal patients were treated. There were 4 males and 3 females, one of them aged 23 and the remaining patients from 53 to 79 years of age. Five patients had less than a year history of the disease and two patients from 3 to 5 years history of the disease. All patients were diagnosed with non-small cell carcinoma. Among them was a single case of squamous cell carcinoma and six cases of adenocarcinoma. The patients had widely spread metastatic disease including lymph nodes, lung, pleura, liver, brain, bones, peritoneal, pericardial, adrenal, thyroid, spleen and muscle metastases. The estimated survival of two patients was less than 3 months for one patient less than 4 months and for 4 patients, less than 6 months. Two patients were previously treated with surgery, radiation therapy and chemotherapy and a single patient had two types of radiation therapy and three regimens of chemotherapy, one patient had

TABLE 17

Evaluable Patients Treated with Antineoplaston AS2-1 in Combination with Other Drugs; Kidney Cancer, Stage IV.

| | | | | | Response | | | Survival from | |
|---|---|---|---|---|---|---|---|---|---|
| Patient | Diagnosis | Duration of Cancer (Years) | Prior Treatment | Treatment at BC (study) | RT and by PE | Genes Affected By AS | Estimated Survival (Months) | Treatment Start (Months) | Comments |
| 1KI | RCC, Stage IV LYM, PUL, BRA, opposite kidney | 1 | SU, 3RT, TT | AS, TT | PR, BRA SD LYM | CDKN2A/B SDKN2A | <2 | >11 | TT at BC - nivolumab, ipilimumab, vorinostat DAMA |
| 2KI | RCC, Stage IV LYM, PUL, OSS, BRA | 3 | 2SU, TT | AS,TT | CR | PTEN Y27C AKT2 multiplication | <6 | >7 | TT at BC - pembrolizumab, axitinib. DAMA |

RCC = Renal Cell Carcinoma

TABLE 18

Treatment of Kidney Cancer, Stage IV with Antineoplaston AS2-1 and Targeted Drugs in Comparison with AS2-1 Alone and Prior Targeted Therapy.

| | Treatment Type (Number of Patients) | | | | | |
|---|---|---|---|---|---|---|
| Cancer Type | AS2-1 + TT | Response | AS2-1 + A10 Protocol RN-02 | Response | Prior TT | Response |
| Renal Cell | 1 | CR | 5 | SD | 1 | PD |
| Carcinoma, | 1 | PR | 3 | PD | | |
| Stage IV | | | 7 | NE | | |

TABLE 19

Genes Possibly Affected by Antineoplaston AS2-1 Based on Clinical Results (Tissue Genomic Analysis) in Kidney Cancer, Stage IV.

| Patient | Mutation |
|---|---|
| 1KI | CDKN2A/B, SDKN2A |
| 2KI | PTEN Y27C, AKT2 multiplication |

The estimated survival before the treatment was less than 2 and 6 months but after the treatment increased to over 7 and 11 months and was associated with clinical improvement. There was only one additional patient with this type of cancer treated under the Right to Try who discontinued the treatment within less than 60 days and died from unknown cause.

only surgery and two patients had only targeted therapy. There was a single patient who did not have prior treatment (Table 20).

TABLE 20

| Lung Cancer Patient Demographics. | |
|---|---|
| Characteristics | N = 7 |
| Age (Years) | N |
| Range 23 | 1 |
| 53-79 | 6 |

TABLE 20-continued

| Lung Cancer Patient Demographics. | |
|---|---|
| Characteristics | N = 7 |
| Estimated Survival (Months) | |
| Less than 3 | 2 |
| Less than 4 | 1 |
| Less than 6 | 4 |
| Duration of the Disease (Years) | |
| Less than 1 year to 1 year | 5 |
| 3-5 | 2 |
| Metastatic Sites | |
| LYM, OSS, thyroid | 1 |
| LYM, BRA, HEP, PUL, OSS, ADR, muscles | 1 |
| LYM | 1 |
| LYM, OSS | 1 |
| LYM, PUL | 1 |
| LYM, PUL, PLE, BRA, OSS, PER | 1 |
| LYM, PUL, BRA, HEP, OSS, spleen, pericardium | 1 |
| Prior Treatment | |
| SU, RT, CH | 1 |
| 2RT, 3CH | 1 |
| SU | 1 |
| TT | 1 |
| 2TT | 1 |
| NONE | 1 |

Patients were treated as described above. The details of the treatment and responses are provided in Tables 21 and 22. One patient accomplished CR, four accomplished PR and two accomplished MR. Table 22 summarizes the responses and compares them to responses in clinical trials of AS and A10 and prior targeted therapy and shows no OR's. The list of the genes affected by AS is in Table 23.

TABLE 21

Evaluable Patients Treated with Antineoplaston AS2-1 in Combination with Other Drugs; Lung Cancer with Multiple Metastases, Stage IV.

| Patient | Diagnosis | Duration of Cancer (Years) | Prior Treatment | Treatment at BC (study) | Response: RT and by PE | Genes Affected By AS | Estimated Survival (Months) | Survival from Treatment Start (Months) | Comments |
|---|---|---|---|---|---|---|---|---|---|
| 1LU | Squamous Cell Carcinoma, Stage IV LYM, OSS, Thyroid | 1.5 | 2RT, 3CH | AS, TT | PR - PUL PD - OSS | EWSR1-FLI1 fusion | <6 | >6 | TT at BC - bevacizumab, nivolumab. DAMA |
| 2LU | Adenocarcinoma, Stage IV LYM, BRA, HEP, PUL, OSS, ADR, Muscles | 0.2 | None | AS, TT, RT | MR | TERT promoter SNV | <3 | 18 | TT at BC - nivolumab, ipilimumab, bevacizumab, rucaparib, vorinostat. RT at BC DAMA |
| 3LU | Adenocarcinoma, Stage IV PUL, BRA, OSS | 4 | SU, 2RT, CH | AS, TT | PR* | FBXW7 Y545C | <6 | >6 | TT at BC - nivolumab, pembrolizumab. DAMA |
| 4LU | Adenocarcinoma, Stage IV LYM, OSS | 1 | SU | AS, TT | CR - LYM, PUL PR - OSS | SMAD4 A406T | <4 | >22 | TT at BC - alectinib. |
| 5LU | Adenocarcinoma, Stage IV LYM, PUL | 0.7 | TT | AS, TT | PR | EGFR P753L (possibly) | <6 | >12 | TT at BC - erlotinib, pembrolizumab. DAMA |
| 6LU | Adenocarcinoma, Stage IV LYM, PUL, PLE, BRA, OSS, PER | 1 | 2TT | AS, TT | MR | NF1 Splice Site SNV | <6 | >4 | TT at BC - osimertinib. DAMA |
| 7LU | Adenocarcinoma, Stage IV LYM PUL, BRA, HEP, OSS, Spleen, Pericardium | 1 | SU, RT, CH | AS, TT, RT | PR | TP53 Y126D and R273H | <3 | >4 | TT at BC -fam-trastuzumab deruxtecan-Nxki RT at BC |

TABLE 22

Treatment of Lung Cancer with Multiple Metastases, Stage IV with Antineoplaston AS2-1 and Targeted Drugs in Comparison with AsS2-l Alone and Prior Targeted Therapy.

| | Treatment Type (Number of Patients) | | | | | |
|---|---|---|---|---|---|---|
| Cancer Type | AS2-1 + TT | Response | AS2-1 + A10 | Response | Prior TT | Response |
| Squamous Cell | 1 | PR | LA-05 | 4NE | | |
| Adenocarcinoma | 6 | 1CR<br>3PR<br>2MR | LA-06 | 1SD<br>6NE | NA | |

TABLE 23

Genes Possibly Affected by Antineoplaston AS2-1 Based on Clinical Results (Tissue Genomic Analysis) in Lung Cancer with Multiple Metastases, Stage IV.

| | |
|---|---|
| 1LU | EWSR1-F LI1 fusion |
| 2LU | TERT promoter SNV |
| 3LU | FBXW7 Y545C |
| 4LU | SMAD4 A406T |
| 5LU | EGFR P753L (possibly) |
| 6LU | NF1 Splice Site SNV |
| 7LU | TP53 Y126D and R273H |

The estimated survival of two patients was less than 3 months, one patient less than 4 months and the remaining patients less than 6 months. After the treatment, the survival of three patients was over 12 to over 22 months and the remaining patients over 4 to 8 months. Overall survival at 14 months was 75%.

There was an additional group of four patients treated under the Right to Try law who were not evaluable for this review. The responses of two were classified as SD and two other patients died from cancer and were counted as PD. In the expanded group of 12 patients there are the following responses: CR (1) 8.3%; PR (4) 33.3%; MR (2) 16.6%; SD (3) 25.0%; PD (2) 16.6%; OR 7 58.2%.

Ovarian Cancer. The group of four patients diagnosed with terminal serous carcinoma of the ovary qualified for this review. The patients were from 54 to 80 years of age and their history of disease was from less than a year to 4 years. The patient had widely spread metastatic disease to the lymph nodes, liver, lungs, pleura, peritoneum and spleen. Their estimated survival was from less than 3 to 6 months. The prior treatment included surgery, radiation and targeted therapy in two cases, surgery and chemotherapy in one case and no treatment in another case (Table 24).

TABLE 24

Ovarian Cancer Patient Demographics.

| Characteristics | N = 4 |
|---|---|
| Age (Years) -54-80 | 4 |
| Duration of the Disease (Years) | 0.2-4 |
| Estimated Survival (Months) | <3-<6 |
| Metastatic Sites | |
| LYM, PER | 1 |
| LYM, PUL, HEP, PER, spleen | 1 |
| LYM, HEP | 1 |
| HEP, PER, PLE | 1 |
| Prior Treatment | |
| 1OA | SU, 3CH, TT |
| 2OA | NONE |
| 3OA | SU, 2CH, 2TT |
| 4OA | SU, CH |

Patients were treated as described above. The details of the treatment and responses are provided in Tables 25 and 26. All patients had objective responses: 3PR and 1MR. Table 26 compares the responses to the results of the clinical trials with AS and A10 and prior targeted therapy. There were no ORs in clinical trials and a single PR after prior targeted therapy. In the follow-up blood genomic test, a number of the mutated genes which were previously seen were gone or had a decrease in the concentration (Table 27).

TABLE 25

Evaluable Patients Treated with Antineoplaston AS2-1 in Combination with Other Drugs; Ovarian Cancer with Multiple Metastases, Stage IV.

| | | | | | Response | | | Survival from | |
|---|---|---|---|---|---|---|---|---|---|
| Patient | Diagnosis | Duration of Cancer (Years) | Prior Treatment | Treatment at BC (study) | RT and by PE | Genes Affected By AS | Estimated Survival (Months) | Treatment Start (Months) | Comments |
| 1OA | Serous Papillary Carcinoma, Stage IV LYM, PER | 2 | SU, 3CH, TT | AS, H, 4TT | MR | NTRK1 | <6 | >28 | TT at BC - nivolumab, pazopanib, sorafenib, rapamycin. H at BC - anastrozole. DAMA |

TABLE 25-continued

Evaluable Patients Treated with Antineoplaston AS2-1 in Combination with Other Drugs; Ovarian Cancer with Multiple Metastases, Stage IV.

| Patient | Diagnosis | Duration of Cancer (Years) | Prior Treatment | Treatment at BC (study) | Response: RT and by PE | Response: Genes Affected By AS | Estimated Survival (Months) | Survival from Treatment Start (Months) | Comments |
|---|---|---|---|---|---|---|---|---|---|
| 2OA | Serous Carcinoma, Stage IV LYM, PUL, HEP, PER, Spleen | 0.5 | None | AS, CH, 2TT | PR* | TP53 R248W NF1 K583R MYC amplification PIK3CA amplification RAF1 amplification AR M887V ALK N1544K PIK3CA Q597H ARID1A R1889W | <3 | >18 | CH at BC - paclitaxel, carboplatin. TT at BC - bevacizurnab, palbociclib. DAMA |
| 3OA | Serous Carcinoma, Stage IV LYM, HEP | 4 | SU, 2CH, 2TT | AS, TT | IM | TP53 R176H CCND1 R291W BRAF amplification PIK3CA amplification ND Decreased more than 50% of TP53 R209fs ARID1A G246V Molecular PR | <6 | >8 | TT at BC - Olaparib embrolizumab. p DAMA |
| 4OA | Carcinoma, Stage IV HEP, PER, PLE | 0.2 | SU, CH | AS, CH, TT | PR | TP53 N235-Y236del decreased more than 50% | <6 | >9 | CH at BC - paclitaxel, carboplatin. TT at BC - bevacizurnab. |

TABLE 26

Treatment of Ovarian Cancer with Multiple Metastases, Stage IV with Antineoplaston AS2-1 and Targeted Drugs in Comparison with AS2-1 Alone and Prior Targeted Therapy.

| Cancer Type | Treatment Type (Number of Patients): AS2-1 + TT | Response S2-1 + A10 | A Protocol OO-02 | Response | Prior TT | Response |
|---|---|---|---|---|---|---|
| Serous Carcinoma, Stage IV | 3 | PR | 3 | PD | 1 | PD |
| | 1 | MR | 4 | NE | 1 | PR |

TABLE 27

Genes Possibly Affected by Antineoplaston AS2-1 Based on Clinical Results (Tissue Genomic Analysis) in Ovarian Cancer with Multiple Metastases, Stage IV.

| Patient | Mutation |
|---|---|
| 1OA | NTRK1 |
| 2OA | TP53 (R248W), NF1 (K583R), MYC amplification, PIK3CA amplification, RAF1 amplification, AR (M887V), ALK (N1544K), PIK3CA (Q597H), ARID1A (R1889W) |
| 3OA | TP53 (R176H), CCND1 (R291W), BRAF amplification, PIK3CA amplification, ND, Decreased more than 50% of TP53 (R209fs), ARID1A (G246V) |
| 4OA | SMAD4 (P511L), ND, TP53 (N235-Y236del) decreased more than 50% |

The patients obtained marked symptomatic improvement and life extension to over 8 to 28 months compared to less than 3 to 6 months before treatment.

Pancreatic Cancer. A total of three patients were treated. The patients were male and in the age range of 46 to 77 years. All of them were diagnosed with adenocarcinoma of the pancreas, Stage IV, and carried a life expectancy from less than 3 months to less than 6 months. They had less than a year to 2-year history of the disease. Metastatic sites included lymph nodes, liver and stomach. One patient underwent prior surgery, radiation and chemotherapy and another had surgery and chemotherapy. The third patient did not have any prior treatment (Table 28).

TABLE 28

Pancreatic Cancer Patient Demographics.

| Characteristics | N = 3 |
|---|---|
| Age (Years) 46-77 | 3 |
| Estimated Survival (Months) | |
| <3-<6 | 3 |
| Duration of the Disease (Years) | |
| <1-2 | 3 |
| Metastatic Sites | |
| LYM | |
| PUL, stomach | 1 |
| HEP | 1 |
| Prior Treatment | |
| SU, RT, CH | 1 |
| SU, CH | 1 |
| NONE | 1 |

Patients were treated as described above. The details of the treatment and the results are provided in Tables 29 and 30. Two patients accomplished PR and one had MR. Table 30 summarizes the responses and compares them to the responses in Phase 2 trial of AS and A10 and prior targeted therapy. As shown in Table 30, all three patients in this review objectively responded, but there was not an OR in the clinical trial. The patients had marked improvement and decrease of concentration of mutated genes in blood which is shown in Table 31.

In the expanded group, there were the following responses: PR (2), 33.3%; MR (2), 33.3%; PD (2), 33.3%: OR (4), 66.6%.

Prostate Cancer. A total of 4 patients were treated. The patients were in the age range of 59 to 69 years. All of them were diagnosed with aggressive adenocarcinoma of the prostate, Stage IV. The Gleason Score of two patients was 9 and the remaining patients were Gleason Score 10 and 8. The patients had from less than a year to a 5-year history of the disease. They had widely spread metastatic disease to the lymph nodes, bones and lungs. The estimated survival was less than 3 months for one patient and less than 6 months for the remaining patients. Prior treatments included surgery, radiation, chemotherapy, hormonal and targeted therapy. The details are compiled in Table 32.

TABLE 29

Evaluable Patients Treated with Antineoplaston AS2-1 in Combination with Other Drugs; Pancreatic Cancer with Multiple Metastases, Stage IV.

| Patient | Diagnosis | Duration of Cancer (Years) | Prior Treatment | Treatment at BC (study) | Response: RT and by PE | Response: Genes Affected By AS | Estimated Survival (Months) | Survival from Treatment Start (Months) | Comments |
|---|---|---|---|---|---|---|---|---|---|
| 1PT | Poorly Differentiated Adenocarcinoma, Stage IVA LYM | 2 | SU, RT, CH | AS, 2CH, 2TT | PR | Possibly KRAS G12D NF1 H415Y ARID1A O1334-R1335InsQ SMAD4 R135 | <6 | >7 | CH at BC - capecitabine, gemcitabine, nab-paclitaxel. TT at BC - bevacizumab, sorafenib, rapamycin, vorinostat. DAMA |
| 2PT | Moderately Differentiated Adenocarcinoma, Stage IVB PUL, Stomach | 1 | SU, CH | AS, CH, 3TT | PR | Possibly TP53 C1355 | <3 | 19 | CH at BC - capecitabine. TT at BC - sorafenib, rapamycin, vorinostat, olaparib, osimertinib, erlotinib. |
| 3PT | Moderately Differentiated Adenocarcinoma, Stage IVB HEP | 0.2 | None | AS, CH, TT | MR | Possibly SMAD4 R497H KIT H630D | <6 | >10 | CH at BC - capecitabine. TT at BC - sorafenib, rapamycin, vorinostat, bevacizumab. DAMA |

TABLE 30

Treatment of Pancreatic Cancer with Multiple Metastases, Stage IV with Antineoplaston AS2-1 and Targeted Drugs in Comparison with AS2-1 Alone and Prior Targeted Therapy.

| | Treatment Type (Number of Patients) | | | | | |
|---|---|---|---|---|---|---|
| Cancer Type | AS2-1 + TT | Response | AS2-1 + A10 Protocol BR-12 | Response | Prior TT | Response |
| Adenocarcinoma of the Pancreas | 2 | PR | SD | 1 | None | |
| | 1 | MR | PD | 4 | | |
| | | | NE | 10 | | |

TABLE 31

Genes Possibly Affected by Antineoplaston AS2-1 Based on Clinical Results in Pancreatic Cancer.

| Patient | Mutation |
|---|---|
| 1PT | Possibly KRAS (G12D), NF1 (H415Y), ARID1A (Q1334-R1335InsQ), SMAD4 (R135) |
| 2PT | Possibly TP53 (C1355) |
| 3PT | Possibly SMAD4 (R497H), KIT (H630D) |

There was marked improvement of overall survival from the pretreatment estimation of less than 3 months to 6 months to over 7 months to 19 months and there was also clinical improvement of patients treated. There were three additional patients treated under the Right to Try law who were not evaluable for this review. One of them had MR, one had PD and one died from cancer and was classified as PD.

TABLE 32

Prostate Cancer Patient Demographics.

| Characteristics | N = 4 |
|---|---|
| Age (Years) 59-72 | 4 |
| Estimated Survival (Months) | |
| Less than 3 | 1 |
| Less than 6 | 3 |

TABLE 32-continued

Prostate Cancer Patient Demographics.

| Characteristics | N = 4 |
|---|---|
| Duration of the Disease (Years) | |
| <1-5 | 4 |
| Metastatic Sites | |
| LYM, OSS | 1 |
| LYM, OSS, PUL | 2 |
| OSS | 1 |
| Prior Treatment | |
| SU, RT, H | 1 |
| 3CH, 2H, TT | 1 |
| 2SU, H | 1 |
| SU, 2H | 1 |

Patients were treated as described above. The details and results of treatment are provided in Tables 33 and 34. There were 2CR, 1 MR and 1 PD. Table 34 summarizes the responses and compares them to Phase 2 clinical trial with AS and A10 and targeted therapy, which showed no OR. The patients had improvement and marked decrease of concentration or elimination of mutated genes in the follow-up blood tests which is shown in Table 35.

TABLE 33

Evaluable Patients Treated with Antineoplaston AS2-1 in Combination with Other Drugs; Prostate Cancer with Multiple Metastases, Stage IV.

| Patient | Diagnosis | Duration of Cancer (Years) | Prior Treatment | Treatment at BC (study) | Response: RT and by PE | Response: Genes Affected By AS | Estimated Survival (Months) | Survival from Treatment Start (Months) | Comments |
|---|---|---|---|---|---|---|---|---|---|
| 1PS | 1PS0.2 Adenocarcinoma, Gleason Score 9, Stage IV LYM, OSS | | 2SU, H | AS, H, TT | CR | PTEN G1435 SMAD R189H ND | <6 | >8 | TT at BC - nivolumab, ipilimumab. H at BC - Casodex, Lupron. |
| 2PS | Adenocarcinoma, Gleason Score 8, Stage IV LYM, PUL, OSS | 5 | SU, 2H, TT | AS, 2H, TT | CR | MYC amplification PIK3CA mutation CCNE1 mutation | <6 | >7 | H at BC - Casodex, Zoladex, degarelix. TT at BC - rapamycin. DAMA |
| 3PS | Poorly Differentiated Adenocarcinoma, Gleason Score 10, Stage IV LYM, PUL, OSS | 2 | 3CH 2H TT | AS, CH, H, TT | PR | Decrease of TP53 H178 - S183del APCS197F ND of EGFR V742V EGFR amplification | <3 | >5 | CH at BC - carboplatin, paclitaxel. H - leuprorelin, abiraterone. TT at BC - denosumab, olaparib. DAMA |
| 4PS | Adenocarcinoma, Gleason Score 9, Stage IV OSS | 2 | SU, RT, H | ASH, TT | PD | NF1 T1295S ND | <6 | >4 | H at BC - abiraterone TT at BC - pembrolizumab, rucaparib DAMA |

TABLE 34

Treatment of Prostate Cancer with Antineoplaston AS2-1 and Targeted Drugs in Comparison with AS2-1 Alone and Prior Targeted Therapy

| Cancer Type | Treatment Type (Number of Patients): AS2-1 + TT | Response | AS2-1 + A10 Protocol PR-07 | Response | Prior TT | Response |
|---|---|---|---|---|---|---|
| Adenocarcinoma Gleason Score 8-10 | 2 | CR | 1 | PD | 1 | PD |
| | 1 | MR | | | | |
| | 1 | PD | | | | |

TABLE 35

| Genes Affected by Antineoplaston AS2-1 Based on Clinical Results in Prostate Cancer. | |
|---|---|
| Patient | Mutation |
| 1PS | PTEN (G143S), SMAD (R189H), ND |
| 2PS | MYC amplification, PIK3CA mutation, CCNE1 mutation |
| 3PS | Decrease of TP53 (H178_S183del), APCS197F, ND of EGFR V742V, EGFR amplification |
| 4PS | NF1 (T1295S), ND |

The estimated survival before treatment was from less than 3 months to less than 6 months and increased after the treatment to over 4 months to over 8 months. There was an additional group of 3 patients treated under the Right to Try law who were not evaluable for this review. Among them there were single cases of PR, SD and PD. In the expanded group there were the following responses: CR 2, 25%; PR 1, 12.5%; MR 1, 12.5%; PD 2, 25%; OR 6, 75%.

Part II—Uncommon Cancers (Neoplastic Disorders).

Adenoid Cystic Carcinoma. There was a single patient diagnosed with Stage IV disease with metastases to the liver and peritoneum. The patient was a 37-year-old male who had a 5-year history of disease and was treated with surgery, radiation (twice), and chemotherapy. He had an estimated survival of less than 6 months.

Patient was treated as described above. In brief, the patient received AS and TT at study site wherein the TT was nivolumab, ipilimumab DAMA. The patient's radiological response was SD. Due to the rarity of his cancer, the results could not be compared to AS and A10 and targeted therapy. It was suspected that the treatment affected ATM mutation, possibly at Exon 8 SNV.

Estimated survival before the treatment was less than 6 months. The patient discontinued the treatment in good condition after 7 months. There were no other patients treated with this diagnosis.

Anaplastic Astrocytoma. The group of three patients with terminal anaplastic astrocytoma qualified for inclusion of this review. There were two females and one male in this group. One patient was 10 years old and two others were between 34 and 49 years old. The youngest patient with a very aggressive tumor had less than a year history of her disease and the remaining two had 4 to 13 years duration of their tumors. The estimated survival was from less than 2 months to less than 6 months. Prior treatments included surgery in all the patients and radiation in two of them. The third patient was also treated with chemotherapy and targeted therapy.

Patients were treated as described above. In brief, patients received AS and TT at study site wherein the TT was bevacizumab, pazopanib, dasatinib, everolimus, and/or vorinostat DAMA. There was one CR, one PR and one PD. In the Phase 2 study with AS and A10 there was a smaller percentage of OR in a larger population of patients: 5 ORs in 27 patients and no ORs on prior targeted therapy. Table 36 compiles mutated genes possibly affected by AS.

TABLE 36

| Genes Affected by Antineoplaston AS2-1 Based on Clinical Results in Anaplastic Astrocytoma. | |
|---|---|
| Patient | Mutations |
| 1AA | IDH1 (R132H), ATRX (S850fs*2), TP53 (R273C) |
| 2AA | IDH1 (R132H), ARID2 (N127fs18), ATRX (N179fs*26), TP53 (R273H) |
| 3AA | None |

The estimated survival before the treatment was from less than 2 months to less than 6 months and after the treatment from 3 months to over 12 months with clinical improvement. There was an additional group of 3 patients treated under the Right to Try law who were not evaluable for this review. Two of them had SD and one PD. In the expanded group there were the following responses: CR 1, 16.6%; PR 1, 16.6%; SD 2, 33.3%; PD 2, 33.3%; OR 2, 33.2%.

Anaplastic Oligodendroglioma. There were two patients diagnosed with terminal anaplastic oligodendroglioma treated under the Right to Try law. One of them was a 40-year-old male with a 3-year history of the disease. His tumor recurred after surgical resection and his life expectancy was less than 6 months. The second patient had a recurrence and leptomeningeal carcinomatosis after 34 weeks of 2 surgeries, 5 chemotherapy regimens, radiation therapy, a clinical trial and targeted therapy. His life expectancy was less than 2 months.

Patients were treated as described above. In brief, patients received AS and TT at study site wherein the TT was bevacizumab, pazopanib, dasatinib, and everolimus. One patient accomplished MR and the second patient had PD. The comparison to Phase 2 study of AS and A10 indicates that there were no objective responses. Table 37 shows mutated genes possibly affected by AS. The estimated survival before treatment was less than 2 and 6 months but after the treatment it was over 8 and 6 months.

TABLE 37

| Genes Affected by Antineoplaston AS2-1 Based on Clinical Results in Anaplastic Oligodendroglioma. | |
|---|---|
| Patient | Mutations |
| 1AO | PIK3CA (E453K), IDH1 (R132H), PIK3R1 (S399Y408del splice site 917-1G > A), TERT promoter (146C > T), TP53 (splice site 37G-1G > A) |
| 2AO | |

Diffuse Astrocytoma. A single patient diagnosed with terminal diffuse astrocytoma, Grade 2, qualified for this review. This was a 54-year-old male, practicing physician with a one-year history of the disease and estimated survival of less than 6 months. His prior treatment consisted of chemotherapy and radiation.

Patient was treated as described above. In brief, the patient received AS and TT at study site wherein the TT was bevacizumab, pazopanib, dasatinib, and everolimus. The patient accomplished CR documented by MR spectroscopy. Mutated genes affected by AS included NF1 V2378fs*8; PTENN323fs*23; and TERT Promoter 124 C>T.

The estimated survival before treatment was less than 6 months but after the treatment, he survived over 6 months, possibly over 24 months. There was an additional group of 3 patients treated under the Right to Try law that did not qualify for inclusion in this review. One of them had PR and the other two patients had SD. In the expanded group there are the following responses: CR 1, 25°/u; PR 1, 25%; SD 2, 50%;

Cholangiocarcinoma. There was a single patient diagnosed with terminal cholangiocarcinoma, Stage IV, who qualified for inclusion in this review. The patient was a 51-year-old female who had a 3-year history of her disease, failed chemotherapy and had an estimated survival of less than 1 month. She had widespread metastatic disease to the lymph nodes, liver, brain, pleura and leptomeningeal carcinomatosis.

Patient was treated as described above. In brief, the patient received AS and TT at study site wherein the TT was sorafenib, everolimus, vorinostat, bevacizumab and capecitabine (a chemotherapy). The patient had MR evidenced by a follow-up MRI which showed 31% decrease in the size of metastatic lesions in the brain and leptomeningeal carcinomatosis. Phase 2 studies with AS and A10 were not conducted in this indication and the responses to targeted therapy are not available. The patient survived longer than the expected 1 month and died after 4 months from pneumonia. Mutated genes affected by AS included: NF1 F710C and KRAS G12V.

There were two additional patients treated under the Right to Try law who did not qualify for inclusion in this review. One of them had PD and another died from cancer and was classified as PD. In the expanded group, there were the following responses: MR 1, PD 2.

Chronic Atypical Myelogenous Leukemia. There was a single patient diagnosed with this type of leukemia who qualified for inclusion in this review. The patient was a 72-year-old male who had a 3-year history of the disease, no prior treatment and a less than 6 months life expectancy.

Patient was treated as described above. In brief, the patient received AS and TT at study site wherein the TT was ruxolitinib and vorinostat. The patient accomplished PR. There are no data on the responses to AS and A10 and targeted therapy for comparison. The estimated survival before the treatment was less than 6 months, but it was 26 months after the treatment. The patient died from an opportunistic infection. Mutated genes affected by AS included: BRACA2 12040V, HIST1H1D K185-A186>T, MAP3K6 P646L, NOTCH2 S2379F, SPEN A2510V, STAT5B R110H, TET2 C1875G, MPL Y591D, RUNX1 R107C, ASXL1 R1273f*s, and SRSF2 P95H.

DIPG. There was a single patient who qualified for inclusion in this review. He was an 8-year-old male with less than a year of history of the disease. He was treated before with radiation therapy and had an expected survival of less than 6 months.

Patient was treated as described above. In brief, the patient received AS and TT at study site wherein the TT was bevacizumab, pazopanib, dasatinib, and everolimus. The follow-up MRI after two months of treatment showed an over 40% decrease of tumor size which was classified as MR. The patient continued the treatment and approached approaching PR. In comparison to the results of Phase 2 trials of AS and A10, there were 6 ORs in 49 patients. There are no data on the effect of targeted therapy. Mutated genes affected by AS included: PTEN C136Y, and H3F3A K28N The patient was surviving over 7 months from the treatment start and continued to improve compared to less than 6 months life expectancy before the treatment.

Esophageal Cancer. A single patient diagnosed with terminal adenocarcinoma of the esophagus, Stage IV, qualified for this review. This was a 61-year-old male with a 4-year history of the disease which also involved liver, pleura and peritoneum. He failed prior chemotherapy and targeted therapy and had less than a 2-month life expectancy.

Patient was treated as described above. In brief, the patient received AS and TT at study site wherein the TT was nivolumab, olaparib, ramucirumab and chemotherapy including carboplatin and nab-paclitaxel DAMA. The patient accomplished marked improvement of liver metastases and reduction of pain. Instead of multiple liver metastases at baseline, there was only one after the treatment which decreased by 30%. The response was classified as MR. In comparison to the results of the Phase 2 study, there was 1CR in 8 patients. The estimated survival was less than 2 months, but the patient survived over 6 months. He discontinued the treatment against medical advice. Mutated genes affected by AS included: TP53 C1104, TP53 P151H, KRAS G12D, BRAF E264, NF1 I1719T, and ERBB2 C584G.

Ewing Sarcoma. There was a single case of terminal Ewing sarcoma, Stage IV, which qualified for inclusion in this review. The patient was a 23-year-old female who had an approximate 2-year history of her disease which spread to the lymph nodes, bones and thyroid. She failed surgery, radiation and chemotherapy and her life expectancy was less than 6 months.

Patient was treated as described above. In brief, the patient received AS and TT at study site wherein the TT was nivolumab, bevacizumab DAMA. She accomplished PR of the largest right clavicular mass but there was new hypermetabolic activity in the left sacrum and ilium. There were no cases of Ewing sarcoma treated in Phase 2 clinical studies or by targeted therapy for comparison. The patient survived over 6 months compared to the less than 6-month life expectancy before treatment. She discontinued the treatment against medical advice. Mutated gene affected by AS was EWSR1-FLI1 fusion.

Ganglioglioma. There was a single patient diagnosed with terminal ganglioglioma with leptomeningeal carcinomatosis who qualified for this review. The patient was an 11-year-old male who had less than a year history of the disease. He was treated surgically but developed recurrence and had a life expectancy of less than 4 months.

Patient was treated as described above. In brief, the patient received AS and TT at study site wherein the TT was bevacizumab, pazopanib, dasatinib, everolimus, vorinostat DAMA. After 4 months of treatment there was more than 50% decrease of the enhancing lesions which included a decrease of leptomeningeal carcinomatosis and resolution of the lesions in the mid thoracic region. In comparison to the results of the Phase 2 clinical studies with AS and A10, there were three cases of PR, but they did not have leptomeningeal carcinomatosis. The data on results of targeted therapy are not available. The patient survived over 12 months compared to the pretreatment estimated survival of less than 4 months. He discontinued treatment against medical advice. Mutations affected by AS included: NF1 c.6655>T and p.D2219Y.

Gastrointestinal Stromal Tumor, Stage IV (GIST). A single patient diagnosed with terminal GIST qualified for this review. He was 72 years old and had a 5-year history of his disease. He had metastatic involvement of the bones and pelvis. He failed surgery and targeted therapy and had a life expectancy of less than 6 months.

Patient was treated as described above. In brief, the patient received AS and TT at study site wherein the TT was sunitinib. The patient accomplished 39.7% decrease of the size of pelvic mass after 6 weeks of treatment which was classified as MR. There are no data on the treatment of GIST in the Phase 2 studies of AS and A10. The patient failed to respond to targeted therapy with imatinib and sunitinib but had a very good response to the combination of AS and sunitinib. Mutations affected by AS included NOTCH1 A465V and NF1A2617A. The patient developed perforation of a necrotic tumor and died after 5 months.

Leptomeningeal Carcinomatosis. Three patients diagnosed with leptomeningeal carcinomatosis (LMN) were included in this review. One of each had metastases to the brain and spinal cord correspondingly and the third patient had involvement of the lymph nodes, liver, pleura and brain. One of them failed surgery, two regimens of radiation, chemotherapy and hormonal therapy. The second patient was treated with chemotherapy and the third with surgery. Their life expectancy was estimated as less than 1 month.

Patients were treated as described above. In brief, patients received AS and TT at study site wherein the TT was either: 1) capecitabine (CH) and bevacizumab DAMA; 2) sorafenib, everolimus, vorinostat, bevacizumab, and capecitabine (CH); or 3) bevacizumab, pazopanib, dasatinib, everolimus, vorinostat DAMA. All patients responded to the treatment. There was one of each: CR, PR and MR. The data on LMN coming from Phase 2 clinical trials with ANP are showing 3PR's in primary malignant brain tumors, but no CR. There are no data on responses to targeted therapy. Molecular responses are listed in Table 38. The patients survived much longer than the expected 1 month; from over 4 to 15 months.

TABLE 38

Genes Affected by Antineoplaston AS2-1 Based on Clinical Results in Leptomeningeal Carcinomatosis

| Patient | Mutations |
|---|---|
| 1BE | PTEN, TP53, NF1, MAP3K1 |
| 1CC | NF1 (F710C), KRAS (G12V) |
| 1GG | NF1 (c.6655 > T, p.D2219Y) |

Medulloblastoma. Two patients with terminal medulloblastoma qualified for this review. There was one male and one female in this group, and both were 11 years old. Both patients had widely disseminated disease of the brain and spinal cord and one patient had leptomeningeal carcinomatosis. One of them was treated with surgery, radiation and chemotherapy and the second patient underwent 3 surgical resections, 2 types of radiation therapy and 2 types of chemotherapy and a bone marrow transplant. They developed recurrence and estimated survival was less than 2 months.

Myelodysplastic Syndrome (MDS). Two patients diagnosed with MDS were qualified for the inclusion in this review. In one of the patients, it was possible to identify four distinct diagnoses: 1) chronic atypical myelogenous leukemia, 2) myelofibrosis, 3) refractory anemia and 4) thrombocytopenia. The results of treatment of three diagnoses: 1) to 3) will be evaluated separately. The second patient, in addition to MDS, carried diagnosis of non-Hodgkin's small-cell, B-cell lymphoma (SLL). Both patients were males in the age range of 63 to 72 and had 3 to 5-year histories of the disease. One of them relapsed after targeted therapy and the other did not have any treatment. Their estimated survival was less than 6 months.

Patients were treated as described above. In brief, patients received AS and TT at study site wherein the TT was either vorinostat and ruxolitinib or vorinostat and rituximab. One patient accomplished PR and the other had SD. There are no data for comparison with the results of clinical studies and targeted therapy, except that one patient relapsed after targeted therapy. The affected mutated genes are listed in Table 39.

TABLE 39

Evaluable MDS Patients Treated with Antineoplaston AS2-1 in Combination with Other Drugs

| Patient | Radiological and By PE | Molecular Genes Affected By AS | Comments: |
|---|---|---|---|
| 1MD | PR | BRACA2 12040V, H1ST1H1D K185-A186 > T, MAP3K6 P946L, SPEN A2510V, STAT5B R110H TET2 Cl875G | TT at BC: vorinostat, ruxolitinib |
| 2MD | SD | CD79B Y196C-subclonal MYD88 L265P-subclonal AR1D1A Q1334-R1335insQ CXCR4 E338-subclonal KLHL6 L65P-subclonal RUNX1 R204O | TT at BC: vorinostat, rituximab |

Both patients survived much longer than the expected less than 6 months. One of them died from cerebral hemorrhage after 26 months and the second patient continued the treatment and survived over 36 months. In both cases, there was marked symptomatic improvement.

Myelofibrosis. There was only a single patient with this diagnosis who was also described in the MDS section. He was 72 years of age and had a 3-year history of the disease. He was not treated before and his life expectancy was less than 6 months.

Patient was treated as described above. In brief, patient received AS and TT at study site wherein the TT was vorinostat and ruxolitinib. The patient accomplished PR. There are no data for comparison with the results of clinical studies and treatment with targeted therapy. AS-affected mutated genes included: BRACA2 12040V, HIST1H1D K185-A186>T, MAP3K6 P646L, NOTCH2 52379F, SPEN A2510V, STAT5B R110H, TET2 C1875G, MPL Y591D, RUNX1 R107C, ASXL1R1273f*s, SRSF2 P95H. The patient survived over 26 months compared to the estimated less than 6 months before the treatment. He died from cerebral hemorrhage.

Neuroendocrine Carcinoma. There was a single patient diagnosed with terminal neuroendocrine cancer, Stage IV, who qualified for this review. She was also described in the Lung Cancer section. The patient was a 23-year-old female with an approximate 2-year history of the disease which spread to the lymph nodes, bones and thyroid. She failed surgery, radiation and chemotherapy and her life expectancy was less than 6 months.

Patient was treated as described above. In brief, patient received AS and TT at study site wherein the TT was nivolumab and bevacizumab. She accomplished PR of the largest right clavicular mass but there was new hypermetabolic activity in the left sacrum and ilium. There were no cases of neuroendocrine carcinoma treated in Phase 2 clinical studies or by targeted therapy for comparison. The mutated gene affected by AS was EWSR1-FLI1 fusion. The patient survived over 6 months compared to the less than 6-month life expectancy before treatment. She discontinued the treatment against medical advice.

Pilocytic Astrocytoma. There was a single patient with terminal pilocytic astrocytoma who qualified for this review. He was a 3-year-old male with less than a year history of the disease. His tumor relapsed after two surgical procedures and his life expectancy was less than 6 months.

Patient was treated as described above. In brief, patient received AS and TT at study site wherein the TT was bevacizumab, pazopanib, dasatinib, and everolimus. The patient had a pilocytic astrocytoma of unusual aggressiveness. He accomplished CR. There were no OR's in the Phase 2 study with AS and A10 and no data on targeted therapy. The mutated genes affected by AS included: PIK3CA Q546R and PIK3CA K567E. Patient survived over 12 months compared to the estimated survival of less than 6 months before treatment and had marked symptomatic improvement. The parents decided to discontinue the treatment.

Pleomorphic Carcinoma. There was a single patient who qualified for this review. She was 50 years of age and had a 27-year history of her disease. Her sarcoma was widely metastatic to the lymph nodes, lungs and bones. She failed two surgical procedures, radiation and chemotherapy and her estimated survival was less than 3 months.

Patient was treated as described above. In brief, patient received AS and TT at study site wherein the TT was pembrolizumab, bevacizumab, pazopanib, and dasatinib and CH was gemcitabine, docetaxel. The patient accomplished PR. There are no data on the clinical study with AS and A10 or for comparison with targeted therapy. Mutated genes affected by AS included: TP53 R249T and TP53 c.97-28_99 del. The patient survived 12 months compared to the less than 3 months estimated before the treatment.

PNET. There was a single patient diagnosed with terminal primitive neuroectodermal tumor, Stage IV, who qualified for this review. She was also described in the Lung Cancer section. The patient was a 23-year-old female with an approximate 2-year history of the disease which spread to the lymph nodes, bones and thyroid. She failed surgery, radiation and chemotherapy and her life expectancy was less than 6 months.

Patient was treated as described above. In brief, patient received AS and TT at study site wherein the TT was nivolumnab and bevacizumab. She accomplished PR of the largest right clavicular mass but there was new hypermetabolic activity in the left sacrum and ilium. There were no cases of neuroendocrine carcinoma treated in Phase 2 clinical studies or by targeted therapy for comparison. The mutated gene affected by AS was EWSR1-FLI1 fusion.

The patient survived over 6 months compared to the less than 6-month life expectancy before treatment. She discontinued the treatment against medical advice.

Refractory Anemia. There was only a single patient with this diagnosis who was also described in the MDS section. He was 72 years of age and had a 3-year history of the disease. He was not treated before and his life expectancy was less than 6 months.

Patient was treated as described above. In brief, patient received AS and TT at study site wherein the TT was ruxolitinib and vorinostat. The patient accomplished PR. There are no data for comparison with the results of clinical studies and treatment with targeted therapy. AS-affected mutated genes included: BRACA2 12040V, HIST1H1D K185-A186>T, MAP3K6 P646L, NOTCH2 52379F, SPEN A2510V, STAT5B R110H, TET2 C1875G, MPL Y591 D, RUNX1 R107C, ASXL1 R1273f*7, SRSF2 P95H. The patient survived over 26 months compared to the estimated less than 6 months before the treatment. He died from cerebral hemorrhage.

Salivary Gland Cancer. There was a single patient diagnosed with terminal mucoepidermoid carcinoma of the submandibular gland, Stage IV. His case was also described in the Head and Neck Cancer section. He was 54 years of age and had approximately 2 years history of the disease. He had widely spread metastatic disease to the lymph nodes, lungs and liver. He was treated with two surgeries, two different types of chemotherapy and two different targeted therapies as well as radiation therapy. His life expectancy was estimated at less than 2 months.

Patient was treated as described above. In brief, patient received AS and TT at study site wherein the TT was pembrolizumab, trastuzumab, paclitaxel, and carboplatin DAMA. The patient accomplished PR. There are no data for comparison with the results of clinical studies and targeted therapy. Mutated genes affected by AS included: ARID1A and GNAQ. The patient survived more than 12 months over the estimated less than 2 months before the treatment. He also obtained marked symptomatic improvement. He discontinued the treatment against medical advice.

Skin Cancer. There was a single case of terminal squamous cell carcinoma of the skin who qualified for this review. He was 70 years of age and had a year history of his disease. It was thought that the cancer developed as the result of immunosuppression necessary to maintain his kidney transplant for polycystic disease. His cancer rapidly relapsed after surgical resection and he had no curative options available due to his overall condition. His survival was estimated as less than 3 months.

Patient was treated as described above. In brief, patient received AS and TT at study site wherein the TT was A10, ipilimumab, cetuximab, rucaparib and RT. The patient accomplished PR of a very large and aggressive tumor. There are no data for comparison with the results of clinical studies of AS and A10 or with targeted therapy. Mutated genes affected by AS included decreased expression of GNAS R201H*, ND of PDGFRA E86A, APC E918E, TP53 H179Y, ARID1A S1167F, METT7591, NOTCH1 V220M. The patient survived 12 months compared to the estimated less than 3 months before the treatment started. He died from pneumonia.

Stomach Cancer. There was a single patient diagnosed with terminal adenocarcinoma of the stomach, Stage IV, who qualified for this review. He was 69 years of age and had a one-year history of the disease. He was treated with chemotherapy but developed progressive peritoneal metastases. His survival was estimated at less than 6 months.

Patient was treated as described above. In brief, patient received AS and TT at study site wherein the TT was vorinostat; CH was oxaliplatin, 5-fluorouracil DAMA. The patient accomplished CR. There are no data for comparison with the results of clinical studies of AS and A10 or with targeted therapy. The mutation affected by AS included ND-EGFR V7421. The patient discontinued the treatment after 3 months against medical advice. He was in remission and free from symptoms.

Synovial Sarcoma. There was a single patient with this diagnosis who qualified for this review. Her case was described in the section on Pleomorphic Sarcoma. She was 50 years of age and had a 27-year history of her disease. Her sarcoma was widely metastatic to the lymph nodes, lungs and bones. She failed two surgical procedures, radiation and chemotherapy and her estimated survival was less than 3 months.

Patient was treated as described above. In brief, patient received AS and TT at study site wherein the TT was pembrolizumab, bevacizumab, pazopanib, dasatinib, gemcitabine, and docetaxel. The patient accomplished PR. There are no data on the clinical study with AS and A10 or for comparison with targeted therapy. Mutated genes affected by AS included: TP53 R249T and TP53 c.97-28_99 del. The patient survived 12 months compared to the less than 3 months estimated before the treatment.

T-Cell Lymphoma. There was a single patient diagnosed with terminal T-cell lymphoma with peritoneal and brain involvement who qualified for this review. He was a 45-year-old male with a 3-year history of his disease. He failed two types of chemotherapy, three types of targeted therapy and two bone marrow transplants and he was not given any further options for successful treatment. His survival was estimated as less than 2 months.

Patient was treated as described above. In brief, patient received AS and RT at study site. The patient accomplished PR with the contribution of radiation therapy. There are no data for comparison of the results from clinical studies of AS and A10 or for targeted therapy. Mutated genes affected by AS included: CDKN1B K59fs*, RB1 Y173fs*, TP53 K320*. The patient discontinued the treatment against medical advice after 4 months.

Thyroid Cancer. There was a single patient diagnosed with terminal carcinoma of the thyroid, Stage IV, who qualified for this review. He was a 71-year-old male who had an 11-year history of the disease. He was treated with surgery and radiation therapy and his life expectancy was less than 6 months. His cancer metastasized to the lymph nodes and lungs.

Patient was treated as described above. In brief, patient received AS and TT at study site wherein the TT was lenvatinib, everolimus, and dasatinib. The patient accomplished PR. There are no data for comparison of the results with the responses from clinical studies of AS and A10 or for targeted therapy. The mutated gene which was possibly affected by AS was MET F462F. The patient survived over 21 months and was taking maintenance treatment.

Urothelial Cancer. There were two patients diagnosed with terminal high-grade urothelial carcinoma, stage IV, who qualified for this review. There was a female and a male in the age range of 57 to 73 and a one to eight-year history of the disease. There were metastases to the lymph nodes and lungs in both. One patient also had metastases to the bones and brain. One of the patients had extensive prior treatments with two surgeries, two chemotherapies and two targeted therapies and the other was not treated before. The estimated survival was from less than 2 months to less than 6 months.

Patients were treated as described above. In brief, patients received AS and TT at study site wherein the TT is described in Table 40. There was a 33% decrease of size of brain metastases in one patient classified as MR. The second patient accomplished PR. There are no data for comparison with clinical studies of AS and A10 or for targeted therapy. Table 40 lists mutated genes affected by AS.

TABLE 40

Evaluable Patients Treated with Antineoplaston AS-1 in Combination with Other Drugs Invasive, High-Grade Urothelial Carcinoma, Stage IV.

| Patient | Radiological and by PE | Molecular Genes Affected By AS | Treatment at BC (Study Site) |
|---|---|---|---|
| 1UR | MR | ND - BRAF amplification, Decrease of TERT, Promoter SNV, TP53 T253A, ERRB2 amplification | TT at BC: AS, ado-trastuzumab emtansine, trastuzumab, tucatinib, RT, CH at BC: capecitabine, DAMA |
| 2UR | PR | Decrease of KRAS (G12D) | TT at BC: AS, nivolumab, ipilimumab, DAMA |

Both patients discontinued the treatment against medical advice. One of them survived over 14 months compared to less than 2 months before treatment. The second patient discontinued the treatment after 4 months.

Part III—All Evaluable Patients.

Radiological Responses and Survival. The total of 155 evaluable patients were treated at Burzynski Clinic under RTT from Jul. 15, 2015 to Jul. 15, 2020 by using a combination of AS, A10 and other treatments. The largest diagnostic group of glioblastoma and a small group of patients with brainstem glioma, without pathology diagnosis, are described separately. The patients treated only with AS/A10 are evaluated separately. There was also a group of three patients diagnosed with rare brain tumors whose best response was SD which was also described separately. Exclusion of these patients limits the number of patients in this review to 75. Both sexes were equally represented. There were 6 children, 8 young adults and 61 adult patients. Four ethnic groups were represented with 76% of patients in the Caucasian group. A group of 10 patients were diagnosed with more than one malignancy. This would add eight additional diagnostic groups increasing the number of cancer diagnoses to 34. They include chronic atypical myelogenous leukemia, Ewing sarcoma, leptomeningeal carcinomatosis (3 patients), myelofibrosis, neuroendocrine carcinoma, PNET, refractory anemia, and synovial sarcoma. The largest number of patients carried the diagnosis of breast cancer followed by colorectal, lung, head and neck, ovarian and prostate cancers. The patients received the average from 219 to 295 days of treatment with AS and A10 (Table 41).

TABLE 41

Duration and Response to Treatment of All Evaluable Patients.

| DURATION | | | | |
|---|---|---|---|---|
| BC treatment (days between first and last dose, including days OFF) | <21 | <=40 | >40 | all |
| Median | 271 | 219 | 295 | 266 |
| Average | 275 | 256 | 336 | 330 |
| Range | 89-477 | 118-490 | 63-1183* | 63-1183* |
| RESPONSE | | | | |
| Response | <21 | <=40 | >40 | Total |
| CR | 1 | 2 | 20 | 23 |
| PR | 2 | 4 | 21 | 27 |
| MR | 2 | | 15 | 17 |
| SD | | 1 | 3 | 4 |
| PD | 1 | 1 | 2 | 4 |
| Total | | | | 75 |

TABLE 41-continued

Duration and Response to Treatment of All Evaluable Patients.

| | | | | |
|---|---|---|---|---|
| CR | 1.3% | 2.7% | 26.6% | 30.6% |
| PR | 2.7% | 5.3% | 28.1% | 36.1% |
| MR | 2.7% | | 20.0% | 22.7% |
| SD | | 1.3% | 4.0% | 5.3% |
| PD | 1.3% | 1.3% | 2.7% | 5.3% |
| Total | | | | 100.0% |

Figure 1:
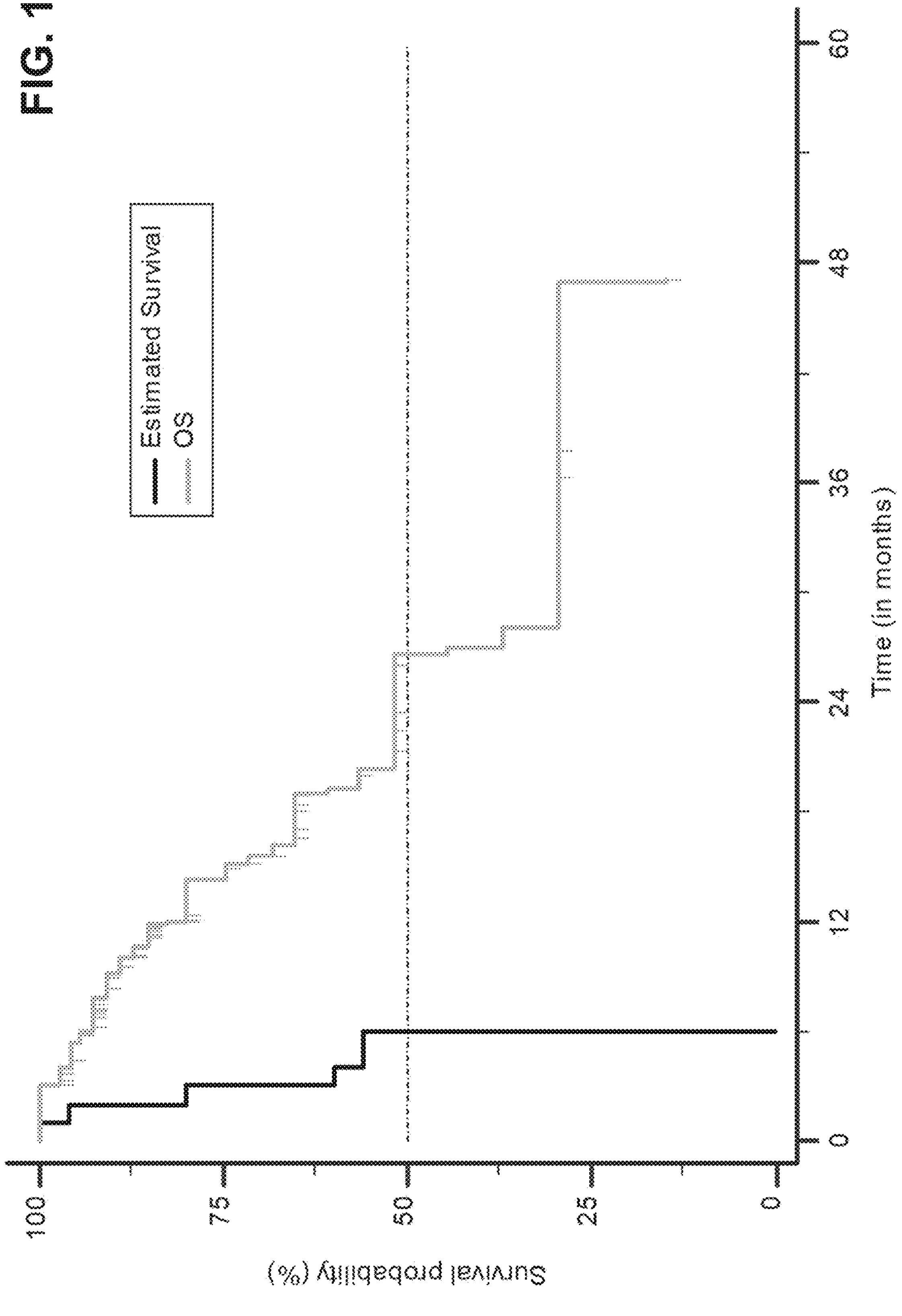
FIG. 1 shows a Kaplan-Meier survival curve for all evaluable, terminal cancer patients treated with or without AS therapy.

In most cases, the additional medications were selected based on data from genomic analysis or data coming from medical literature. The objective response rate, which included CR, PR and MR, was very high and equal to 85.4%. Stable disease was determined in 9.3% and progressive disease in 5.3%. The survival analysis revealed 94.4% survival at 6 months, 80.3% at 1 year and 51.8% at 2 years compared to the estimated no survival at 6 months without this treatment (FIG. 1).

Figure 2:
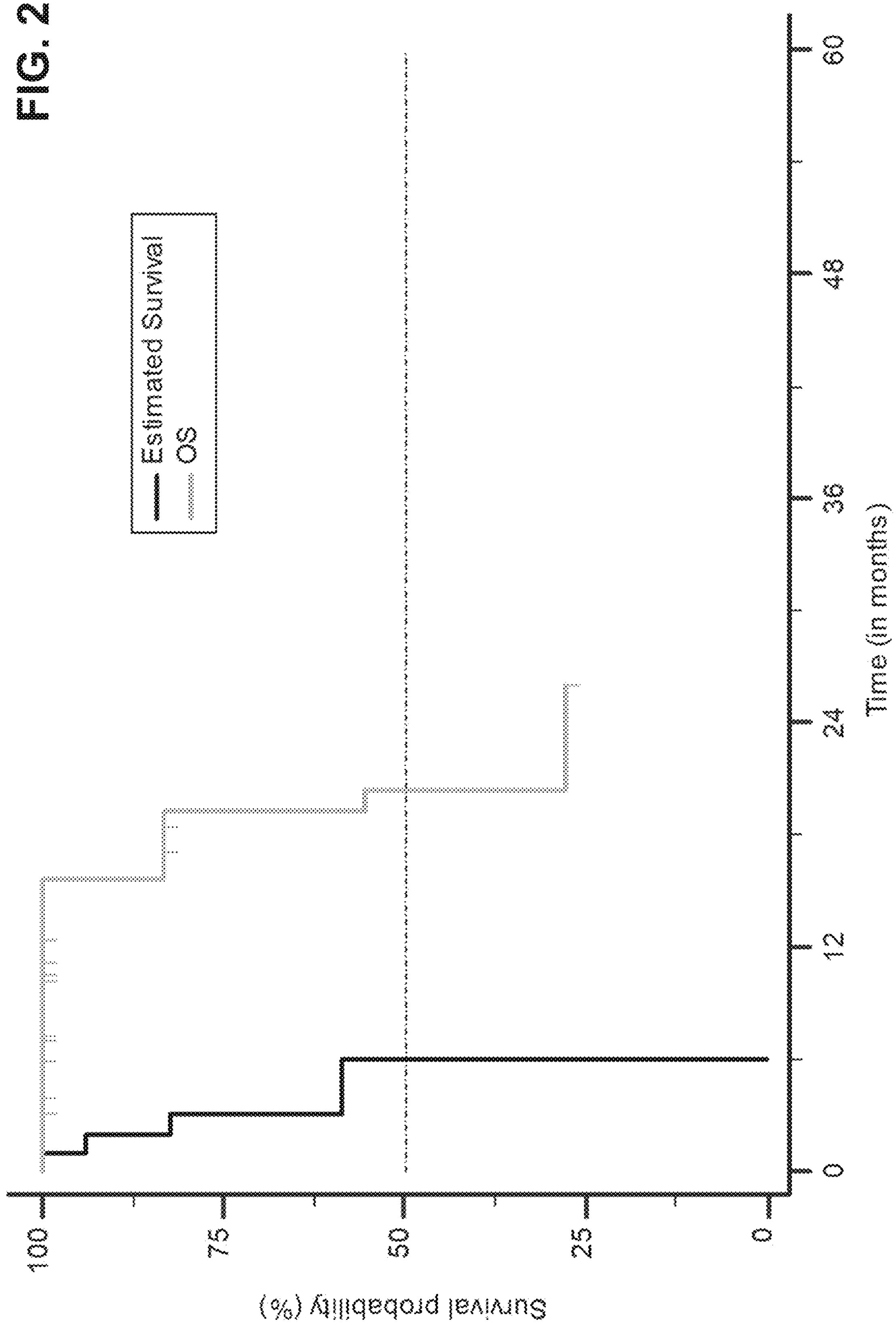
FIG. 2 shows a Kaplan-Meier survival curve for evaluable, terminal cancer patients treated with or without AS therapy wherein the patients were diagnosed as having head and neck, kidney, ovarian, pancreatic, or prostate cancer (e.g., common cancers excluding BE, CL, and LU).

The results of treatment of common cancers excluding breast, colorectal and lung (described separately) and including head and neck, kidney, ovarian, pancreatic, and prostate cancer are illustrated by FIG. 2. Survival at 6 months was 100%, 1 year was 100% and 2 years was 27.8%.

Figure 3:
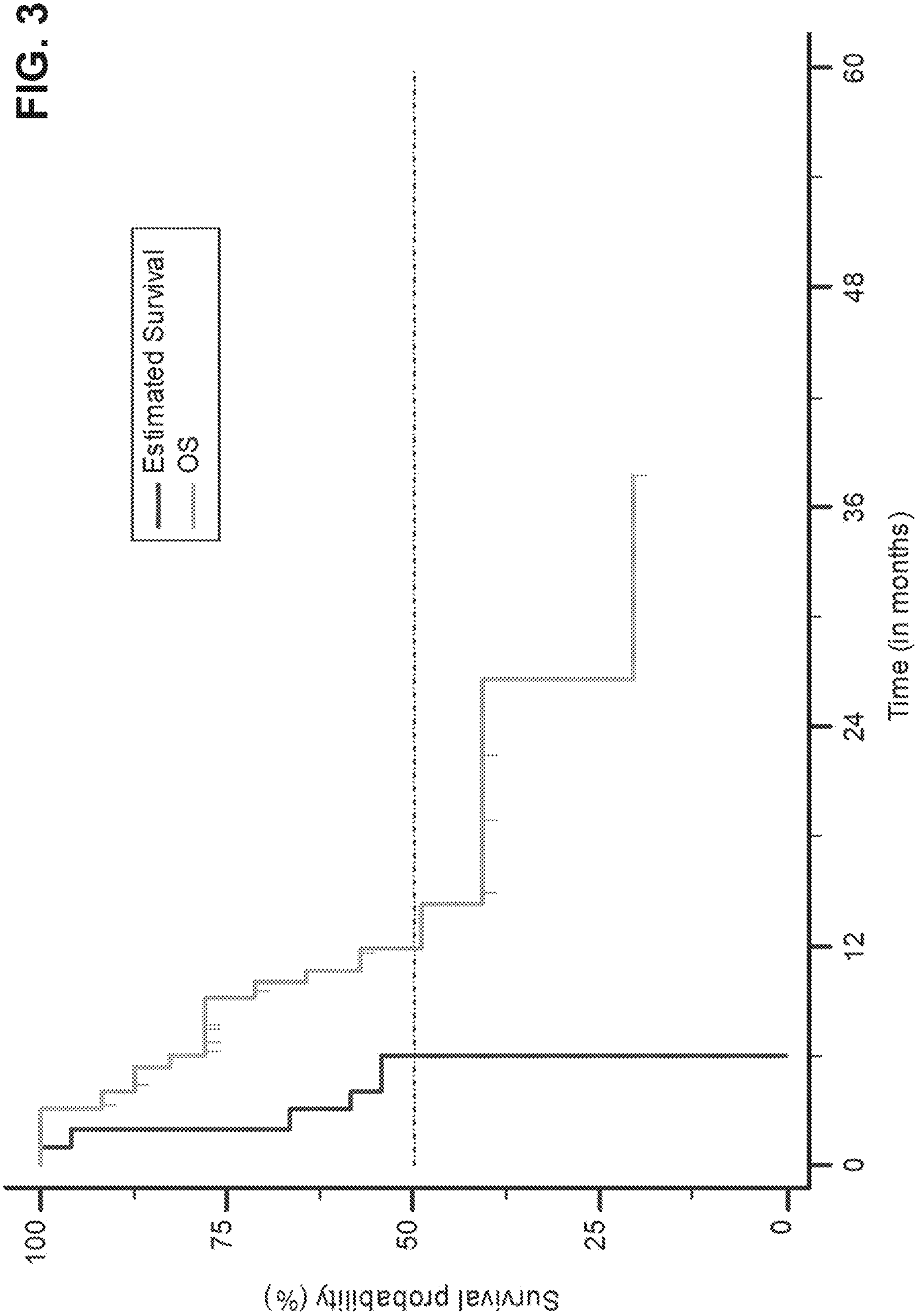
FIG. 3 shows a Kaplan-Meier survival curve for evaluable, terminal cancer patients treated with or without AS therapy wherein the patients were diagnosed as having an uncommon cancer. Patients with multiple diagnoses are listed only once.

The group of 24 patients with uncommon cancers was evaluated separately. The details are shown in FIG. 3. There were 6 pediatric cases, 17 males and 7 females in this group. The average duration of treatment was 295 days. CR was documented in 16.7%, PR in 37.5%, MR in 29.2%, SD in 8.3% and PD in 8.3%. The total objective response rate was 83.4%. Overall survival at 6 months was 77.8%, at one year it was 48.9% and at 2 years it was 20.4%.

Molecular Responses. In addition to radiological response, the second goal of the treatment was to accomplish molecular response indicated by no longer detectable abnormal genes or marked decrease of the concentration of the DNA of these genes in blood tests such as Guardant 360, Foundation One or Tempus. Based on laboratory results the listing of the genes affected by AS is provided in Table 1. Table 42 provides alphabetic listing of 152 specific genomic abnormalities including mutations and amplifications which were affected by AS in different diagnostic groups based on clinical results. This is a more detailed listing than in Table 1 of the genes affected by ANP in laboratory tests. For instance, instead of a single abnormality of TP53, there are 25 mutations of this gene based on clinical observation. Contrary to prescription targeted drugs which typically affect a single mutation of the genes, AS seems to have a broad spectrum of activity which covers numerous mutations and amplifications.

TABLE 42

Gene Abnormalities Affected by Antineoplastons
Based on Clinical Results in All Cancers.

Mutations of ALK
N1544K - Ovarian Cancer
Mutations of AKT1
E17K - Breast Cancer
Mutations of APC
G29G - Breast Cancer
K445K - Breast Cancer
E918E - Squamous Cell Carcinoma of the Skin
E888fs - Colorectal Cancer
R230C - Colorectal Cancer
Mutations of AR
M887V - Ovarian Cancer
Mutations of ARAF
Y495Y - Breast Cancer
Mutations of ARID1A
51798L - Breast Cancer, Salivary Gland Cancer,
Head & Neck
S1167F -Squamous Cell Carcinoma of the Skin
G246V - Ovarian Cancer
R1889W - Ovarian Cancer
Q802fs - Colorectal Cancer
Mutations of AR1D2
N127fs18 - Anaplastic Astrocytoma
Mutations of ASXL1
R1273f*s - Chronic Atypical Myelogenous Leukemia
Mutations of ATRX
S850fs*2 -Anaplastic Astrocytoma
N179fs*26 - Anaplastic Astrocytoma
Mutations of BRACA1
H662Q - Breast Cancer
Mutations of BRACA2
D237N - Breast Cancer
12040V - Chronic Atypical Myelogenous Leukemia
Mutations and amplifications of BRAF
BRAF amplification - Urothelial Carcinoma & Ovarian Cancer
E264 - Esophagus
V600E - Colorectal Cancer
Mutations and amplifications of CCND1
Mutations of MAP3K6
P646L - Chronic Atypical Myelogenous Leukemia
Mutations of MET
T895M - Breast Cancer
T7591 -Squamous Cell Carcinoma of the Skin
Mutations of MPL
Y591D - Chronic Atypical Myelogenous Leukemia
Mutations and amplifications of MYC
Amplifications - Breast Cancer & Ovarian Cancer
S244S - Breast Cancer
Mutations of NF1
Splice cite 480-11_4801del11 - Breast Cancer
Splice cite SNV - Lung Cancer
c.6655 > T - Ganglioglioma
p.D2219Y - Ganglioglioma
A2617A - GIST
F710C - Cholangiocarcinoma
V2378fs*8 - Diffuse Astrocytoma
I1719T - Esophagus
K583R - Ovarian Cancer
Mutations of NOTCH1
A465V - GIST
V220M - Squamous Cell Carcinoma of the Skin
Mutations of NOTCH2
52379F - Chronic Atypical Myelogenous Leukemia
Mutations of NOTCH2
52379F - Chronic Atypical Myelogenous Leukemia
Mutations of NTRK1
Ovarian Cancer
P387L (possibly) - Lung Cancer
Mutations of PDGFRA
V299G - Breast Cancer
E86A - Squamous Cell Carcinoma of the Skin
Mutations and amplifications of PIK3CA
Q546H - Breast Cancer
Q546R - Pilocytic Astrocytoma
Q597H - Ovarian Cancer
Amplification - Breast Cancer TABLE 42-continued Gene Abnormalities Affected by Antineoplastons Based on Clinical Results in All Cancers.

Amplification - Breast Cancer
R291W - Ovarian Cancer
Mutations and amplifications of CCND1
Amplification - Breast Cancer
R291W - Ovarian Cancer
Mutations of CCNE1
P268P - Breast Cancer
CDK4 amplifications - Breast Cancer
Mutations and amplifications of CDK6
Breast Cancer
Mutations of CDKN1B
K59fs* - T-Cell Lymphoma
Mutations of CDKN2A
D74N - Breast Cancer
Mutations and amplifications of EGFR
Amplification - Breast Cancer
P753L (possibly) - Lung Cancer
V524I - Breast Cancer
Mutations and amplifications of EGFR
Amplification - Breast Cancer
P753L (possibly) - Lung Cancer
V524I - Breast Cancer
V7421 - Stomach Cancer
D321D - Colorectal Cancer
Mutations and amplifications of ERRB2
amplification - Urothelial Carcinoma
C584G - Esophagus
Mutations of EWSR1
FLI1 fusion - Ewing Sarcoma & Lung Cancer
Mutations of FBXW7
Y545C - Lung Cancer
Mutations and amplification of FGFR
Amplification - Breast Cancer
T320T - Breast Cancer
S726F - Breast Cancer
H791H - Breast Cancer
P47P - Breast Cancer
Mutations and amplifications of FGFR1
Amplifications - Breast Cancer
S726F - Breast Cancer
Mutations of GATA 3
P433fs43 - Breast Cancer
P409fs - Breast Cancer
PS405fs - Breast Cancer
D336fs - Breast Cancer
c.1213_1214del - Breast Cancer
Multiplication - Head & Neck
Mutations of GNAQ
Salivary Gland Cancer
Head & Neck
Mutations of GNAS
R201H* - Squamous Cell Carcinoma of the Skin
Mutations of H3F3A
K28N - DIPG
K27 - DIPG
Mutations of HIST1H1D
K185-A186 > T- Chronic Atypical Myelogenous Leukemia
Mutations of IDH1
R132H - Anaplastic Oligodendroglioma & Anaplastic Astrocytoma
Mutations of KDMGA
loss - Breast Cancer
Mutations of KRAS
G12V - Cholangiocarcinoma
G12D - Urothelial Carcinoma & Esophagus
G13D - Colorectal Cancer
Mutations of MAP2K1
E542K - Breast Cancer & Colorectal Cancer
E545K - Breast Cancer
E726K - Breast Cancer
E39K - Breast Cancer
E453K - Breast Cancer & Anaplastic Oligodendroglioma
R4-P18del - Breast Cancer
H1047L - Breast Cancer
K567E - Pilocytic Astrocytoma
Amplification - Ovarian Cancer
115431 - Colorectal Cancer
Mutations of PIK3R1
S399Y408del splice site 917-1G > A - Anaplastic Oligodendroglioma
Mutations of PTEN
C136Y - DIPG
Loss exons 4-7 - Breast Cancer
D252Y - Breast Cancer
R130* - Breast Cancer
Y27C - Breast Cancer
N323fs*23 - Diffuse Astrocytoma
R55fs - Colorectal Cancer
Mutations of RAF1
P63P - Breast Cancer
Amplification - Ovarian Cancer
Mutations of RB1
O217* - Breast Cancer
Y173fs* -T-Cell Lymphoma
Mutations of RUNX1
R107C - Chronic Atypical Myelogenous Leukemia
Mutations of SMAD4
A406T - Lung Cancer D537V - Colorectal Cancer P511L - Ovarian Cancer
Mutations of SPEN
A2510V - Chronic Atypical Myelogenous Leukemia
Mutations of SRSF2
P95H - Chronic Atypical Myelogenous Leukemia
Mutations of STAT5B
R110H - Chronic Atypical Myelogenous Leukemia
Mutations of Tert promoter
SNV - Lung Cancer and Urothelial Carcinoma
124 C > T - Diffuse Astrocytoma
146C > T - Anaplastic Oligodendroglioma
Mutations of TET2
C1875G - Chronic Atypical Myelogenous Leukemia
Mutations of TP53
V73fs - Breast Cancer
R175G - Breast Cancer
R196 - Breast Cancer
R249T- Pleomorphic Sarcoma
C176F - Breast Cancer
G187D - Breast Cancer
R282W - Breast Cancer & Colorectal Cancer
E287* - Breast Cancer
E285K - Breast Cancer
c.97-28_99del - Pleomorphic Sarcoma
Y126D - Lung Cancer
R273H - Lung Cancer & Anaplastic Astrocytoma & Colorectal Cancer
K320* -T-Cell Lymphoma
T253A - Urothelial Carcinoma
Splice site 37G-1G > A - Anaplastic Oligodendroglioma
O104 - Esophagus
P151H - Esophagus TABLE 42-continued

| Gene Abnormalities Affected by Antineoplastons Based on Clinical Results in All Cancers. | |
|---|---|
| K57E - Breast Cancer | H179Y -Squamous Cell Carcinoma of the Skin |
| Mutations of MAP2K4 | R273C - Anaplastic Astrocytoma |
| Loss exon 2 - Breast Cancer | R248W - Ovarian Cancer |
| Mutations of MAP3K1 | R176H - Ovarian Cancer |
| S398 - Breast Cancer | R209fs - Ovarian Cancer |
| | N235-Y236del - Ovarian Cancer |
| | C176Y - Colorectal Cancer |
| | S241F - Colorectal Cancer |

Toxicity. The adverse events possibly related to AS and A10 occurred in a small percentage of patients and were only Grade 1 and 2 (minor toxicity). The adverse events possibly related to the additional drugs were less common compared to the published data due to reduced dosages resulting from synergistic effects. The details are described in a separate report.

Conclusions and Discussion of Example 1

This study provided results of treatment of 75 terminal cancer patients diagnosed with 34 different malignancies. The report was limited to evaluable cases. Some patients were close to death on admission and died from cancer or additional medical complications within the first 60 days before the treatment could take effect. The other group of patients discontinued the treatment for personal reasons or was not willing to have radiology evaluation of the results. Such cases were not included in this report and were described separately. In the glioblastoma group, the patients who were on the treatment less than 30 days are also evaluated based on rapid responses in these patients. All patients were treated under the Texas Right to Try Law. The treatment plans were formulated based on genomic analysis or genomic published data. The principle was to treat “cancer” genes and remove them from the patient’s body.

The reported results of this treatment were better than expected and the average number of patients who accomplished objective responses are 85%. The aim of this report was to prove the validity of the hypothesis that targeting abnormal genes can lead to the objective reduction of tumor size and extend the patient’s life. A number of patients had many years of history of cancer and their disease had heterogenous genomics depending on the site of metastasis. This could explain CR of one site and no response in the other. Such cases would not be described in rigorous clinical trials as CR’s, but on the other hand terminal cancer patients are typically not admitted to clinical trials. A summary of the response rates for terminal cancer patients treated with antineoplastons in combination with prescription medications/standard-of-care/off label under the Texas right to try from Jul. 15, 2015 to Apr. 1, 2021 according to the methods of Example 1 are provided in Tables 43-50.

TABLE 43

Common Cancer Diagnoses.

| Diagnosis | CR + PR % | MR % | SD % | PD % |
|---|---|---|---|---|
| Breast | 84 | 8 | 8 | |
| Colorectal | 50 | 40 | 10 | |
| Head & Neck | 33 | 33 | | 34 |
| Kidney | 66 | 33 | | |
| Lung | 71 | 29 | | |

TABLE 43-continued

Common Cancer Diagnoses.

| Diagnosis | CR + PR % | MR % | SD % | PD % |
|---|---|---|---|---|
| Ovarian | 66 | 34 | | |
| Pancreatic | 66 | 34 | | |
| Prostate | 83 | | | 17 |
| Total | 71 | 21 | 5 | 3 |

Tumors were gone or shrunk in 92% of the total cases and progressed in 3%; Glioblastoma is not included.

TABLE 44

Uncommon Cancer Diagnoses.

| Diagnosis | CR + PR (Number of Cases) | MR | SD | PD |
|---|---|---|---|---|
| Adenoid Cystic Carcinoma | | | 1 | |
| Brain Tumor - Anaplastic Astrocytoma | 2 | | | 1 |
| Brain Tumor - Anaplastic Ependymoma | 1 | | | |
| Brain Tumor - Anaplastic Oligodendroglioma | | 1 | | 1 |
| Brain Tumor - Brainstem Glioma | 1 | | | |
| Brain Tumor - Diffuse astrocytoma | 1 | | | |
| Brain Tumor - DIPG | 1 | 2 | | |
| Brain Tumor - Ganglioglioma | 1 | | | |
| Brain Tumor - Medulloblastoma | 1 | 1 | | |
| Brain Tumor - Pilocytic Astrocytoma | 1 | | | |
| Cholangiocarcinoma | | 2 | | |
| Chronic Atypical Myelogenous Leukemia | | 1 | | |
| Endometrial Carcinoma | | 1 | | |
| Esophageal Cancer | | 1 | 1 | |
| Ewing Sarcoma | 1 | | | |
| GIST | | 1 | | |
| Leptomeningeal Carcinomatosis | 2 | 2 | | |
| Multiple Myeloma | | 1 | | |
| Myelodysplastic Syndrome | 1 | | 1 | |
| Neuroendocrine Carcinoma | 1 | | | |
| Non-Hodgkin’s Lymphoma | 1 | | | |
| Pleomorphic Sarcoma | 1 | | | |
| PNET | 1 | | | |
| Refractory Anemia | 1 | | | |
| Salivary Gland Carcinoma | 1 | | | |
| Skin Cancer | 1 | | | |
| Stomach Cancer | 1 | | | |

TABLE 44-continued

Uncommon Cancer Diagnoses.

| Diagnosis | CR + PR | MR | SD | PD |
|---|---|---|---|---|
| | Number of Cases | | | |
| Thyroid Cancer | 1 | | | |
| Urothelial High-Grade Cancer | 1 | 1 | | |
| Total of 29 diagnoses in 42 cases Percentage of Responses | 55% | 33.3% | 7% | 4.7% |

Tumors were gone or shrunk in 88.3% of the total cases and progressed in 4.7%.

TABLE 45

Subgroups of Breast Cancer.

| | Responses % | | | |
|---|---|---|---|---|
| Subgroup | CR + PR | MR | SD | PD |
| Breast Cancer HER-2 Neg. | 80 | 13.4 | | 6.6 |
| Breast Cancer HER-2 Pos. | 100 | | | |
| Breast Cancer Triple Negative | 67 | | 33 | |

TABLE 46

Subgroups of Glioblastoma.

| | Responses % | | | | |
|---|---|---|---|---|---|
| Subgroup | CR + PR | MR | SD | PD | Tumor reduction or tumor gone from MRI |
| GBM recurrent after SOC | 52 | 4 | 22 | 22 | 56 |
| GBM recurrent after SOC Less than 60 days of treatment | 40* | | | 60* | 40* |
| GBM - no SOC | 43 | 14 | | 43 | 57 |
| GBM - no SOC Less than 60 days of treatment | 100* | | | | 100* |

SOC—standard-of-care;
*Small number of patients

TABLE 47

Brain Cancer, Metastatic.

| | Patient Number | | | | |
|---|---|---|---|---|---|
| Primary Tumor | All | CR + PR | MR | SD | PD |
| Breast Cancer | 9 | 7 | | 1 | 1 |
| Kidney Cancer | 2 | 2 | | | |
| Lung Cancer | 3 | 2 | 1 | | |
| Prostate Cancer | 1 | 1 | | | |
| Biliary Tract | 1 | | 1 | | |
| Urothelial, High-Grade | 1 | | 1 | | |
| | Responses % | | | | |
| ALL | 17 | 70 | 18 | 6 | 6 |

Tumors were gone or shrunk in 86% of the total cases and progressed in 6%.

TABLE 48

Liver Cancer, Metastatic.

| | Patient Number | | | | |
|---|---|---|---|---|---|
| Primary Tumor | All | CR + PR | MR | SD | PD |
| Adenoid Cystic Cancer | 1 | | | 1 | |
| Breast Cancer | 8 | 4 | 1 | 2 | 1 |
| Colorectal Cancer | 6 | 3 | 1 | 2 | |
| Endometrial Cancer | 1 | | 1 | | |
| Head & Neck Cancer | 1 | 1 | | | |
| Lung Cancer | 2 | 1 | 1 | | |
| Ovarian Cancer | 4 | 4 | | | |
| Pancreatic Cancer | 1 | 1 | | | |
| Biliary Tract Cancer | 2 | | 2 | | |
| Esophageal Cancer | 1 | 1 | | | |
| | Responses % | | | | |
| ALL | 27 | 56 | 22 | 18 | 4 |

Tumors were gone or shrunk in 78% of the total cases and progressed in 4%.

TABLE 49

Bone Cancer, Metastatic.

| | Patient Number | | | | |
|---|---|---|---|---|---|
| Primary Tumor | All | CR + PR | MR | SD | PD |
| Breast Cancer | 18 | 6 | 5 | 6 | 1 |
| Colorectal Cancer | 1 | | | 1 | |
| Lung Cancer | 5 | 2 | 1 | 1 | 1 |
| Prostate Cancer | 3 | 2 | | | 1 |
| Sarcoma | 1 | | 1 | | |
| Urothelial Cancer | 1 | | | 1 | |
| | Responses % | | | | |
| ALL | 29 | 35 | 24 | 31 | 10 |

Tumors were gone or shrunk in 59% of the total cases and progressed in 10%.

TABLE 50

| Lung Cancer, Metastatic. | | | | | |
|---|---|---|---|---|---|
| | Patient Number | | | | |
| Primary Tumor | All | CR + PR | MR | SD | PD |
| Breast Cancer | 8 | 2 | 1 | 4 | 1 |
| Colorectal Cancer | 5 | 2 | 1 | 2 | |
| Endometrial Cancer | 1 | | 1 | | |
| Head & Neck Cancer | 3 | 1 | | 1 | 1 |
| Lung Cancer with Metastases to the Lung | 4 | 2 | 2 | | |
| Ovarian Cancer | 3 | 3 | | | |
| Prostate Cancer | 1 | 1 | | | |
| Sarcoma | 1 | | 1 | | |
| Thyroid Cancer | 1 | 1 | | | |
| Urothelial Cancer | 2 | 1 | | 1 | |
| | Responses % | | | | |
| ALL | 29 | 45 | 21 | 27 | 7 |

Tumors were gone or shrunk in 66% of the total cases and progressed in 7%.

It may be necessary to study the genomics of non-responding tumors and use additional drugs to affect them. Unfortunately, there may not be enough time to do it in terminal patients. Inclusion of patients who had CR in some metastases but not in all metastases increased the number of objective responses. For instance, in breast cancer all patients responded to the treatment. For comparison purposes, cases from the group which received less than 60 days of treatment were added. In this expanded group the response in breast cancer was reduced to 84.7%. The survival analysis revealed 94.4% survival at 6 months versus the estimated no survivors for terminal cancer patients. The survival rate decreased to 51.8% at 2 years. This drop in the survival rate can be explained by many patients deciding to discontinue the treatment after determination of CR.

Example 2

A 54-year-old Caucasian female presented to Burzynski Clinic for AS2-1 treatment on Jun. 28, 2016 and was diagnosed with invasive ductal carcinoma, $ER^+$, $PR^-$, HER-$2^+$ with metastases to the liver, stage IV. The history of her cancer 15 years before. In December 2001 she underwent left lumpectomy and was followed with doxorubicin/cyclophosphamide chemotherapy (January 2002-March 2002) and docetaxel/trastuzumab (March 2002-June 2002). Trastuzumab continued until June 2003. From June to August 2002, she received radiation therapy to the left breast. She also took tamoxifen for 6 months. In 2005 she underwent a hysterectomy and in 2007 she had a bilateral scalpingo-oophorectomy. In August 2012 she developed liver involvement and CT of Oct. 12, 2012 documented numerous liver metastases. Liver biopsy on Oct. 22, 2012 confirmed metastatic breast cancer. Follow-up PET on Oct. 31, 2012 confirmed these findings. On Nov. 6, 2012 she commenced docetaxel, trastuzumab and pertuzumab and completed 6 cycles. The 7th cycle was without docetaxel. She obtained moderate improvement. In August of 2015 she developed progressive disease and resumed docetaxel, trastuzumab and pertuzumab for 3 cycles; the last cycle without docetaxel through Oct. 15, 2015. In February 2016 her cancer progressed again. From May 26, 2016-Jun. 30, 2016 she was treated with sodium phenylbutyrate with symptomatic improvement and on Jun. 16, 2016 received trastuzumab/pertuzumab at 80% dose reduction.

Treatment: Her treatment at Burzynski Clinic started on Jun. 29, 2016 with AS2-1. The dose was gradually increased to 19.2 g daily. She continued trastuzumab/pertuzumab according to her previous schedule and added capecitabine 2500 mg daily in 2 weeks on and 1 week off cycles. She decided to discontinue the treatment against medical advice on Apr. 20, 2017. The last contact with her was on Feb. 28, 2018. Her treating physician informed us in October 2019 that she was doing reasonably well but developed recurrence.

Figure 4:
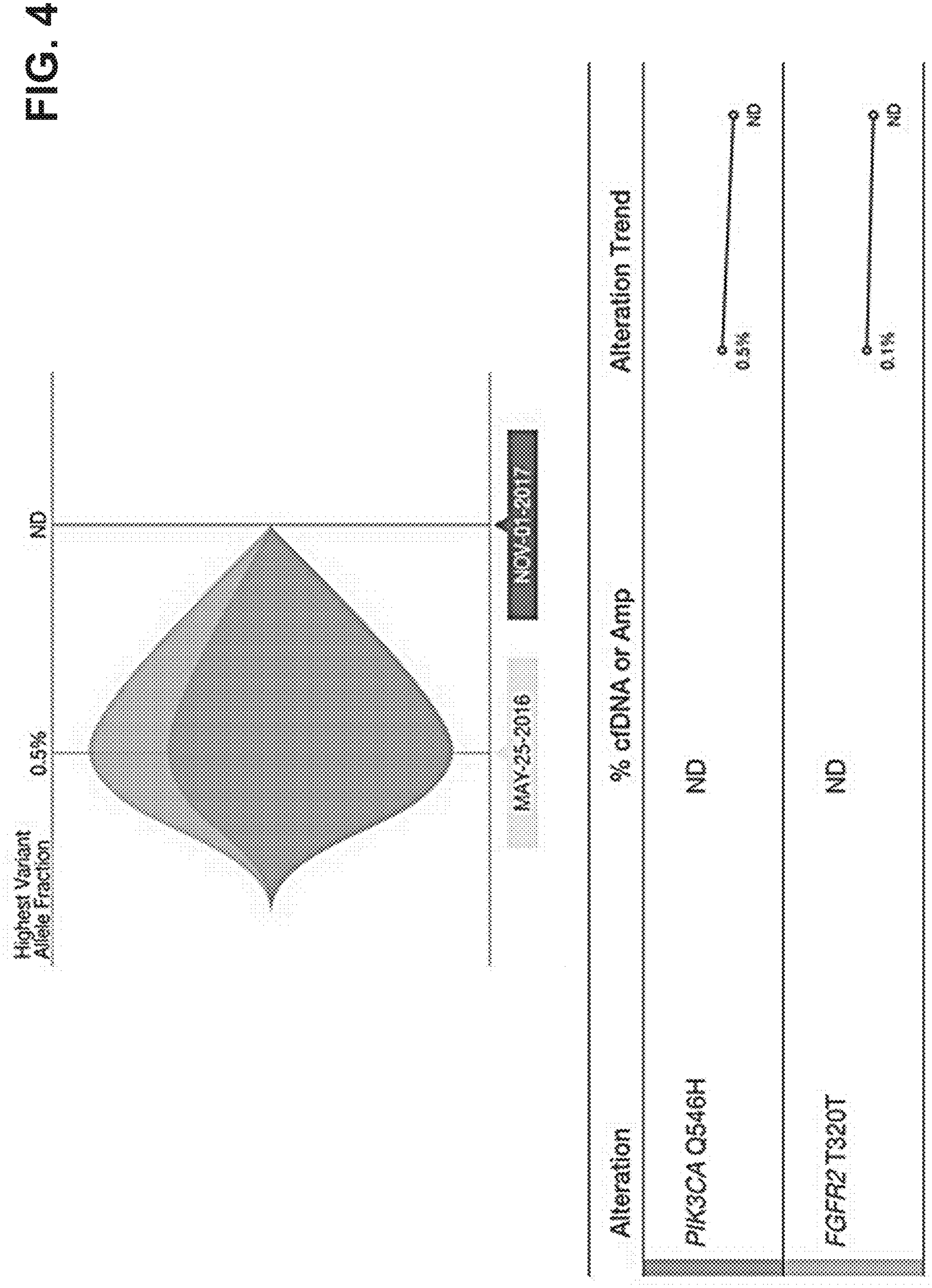
FIG. 4 shows a variant allele frequency map of ctDNA-detected mutations in an individual patient diagnosed with invasive ductal carcinoma, $ER^+$, $PR^-$, HER-$2^+$ with metastases to the liver (stage IV) in response to AS therapy. Mutated genes PIK3CA and FGFR2 were no longer present as of Nov. 1, 2017 due to successful treatment.

Response to Treatment: Baseline PET/CT on May 16, 2016 has shown multiple liver metastases but follow-up scans on Oct. 28, 2016 and Apr. 7, 2017 were normal. Guardant 360 on May 25, 2016 revealed mutations of two genes: PIK3CA Q546H and FGFR T320T. PIK3CA was the target of AS2-1. The follow-up Guardant 360 on Nov. 1, 2017 did not show any abnormalities (Guardant 360 report provided in FIG. 4).

Conclusion: This patient had a 15-year history of breast cancer which was treated with four surgeries, radiation therapy, hormonal treatment and three courses of docetaxel/trastuzumab/pertuzumab. Despite numerous treatments, she presented with multiple liver metastases. She obtained radiological complete response after 4 months of treatment and molecular complete response was documented 16 months since the beginning of the treatment. Unfortunately, after premature discontinuation, she developed progressive disease two and half years later. The patient's estimated survival was less than 3 months, but she was alive over 30 months later.

Example 3

A 56-year-old Caucasian female presented to Burzynski Clinic on Nov. 21, 2017 and was diagnosed with invasive ductal carcinoma with extensive DCIS, ER−, PR−, HER-$2^+$ with metastases to the lymph nodes and skin, stage IV. Her symptoms began in August 2015. The patient was diagnosed on Feb. 1, 2016 based on biopsy of the breast mass and axillary lymph node positive for cancer. She underwent neoadjuvant therapy ATCHP protocol from Feb. 17, 2016 to Jun. 1, 2016 and followed with modified radical mastectomy on Jul. 5, 2016. She was found to have diffuse involvement of the breast with extensive lymphatic invasion. She followed with radiation therapy with capecitabine from Aug. 11, 2016 to Sep. 27, 2016 and started trastuzumab on Aug. 19, 2016 to Apr. 18, 2017. Capecitabine was discontinued on Oct. 21, 2016. PET/CT on Jan. 20, 2017 had shown involvement of the skin which was confirmed by biopsy of Apr. 4, 2017.

Treatment: The patient started AS2-1 on Nov. 21, 2017, 9.6 g daily. She was unable to take the optimal dose of the medication and for this reason was also taking sodium phenylbutyrate (PB), 3 g 4× p.o. daily (PB was metabolized to AS2-1). The additional medications included lapatinib 1000 mg daily, capecitabine 2000 mg daily in 2 weeks on and one week off cycles, sorafenib 200 mg every other day and trastuzumab 6 mg/kg every 3 weeks. On Dec. 13, 2017 vorinostat, 100 mg daily was added to the treatment. On May 7, 2018 lapatinib was replaced by neratinib, 240 mg daily. Due to poor tolerance neratinib was discontinued on May 23, 2018. On Jun. 20, 2018 her treatment plan was changed and included AS2-1, ado-trastuzumab emtansine 3.6 mg/kg every 3 weeks, sorafenib 200 mg daily and capecitabine 1500 mg daily in 2 weeks on and 1 week off cycles. PB and sorafenib were discontinued on Sep. 11, 2018. Ado-trastuzumab was discontinued on Oct. 9, 2018 because it was suspected to cause ascites (negative for cancer cells). Her skin lesions were almost gone on Oct. 16, 2018 but on Nov. 12, 2018 she developed new lesions. Ado-trastuzumab was restated on reduced dose on Dec. 4, 2018. There was a mixed response on Feb. 7, 2019. Ado-trastuzumab was increased to full dose and on Mar. 14, 2018, neratinib, 240 mg daily was restarted. Neratinib was discontinued on Jun. 19, 2019 and replaced by alpelisib, 50 mg po daily. There was a reduction of skin lesions. On Aug. 19, 2019 she was hospitalized for pneumonia and AS2-1, alpelisib and ado-trastuzumab were discontinued. The patient was discharged from the hospital and on Sep. 2, 2019 the local oncologist advised to take trastuzumab and navelbine. The patient restarted AS2-1 and received 2 cycles (weekly) of trastuzumab/navelbine. On Sep. 23, 2019 she developed a herpes zoster infection. Cancer treatment was discontinued, and she was admitted to the hospital. On Sep. 30, 2019 she developed a subdural hematoma and went into a coma. The hematoma was evacuated through the left craniotomy. She remained hospitalized and off cancer treatment until Oct. 29, 2019, when she restarted alpelisib and trastuzumab/navelbine on Oct. 30, 2019 but discontinued again on Nov. 14, 2019 due to leukopenia. AS2-1 was restarted on Nov. 1, 2019. On Nov. 21, 2019 she restarted trastuzumab and navelbine with 20% dose reduction and continued alpelisib and AS2-1. Evaluation of her condition on Dec. 12, 2019 has shown improvement. She discontinued treatment on Jan. 9, 2020. The patient passed away from subdural hematoma on Mar. 23, 2020.

Response to Treatment:

Radiological. PET/CT on Jan. 20, 2017 revealed progression of cancer with involvement of the left side of the chest but follow-up scan on Aug. 10, 2018 had shown resolution of the involvement. PET/CT on Nov. 3, 2019 revealed a new lesion in the right axillary area.

By physical examination. Physical examination on Feb. 22, 2018 indicated a marked improvement of skin lesions consistent with Partial Response which was confirmed by further improvement on Mar. 26, 2018. The patient had poor tolerance of targeted medications which resulted in lowering of the doses, interruptions of the treatment and changes in the treatment plan. The initial response was produced by AS2-1, trastuzumab, lapatinib, sorafenib and capecitabine. Ado-trastuzumab, AS2-1 and alpelisib were responsible for improvement in June 2019. Additional complications including pneumonia, herpes zoster and subdural hematoma caused almost 2 months of cancer treatment discontinuation. Further improvement of skin lesions was documented on Dec. 12, 2019 as the result of the treatment with AS2-1, alpelisib, trastuzumab and Navelbine.

Molecular. The baseline Guardant 360 analysis (FIG. 5) of blood samples revealed a high percentage of TP53 V73fs and ERBB2 amplification (Apr. 25, 2017). The next analysis on Nov. 14, 2017 indicated a 97% decrease of TP53 V73fs and a 48% decrease of ERRB2 amplification. On Sep. 13, 2018 both abnormalities were no longer present consistent with partial response by radiology and physical examination. The test of Sep. 13, 2018 had shown 0.1% of new mutation of TP53-R175G. This mutation was gone on Jan. 16, 2019 but initial TP53 V73f and ERBB2 amplification came back again on lower levels.

Conclusion: The treatment was based on activity directed against TP53 by AS2-1 and ERBB2 by trastuzumab, ado-trastuzumab, lapatinib and neratinib. Tissue genomic analysis by Foundation Medicine of Apr. 18, 2017 and Nov. 6, 2018 confirmed TP53 and ERBB2 abnormalities as well as RET and MCL1 amplifications which provided the rationale for sorafenib. H3F3A amplification gave rationale for vorinostat. She obtained partial response, but her course of treatment was erratic due to poor tolerance of medications and complications. Her TP53 and ERBB2 abnormalities normalized on the treatment. The patient's life expectancy was less than 6 months, but she survived 29 months.

Example 4

A 53-year-old Caucasian female presented to Burzynski Clinic on Jan. 18, 2018 and was diagnosed with an invasive ductal carcinoma of the right breast with extensive bone metastases, Stage IV. Her cancer was ER/PR$^+$, HER-2$^-$, ATM germ line mutation. Her history of cancer began 3 years before. On Sep. 17, 2015 she underwent a right mastectomy with axillary node dissection. She was followed with AC chemotherapy every 3 weeks for 4 cycles and paclitaxel for 12 cycles after that, to Apr. 5, 2016. She also was treated with radiation therapy of 60 Gy which was completed on Jun. 20, 2016. On Jul. 8, 2017 she was found to have metastases to the bones confirmed by biopsy Aug. 16, 2017. Letrozole was added to the treatment in July 2017. Progression was documented by PET/CT of Sep. 15, 2017. Fulvestrant and abemaciclib were started on Oct. 19, 2017 and letrozole was discontinued. Bone scan on Dec. 11, 2017 showed progression.

Treatment: The treatment at Burzynski Clinic started on Jan. 18, 2018 with AS2-1 up to 19.2 g daily and capecitabine 1000 mg daily in 2 weeks on and 1 week off cycles. On Jan. 24, 2018 bevacizumab, 10 mg/kg every 2 weeks and rucaparib 600 mg were added to her regimen. Capecitabine daily dose was increased to 2000 mg on Jan. 25, 2018. Bone scan on Mar. 13, 2018 revealed marked improvement. Rucaparib was discontinued on May 31, 2018 due to lack of insurance coverage. The patient was advised to take olaparib, but she decided against it. On Jul. 30, 2018 denosumab, 60 mg every 6 months was added to the treatment. Rapamycin, 1 mg daily was added on Nov. 8, 2018. PET/CT on Feb. 21, 21019 indicated progression, possibly due to discontinuation of rucaparib. Rapamycin was replaced by everolimus, 5 mg and exemestane, 25 mg daily. On Aug. 1, 2019 she developed vagino-rectal fistula which improved on antibiotics and after discontinuation of bevacizumab, capecitabine, exemestane and everolimus. Exemestane and everolimus were restarted on Sep. 10, 2019. Capecitabine was restarted on Apr. 20, 2020. On May 5, 2020 she started radiation therapy to the right sacroiliac joint (8 treatments) and capecitabine was discontinued. PET/CT on Jul. 15, 2020 was within normal limits, as well as PET/CT of Oct. 28, 2020.

Response to Treatment:

Radiological. Baseline bone scan on Dec. 11, 2017 has shown multiple metastases. Numerous follow-up PET/CTs (Mar. 13, 2018, May 17, 2019, Aug. 21, 2019 and Jan. 14, 2020) documented continuous improvement and finally PET/CT on Jul. 15, 2020 was within normal limits confirming complete response.

Molecular. Baseline genomic analysis by Guardant 360 (FIG. 6) revealed PIK3CA amplification and PIK3CA E545K mutation. They were no longer present in the follow-up tests of Oct. 2, 2018, Dec. 18, 2019 and Sep. 14, 2020. The last test indicated ATM mutation of unknown significance. The patient had known germ line mutation of ATM. AS2-1 targets PIKCA, and rapamycin and everolimus were applied to target ATM.

Conclusion: The patient had complete response of difficult to treat multiple bone metastases. There was a contribution from radiation therapy to the resolution of a single right sacro-iliac metastasis. There was also complete molecular response. Her cancer recurred before and after surgery, radiation, two lines of chemotherapy and hormonal therapy. Her estimated survival was less than 6 months; however she survived at least 33 months.

Example 5

In another exemplary method, a 40-year-old Caucasian female presented to Burzynski Clinic on Jan. 1, 2018 and was diagnosed with invasive ductal carcinoma, $ER^+$, $PR^+$, $HER\text{-}2^-$, with multiple metastases to the lymph nodes, bones and brain, Stage IV. The patient had 5 years history of cancer. Her diagnosis was established based on a biopsy of the right breast nodule in March 2013. She underwent right modified mastectomy with dissection of axillary lymph nodes on May 7, 2013. She was followed with adjuvant chemotherapy FEC for 5 cycles from May to August 2013 and radiation therapy to the right side of the chest to March 2014. In July 2017 the MRI of the spine and PET/CT on Jul. 14, 2017 revealed multiple bone metastases. MRI of Jan. 23, 2018 showed multiple brain metastases.

Treatment: The treatment at the Burzynski Clinic began on Jan. 25, 2018 with AS2-1 up to 19.2 g daily, Zoladex 3.6 mg, and letrozole 2.5 mg daily. On Feb. 1, 2018 she started standard radiation therapy to the brain at MDACC. On Feb. 14, 2018 she started trastuzumab 2 mg/kg weekly and lapatinib 750 mg daily. MRI on Apr. 19, 2018 showed a decrease of brain metastases and PET/CT, a mixed response. On Jul. 11, 2018, pertuzumab 840 mg was added and to be continued every 3 weeks by 420 mg together with trastuzumab 6 mg/kg. Lapatinib was discontinued on Jul. 25, 2018 because the insurance did not cover the cost. MRI on Aug. 2, 2018 showed a mixed response and PET/CT on Aug. 31, 2018 showed progression. It was advised to switch from trastuzumab/pertuzumab to ado-trastuzumab emtansine which was started on Sep. 5, 2018, 3.6 mg/kg every 3 weeks and continue Zoladex, exemestane and AS2-1. On December 4, she completed 5 treatments of Gamma-Knife to the brain metastases. PET/CT on Dec. 5, 2018 revealed a decrease of bone and brain metastases and MRI on Jan. 17, 2019 further improvement. Patient's response was determined as partial response. PET/CT on Mar. 5, 2019 showed progression and the medications were discontinued except for AS2-1, which was also discontinued by patient on May 15, 2019 for personal reasons.

Response to Treatment:

Radiological. PET/CT of Dec. 5, 2018 showed resolution of numerous bone metastases and MRI of the head of Jan. 17, 2019 revealed 71.8% decrease of the size of cerebellar vermis nodule indicating partial response. There was no follow-up MRI to confirm the response and CT/PET of Mar. 5, 2019 showed increase of the intensity of hypermetabolic uptake without change in size and number of lesions. The contribution of radiation therapy to the response in the brain can't be excluded.

Molecular. This patient had numerous genomic abnormalities, totaling 19 by Guardant 360 blood test (FIG. 7). Four mutations were of unknown significance. Plasma copy number of amplified ERBB2 has decreased on Aug. 22, 2018 as the result of treatment with trastuzumab, pertuzumab and lapatinib. After denial of insurance coverage for lapatinib and its discontinuation, ERBB2 level of amplifications increased on Apr. 8, 2019 despite treatment with ado-trastuzumab. ERBB2 V219V seemed to respond to ado-trastuzumab and was not present on Apr. 8, 2019. BRACA2 D237N, PIK3CA E726K, APC G29G, BRACA1 H662O, FGFR H791H, RAF1 P63P, ARAFY495Y mutations and MYC amplifications were gone on Apr. 8, 2019 possibly due to action of AS2-1. On the other hand, CCND1 and PIK3CA amplifications and PIK3CA E545K and E453K mutations have increased.

Conclusion: This was a very aggressive and complex breast cancer case with a 5-year history of cancer which failed surgery, radiation, and combination chemotherapy. The patient accomplished a partial response of multiple bone and brain metastases. Out of 15 genomic abnormalities of known significance, 8 were eliminated by AS2-1 and one by ado-trastuzumab. Among them were important mutated genes including BRACA1 and 2, PIK3CA, APC, FGFR, RAF, ARAF and ERBB2. Three different mutations of PIC3CA, one of CCND1 and ERBB2 amplifications have increased at the end of treatment. The patient's life expectancy was estimated for less than 3 months but she has survived over 18 months.

Example 6

A 60-year-old Caucasian female presented to Burzynski Clinic in April 2019 and was diagnosed with infiltrating ductal carcinoma of the left breast, $ER^+$, $PR^-$, HER-2+, with extensive metastases to the brain, bones, liver, lungs and epidural involvement at T6-T12, Stage IV. The patient was diagnosed based on the biopsy of May 26, 2018. MRI of May 24, 2018 revealed numerous metastases to the bones, liver, lungs and involvement of the left breast and dura from T6 to T12. From May 31, 2018 she was given radiation therapy of 2000 cGy to T5 7, T11-L1, L4 and sacrum. On Jun. 12, 2018 she started paclitaxel, trastuzumab, Zometa and anastrozole for 8 cycles to Nov. 13, 2018. In the last cycle, paclitaxel was replaced by docetaxel. MRI of Nov. 30, 2018 confirmed multiple brain metastases and CT on the same date confirmed the progression of liver metastases. The treatment plan was changed on Dec. 4, 2018 to ado-trastuzumab emtansine for 6 cycles, Zometa and 15 fractions of brain radiation. There was further progression in the liver documented by CT of Apr. 11, 2019. The patient was complaining or memory loss, speech abnormalities, muscle weakness, nausea, urinary frequency, insomnia and left breast tumor.

Treatment: The treatment at Burzynski Clinic started on Apr. 19, 2019 with AS2-1 up to 12 g daily, lapatinib 750 mg daily, capecitabine 1000 mg daily and anastrozole 1 mg daily. On Nov. 5, 2019 the treatment plan was changed to AS2-1, trastuzumab, pertuzumab and navelbine under the care of local oncologist. On Feb. 17, 2020 she discontinued the treatment under the disclosed care.

Response to Treatment:

Radiological. CT of Sep. 9, 2019 showed a 58.8% decrease of the size of liver metastases and follow-up CT on Jan. 24, 2020 showed further decrease compared to baseline of Apr. 11, 2019. Bone and lung lesions were stable. MRI of the head of Jun. 18, 2019 showed a 10% decrease of the size of cerebellar tumor compared to baseline of Apr. 11, 2019, but MRI of Jan. 24, 2020 revealed progression. There was documented partial response of liver metastases and stabilization of brain, lung and bone metastases.

Molecular. Initial genomic analysis of blood by Guardant 360 revealed amplifications of ERBB2, EGFR and PIK3CA and CCNE1 P268P mutations (FIG. 8). On the follow-up test on Dec. 30, 2019, all three amplifications were gone and the concentration of CCNE1 mutated DNA decreased by 86%. AS2-1 was instrumental in elimination of PIK3CA and EGFR amplification and decrease of CCNE1 mutation, and HER-2 inhibitors in elimination of ERBB2 amplification. The best results were obtained through a combination of AS2-1, capecitabine and anastrozole. The change to trastuzumab, pertuzumab and Navelbine resulted in progressive disease.

Conclusion: The patient was diagnosed with very aggressive and wiμ°wly metastatic breast cancer and had an estimated survival of less than 2 month. She obtained partial response of liver metastases and stabilization of brain, lung and bone metastases and elimination of amplified genes ERBB2, EGFR, PIK3CA and marked decrease in concentration of DNA of mutated CCNE1 in blood. She survived over 10 months.

Example 7

A 38-year-old Caucasian female presented to Burzynski Clinic in June 2019 and was diagnosed with adenocarcinoma of the breast, $ER^+$, PR–, $HER-2^+$ with metastases to the lymph nodes, brain, lungs, pleura, bones, peritoneum and ovaries. The primary tumor was in the left breast, but the biopsy was performed on left axillary lymph node on Jan. 18, 2017. The initial treatment consisted with vinorelbine and capecitabine chemotherapy in a clinic in Mexico which resulted in progression. The next regimen with cisplatin, doxorubicin and cyclophosphamide was unsuccessful as well, indicated by the PET/CT on Aug. 3, 2018. At that time, she developed lymphogenic spread in the lungs. She was started on trastuzumab and paclitaxel and continued until May 2019. CT of the chest of Feb. 6, 2019 revealed a minor response. On Apr. 16, 2019 she started etoposide, advised by the Mexican clinic, which was discontinued in the second week of May 2019 when the MRI revealed disseminated brain metastases. From May 23 to Jun. 6, 2019 she received 3000 cGy of radiation therapy to the brain. Upon the admission to Burzynski Clinic, she was complaining on fatigue, muscle weakness and stiffness, memory loss, mood changes, irritability, double vision, decreased hearing, dizziness, numbness and tingling of fingers and toes, cough, bone pain, lack of appetite, thirst and a breast tumor.

Treatment: The treatment at Burzynski Clinic started on Jun. 25, 2019 with AS2-1 up to 19.2 g daily. On Jul. 7, 2019 letrozole, 2.5 mg daily, was started and on Jul. 19, 2019 ado-trastuzumab emtansine 3.6 mg/kg every 3 weeks was started. On Aug. 23, 2019 the patient was started on Lupron and denosumab by her local oncologist. On Oct. 11, 2019 letrozole was replaced by Fulvestrant by the local oncologist. The local oncologist discontinued ado-trastuzumab on Nov. 19, 2019 due to nose and vaginal bleeding. She discontinued all cancer treatments on Nov. 21, 2019 due to hospitalization for fungal pneumonia. She was discharged on Nov. 29, 2019 and was advised to continue anti-fungal treatment with voriconazole and restarted AS2-1. On Jan. 21, 2020 the patient decided to discontinue all medications. She passed away on Feb. 19, 2020.

Response to Treatment:

Radiological. MRI of the head of Oct. 14, 2019 was compared to baseline MRI of Jun. 28, 2019 and revealed 51% decrease of the size of the lesions and some innumerable lesions were no longer visible. The follow-up MRI of Nov. 21, 2019 has shown further decrease of the size of the lesions by 57.2% vs. baseline. CT of the chest and abdomen of Oct. 17, 2019 compared to baseline PET/CT of Jul. 15, 2019 documented marked improvement and decrease of lungs and lymph node metastases. Liver metastases were no longer seen. The patient obtained partial response of brain, lung and lymph node metastases and a complete response of liver metastases; the follow-up conformation of complete response was not done. There was a contribution from radiation therapy to the response in the brain.

Molecular. The patient had numerous genomic abnormalities including 5 amplifications and 9 mutations of known significance by Guardant 360 test from blood sample of Jun. 24, 2019 (FIG. 9). None of them were present in the follow-up test report of Jan. 8, 2020 indicating complete molecular response. In the follow-up report there was an occurrence of minute amounts (0.02%) of BRAF V765fs of unknown significance. Elimination of ERBB2 amplification from blood was affected by ado-trastuzumab. There was no other explanation for the elimination of the remaining 13 genomic abnormalities except for the activity of AS2-1. They include: CCND1, CDK6, FGFR1, and PIK3CA amplifications and mutations PTEN D252Y, PIK3CA E542K, PIK3CA E545K, PIK3CA E726K, APC K445K, PIK3CA R4_P18del, ARID1A S1798L, FGFR1 S726F and PDGFRA V299G.

Symptomatic and Physical. The patient was showing continuous improvement in her symptoms. Unfortunately, after contracting fungal pneumonia after 5 months of treatment and discontinuation of her treatment plan, her condition deteriorated, and she decided to discontinue these services in January 2020.

Conclusion: This patient was diagnosed with a very aggressive form of breast cancer, which despite two and a half years of treatment, progressed widely through her body with over 50 metastatic lesions and 14 genomic abnormalities. She responded rapidly to the treatment at Burzynski Clinic. ERBB2 amplification was affected by ado-trastuzumab and the remaining 13 abnormal genes were affected with AS2-1. As the result, the patient's condition improved, and she accomplished a complete response of liver metastases and partial response of brain, lungs and lymph nodes metastases. The interruptions of the treatment plan due to possible adverse events from ado-trastuzumab, fungal pneumonia and serious logistic problems (after initial month of treatment the patient was 1,700 miles away), caused the premature discontinuation of the treatment and her death 4 weeks later. At the admission to the Clinic her life expectancy was less than 2 months, but she was able to live over 7 months.

Example 8

A 54-year-old Caucasian female presented to Burzynski Clinic in February 2020 and was diagnosed with invasive ductal carcinoma of the left breast, $ER^+$, $PR^+$, $HER-2^-$, with extensive bone, lung and skin metastases, Stage IV. She had a 5-year history of her cancer. The patient underwent a bilateral mastectomy on May 19, 2015 followed by breast reconstruction. From February 2016 to December 2016 she was treated with tamoxifen and in December 2016 she underwent standard radiation therapy to the chest. On Feb. 4, 2020 she developed multiple skin metastases. CT/PET of Feb. 24, 2020 showed extensive bone metastases and questionable lung metastasis. The estimated survival was less than 6 months.

Treatment: The treatment at Burzynski Clinic started on Feb. 25, 2020 with A52-1 up to 19.2 g daily. She also began a standard regimen with abemaciclib and fulvestrant at MDACC. On Sep. 20, 2020 sorafenib 400 mg daily was added. She continues the treatment currently. She survived at least more than a year from treatment start.

Response to Treatment:

Radiological. Follow-up PET/CT of May 20, 2020 compared to baseline study of Feb. 24, 2020 showed a marked improvement with only minimal metabolic activity left. A small skin lesion on the scalp was still present and a biopsy specimen was analyzed and showed BRAF G469A mutation, not present in initial surgical specimen of May 19, 2015. PET/CT on Oct. 21, 2020 was within normal limits indicating beginning of complete response.

Molecular. Patient's baseline Guardant 360 blood genomic analysis did not show any abnormalities. Foundation One report based on May 19, 2015 specimen showed the following mutations: CTNNB1 S45P-subclonal and GATA3 P433fs43. The test based of skin metastasis found the following: BRAF G469A, BTG1 rearrangement of exon 2, MAP2K4 loss exon 2 and GATA3 P433 fs43. Based on this report, sorafenib was added to the treatment. It was expected that AS2-1 affected CTNNB1 and GATA3 mutations.

Conclusion: The patient has the beginning of complete response which should be confirmed by the next PET/CT. Lack of abnormalities in the Guardant 360 report did not permit us to follow the changes of genomic abnormalities in the blood.

Example 9

A 65-year-old Chinese female presented to Burzynski Clinic in March 2020 and was diagnosed with invasive carcinoma of the right breast, $ER^+$, $PR^+$, $HER\text{-}2^-$, with extensive skin and chest wall involvement and metastases to the lymph nodes, lungs and bones, Stage IV. The history of her cancer began 10 years before with a nodule in the right breast found by the patient in 2010. She did not have treatment and finally, she developed fungating involvement of the entire anterior chest and multiple metastases. The biopsy of the right breast tumor, on Feb. 25, 2020, established the pathology diagnosis. The estimated survival was less than 3 months.

Treatment: The treatment at Burzynski Clinic started on Mar. 5, 2020 with AS2-1 up to 19.2 g/day, letrozole 2.5 mg daily, and palbociclib 125 mg daily in 3 weeks on and 1 week off cycles. The patient continues the treatment at present. She survived at least more than a year from the treatment start.

Response to Treatment:

Radiological. CT of Jun. 5, 2020 revealed a decrease of bilateral breast masses and thickness of the chest wall, lymph nodes and pulmonary metastases. The next CT of Oct. 6, 2020 has shown further decrease, but less than 50%.

By Physical Examination. Physical examination of Mar. 5, 2020, before the treatment, showed very extensive involvement of the entire anterior chest wall. Follow-up examination of Jul. 1, 2020 indicated more than 50% decrease of the involvement with progressive healing.

Molecular. Baseline genomic analysis on Mar. 5, 2020 by Guardant 360 showed FGFR2 P47P mutation which was no longer seen on the follow-up test of Jul. 14, 2020.

Conclusion: The patient was diagnosed with very advanced breast cancer with very extensive skin and chest wall involvement and metastases to the lymph nodes, lung and bones. She accomplished a partial response of skin involvement and a decrease of lymph node and lung metastases and a decrease of tumors in both breasts. These improvements are the result of combination treatment with AS2-1 and hormonal and targeted medications, but the elimination of FGFR2 P47P mutation was due to AS2-1.

Example 10

A 47-year-old Caucasian female presented to Burzynski clinic in November 2015 and was diagnosed with invasive ductal carcinoma of the breast, ER+, PR−, HER-2+, with metastases to the lymph nodes, bones and skin, Stage IV. The patient had a 6-year history of her disease. In June 2009 she was diagnosed with invasive ductal carcinoma and extensive ductal carcinoma in situ and underwent a modified radical mastectomy of the right breast. From October 2009 to February 2010 she was treated with FEC chemotherapy and from November 2009 to February 2010 she was given paclitaxel and trastuzumab. From February to August 2010 she was given only trastuzumab and accomplished remission. From March to April 2010 she received radiation therapy to the right chest wall. From Mar. 20, 2010 to December 2011 she received daily tamoxifen. In June 2011 she underwent plastic reconstruction of the right breast. The CT on Dec. 19, 2011 revealed metastasis to the bone which was proven by biopsy as cancerous. From August 2012 to February 2013 she was taking daily capecitabine, one week on and one week off and trastuzumab every 3 weeks. MRI of the chest and abdomen on May 5, 2014 showed progression of bone metastases and lymph nodes. The biopsy of the right axillary lymph node on Oct. 20, 2014 confirmed her original diagnosis. On Oct. 23, 2014 she started PB, capecitabine and trastuzumab/pertuzumab. On Nov. 19, 2014 everolimus and pazopanib were added to her treatment. She obtained a decrease in the size of the lymph nodes and a decrease in bone pain. In January 2015 her local oncologist discontinued trastuzumab/pertuzumab and in February 2015 she discontinued capecitabine. In March 2015 she discontinued everolimus and started denosumab. A CT of Oct. 26, 2015 showed an increase in the size of the soft tissue mass in the right lower chest, but the lymph node and bone metastases were stable. Her life expectancy was estimated as less than 6 months.

Treatment: The treatment began on Dec. 2, 2015 with AS up to 19.2 g daily and A10 up to 184 g daily. Everolimus 2.5 mg PO daily, pazopanib 200 mg PO daily and dasatinib 50 mg PO daily were added on Dec. 10, 2015. On Dec. 25, 2015 she added ado-trastuzumab emtansine IV every 3 weeks. On Jun. 6, 2016 she discontinued pazopanib and everolimus but added pembrolizumab 200 mg IV every 3 weeks under the care of her local oncologist. She discontinued pembrolizumab, ado-trastuzumab and dasatinib on Jul. 5, 2016 and added bevacizumab 10 mg/kg IV every 2 weeks. She discontinued bevacizumab on Nov. 22, 2016 and started carboplatin, docetaxel, trastuzumab and pertuzumab every 3 weeks×6 cycles under the care of her local oncologist. On Jan. 8, 2017 she increased the dose of A10 to 300 g daily and restarted everolimus 5 mg PO daily and dasatinib 50 mg PO daily. She restarted pazopanib 200 mg PO daily on Feb. 17, 2017. On Apr. 24, 2017 her local oncologist discontinued docetaxel but continued trastuzumab/pertuzumab. She also discontinued A10. On Jun. 27, 2017 she started 5 days of radiation therapy to the right arm and shoulder. On Jun. 28, 2017 vorinostat 100 mg PO daily was added to the regimen. On Dec. 27, 2017 vinorelbine was added by the local oncologist. The patient discontinued the treatment under the disclosed care on Apr. 21, 2018. The passed away on Nov. 1, 2019.

Response to Treatment: The patient was taking treatment under the disclosed care for over 30 months. During the first 5 months she had stable disease which was followed by progression for the next 5 months and by objective response indicated by resolution of the right upper chest mass during the final 8 months (CT of May 4, 2017) and stabilization of bone metastases (CT of Feb. 2, 2018). She also had significant symptomatic improvement. Blood genomic analysis by Guardant 360 of Apr. 18, 2019 showed ND for MYC S244S. Tissue analysis by Foundation Medicine of May 16, 2018 supported the treatment with AS and HER2 inhibitors.

Conclusion: This patient had a very long history of the disease and failed surgery, multiple chemotherapy and targeted therapy regimens and radiation therapy. She responded objectively to treatment under the disclosed care and had a long period of stabilization of her cancer interrupted by short periods of disease progression. She survived an additional 4 years despite her prior estimated survival of less than 6 months. She responded again to the HER2 inhibitors when ANP was added, despite the progression on the same regimen before the addition of ANP.

Example 11

A 54-year-old Caucasian female presented to Burzynski Clinic in June 2020 and was diagnosed with poorly differentiated invasive ductal carcinoma of the right breast, triple negative with multiple metastases to the lymph nodes, bones and skin, Stage IV. The patient had a 4-year history of her disease. Her diagnosis was established based on the biopsy of the right breast on Mar. 3, 2016. She underwent bilateral mastectomy on Mar. 31, 2016. She was started on CMF chemotherapy in May 2016 but discontinued because of poor tolerance and was switched to letrozole. PET/CT of May 22, 2020 showed multiple lymph node, bone and skin metastases. Her life expectancy was less than 6 months.

Treatment: The treatment began on Jun. 5, 2020 with AS up to 19.2 g daily. On Jul. 2, 2020 atezolizumab and nab-paclitaxel IV every 2 weeks was recommended and added under the care of her local oncologist. Denosumab SC was also added by her local oncologist on Aug. 2, 2020. She continues the treatment at present.

Response to Treatment: The follow-up PET/CT of Aug. 24, 2020 compared to May 22, 2020 showed a marked improvement. Only one lesion was identified in the chest wall and skin compared to numerous lesions visible before. There were no longer metabolically active measurable lymph nodes identified. There was marked decreases of metabolic activity in all the bone metastases. The next PET/CT of Nov. 10, 2020 revealed further decrease of a single remaining chest wall nodule and resolution of metabolic activity in the bone metastases. PET/CT of 02/15/2021 was within normal limits indicating the beginning of CR. Blood genomic analysis by Guardant 360 of Dec. 3, 2020 showed ND of all mutated genes from the test of Jun. 3, 2020 including: TP53 G187D, MAP2K1 K57E, PTEN R130*, METT 895M and PTEN Y27C. The patient's condition markedly improved and she became asymptomatic.

Conclusion: This the case of aggressive, metastatic triple negative breast cancer. The patient accomplished a CR after 9 months of treatment and all of her mutated genes were no longer identified by Guardant 360.

Example 12

A 39-year-old Latin American female presented to Burzynski Clinic in January 2019 and was diagnosed with invasive ductal carcinoma of the right breast, triple positive, with metastases to the lymph nodes, lungs, pleura, liver, bones and brain, Stage IV. The patient had a 2-year history of her disease. Her initial diagnosis was made in February 2017 based on the biopsy of a right breast nodule. MRI of June 2018 showed marked increase of breast mass and lymph nodes and liver metastases. She underwent a radical resection of the right chest wall tumor and modified radical right mastectomy on Jul. 23, 2018. PET/CT of Aug. 18, 2018 showed multiple metastases to the lymph nodes, lungs, pleura, liver and bones. In September 2018 she started trastuzumab, pertuzumab and docetaxel with initial response followed by progression in January 2019 when she developed a pathological fracture of her left hip. Her treatment was changed to ado-trastuzumab emtansine. Her life expectancy was estimated at less than 3 months.

Treatment: The treatment began on Jan. 29, 2019 with AS up to 18 g daily. She also continued ado-trastuzumab emtansine until Mar. 25, 2019 under the care of her local oncologist and was advised to add vorinostat 100 mg PO daily. On Mar. 26, 2019 she began trastuzumab, pertuzumab, and capecitabine under the care of local oncologist. On Jun. 4, 2019 vorinostat was discontinued and neratinib 400 mg PO daily and A10 up to 150 g daily was added to the regimen. On Sep. 25, 2019 she was started on fulvestrant by her local oncologist. On Jan. 23, 2020 the local oncologist discontinued trastuzumab, pertuzumab, capecitabine and neratinib and started fam-trastuzumab deruxtecan-nxki. She discontinued the treatment under the disclosed care on May 5, 2020 and passed away on Jun. 4, 2020 from subdural hematoma.

Response to Treatment: Baseline PET/CT of Jan. 2, 2019 showed multiple lymph node, pulmonary, pleural and bone metastases which progressed and an axillary lymph node and hepatic metastases which improved. Follow-up CTs of Mar. 18, 2019, Jun. 17, 2019 and Aug. 16, 2019 showed continuous decrease and finally resolution of the right axillary adenopathy indicating CR. There was improvement of pleural masses and SD of pulmonary and bone metastases. There was improvement of some hepatic metastases but progression of the other. MRI of the brain showed progression. Blood genomic analysis of Apr. 13, 2020 compared to Mar. 27, 2019, Jun. 4, 2019, Sep. 5, 2019 and Dec. 19, 2019 by Guardant 360 revealed ND of CCND1, EGFR, ERBB2, MYC, and PIK3CA amplifications and ND of AR G432D, GATA3 P409fs, ERRB2 S11071 and EGFR V5241. There was molecular CR based on blood genomic analysis. Despite these improvements there was final deterioration in the patient's condition and progression of some of her metastases.

Conclusion: This was a very complex and heterogenous case of advanced breast cancer. The ND of ERRB2 abnormalities indicates that the HER+ part of her disease responded but the HER− part progressed. There were difficulties in execution of treatment plans due to the lack of insurance coverage and different opinions of local oncologists.

Example 13

A 48-year-old Caucasian female presented to Burzynski Clinic in April 2019 and was diagnosed with invasive lobular carcinoma of the left breast, HER-2 negative, with metastases to the bones, Stage IV. The patient had a 6-year history of her disease. In August 2013 she noted a lump in the left breast. The biopsy of Jun. 25, 2014 established the diagnosis. From May 20, 2014 to Jul. 20, 2014 she was treated with neoadjuvant Adriamycin and followed with bilateral mastectomy. At the beginning of 2019 she developed metastases to the bones and underwent internal fixation of the left hip. The pathology examination confirmed original diagnosis. On Apr. 8, 2019 she finished 7 days radiation therapy to the left hip and started letrozole. Her life expectancy was less than 6 months.

Treatment: The treatment began on Apr. 27, 2019 with AS up to 19.2 g daily and letrozole 2.5 mg PO daily. On May 16, 2019 abemaciclib 300 mg PO daily was added to the treatment. The patient decided to discontinue the treatment on Aug. 14, 2019 for personal reasons against medical advice.

Response to Treatment: PET/CT of Aug. 12, 2019 compared to PET/CT of Apr. 18, 2019 showed resolution of multiple hypermetabolic lesions. Blood genomic analysis by Guardant 360 on Apr. 23, 2019 showed PIK3CA H1047L and TP53 R282W. They were no longer seen on follow-up analysis of Nov. 6, 2019. The patient had marked symptomatic improvement. CR without confirmation by the second scan.

Conclusion: This was a very advanced and rapidly progressive cancer which responded rapidly to the treatment. Unfortunately, she decided too prematurely discontinue the treatment.

Example 14

A 40-year-old Caucasian female presented to Burzynski Clinic in December 2019 and was diagnosed with carcinoma of the right breast, HER-2 negative, with multiple metastases to the liver, lungs, bones and brain, Stage IV. The patient had a 3-year history of her disease. In 2016 the biopsy of the right breast nodule revealed $ER^+/PR^+/HER\text{-}2^-$ breast cancer. She was treated with adjuvant AC chemotherapy and radiation therapy until February 2017. She took tamoxifen thereafter for a short time. In October 2018 she developed biopsy-confirmed lung metastases. In May 2019 she underwent bilateral oophorectomy. In November 2019 she was started on letrozole which she continues. Her estimated survival was less than 3 months.

Treatment: The treatment began on Dec. 4, 2019 with AS up to 19.2 g daily, palbociclib 125 mg PO daily and letrozole 2.5 mg daily. On Dec. 10, 2019 palbociclib and letrozole was discontinued and replaced by abemaciclib 150 mg PO daily and fulvestrant 500 mg IM monthly based on genomic analysis. She decided to discontinue the disclosed services on Jul. 9, 2020.

Response to Treatment: MRI of the brain of Jan. 21, 2020 compared with Dec. 3, 2019 MRI showed disappearance of one metastasis and overall, a 66.4% decrease of the size of both lesions. The next MRI of Jun. 18, 2020 showed 73.5% decrease indicating PR. PET/CTs of Jan. 24, 2020 and Jun. 19, 2020 compared to Nov. 27, 2019 showed SD. Blood genomic analysis by Guardant 360 of Dec. 2, 2019 showed ESR1 E380G, ESR1 Y537N, PIK3CA E545K and E542K and E39K, CDK4 amplification, AKT1 E17K, FGFR1 amplification, TP53 E287* and E285K. It was expected that all genomic abnormalities except for ESR1 and CDK were affected by AS. There was no follow-up analysis. The patient had marked symptomatic improvement.

Conclusion: This was a very advanced case of HER− breast cancer with numerous metastases. She accomplished CR of brain metastases and SD elsewhere and marked symptomatic improvement.

Example 15

In another exemplary method, a 42-year-old Caucasian female presented to Burzynski Clinic in June 2019 diagnosed and was with invasive ductal carcinoma of the left breast, $ER^+$, PR−, $HER\text{-}2^-$ with metastases to liver, lungs, pleura, bones and brain, Stage IV. The patient had a 2-year history of her disease. In November 2017 her gynecologist found the nodule in the left breast. The biopsy of Jan. 2, 2018 established the diagnosis. PET/CT of Jan. 25, 2018 showed breast, lymph node and lung involvement. From Jan. 30, 2018 to May 9, 2018 she was treated with neoadjuvant AC chemotherapy and followed with left total mastectomy, lymph node dissection and plastic reconstruction on Jun. 6, 2018. On Aug. 21, 2018 she completed 5000 cGy of radiation therapy. PET/CT on Apr. 12, 2019 showed progression with lymph node, lung, pleural, liver and bone metastases. The biopsy of bone metastasis on May 2, 2019 confirmed original diagnosis. MRI of the head of Aug. 16, 2019 showed brain metastases. Her life expectancy was estimated as less than 2 months.

Treatment: The treatment began on Oct. 16, 2019 with AS up to 19.2 g daily. Fulvestrant and Lupron were added by her local oncologist. She discontinued the treatment on Jan. 28, 2020 and decided on hospice care. She passed away in March 2020.

Response to Treatment: MRI of the brain of Dec. 14, 2019 compared to MRI of Aug. 16, 2019 showed a 55.6% decrease of brain metastases indicating beginning of PR. CT of Jan. 10, 2020 showed progression of liver metastases. Blood genomic analysis by Guardant 360 of Jun. 3, 2019 showed PIK3CA E542K and E453K, CDKN2A D74N and GATA3 D336fs. There was improvement in the patient's condition during the treatment. The patient survived 10 months longer than expected.

Conclusion: This was a case of very aggressive and advanced $HER\text{-}2^-$ breast cancer. The patient accomplished the beginning of PR of brain metastases but PD of liver metastases. She declined modification of the treatment plan based on genomic analysis for personal concerns.

Example 16

A 57-year-old Caucasian female presented to Burzynski Clinic in August 2019 and was diagnosed with invasive ductal carcinoma of the right breast, $ER^+$, PR−, HER-2−, BRCA1 germLine mutation with multiple metastases to the liver, bones and brain, Stage IV.

The patient had a 15-year history of her disease. She was first diagnosed with right breast DCIS in 2004 and underwent bilateral mastectomy with plastic reconstruction. She developed recurrence in the right postmastectomy site which was confirmed by biopsy of Jul. 11, 2016. PET/CT showed metastases to the bones. On Jun. 25, 2018 she had a right hip replacement for pathological fracture and also had a left femur rodding and emergent spinal surgery for spinal cord compression on Jul. 19, 2018. She began taking letrozole on Jun. 22, 2018 and palbociclib on Aug. 20, 2018 and continued until the progression in the bones and liver in March 2019. She took olaparib after that but discontinued after 1 week due to adverse effects. She decided to restart letrozole in April 2019. MRI of the brain of Aug. 23, 2019 showed brain metastasis. Her life expectancy was estimated at less than 3 months.

Treatment: The treatment began on Aug. 26, 2019 with AS up to 19.2 g daily and fulvestrant 500 mg IM monthly. Upon the recommendation, she started talazoparib under the care of local oncologist on Sep. 25, 2019. She decided to stop AS for personal reasons on Jan. 2, 2020 and began treatment with PB under the disclosed care.

Response to Treatment: MRI of the brain of Jan. 22, 2020 showed 11.3% decrease of the size of brain metastasis and the next MRI revealed 43% decrease. PET/CT of Oct. 23, 2019 compared to the scan of Aug. 22, 2019 showed marked improvement of numerous liver and bone metastases indicating the beginning of PR and the next PET/CT of Jan. 24, 2020 confirmed PR. Blood genomic analysis of Aug. 21, 2019 showed ESR1 E380Q, Y537C, E330dup, H524L and BRAC1 [908*], PIK3CA amplification, and RB1 O217*. The patient had marked symptomatic improvement.

Conclusion: The patient had a 15-year history of her disease which was very advanced and difficult to treat HER– and BRA C1 mutated breast cancer. She obtained a rapid PR but her response slowed down after she decided to discontinue AS after 4 months of treatment.

Example 17

A 48-year-old Chinese female presented to Burzynski Clinic in April 2020 and was diagnosed with invasive ductal carcinoma of the right breast, $ER^+$, $PR^+$, HER-$2^-$, with metastases to the left breast, lymph nodes, liver, lungs, bones, thyroid and peritoneum, Stage IV.

The patient had an 11-year history of her disease. In 2009 she had resection of the right adrenal tumor. The pathology diagnosis was not available. In April 2018 she developed a nodule in the right breast and biopsy confirmed above diagnosis. On Nov. 6, 2019 she was found to have marked progression of the disease with the large tumor in the right breast infiltrating the skin, the tumor in the left breast and metastases to the lymph nodes, liver, bones and peritoneum. On Nov. 20, 2019 she had embolization of the hepatic artery and followed with ablation of both breasts and the liver on Dec. 9, 2019. She developed further progression at the beginning of 2020. Her life expectancy was less than 3 months.

Treatment: The treatment began on Apr. 16, 2020 with AS up to 14.4 g daily and capecitabine 1000 mg PO daily in 14 days on/7 days off cycles. On Sep. 9, 2020 she underwent right breast mastectomy. Upon advice provided on Oct. 14, 2020, she started abemaciclib and letrozole and on Dec. 4, 2020, Zoladex under the care of her local oncologist. She continues the treatment at present.

Response to Treatment: PET/CT of Sep. 2, 2020 showed improvement of hepatic, bone and thyroid metastases and slight increase of pulmonary nodules and right breast tumor and no peritoneal metastases. The next PET/CT of Dec. 9, 2020 showed stable liver, bone and thyroid metastases and increasing lung and right axillary metastases. There was status post right mastectomy. Blood genomic analysis of Apr. 28, 2020 showed CCND1 amplification and blood genomic analysis of Apr. 14, 2020 showed GATA3 c.1213_1214del and p.S405fs. HER2 amplification was suspected but not confirmed. The patient obtained mark symptomatic improvement.

Conclusion: This was a very aggressive and advanced case of HER2 negative breast cancer which showed OR of liver, bone, peritoneal and thyroid metastases and marked symptomatic improvement. Some of the recommended treatment plan changes, like abemaciclib and hormonal treatments, were implemented with marked delay due to insurance authorization. The patient survived at least over 9 months in good condition versus the estimated less than 3 months.

Example 18

A 51-year-old Caucasian female presented to Burzynski Clinic in June 2018 and was diagnosed with invasive ductal carcinoma, high-grade, $ER^+$, $PR^+$, HER-$2^-$, Stage IV with extensive metastases to the bones. The patient had a 16-year history of her disease. In 2002 she was diagnosed with DCIC of the left breast which was treated with surgical excision. On Mar. 20, 2015 she under-went a left breast biopsy which revealed intermediate grade DCIC. She denied the recommended mastectomy at that time but on Aug. 25, 2015 she decided to do it and also had breast reconstruction. The pathology examination provided the above diagnosis. She declined radiation, chemotherapy and hormonal treatment and was treated with PB from October 2015 to August 2017 without any recurrence. Eight months later she underwent an excisional biopsy of the left chest nodule which revealed the same features of this recurrence as examination in August 2015. The PET/CT of May 15, 2018 showed several bone metastases. On Jun. 11, 2018 she underwent laparoscopic BSO and was started on denosumab. Her life expectancy was less than 6 months.

Treatment: On Jul. 2, 2018 she started AS up to 12 g/d at Burzynski Clinic. Subsequently letrozole, palbociclib and denosumab were added by her local oncologist. Palbociclib was discontinued on Apr. 9, 2019 and on May 2, 2019 she was switched from letrozole to fulvestrant. A10 was added on May 14, 2019 up to 159 g/d. She was advised to add abemaciclib, but it was denied by insurance. She discontinued the treatment on Jul. 9, 2019. She survived over 12 months.

Response to Treatment: Follow-up PET/CT of Oct. 31, 2018 compared to May 17, 2018 revealed resolution of all metastatic hypermetabolic bone lesions indicating the beginning of CR. Follow-up PET/CT of Apr. 16, 2019 showed a couple of hypermetabolic densities in the liver and the bones indicating PD. Blood genomic analysis of Aug. 15, 2018 compared to baseline of Oct. 16, 2017 showed ND for ESR1 Y537S and CCND1 Q264K. Both of these mutants showed again on Apr. 10, 2019 and MTOR R454R occurred. ND of CCND1 Q264K was likely due to AS. Patient response was classified as CR, but was not confirmed by repeated scan, and followed by PD.

Conclusion: Beginning of CR of bone metastases after 5 months of treatment and ND of CCND1 Q264K.

Example 19

A 67-year-old Caucasian female presented to Burzynski Clinic in March 2017 and was diagnosed with invasive poorly differentiated adenocarcinoma of the hepatic flexure of the colon with metastases to the lymph nodes, liver and peritoneum, Stage IV. She was complaining of fatigue, abdominal and back pain, nausea, vomiting, poor appetite, and the loss of 50 lbs. of weight in 5 months. The history of her cancer began 6 months before, with mid abdominal and back pain. She was initially diagnosed with diverticulitis, GERD and hiatal hernia. On Dec. 12, 2016 she was found to be positive for *H. pylori* and was treated with standard regimen, then found to be negative in March 2017. On Dec. 12, 2016 her CT identified the tumor in the hepatic flexure of the colon. On Jan. 25, 2017 she underwent right hemicolectomy at Mayo Clinic. The tumor was not completely respectable because it invaded the duodenum and pancreatic head and penetrated the visceral peritoneum. 2/18 lymph nodes were positive for metastatic carcinoma. Pathology examination confirmed the above diagnosis. There was loss of MLH-1 and PMS-2 expression, but intact MSH-2 and MSH-6 expression. She did not receive further treatment. Baseline PET/CT of Mar. 15, 2017 revealed massive metastatic involvement of the lymph nodes, liver and peritoneum. Her life expectancy was less than 4 months.

Treatment: Her treatment started with pembrolizumab infusions on Mar. 16, 2017 which continued every 3 weeks. She also received FOLFOX every 2 weeks. On Apr. 6, 2017 the infusions of AS were added to the treatment up to 19.2 g daily. On Nov. 6, 2017 FOLFOX was switch to XELOX which continued until May 21, 2018. Pembrolizumab was discontinued on Aug. 15, 2018 and AS on Feb. 28, 2019.

Response to Treatment: The follow-up PET/CT of Apr. 20, 2017 revealed a decrease of all metastases. The next PET/CT of Jun. 26, 2017 did not show any measurable lesion, but the scan of Sep. 20, 2017 showed a new lesion in the central abdomen. This lesion was resolved on the Nov. 6, 2017 scan. The follow-up scans of Jan. 18, 2018, Apr. 23, 2018 and Jul. 24, 2018 were normal, as well as Jan. 2, 2019, Apr. 4, 2019, Jul. 30, 2019 and Nov. 15, 2019 except for the inflammatory changes in the T11 vertebra. The PET/CTs of Feb. 28, 2020 and Aug. 24, 2020 did not show any recurrence, confirming radiological CR. The patient's symptoms improved and were gone at the beginning of the treatment. Her repeated Guardant 360 tests on Jul. 12, 2017, May 1, 2018, Aug. 6, 2018, Nov. 8, 2018 and Feb. 7, 2019 were all negative. There was BRAF V600E mutation in tumor tissue. Pembrolizumab was selected based on the loss of MLH-1 and PMS-2 expression by tissue genomics (Mayo Clinic, Feb. 24, 2017).

Conclusion: The patient accomplished a CR of over 3 years duration and continues to do very well at present. Her blood genomic test was negative, and tissue genomics guided the preparation of her treatment plan. Her estimated survival was 4 months, but she continues to be cancer-free for over 3 years.

Example 20

A 60-year-old Caucasian male presented to Burzynski Clinic in January 2018 and was diagnosed with invasive moderately differentiated adenocarcinoma of the sigmoid colon with metastases to the lymph nodes, liver, lungs and lymphangitic spread, Stage IV. The history of his cancer began a year before when he reported to the emergency room with intestinal obstruction from a cancerous tumor. In February 2017 he underwent partial colectomy with tumor resection which was complicated by rectal sheath hematoma and intestinal obstruction. One out of 16 lymph nodes was positive for cancer. He decided not to have additional treatment and the CT on Jan. 2, 2018 showed bulky liver metastases as well as metastases to the lymph nodes and lungs with lymphangitic spread. His life expectancy was estimated at less than 6 months.

Treatment: His treatment at Burzynski Clinic started on Jan. 17, 2018 and included AS up to 19.2 g daily, capecitabine, oxaliplatin and bevacizumab at regular doses. Oxaliplatin was discontinued on Jul. 10, 2018 due to adverse events. Oxaliplatin was restarted On Oct. 24, 2018. Capecitabine, oxaliplatin and bevacizumab were discontinued on Dec. 6, 2018 and the patient was advised to start cetuximab, encorafenib, and binimetinib. He received a single infusion of cetuximab on Dec. 4, 2018 and continued weekly until Jan. 4, 2019. He took encorafenib and binimetinib only for two days (January 8 and 9, 2019). The treatments were discontinued on Jan. 10, 2019 for worsening of liver tests. He passed away on Jan. 15, 2019.

Response to Treatment: The follow-up PET/CTs of Mar. 27, 2018, Jun. 15, 2018 and Sep. 26, 2018 have shown continuous decrease in size, number and metabolic activity of the lesions. On Jun. 15, 2018 the metabolic activity resolved in the lungs and dome of the liver. The maximum decrease in the size of the lesion was 31%. PET/CT of Sep. 26, 2018 showed no metabolic activity in the lungs, but 15% increase in the size of the liver lesions. The next PET/CT of Nov. 30, 2018 revealed progression. The patient did not have baseline Guardant 360. His first test was done on Jul. 12, 2018 and the follow-up on Oct. 15, 2018 when there was progression. It showed increased levels of TP53 Y220C, TP53 V143M and BRACA1 T17201. EGFR D321D was ND.

Conclusion: The patient obtained an objective decrease in the size, number, and activity of numerous metastases to the lymph nodes, lungs and the liver. Activity in the dome of the liver, in a number of enlarged lymph nodes, and in the pulmonary metastases were no longer seen and the lymphangitic spread was no longer seen. His EGFR D321D mutation was eliminated. His estimated survival was less than 6 months, but he lived a year.

Example 21

A 63-year-old Caucasian female presented to Burzynski Clinic in May 2018 and was diagnosed with moderately differentiated adenocarcinoma of the colon with metastases to the lungs and pleura, Stage IV. The patient had seven years history of her cancer. In 2011 she underwent partial colectomy for adenocarcinoma of the colon. In 2015 she presented with an adnexal tumor and underwent a total abdominal hysterectomy and bilateral salpingo-oophorectomy with pathology diagnosis of metastatic adenocarcinoma of the colon. She was followed with FOLFOX chemotherapy and panitumumab from September 2015 through April 2016 and suffered severe toxicity from panitumumab. In October 2017 she developed metastasis to the left lower lobe of the lung and in January 2018 metastases to perihilar lymph node, right lung and pelvis. She underwent radiation therapy to the right lung lesion on Feb. 14, 2018 and Feb. 15, 2018 and on Mar. 5, 2018 exploratory laparotomy with lysis of adhesions, small bowel resection with anastomosis, and en block resection of right obturator fossa with resection of the ureter and reimplantation. The pathology of the right uterine mass showed metastatic colon adenocarcinoma, moderately differentiated. PET/CT of Apr. 23, 2018 showed metastases to the right lung and pleura. Her estimated survival was less than 6 months.

Treatment: Her treatment at Burzynski Clinic began on Jun. 6, 2018 with AS up to 19.2 g daily and chemotherapy with FOLFIRI and bevacizumab every 2 weeks. The chemotherapy and AS was discontinued on patient's request on Aug. 27, 2018. AS was restarted on Nov. 27, 2018. On Dec. 20, 2018 she restarted FOLFIRI with bevacizumab which was discontinued on Mar. 25, 2019. At that time, she was started on atezolizumab infusions every 2 weeks and cobimetinib administered orally and continued until May 22, 2019. On Jun. 11, 2019 A10 was added to the treatment, up to 1 g/kg/day. On Jun. 20, 2019 she started radiation therapy to the right lung metastasis for 36 treatments (6480 cGy). On Nov. 20, 2019 she started the regimen of nivolumab infusions every 2 weeks and regorafenib given orally. On Mar. 15, 2020 she started radiation therapy to the scalp lesion which continued to Mar. 30, 2020. She decided to discontinue the treatment at Burzynski Clinic on Mar. 31, 2020.

Response to Treatment: Follow-up CTs of Aug. 2, 2018 and Oct. 9, 2018 revealed a decrease in the size of the lung metastases. After discontinuation of the treatment, by patient request, for 3 months there was a continuous increase in the size, documented by follow-up CTs and progression of the disease with a new lesion on the scalp. PET/CTs documented progression at the baseline on Apr. 23, 2018, but complete resolution of metabolic activity was documented on Aug. 2, 2018 and Oct. 9, 2018 indicating CR by PET criteria. Follow-up PET/CTs on Dec. 12, 2018 and Mar. 22, 2019 revealed progression but PET/CT of May 21, 2019 showed mixed response. The final PET/CT of Nov. 15, 2019 showed progression. The baseline blood genomics by Guardant 360 on May 6, 2018 showed TP53 R273H and PTEN R55fs mutations which were gone on the follow-up tests of Aug. 2, 2018 and Oct. 10, 2018 coinciding with CR by PET/CT. Thereafter, starting Aug. 27, 2019 to Feb. 19, 2020 there was recurrence of these two mutations as well as a new finding of BRAF amplification on Feb. 19, 2020 from metastasis in the scalp. APC E888fs occurred on Aug. 27, 2019 but was gone on Nov. 20, 2019 and Feb. 19, 2020. The patient had several interruptions of the treatment which compromised her initial response. Most of the time she was asymptomatic and had good quality of life with several vacations overseas. The elimination of TP53 R273H, PTEN R55fs, APC E888fs and APC R230C was possibly affected by AS.

Conclusion: The patient had a very long (7 years) history of her cancer and failed 2 surgeries, standard chemotherapy, immunotherapy and radiation therapy. She obtained CR by PET/CT and ND of two important mutated$^-$ genes, TP53 and PTEN. Unfortunately, after discontinuation of the treatment for 3 months her disease progressed and was not sufficiently controlled by additional treatments. As the resulting new mutations developed during this time but some of them (APC) were eliminated. She was advised a new regimen with targeted therapy directed against BRAF amplification but decided to discontinue: She survived 2 years when her estimated survival was less than 6 months.

Example 22

A 50-year-old African American male presented to Burzynski Clinic in December 2018 and was diagnosed with infiltrating moderately differentiated adenocarcinoma of the sigmoid colon with metastases to the lymph nodes, peritoneum and ureteral pelvic junction with blockage of the left kidney, Stage IV. The patient had a 3-year history of his cancer. On May 18, 2015 he was operated on for intestinal obstruction caused by the tumor and underwent partial colectomy with sigmoid tumor resection. The pathology examination provided the above diagnosis and RAS and BRAF wild type. He was treated with FOLFOX for 12 cycles from July 2015 to December 2015. In April 2017 he was found to have recurrence with tumor obstructing the left kidney. The pathology confirmed the recurrence. He had placement of nephrostomy and continued with 5-fluorouracil and bevacizumab every 2 weeks from July 2017 to September 2017. He decided to discontinue due to toxicity. He was treated with capecitabine by another physician but developed progression in November 2018. His life expectancy was estimated for less than 6 months.

Treatment: His treatment at Burzynski Clinic started on Dec. 27, 2018 with AS up to 19.2 g/day. On Jan. 15, 2019 capecitabine was added to his treatment and on Feb. 14, 2019 panitumumab was started every 2 weeks and discontinued on May 29, 2019. He decided to discontinue AS and the disclosed care on Aug. 3, 2019 against medical advice and despite the offer of free services for the next month.

Response to Treatment: The patient had very good response to treatment. The follow-up PET/CTs of Apr. 4, 2019 and Jun. 10, 2019 showed complete resolution of metastatic lesions indicating CR. Baseline blood genomics by Guardant 360 on Dec. 11, 2018 revealed TP53 S241F which was ND on Apr. 10, 2019. However, after discontinuation of panitumumab by the patient, the mutated gene occurred again at a much lower concentration. The patient survived over a year despite his life expectancy of less than 6 months upon admission to Burzynski Clinic.

Conclusion: The patient obtained radiological and molecular CR but discontinued the treatment prematurely against medical advice which caused progression of the disease. Mutated TP53 was no longer detected in his blood after 3 months of treatment. The patient obtained good symptomatic improvement and surpassed his estimated life expectancy by over 6 months.

Example 23

A 62-year-old Caucasian female presented to Burzynski Clinic in October 2019 and was diagnosed with moderately differentiated adenocarcinoma of the rectum with metastases to the lymph nodes, liver and lungs, Stage IV. The patient had a 2-year history of her cancer. Her initial diagnosis of rectal adenocarcinoma was established in July 2017. She denied surgery, chemotherapy and radiation and did not have any standard treatment. The CT of Sep. 10, 2019 showed a large rectal tumor and numerous metastases as described above. Her life expectancy was less than 6 months.

Treatment: Her treatment at Burzynski Clinic began on Oct. 18, 2019 and included AS up to 19.2 g/day and XELOX chemotherapy with bevacizumab by standard regimen. She discontinued the treatment against advice on Feb. 13, 2020 because of lack of support from her local oncologist.

Response to Treatment: Follow-up CT of Jan. 4, 2020 showed stable number and size of metastatic lesions. Her rectal tumor markedly decreased by physical examination on Jan. 16, 2020 and there was marked decrease of her pain. Her response was classified as SD. Blood genomics by Guardant 360 of Jan. 13, 2020 compared to baseline of Oct. 16, 2019 showed a 95% decrease of concentration of KRAS G13D and a 99% decrease of TP53 R282W and SMAD4 D537V. PIK3CA E542K, PIK3CA 115431, ARID1A Q802fs and AR Splice Site SNV were no longer detectable.

Conclusion: The patient accomplished radiological SD and marked improvement by physical examination and blood genomics. Her comfort and quality of life also significantly improved.

Example 24

A 64-year-old Vietnamese female presented to Burzynski Clinic in October 2019 and was diagnosed with poorly differentiated adenocarcinoma of rectosigmoid with diffuse metastases to the lungs, liver, spleen, bones and peritoneum, Stage IV. The patient had a 7-year history of cancer. In 2012 she underwent right breast lumpectomy for DCIS. On Apr. 10, 2019 she developed perforation of the colon and underwent rectosigmoid resection, partial hysterectomy, evacuation of pelvic abscess and a colostomy. The pathology examination confirmed the above diagnosis. She had delayed primary closure and hematoma requiring percutaneous drainage. On Jun. 19, 2019 she started FOLFIRI chemotherapy at MDACC. On Jun. 19, 2019 the treatment was discontinued for small bowel obstruction. She then followed with 6 cycles of FOLFOX; the last one with bevacizumab. The CT of Sep. 11, 2019 showed progression. Her life expectancy was less than 6 months.

Treatment: The treatment began on Oct. 10, 2019 with AS up to 19.2 g daily. On Dec. 23, 2019 the FOLFOX was restarted at MDACC. The treatment was interrupted on Mar. 9, 2020 due to viral pneumonia which required hospitalization for suspected COVID-19 infection (which was excluded). On Apr. 17, 2020 she restarted FOLFIRI under the care of MDACC. On Jul. 21, 2020 A10 was added to the regimen up to 150 g daily. On Sep. 28, 2020 FOLFIRI was discontinued and regorafenib was started at 80 mg PO daily. The patient discontinued the treatment under care on Oct. 22, 2020.

Response to Treatment: CT scans of Dec. 12, 2019, Jan. 16, 2020, Feb. 15, 2020, Apr. 8, 2020, May 8, 2020 and Jun. 8, 2020 show stable disease. Genomic analysis of tissue specimen collected on Apr. 10, 2019 and reported on Nov. 8, 2019 showed numerous genomic abnormalities including: KRAS A146T, APC G1499*, BRAF D5946, FAM123B R531*, MTOR E1779K, RET E511 K, SMARCB1 R377C, TPS3 C176Y and amplifications of ARFRP1, CDK8, CUL4A, FLT3, GNAS, MYC, RAD21 and ZNF703. Blood genomic analysis of Oct. 9, 2019 was negative. Patient accomplished symptomatic improvement.

Conclusion: This was a case of advanced colon cancer with numerous genomic abnormalities in tumor specimen but normal blood genomic analysis. The execution of the treatment plan was complicated by personal issues.

Example 25

A 66-year-old Caucasian male presented to Burzynski Clinic in July 2018 and was diagnosed with adenocarcinoma of the colon with metastases to the brain, lungs and adrenal gland, Stage IV. The patient had a 3-year history of his disease. In 2015 he developed epileptic seizures and was found by MRI to have a right posterior occipital parietal mass with involvement of the dura which was almost completely resected. On Oct. 17, 2017 he developed balance instability and was found to have a recurrent brain lesion which was resected on Oct. 19, 2017. CT of Oct. 18, 2017 revealed multiple lung metastases which were biopsied. The pathology diagnosis confirmed moderately differentiated adenocarcinoma of the colon, KRAS mutated and MSI stable. On Nov. 7, 2017 he underwent radiosurgery of the brain lesions, SBRT. On Dec. 14, 2017 he started FOLFOXIRI and Avastin. After 6 cycles he had intolerable toxicity and discontinued on Jun. 25, 2018. On Feb. 20, 2018 he started PB as a single drug which he took until Jul. 25, 2018. On May 1, 2018 he was consulted at Burzynski Clinic and advised to take Xeloda, Avastin or Tecentriq with Cotellic and PB. He decided against it and took PB alone. His life expectancy was less than 6 months.

Treatment: The patient started treatment at Burzynski Clinic on Jul. 26, 2018 with AS up to 19.2 g/d. On Jul. 31, 2018 bevacizumab and capecitabine were added under the care of his local oncologist. He discontinued AS on Oct. 3, 2018 and was discharged from Burzynski Clinic on Jan. 22, 2019.

Response to Treatment: Baseline PET/CT on Aug. 3, 2018 showed progression of multiple lung and adrenal metastases, but follow-up PET/CT on Oct. 2, 2018 showed 24% decrease in the size of the right upper lung mass, as well as decrease in size and metabolic activity of other pulmonary metastases. Left adrenal gland metastasis had a decrease in the metabolic uptake. The patient accomplished MR. MRI's of the head of Aug. 16, 2018 and Sep. 13, 2018 did not show any recurrence. The patient survived over 6 months.

Conclusion: This was an unusual case of a terminal colon cancer patient with brain, lung and adrenal metastases which failed two tumor resections, chemotherapy and radiation therapy but responded to the treatment at Burzynski Clinic. The patient discontinued the treatment against medical advice.

Example 26

A 78-year-old Caucasian male presented to Burzynski Clinic in October 2019 and was diagnosed with adenocarcinoma of the cecum with metastases to the peritoneum and pericardium, Stage IV. The patient had over one-year history of his disease. In July 2018 he was found to have a cecal mass and pericardial infusion. On Feb. 17, 2019 he underwent partial resection of the tumor; a complete resection was not possible due to infiltration of the abdominal wall and adhesions. He refused the recommended chemotherapy. In October 2019 the patient presented with a large abscess continuous with the intestine and extending into the psoas muscle and multiple peritoneal metastases. His life expectancy was less than 6 months.

Treatment: The treatment at Burzynski Clinic started on Oct. 30, 2019 with AS up to 19.2 g/d, nivolumab 3 mg/kg IV every 3 weeks and regorafenib 80 mg in 21 days on and 7 days off cycles. On Dec. 4, 2019 capecitabine 500 mg 2× daily in 14 days on/7 days off cycle was added. The Patient returned to Europe on Dec. 24, 2019 and could not continue the treatment because of lack of cooperation from local oncologists. The last contact with the patient was on Mar. 16, 2021. The fact that he was reasonably well was conveyed to us.

Response to Treatment: The PET/CT of Dec. 2, 2019 vs. CT of Oct. 29, 2019 showed a 18.7% decrease of the size of the largest mesenteric lesion and improvement of the right illiopsoas muscle infiltration and multiple peritoneal metastases documenting MR. The patient survived at least 17 months from the treatment start.

Conclusion: This was a difficult-to-treat case of colon cancer due to a large intra-abdominal abscess involving the intestines. Standard chemotherapy was associated with the risk of septicemia. The patient could not continue the treatment for logistic reasons: lack of cooperation with local oncologists and COVID-19 pandemics.

Example 27

A 54-year-old Caucasian male presented to Burzynski Clinic in October 2015 and was diagnosed with mucoepidermoid carcinoma of right submandibular gland with metastases to the lymph nodes, lungs and liver, Stage IV. The patient had over two years of cancer history. He also had a history of HIV infection since 2001. His pathology diagnosis was established on Mar. 15, 2013 based on biopsy of the right neck submandibular mass. ACT on Apr. 9, 2013 showed extensive lymph node and pulmonary metastases. Their metastatic origin was confirmed by biopsy of the lung lesion on Apr. 16, 2013. On May 24, 2013 he underwent a right modified neck dissection. In June 2013 he was followed with radiation therapy to the right neck for five treatments. From July to the end of August he was treated with reduced dosage docetaxel and pemetrexed with slightly decreased size of metastatic lesions. At the beginning of 2014 he had investigational supportive oligonucleotide therapy (SOT) and the follow-up PET/CT on Mar. 25, 2014 indicated a response. On Apr. 21, 2015 he was started on reduced dose 5FU, docetaxel and cisplatin which was followed by progression. On Aug. 20, 2015 he started the treatment in clinic with PB, pembrolizumab, paclitaxel, carboplatin and trastuzumab. Due to approval of the Right to Try Law he discontinued PB and was switched to IV ANP. His life expectancy was less than 2 months.

Treatment: The treatment with AS and A10 started on Oct. 16, 2015. The dose of AS was increased to 19.2 g/day and A10 to 3.5 g/kg/day. He also continued pembrolizumab, paclitaxel, carboplatin, and trastuzumab IV every 3 weeks. The treatment was held from Nov. 18, 2015 to Dec. 2, 2015 due to hospitalization for pneumonia. He restarted ANP on Feb. 5, 2016 but discontinued again on Feb. 26, 2016. He decided to restart AS again on Jul. 25, 2016 and discontinued on Oct. 25, 2016.

Response to Treatment: Since Aug. 20, 2015 the patient had marked improvement in size and number of metastatic lesions. The lung lesions decreased by 75% and the liver lesion had dissolved. There was further improvement documented by CT of Nov. 22, 2015. Further 30% of lung metastasis shown by PET/CT of Feb. 11, 2016. CT of Mar. 22, 2016 showed mild progression, possibly the result of poor compliance with the treatment plan. The patient had also marked symptomatic improvement. He decided to have only one blood genomic test by Guardant 360 on Aug. 18, 2015 which revealed ERBB2, ARID1A and GNAQ mutations indicating a good target for trastuzumab.

Conclusion: The patient obtained marked reductions of tumor size and number consistent with PR. He was susceptible to infection due to an underlying HIV infection. His response was compromised by interruptions due to infections and poor compliance. He survived over a year when his life expectancy was only 2 months.

Example 28

A 66-year-old Caucasian female presented to Burzynski Clinic in January 2018 and was diagnosed with poorly differentiated acinic cell carcinoma of right parotid gland with metastases to the lymph nodes, lungs and pleura, Stage IV. The patient had 14 years history of cancer. In 2004 she was diagnosed with left breast cancer and underwent left partial mastectomy and radiation therapy and has been in remission. In 2016 she developed a right neck mass and bilateral thyroid nodules which were diagnosed as Warthin's tumor. She was scheduled for surgery but declined. She presented for a second opinion in January 2017 and was diagnosed with high-grade carcinoma with squamous differentiation of the right parotid gland. On Jul. 7, 2017 she underwent a right modified radical neck dissection and received post-operative diagnosis of acinic cell carcinoma, high grade, with lymph node metastases. She underwent local radiation therapy from Sep. 12, 2017 to Oct. 25, 2017, had a PEG tube placed due to dysphagia and started pembrolizumab, given PD-01 expression. PET/CT on Dec. 20, 2017 showed progression of the disease as evidenced by the increase in number, size and intensity of multiple metastases to the lymph nodes, lungs and pleura. Her life expectancy was estimated for less than 3 months.

Treatment: The treatment began on Jan. 22, 2018 with a maximum dose of 19.2 g/day. She also continued pembrolizumab under the care of the local physician. On Jan. 25, 2018 vorinostat 100 mg po daily was added to enhance the activity of pembrolizumab. CT of Apr. 3, 2018 revealed progression. The treatment at BC was discontinued on Apr. 26, 2018.

Response to Treatment: The patient was diagnosed with a very aggressive and very rare type of cancer. Her blood genomics by Guardant 360 on Jan. 17, 2018 was negative. Tissue genomic analysis showed GATA3 multiplication. The only possible target for treatment was positive PD-01 which was the basis for pembrolizumab. AS was used for broad spectrum coverage of mutated genes. This was not sufficient, and her cancer progressed.

Conclusion: This case showed unsuccessful treatment due to negative blood genomic results and limited knowledge on genomic abnormalities in this very rare type of cancer.

Example 29

A 45-year-old Indian male presented to Burzynski Clinic in April 2018 and was diagnosed with moderately differentiated squamous cell carcinoma of the left hard palate with metastases to the lymph nodes and bones, Stage IV. The patient had a 2-year history of his cancer. On Aug. 16, 2016 he underwent a biopsy of the tumor in the left hard palate which provided the above diagnosis. The tumor infiltrated the left maxillary bone. On Aug. 24, 2016 he underwent left maxillectomy with reconstruction and right lung nodule resection. He was followed with chemotherapy and radiation therapy of 60 Gy in 30 fractions to the head and neck. He developed recurrence in the hard palate, which was confirmed by a biopsy on Feb. 26, 2018. PET on Feb. 21, 2018 showed a large skull base lesion with erosion of the clivus. There was involvement of the left petrous bone and posterior nasal septum, temporal fossa and left parapharyngeal space, ethmoid sinus and left cavernous sinus and metastases to the lymph nodes including mediastinal, prevascular, pretracheal and subcarinal groups. He was given chemotherapy with carboplatin and Abraxane which did not control the progression. He had difficulty swallowing, pain, left sided vision loss and profound weakness. His life expectancy was estimated to be 1 month.

Treatment: The treatment began on Apr. 11, 2018 with AS up to 19.2 g/day and nivolumab 240 mg IV every 2 weeks. On Apr. 18, 2018 ipilimumab 50 mg IV was added to the treatment but not continued thereafter because it was not available in India. Instead cetuximab, 700 mg IV, was added and continued with nivolumab every 3 weeks. The disclosed services were discontinued on Nov. 7, 2018 because of logistic difficulties.

Response to Treatment: Follow-up PET/CT on May 31, 2018 showed marked decrease of the size and metabolic activity of the skull lesion and slight improvement of the enlarged lymph nodes. There were also new mesenteric foci and new enlarged lymph nodes in the abdomen. The patient also had marked improvement of swallowing and pain. His treatment plan was deficient because blood genomic analysis by Guardant 360 of Apr. 9, 2018 was negative. Tissue genomic analysis showed cytokeratin clone AE1/AE3.

Conclusion: This was a very advanced case of head and neck cancer which responded very well to a combination of AS and monoclonal antibodies and accomplished radiological and symptomatic improvement and increased survival. The treatment was compromised by lack of genomic information and logistic difficulties.

Example 30

A 77-year-old Caucasian male initially presented to Burzynski Clinic in November 2011 for treatment adenocarcinoma of the prostate with metastases to the bones, Stage IV. He achieved a CR, but in 2013 he was diagnosed with invasive squamous cell carcinoma of the right tonsil with metastases to the lymph nodes. He was first treated at MDACC with initial improvement followed by progression and involvement of the mediastinal lymph nodes. On Mar. 30, 2015 he was found to have further progression. He was initially treated with cetuximab and proton radiation at MDACC and his disease progressed further in August 2016. He decided to come to Burzynski Clinic in September 2016 for the treatment of his invasive squamous carcinoma of the head and neck with metastases to the lymph nodes and lungs, Stage IVC, under RU. The patient had a 5-year history of prostate and a 3-year history of head and neck cancer. At the time of starting his treatment under RTT, his prostate cancer was in CR and his head and neck cancer was progressing after cetuximab and proton radiation treatments. His life expectancy was less than 6 months.

Treatment: The treatment under RTT at Burzynski Clinic started on Sep. 8, 2016 and included AS up to 19.2 g/d and pembrolizumab 200 mg IV every 2 weeks. He discontinued the treatment on Mar. 23, 2017. The last contact with the patient was on Apr. 26, 2017 and he was doing well.

Response to Treatment: The baseline PET/CT on Aug. 17, 2016 revealed a large tumor in the right glossopharyngeal region involving the tongue and tonsils, enlarged submental and mediastinal lymph nodes, and pulmonary nodules in the right and left lower lungs. Follow-up PET/CT's on Nov. 17, 2016 and Feb. 27, 2017 showed SD. Genomic blood analysis by Guardant 360 on Aug. 17, 2016 showed TP53 R248Q and C242S, ATM A2688A, APC E1047G and MET R134C. It was thought that two TP53 mutations were affected by AS. The patient survived over 8 months.

Conclusion: This was a complex case of advanced head and neck cancer that relapsed after standard targeted and radiation treatment but stabilized during treatment with AS and immunotherapy. The patient discontinued the treatment prematurely against medical advice.

Example 31

A 39-year-old Latin American male presented to Burzynski Clinic in November 2017 and was diagnosed with renal cell carcinoma, clear cell type of the right kidney with metastases to the opposite kidney, lymph nodes, lungs and brain, Stage IV. The patient had a very aggressive cancer and only a year history of his disease. On Nov. 8, 2016 he underwent right nephrectomy which helped to establish the above diagnosis. There was extension of the tumor to the inferior vena cava. In December 2016 he developed multiple metastases to the brain and was given Gamma-Knife treatment to 5 lesions and began sunitinib 37.5 mg daily on Jan. 1, 2017. On Mar. 31, 2017 he was given another Gamma-Knife treatment. His disease progressed on May 31, 2017 and he was given whole brain radiation therapy from Jun. 6, 2017 to Jun. 19, 2017. CT of Aug. 22, 2017 revealed progression in the opposite kidney, subcarinal lymph node and the lungs. MRI of the head of Sep. 18, 2017 showed progression of brain metastases. The patient was no longer a candidate for radiation therapy. He was complaining of fatigue, diarrhea, nausea and vomiting. His life expectancy was less than 2 months.

Treatment: The patient began treatment with AS on Jan. 3, 2018 with the final dosage of 19.2 g daily. He was also given nivolumab, 3 mg/kg IV every 2 weeks and vorinostat 200 mg po daily. On Jan. 17, 2018 he began ipilimumab 1 mg/kg IV every 6 weeks. The dose of vorinostat was decreased to 100 mg daily on Jan. 22, 2018. On Mar. 8, 2018, based on recommendations of the oncologists from MDACC, the infusions of nivolumab/ipilimumab were rescheduled to every 3 weeks. On Apr. 4, 2018 his coverage for ipilimumab was denied by the insurance company and since then, he continued nivolumab every 2 weeks. On Jul. 18, 2018, the disclosed treatment was discontinued for non-compliance and his care was transferred to MDACC. No information about his condition has been provided since Nov. 7, 2018.

Response to Treatment: MRI of the head on Jan. 29, 2018 showed an 84% decrease of the size and number of brain metastases compared to the Sep. 18, 2017 scan. The follow-up MRI of Mar. 1, 2018 did not show any change and the MRI of Jun. 18, 2018 showed 10% decrease. After discontinuation of the disclosed services, the MRI of Aug. 21, 2018 revealed massive progression. There was also new involvement of the bones based on the bone scan of Aug. 21, 2018. CT's of Mar. 2, 2018, Jun. 18, 2018 and Aug. 21, 2018 confirmed stability of the subcarinal node. There were no other enlarged lymph nodes or lung metastases. The patient refused baseline whole body CT and it was not known if his multiple lymph node and pulmonary metastases were present at baseline. He had difficulty with compliance to the treatment plan due to refusal of insurance coverage. For this reason, he did not have baseline blood genomics by Guardant 360. The baseline tissue genomics by Foundation Medicine of Dec. 6, 2017 revealed mutations targeted by AS: CDKN2A/B and SDKN2A. The patient obtained PR of the brain metastases and SD of the metastasis in the lymph node Conclusion: This was a case of very aggressive and advanced kidney cancer after failure of surgery, radiation therapy, and targeted therapy. The most important was PR of the brain metastases which recurred three times before the disclosed treatment. Previously described metastases to the opposite kidney, lungs and multiple lymph nodes were no longer identified. The patient survived over 8 months versus the estimated 2 months.

Example 32

A 39-year-old Caucasian male presented to the clinic in December 2019 and was diagnosed with renal cell carcinoma of the left kidney with metastases to the lymph nodes, lungs, bones and brain, Stage IV. The patient had a 3-year history of his disease. PET/CT of Nov. 11, 2016 showed a large tumor in the left kidney and left upper lung mass. He underwent nephrectomy and adrenalectomy in the same month and received treatment with interleukin-2 for two cycles with improvement by CT. In July 2019 he developed two metastases to the brain which were resected with clear margins. Pathology confirmed metastatic renal cell carcinoma. MRI of cervical spine of Oct. 17, 2019 revealed metastases to cervical spinal cord. MRI of the brain showed two new lesions out of the prior resection sites. His life expectancy was less than 6 months.

Treatment: The patient began treatment with AS on Dec. 3, 2019 with the final dosage of 19.2 g/kg. On Dec. 5, 2019 it was advised to consider cabozantinib orally and nivolumab and ipilimumab IV under the care of the local oncologist. On Jan. 27, 2020 the patient added axitinib, 5 mg orally and pembrolizumab, 200 mg IV every 3 weeks under the care of his local oncologist due to a lack of insurance coverage. The patient decided to discontinue the disclosed services on Jun. 25, 2020.

Response to Treatment: MRI of the head of Jan. 23, 2020 revealed a resolution of brain metastases which was confirmed by MRI's of Mar. 17, 2020 and Jun. 18, 2020. CT/PET at baseline show a couple of hypermetabolic lesions which could represent metastases to the lymph nodes. They were no longer seen on Mar. 18, 2020 and Jun. 19, 2020 PET/CT's. Patient's baseline blood genomics by Guardant 360 did not show any abnormalities. Tissue genomics by Foundation Medicine of Jan. 24, 2020 revealed PTEN Y27C mutation and AKT2 multiplication which were targets of AS.

Conclusion: The patient obtained a rapid CR of brain metastases on AS and CR of metastases outside the brain on the combination with axitinib and pembrolizumab. He became asymptomatic and was able to return to work after January 2020. He survived over 6 months.

Example 33

A 23-year-old Caucasian female presented to Burzynski Clinic in October 2015 and was diagnosed with atypical small cell neuroendocrine tumor with squamous cell differentiation of the left lung with metastases to the lymph nodes, bones and thyroid gland, Stage IV. The biopsy of metastatic lymph node a year later revealed Ewing sarcoma/PNET. The patient had a three-and-a-half-year history of her disease. Initial bronchoscopy with biopsy of Apr. 12, 2012 revealed primitive neuroectodermal tumor (PNET). On May 8, 2012 she started neoadjuvant VIDE chemotherapy for 6 cycles. She had a decrease in the size in the left hilar mass and metastases in the left inferior lobe of the lung by Nov. 13, 2012. On Jan. 10, 2013 she underwent a left lower lobectomy. The pathology showed atypical small cell neuroendocrine tumor with squamous cell differentiation. From Apr. 23, 2013 to Jun. 3, 2013 she received radiation therapy with the total dose of 50.4 Gy in 28 fractions. CT of Jun. 21, 2013 was consistent with the beginning of CR. From Jul. 4, 2013 to Dec. 4, 2013 she was given adjuvant VAI chemotherapy for 7 cycles. In December 2014 she developed metastasis to the right sternoclavicular node and the biopsy revealed Ewing/PNET. From Feb. 2, 2015 to Mar. 23, 2015 she was given chemotherapy with irinotecan and temozolomide. She progressed with an increase of the right clavicular mass and occurrence of multiple metastases to the bones and thyroid gland. From Sep. 29, 2015 to Oct. 10, 2015 she received 10 treatments of proton therapy to the right clavicular mass. Patient's life expectancy was less than 6 months.

Treatment: The patient began treatment with AS up to 19.2 g/day and A10 up to 50 g/day on Nov. 2, 2015. On Jan. 2, 2016 bevacizumab, 10 mg/kg IV every 2 weeks, was added to the regimen and on Jan. 14, 2016 nivolumab, 220 mg IV every 2 weeks, was also added. She discontinued the disclosed services on Apr. 4, 2016.

Response to Treatment: PET/CT of Dec. 30, 2015 showed a 20% decrease of the size of the right clavicular mass compared to Oct. 30, 2015. Skeletal lesions were stable. The follow-up PET/CT of Mar. 2, 2016 revealed over 50% decrease of the size of the mass and a decrease of metabolic activity. There was, however, new hypermetabolic activity in the left sacrum and ilium. MRI of Sep. 28, 2016 confirmed stable size of clavicular lesion.

Conclusion: The patient was diagnosed with highly malignant neoplasm combining features of neuroendocrine and squamous cell carcinoma and Ewing sarcoma/PNET with multiple metastases. She obtained PR of large clavicular tumor and stabilization of other metastases. She did not have genomic analysis of blood and the tissue showed fusion of EWSR1-FLI1. For this reason, genomic abnormalities did not guide then preparation of her treatment plan.

Example 34

A 65-year-old Indonesian male presented to Burzynski Clinic in October 2017 and was diagnosed with adenocarcinoma of the lung, poorly differentiated with metastases to the lymph nodes, brain, liver, lungs, bones, muscles and adrenal gland, Stage IV. His estimated survival was less than 3 months. The patient had only a 2-month history of his disease. In September 2017 he developed a cough and was treated with antibiotics. PET/CT of Oct. 12, 2017 revealed a tumor in the right upper lobe of the lungs and multiple metastases described above. The biopsy of the lung lesion on Oct. 6, 2017 revealed adenocarcinoma of the lung, poorly differentiated. PD-L1 was +15% and there were no mutations of EGFR, ROS1, MET or ALK. MRI of the brain of Oct. 12, 2017 showed focal lesion of the caudal, periventricular right region with post-contrast enhancement.

Treatment: The patient began the treatment at Burzynski Clinic on Oct. 12, 2017 with AS up to 19.2 g daily, nivolumab 3 m/kg IV every 2 weeks and ipilimumab 1 mg/kg IV every 6 weeks. Vorinostat 100 mg PO daily was added on Dec. 26, 2017. On Mar. 7, 2018 bevacizumab 10 mg/kg every 2 weeks and on May 16, 2018 rucaparib 600 mg PO daily were added to the treatment. On Apr. 2, 2018 he started abscopal radiation therapy to the left hip, 6 Gy for 5 days and vorinostat was discontinued on May 15, 2018. Ipilimumab was discontinued on Jun. 1, 2018 and nivolumab and rucaparib on Jun. 14, 2018. He discontinued the disclosed services on Jul. 1, 2018 and passed away on May 19, 2019.

Response to Treatment: Consultation and MRI of the head at MDACC on Oct. 22, 2017 excluded metastasis to the brain. Follow-up MRI of the head on Nov. 29, 2017 did not show any metastases. PET/CT on Jan. 18, 2018 revealed a decrease in size and metabolic activity of lymph node, pulmonary, liver, adrenal, osseous and intramuscular metastases and a decrease of pleural effusion. The follow-up PET/CT of Mar. 5, 2018 showed stable in size of metastases but an increase of the metabolic activity of osseous metastases and left submental lymph node. The last PET/CT of Jun. 20, 2018 show stability of most of the metastases and progression of intramuscular and pancreatic tail region metastases. Baseline blood genomics by Guardant 360 on Oct. 16, 2017 revealed TERT promoter SNV which was no longer present on May 7, 2018 and Jun. 21, 2018 blood genomics results. He also had marked symptomatic improvement. New mutations occurred on Jun. 21, 2018: NTRK3 F6751 and ERBB2 V777M. The patient obtained PR by PET/CT and CR by molecular study by Guardant 360. The new mutations shown on the Jun. 21, 2018 results caused progression of his cancer.

Conclusion: The patient had a very complex metastatic cancer with metastases to numerous organs. He had a rapid response to combination of AS and check point inhibitors. The lack of mutations typical for lung cancer precluded the addition of other targeted therapy. The new mutations caused progression of his cancer, but he decided not to implement the recommended changes in his treatment plan. He survived a year and a half longer than his life expectancy. The elimination of TERT promoter SNV was affected by AS.

Example 35

A 53-year old Caucasian female presented to Burzynski Clinic in January 2019 and was diagnosed with adenocarcinoma of the left lung (Pancoast tumor) with metastases to the lungs, bones and brain, Stage IV. The patient had a 4-year history of cancer. In 2015 she was found to have a tumor in the posterior left upper lobe of the lung along with a satellite nodule and was treated with pemetrexed and carboplatin from Dec. 2, 2015 and concurrent radiation therapy from Dec. 7, 2015. She received 4 cycles of combination chemotherapy and a fifth cycle only with pemetrexed due to toxicity. She had a response in the left upper lobe but progression in T2 and T3 vertebrae. On Apr. 21, 2016 she underwent resection of the left upper lobe and T2 and T3 vertebral bodies and ribs. The pathology diagnosis revealed moderately differentiated adenocarcinoma, EGFR mutation negative. CT on Feb. 3, 2017 showed enlarging right lung mass. MRI in December 2018 revealed brain metastases. She underwent resection of cerebellar tumors which was over 50% PD-L1 positive but negative for ALK, ROS1 and RER mutations. In March 2019 she had 3 Cyber-knife treatments. Her life expectancy was less than 6 months.

Treatment: The patient began treatment on Sep. 19, 2019 with AS up to 19.2 g daily. On Oct. 4, 2019 nivolumab, 3 mg/kg IV every 3 weeks was added to the treatment. On Dec. 3, 2019 the patient was switched to pembrolizumab 200 mg every 3 weeks. She decided to discontinue treatment under the disclosed care on Feb. 4, 2020.

Response to Treatment: Follow-up MRIs of Oct. 9, 2019 and Dec. 10, 2019 were initially stable and later had a 68% decrease of the size of cerebellar lesion indicating the beginning of PR. CT/PET of Nov. 22, 2019 showed a decrease of pulmonary nodules. Blood genomic analysis of Jan. 15, 2019 revealed FBXW7 Y545C, but the patient did not agree to have a follow-up analysis. Tissue genomics on Jan. 23, 2019 showed tumor mutational burden of 30 Muts/Mb and KRAS G13D, RICTOR amplification, APC 5747, ATR R912fs*1, BCORL1 V1058fs*12, FGF6 R1250, RBM10 E242*, and ZNF217 L546V. The best option based on genomic analysis was the treatment with checkpoint inhibitors which was instituted.

Conclusion: The patient suffered from advanced lung cancer with multiple metastases and was extensively treated with two surgical resections, combination chemotherapy and two different types of radiation therapy. She responded to the combination of AS and nivolumab and accomplished PR of brain metastasis.

Example 36

A 66-year-old Caucasian male presented to Burzynski Clinic in February 2019 and was diagnosed with adenocarcinoma of the right lung with metastases to the lymph nodes and bones, Stage IV. The patient had approximately a 1-year history of his cancer. In May 2018 he was hospitalized because of back pain and numbness of the legs. He was found to have a mass at T6 vertebra compressing the spinal cord and underwent a T5-6 laminectomy, excision of the tumor, bone graft and T4-8 spinal instrumentation with Medtronic pedicle screws and rods. The primary tumor was in the right lower lobe of the lung and was diagnosed as adenocarcinoma with an ALK mutation. PET on Aug. 21, 2018 showed a tumor in the lung and extensive metastases to T5-6 and 7 with invasion of paraspinal soft tissues and spinal canal, right clavicle and multiple lymph nodes in the mediastinum, right hilum and right neck. In December 2018 he became a paraplegic. On Jan. 18, 2019 he was hospitalized for urosepsis and developed multiple pulmonary emboli. When he recovered from these complications, he presented to Burzynski Clinic. His life expectancy was less than 4 months.

Treatment: The patient began treatment on Mar. 20, 2019 with AS up to 28.8 g daily and alectinib 1200 mg PO daily. He continues the treatment at present.

Response to Treatment: Patient had a rapid response to treatment. PET/CT of Jul. 2, 2019 showed a decrease in the size and metabolic activity of the lung mass and on PET/CT of Jan. 7, 2020 this mass did not show any metabolic activity which was confirmed on PET/CTs of Mar. 31, 2020 and Jul. 28, 2020 indicating CR of the lung tumor. Metastatic lymph nodes showed continuous improvement and were no longer seen on the Mar. 31, 2020 and Jul. 28, 2020 PET/CT indicating CR of the lymph nodes. Metabolic activity in the bone metastases almost completely resolved on Jul. 2, 2020 and Oct. 10, 2019 and Jan. 7, 2020 PET/CTs indicating PR of bone metastases. Blood genomic analysis of Aug. 13, 2020 revealed ND of EML4-ALK Fusion and SMAD4 A406T. Follow-up PET/CT of Jul. 28, 2020 showed an increase of T6 lesion and a questionable T5 lesion. In view of the patient's very good condition and negative Guardant 360, the treatment plan was not changed. These lesions will be followed on the next PET/CT. Patient's condition markedly improved and he was able to make a long trip to India in September 2019. Elimination of the ALK fusion was affected by alectinib but SMAD4 A406T by AS.

Conclusion: The patient suffered from very advanced lung cancer which damaged his vertebra and caused paralysis from the waist down as well as serious complications such as sepsis and multiple lung emboli. He accomplished CR of lung and lymph node involvement and PR (near CR) of bone involvement. ALK fusion and SMAD mutation were no longer seen in the follow-up Guardant 360. His physical improvement permitted him to be involved in business and travel. He was approaching a 2-year survival verses his estimated less than 4 months at baseline.

Example 37

A 79-year-old Caucasian male presented to Burzynski Clinic in June 2019 and was diagnosed with adenocarcinoma of the lung with extensive metastases to the lymph nodes and lungs, Stage IV. The patient had a 9-month history of his disease. In the fall of 2018, he developed chest pain and weight loss and on Mar. 25, 2019 he underwent a biopsy of mediastinal lymphadenopathy which confirmed his diagnosis. He was followed with pembrolizumab, but PET/CT of Jun. 5, 2019 revealed extensive involvement of the lymph nodes in the mediastinum and hilum and in the right upper and middle lung. His life expectancy was less than 6 months.

Treatment: The patient began treatment on Jun. 10, 2019 with AS up to 19.2 g daily. Erlotinib 150 mg PO daily was added on Jun. 24, 2019 and pembrolizumab was also restarted 200 mg IV every 3 weeks. He discontinued treatment under the disclosed care on Apr. 10, 2020.

Response to Treatment: PET/CTs of Aug. 28, 2019 and Jan. 13, 2020 showed continuous improvement. Nodular densities in the right mid lung have resolved and there was marked improvement of the size and metabolic activity of all metastatic lymph nodes on the Aug. 28, 2019 scan. There was further improvement of metastases posterior to the left main stem bronchus and in the AP window but slight increase of uptake in the right hilar and subcarinal lymph nodes on Jan. 13, 2020 PET/CT indicating PR. Patient blood genomic analysis of Jun. 18, 2019 showed EGFR P753L mutation which provided the rationale for erlotinib and follow-up analysis of Jan. 13, 2020 was negative.

Conclusion: The patient accomplished radiological PR and molecular CR based on the blood genomic study. He discontinued these services prematurely; however, he was doing well a year after treatment start.

Example 38

A 66-year-old Caucasian female presented to Burzynski Clinic in September 2019 and was diagnosed with adenocarcinoma of the right lung with metastases to the lymph nodes, lungs, pleura, bones, brain and peritoneum, Stage IV. The patient had a year history of her cancer. She first developed symptoms such as persistent cough in August 2018, and in April 2019 she was found to have omental metastases diagnosed as originated from adenocarcinoma of the lungs. On May 17, 2019 the PET showed tumor in the right lung and metastases to the lymph nodes, pleura, bones and peritoneum and the MRI the next day revealed brain metastasis. She was found positive for an EGFR L858R mutation and negative for ROS1, ALK, MET, KRAS and BRAT She had a TP53 variant and she was PD-L1 positive 70%. She started osimertinib in the week of May 31, 2019. she was also treated with SRS to the right frontal lobe on Jun. 6, 2019. On Jul. 22, 2019 she was started on PB. CT of September 2019 showed stable disease and the MRI of the head revealed improvement. Her life expectancy was less than 6 months.

Treatment: The treatment began on Sep. 23, 2019 with AS up to 19.2 g daily. She also continued osimertinib under the care of the local oncologist. She decided to discontinue the treatment against medical advice on Dec. 21, 2019 due to personal issues. The last contact was Mar. 25, 2020 and she was well.

Response to Treatment: Follow-up MRI of the head of Nov. 6, 2019 revealed 25% decrease of the size of right frontal metastasis and CT of the chest showed 22% decrease of right suprahilar mass. Baseline blood genomic analysis by Guardant 360 showed NF1 Splice Site SNV but the patient did not wish to have a follow-up test. Physically she was doing well.

Conclusion: This was an advanced and aggressive lung cancer with multiple metastases including the brain. She had objective response after two months of treatment but decided to discontinue against medical advice.

Example 39

A 69-year-old Caucasian male presented to Burzynski Clinic in May 2020 and was diagnosed with adenocarcinoma of the left lung with metastases to the lymph nodes, lungs, bones, brain, liver, spleen and pericardium, Stage IV. The history of his cancer was very short and of a 1-year duration. He was diagnosed by biopsy in April 2019 and in May 2019 he started 4 cycles of neoadjuvant chemotherapy and underwent left lung tumor resection. In Spring of 2020 he developed metastasis to the right hip, confirmed by biopsy. He was also found to have brain metastasis for which he received stereotactic radiation therapy. His cancer was PD-L1 negative and was showing HER2 exon 20 Y772 mutation and TP53 mutation. His life expectancy was less than 3 months.

Treatment: The treatment began on May 27, 2020 with AS up to 19.2 g daily. On Jun. 11, 2020 fam-trastuzumab deruxtecan-nxki (Enhertu), 5.4 mg/kg IV every 3 weeks and denosumab, 60 mg SC every 3 weeks were added to the treatment. On Jul. 14, 2020 he started 5 days of radiation treatment to the cervical spine and humerus. On Oct. 30, 2020 the patient was admitted to the local hospital and the treatment was discontinued.

Response to Treatment: Follow up PET/CTs of Aug. 13, 2020 and Oct. 9, 2020 have shown continuous marked improvement. Involvement of the hilar and mediastinal lymph nodes left lower lung mass and bony metastases resolved and the liver and spleen metastases resolved. Pericardial effusion was resolved and there was only minimal pleural effusion. Brain metastasis decreased by 33%, however, tiny enhancing lesions were still present as seen on MRI of Oct. 10, 2020. MRI of Oct. 27, 2020 revealed leptomeningeal involvement. Blood genomic analysis of May 26, 2020 showed ERBB2 A775_G776insYVMA, EGFR amplification, TP53 Y126D and TP53 R273H mutations. The patient did not agree to have a follow-up analysis. He had very good symptomatic improvement during the treatment.

Conclusion: This was a case of a very advanced and very aggressive lung cancer. Patient had very good and rapid PR which was followed by occurrence of leptomeningeal involvement. Further recommendations of changes in his treatment plan were not agreed on by the local oncologists.

Example 40

A 63-year-old Vietnamese female presented to Burzynski Clinic in December 2017 and was diagnosed with serous papillary carcinoma of the left ovary with metastases to mediastinal and pelvic lymph nodes and peritoneum, stage IV. The patient had a 2-year history of her disease. At the beginning of 2016 she was found to have diffuse metastatic disease involving abdominal and pelvic peritoneum and thoracic lymph nodes. She began chemotherapy with carboplatin and paclitaxel in Hong Kong in July 2016. Bevacizumab was added to the second cycle. The treatment was complicated with intestinal perforation in August 2016. She underwent laparotomy, bilateral saplingo-oophorectomy, sigmoid colon resection and transverse colostomy. After recovery from surgery she was given two additional cycles of chemotherapy until Oct. 19, 2016. There was still involvement of mesentery and peritoneum and she was switched to gemcitabine and carboplatin. She developed profound bone marrow suppression and her CA125 continued to rise. On Dec. 4, 2016 she was switched to chemotherapy with Doxil, but her cancer continued to progress. On Jan. 2, 2017 she was switched again to gemcitabine for 4 cycles. Her life expectancy was less than 6 months.

Treatment: The treatment began on Dec. 6, 2017 with AS up to 19.2 g daily. She was also taking anastrozole 1 mg PO every other day and nivolumab 3 mg/kg IV every 2 weeks. On Dec. 12, 2017 pazopanib 200 mg PO daily was added to the treatment but was replaced by sorafenib 200 mg PO daily on Jan. 18, 2018. On Mar. 22, 2018 rapamycin 1 mg PO daily was added to the regimen. The patient discontinued sorafenib on Jul. 12, 2018 because she thought it was causing diarrhea. Rapamycin was discontinued on Sep. 10, 2018. The treatment was discontinued on Dec. 3, 2018 and the patient was advised to take an NTRK1 inhibitor based on recent genomic analysis. She decided not to proceed. The last communication with the patient was on Mar. 30, 2019. She was in China and under the care of a different physician.

Response to Treatment: CT/PET on Aug. 7, 2018 revealed a decrease of size and metabolic activity of pretracheal, subcarinal, and cadiophrenic angle metastatic lesions. Mesenteric metastases were stable and pelvic mass was calcified and not changed in size indicating objective response. The patient's blood genomic analysis by Guardant 360 of Mar. 22, 2018 did not show any mutations.

Conclusion: This patient's cancer failed to respond to surgery and 4 regimens of chemotherapy. There was objective response to treatment at the Burzynski Clinic and the patient survived in good condition over 15 months versus a less than 6-month life expectancy.

Example 41

A 54-year-old Vietnamese female presented to Burzynski Clinic in January 2018 and was diagnosed with high-grade serous carcinoma of the ovary with metastases to the lymph nodes, lungs, liver, spleen, peritoneum and pelvis, Stage IV. The patient had a short 6-month history of her disease. CT of Nov. 20, 2017 revealed bilateral adnexal masses and masses in the uterus, peritoneal carcinomatosis, and metastases to the lymph nodes, liver and spleen, Stage IV. The biopsy of the retroperitoneal mass on Dec. 11, 2017 confirmed the above diagnosis. She did not have any treatment yet. Her life expectancy was less than 3 months.

Treatment: The treatment began on Jan. 9, 2018 with AS up to 9.6 g daily. On Jan. 24, 2018 chemotherapy with paclitaxel, carboplatin and bevacizumab every 3 weeks was added to the treatment. She decided to discontinue paclitaxel and carboplatin on Apr. 13, 2018 but continued bevacizumab. On Sep. 20, 2018 she was advised to add palbociclib which she started on Oct. 17, 2018 (75 mg PO daily). She decided to discontinue palbociclib on Jan. 3, 2019. She discontinued the treatment on Jun. 11, 2019.

Response to Treatment: PET/CT of Apr. 6, 2018 showed marked improvement with most of the lesions resolved. PET/CT of Sep. 4, 2018 confirmed reduction and resolution of the lesion with slightly increased metabolic activity in the porta hepatis indicating PR. PET/CT of Feb. 9, 2019 showed PD with new metastatic lymph node. Blood genomic analysis by Guardant 360 of May 15, 2019 showed elimination of multiple mutated genes compared to the baseline of Jan. 4, 2018 including TP53 R248W, NF1 K583R, MYC amplification, PIK3CA amplification, RAF1 amplification, AR M887V, ALK N1544K, PIK3CA Q597H and ARID1A R1889W. The patient also had symptomatic Improvement.

Conclusion: The patient was diagnosed with very advanced and aggressive ovarian cancer. She responded rapidly to the treatment and accomplished almost complete elimination of tumors and mutated genes. She survived over 18 months versus her life expectancy of less than 3 months. The progression of her cancer was caused by her poor compliance with treatment plan.

Example 42

A 73-year-old Caucasian female reported to Burzynski Clinic in May 2019 and was diagnosed with serous carcinoma of the ovary with metastases to the lymph nodes and liver, Stage IV. The patient had a 4-year history of her disease. Her initial diagnosis was established in May 2015. She underwent a standard chemotherapy but developed recurrence in July 2016. At that time, she was started on ribociclib and was in remission in January 2017. She relapsed again in July 2017 and was treated with paclitaxel and carboplatin chemotherapy with 40% tumor reduction after 4 cycles. She decided to stop chemotherapy and was prescribed olaparib and pembrolizumab and obtained 60% tumor reduction. She continued the treatment for one year. In August 2018 she underwent laparoscopic resection of the residual tumor. She continued the treatment and CT of Mar. 19, 2019 showed small, multiple external iliac lymph nodes. Guardant 360 of Nov. 13, 2018 was negative but the follow-up on Apr. 9, 2019 showed BRACA2 K2013, TP53 R209fs, TP53 V143M, TP53 R175H, ARID1A G246V, BRAF amplification, and PIK3CA amplification indicating recurrence. Patient's estimated survival was less than 6 months.

Treatment: The treatment began on May 7, 2019 with AS up to 19.2 g daily. She also continued olaparib and pembrolizumab prescribed by her local oncologist. She decided to discontinue the treatment on Jul. 8, 2019 against medical advice. Her disease progressed but she was still alive as of December 2020.

Response to Treatment: PET/CT on Jun. 12, 2019 at the beginning of the treatment revealed liver and peritoneal metastases. She did not have a follow-up scan at the time of discontinuation. Repeated Guardant 360 Of Jun. 24, 2019 showed marked improvement including reduction of TP53 R209fs by 71%, and ARID1A G246V by 90%. TP53 R176H, BRAF amplification, PIK3CA amplification, CCND1 R291W and BRACA2 S2667N were no longer detected. The patient was asymptomatic.

Conclusion: The patient received prior treatment with two types of standard chemotherapy, and two types of targeted therapy and immunotherapy. She also had a tumor resection. Her cancer relapsed but responded to short treatment with AS. The patient discontinued the treatment after 2 months against medical advice.

Example 43

An 80-year-old Caucasian female presented to Burzynski Clinic in May 2020 and was diagnosed with serous carcinoma of the ovary, high-grade, with metastases to the peritoneum, liver and pleura, Stage IV. The patient has a short history of her disease. PET/CT 2 months before revealed widely spread metastatic disease which was diagnosed based on a biopsy of Apr. 10, 2020. She received one treatment of chemotherapy. At the age of 35 she underwent hysterectomy without saplings-oophorectomy. Her life expectancy was less than 6 months.

Treatment: The treatment began on May 11, 2020 with AS up to 19.2 g daily. She continued chemotherapy with paclitaxel and carboplatin under the care of her local oncologist which was completed on Oct. 7, 2020. On Oct. 10, 2020 she was started on bevacizumab 15 mg/kg IV every 3 weeks and niraparib 300 mg PO daily which was continued.

Response to Treatment: Follow-up PET/CT on Jul. 20, 2020 and Sep. 25, 2020 have shown marked improvement of metastatic involvement with only a small amount of metabolically active peritoneal involvement left. There was resolution of the bilateral pleural effusions and reduction of ascites indicating PR. A CT of Nov. 30, 2020 showed a small amount of ascites and stable mesenteric thickening. Blood genomic analysis by Guardant 360 of Jul. 21, 2020 and Sep. 21, 2020 compared to baseline of Apr. 16, 2020 revealed a marked decrease of concentration of TP53 N235-Y236del (by 88%) and elimination of SMAD4 P511 L. The patient became asymptomatic.

Conclusion: This was a case of very aggressive and advanced ovarian cancer which obtained PR on the treatment with AS and chemotherapy. There was also a marked reduction of mutated genes in the blood.

Example 44

A 46-year-old Turkish male presented to Burzynski Clinic in November 2016 and was diagnosed with poorly differentiated adenocarcinoma of the pancreas with metastasis to the lymph node, Stage IVA. The patient had a 2-year history of his cancer. In May 2015 he was found with a tumor in the pancreatic head which diagnosed as poorly differentiated adenocarcinoma. On Jun. 29, 2015 he underwent a pyloric sparing Whipple procedure with 8/34 positive lymph nodes. In August 2015 he started FOLFIRINOX chemotherapy and received 11 treatments. He then underwent IMRT with concurrent capecitabine, finishing on Mar. 3, 2016. In July 2016 he developed recurrence indicated on PET/CT by a climbing CA19-9 and a metabolically active lymph node. His life expectancy was less than 6 months.

Treatment: The treatment began in November 2016 with AS up to 14.4 g daily. He was also taking sorafenib 200 mg PO daily, rapamycin 2 mg PO daily, vorinostat 100 mg PO daily and capecitabine 500 mg twice a day PO (2 weeks on and 1 week off). He decided to discontinue AS temporarily, as well as other medications, and take gemcitabine and nab-paclitaxel instead starting Dec. 15, 2016. He then decided to restart AS on Jan. 12, 2017 along with gemcitabine 1000 mg/m2 and nab-paclitaxel 125 mg/m2 on day 1, day 8 and day 15 every 4 weeks and bevacizumab 10 mg/kg every 2 weeks. On Feb. 27, 2017 sorafenib, rapamycin and vorinostat were restarted as well. He discontinued the treatment on May 19, 2017.

Response to Treatment: The follow-up PET/CT of Feb. 13, 2017 did not show a hypermetabolic lymph node anymore. The follow-up PET/CT of Apr. 11, 2017 and May 25, 2017 did not show any cancer related hypermetabolic lesions. His tumor marker CA19-9 at the beginning of the treatment was as high as 1005 units/mL but it decreased to 152 units/mL. It never reduced further to normal level. Patient's response was determined as PR. Patient's baseline Guardant 360 on Nov. 4, 2016 was negative. Tissue genomic analysis by Foundation Medicine of Nov. 18, 2016 revealed KRAS G12D, NF1 H415Y, ARID1A Q1334-R1335lnsQ, and SMAD4 R135.

Conclusion: This patient had aggressive pancreatic cancer which recurred after a Whipple surgical procedure, extensive chemotherapy and combination radiation therapy and chemotherapy. He accomplished PR on the treatment plan with AS, targeted agents and modified chemotherapy.

Example 45

A 77-year-old Caucasian male presented to Burzynski Clinic in June 2017 and was diagnosed with moderately differentiated adenocarcinoma of the pancreas with metastases to the stomach and the lung, Stage IVB. The patient had a year history of his cancer. In August 2016 he developed upper abdominal pain. The CT of Oct. 4, 2016 showed superior mesenteric artery encasement with a pancreatic mass. The biopsy confirmed diagnosis of adenocarcinoma. On Oct. 11, 2016 he underwent exploratory laparotomy and retrocolic gastrojejunostomy tube placement. The procedure was not successful, and he underwent a second surgery. On Dec. 9, 2016 he started FOLFIRINOX at 40% dose reduction. On Jan. 28, 2017 he developed right deep vein thrombosis. Due to toxicity of FOLFIRINOX he was switched to gemcitabine at 50% dose reduction on Feb. 13, 2017 and he completed 3 cycles on May 3, 2017. CT of Jun. 13, 2017 showed progression of his cancer. His life expectancy was less than 3 months.

Treatment: The treatment began on Jun. 29, 2017 with AS up to 12 g daily. Starting from Jul. 5, 2017 the following drugs were added: sorafenib 200 mg PO daily, rapamycin 2 mg PO daily, vorinostat 100 mg PO daily and capecitabine 1000 mg PO daily (2 weeks on and 1 week off). He discontinued capecitabine on Jul. 27, 2017 due to diarrhea and discontinued sorafenib, rapamycin and vorinostat on Aug. 24, 2017. Rapamycin was restarted on Oct. 23, 2017. On Feb. 13, 2018 the patient restarted sorafenib, and olaparib 300 mg PO daily was added. Sorafenib and olaparib were discontinued on Apr. 9, 2018 and were replaced by erlotinib 150 mg PO daily. The patient discontinued erlotinib on Sep. 17, 2018. On Sep. 26, 2018 his oral medications were changed to osimertinib 80 mg daily, vorinostat 100 mg and rapamycin 2 mg. The treatment was discontinued on Dec. 29, 2018 when the patient developed pain in the stomach due to blockage of the bypass. He restarted the treatment on Jan. 1, 2019 when the blockage was spontaneously relieved. He discontinued again on Jan. 16, 2019 and was admitted to the hospital due to another blockage incident. He underwent laparotomy and was found with peritoneal carcinomatosis. He passed away on Feb. 4, 2019.

Response to Treatment: PET/CT of Oct. 12, 2017 showed a decrease of the thickening of the gastric wall and reduced metabolic activity. There was further improvement on the PET/CT of Jan. 24, 2018, Jun. 11, 2018 and Sep. 4, 2018. The PET/CT of Nov. 19, 2018 showed a slight worsening (6% increase). The blood genomic study by Guardant 360 showed a stable level of TP53 C135S on multiple analyses of Jan. 22, 2018, Mar. 26, 2018, Jun. 11, 2018, Sep. 4, 2018 and Nov. 20, 2018. EGFR C307W and EGFR T783del were no longer seen on the Nov. 20, 2018 study. EGFR A822T was not detectable on Sep. 4, 2018. BRCA1 T13941 and PDGFRA G652fs were still present despite the treatment with olaparib and sorafenib. The elimination of the two EGFR mutations were possibly affected by osimertinib. Patient response was classified as PR.

Conclusion: This was a challenging case of recurrent pancreatic cancer after surgery and two different chemotherapy plans. The patient's condition and his age created obstacles from continuing his treatment plan as it was necessary to prematurely discontinue his medications. Most of the time he was in good condition and enjoyed a normal life. He survived 20 months versus a 3-month life expectancy.

Example 46

A 71-year-old Caucasian male presented to Burzynski Clinic in May 2019 and was diagnosed with invasive, moderately differentiated adenocarcinoma of the pancreas with metastases to the liver, Stage IVB and adenocarcinoma of the prostate, Stage III. The patient had a 2-year history of localized prostate cancer, not treated before with PSA of 14.98 u on Mar. 6, 2019. MRI of Mar. 28, 2019 showed a pancreatic head mass abutting the superior mesenteric vein and compressing the left renal vein and extending to hepatoduodenal ligament lymph node. PET/CT of Mar. 26, 2017 confirmed hypermetabolic lesions in the head of the pancreas, liver and prostate. Biopsy (FNA) of the pancreatic head on Apr. 30, 2019 confirmed diagnosis of adenocarcinoma of the head of the pancreas. The patient refused surgery and chemotherapy. His life expectancy was less than 6 months.

Treatment: The treatment began on May 15, 2019 with AS up to 19.2 g daily, sorafenib 200 mg PO daily, vorinostat 100 mg PO daily and rapamycin 2 mg PO daily. Capecitabine 1500 mg PO daily (2 weeks on and 1 week off) was added on Jun. 5, 2019 and bevacizumab 10 mg/kg IV every 2 weeks was added on Jun. 6, 2019. On Aug. 12, 2019 the patient discontinued sorafenib, vorinostat, rapamycin and capecitabine due to personal difficulties. He discontinued bevacizumab for personal reasons and restarted capecitabine on Nov. 19, 2019, and on Dec. 9, 2019 increased the dose to 2000 mg PO daily (2 weeks on and 1 week off) and restarted sorafenib 200 mg PO daily. He discontinued AS on Dec. 23, 2019. He restarted AS on Feb. 11, 2020 but discontinued the treatment on Mar. 22, 2020.

Response to Treatment: Follow up PET/CT on Sep. 19, 2019 showed a decrease in the size and metabolic activity of the pancreatic tumor. Hypermetabolic lesions in the prostate gland were no longer seen. There was metabolic activity in the porta hepatis and aortocaval lymph nodes which were enlarged before. CT of Mar. 9, 2020 showed stable size of pancreatic tumor and small lymph nodes. The liver did not show any lesions. The patient had radiation seeds placed recently in the prostate by another physician. Blood tests revealed continuous decrease of tumor markers. CA 19-9 decreased from baseline 364 U/mL to 160.2 U/mL and PSA from baseline 17.6 ng/mL to 10.8 ng/mL on Sep. 12, 2019. The blood genomic analysis by Guardant 360 of Feb. 11, 2020 compared to the baseline of May 13, 2019 showed stable levels of SMAD4 R497H and KIT H630D and an occurrence of KRAS G12R and SMAD4 S517fs.

Conclusion: This patient had objective response in both pancreatic and prostate cancer but because of logistic reasons he could not comply with the treatment plan. He was symptom-free most of the time and survived over a year compared to the less than expected 6 months.

Example 47

A 62-year-old Caucasian male presented to Burzynski Clinic in April 2017 and was diagnosed with adenocarcinoma of the prostate, Gleason's score 9 with metastases to the lymph nodes and bones and obstructive uropathy, Stage IV and renal cell carcinoma, Stage IV. The patient had a short history of his cancers. In February 2017 he developed progressive difficulty with urination and stopped urinating on Feb. 22, 2017 leading to kidney failure. He was found to have a tumor in the prostate and the right kidney and metastases to the lymph nodes and bones. PSA was 16 ng/mL. The biopsy of the prostate and kidney confirmed the above diagnoses. He had placement of bilateral nephrostomies with improvement of kidney function. The biopsy of the left inferior ramus pubis on Feb. 28, 2017 confirmed metastatic adenocarcinoma of the prostate. On Mar. 3, 2017 he was started on Casodex 50 mg PO daily and Lupron 22.5 mg IM every 3 months. The biopsy of the renal mass on Mar. 14, 2017 confirmed renal cell carcinoma. On Mar. 14, 2017 he underwent conversion of the bilateral nephrostomy to double-J ureteral stents. PSA on Mar. 10, 2017 increased to 38 ng/mL. His life expectancy was less than 6 months.

Treatment: The treatment began on Apr. 6, 2017 with AS up to 38.4 g daily. He also continued Casodex and Lupron. On Jun. 8, 2017 pazopanib 400 mg daily was added to the treatment. On Feb. 20, 2018, upon recommendation of his oncologist from MDACC, he started nivolumab 3 ring/kg IV every 2 weeks. Pazopanib was discontinued. On May 10, 2018 ipilimumab 1 mg/kg IV was added and continued every 3 weeks with nivolumab, 3 mg/kg by oncologist from MDACC. On Nov. 1, 2018 he developed bilateral interstitial pneumonia, possibly as an adverse event from nivolumab. He was hospitalized and the treatment was discontinued. He passed away from pneumonitis on Dec. 17, 2018.

Response to Treatment: PET/CTs of Aug. 9, 2017, Jan. 8, 2018, Jul. 31, 2018 and Nov. 8, 2018 showed no hypermetabolic activity that was visible on the PET/CT of May 9, 2017. The PSA on Jun. 19, 2017 was below 0.1 ng/mL. The blood genomic analysis by Guardant 360 of Jan. 10, 2018 compared to Sep. 25, 2017 showed ND PTEN G143S and SMAD R189H. The patient was in very good condition during the treatment. His response was classified as CR of prostate cancer and SD of kidney cancer.

Conclusion: The patient was diagnosed with very aggressive metastatic prostate cancer and kidney cancer. He obtained a rapid CR of bony metastases from the prostate cancer and stabilization of the kidney cancer. Two mutations of PTEN and SMAD were eliminated as the result of treatment. He survived 20 months versus the estimated less than 6 months and died from toxicity of immunotherapy.

Example 48

A 60-year-old Caucasian male presented to Burzynski Clinic in September 2017 and was diagnosed with adenocarcinoma of the prostate, Gleason score 8, with metastases to the lymph nodes, bones and lungs, Stage IV. He had a 5-year history of his disease. In March 2016 he developed acute urinary retention and PSA of 314 ng/mL. On May 13, 2016 he underwent a transurethral resection of the prostate with pathology diagnosis as above. In June 2016 he developed lymph node, bone and lung metastases. On Aug. 17, 2016 his PSA increased to 384 ng/mL. On Sep. 21, 2016 he commenced Lupron 22.8 mg IM every 3 months and on Sep. 22, 2016 he started PB. His PSA decreased to 3.9 ng/mL in November 2016 but on Jan. 23, 2017 it increased to 6.1 ng/mL. On Feb. 16, 2017 he started Casodex 50 mg PO daily, but his PSA continued to rise. He discontinued Lupron on Jun. 27, 2017 and Casodex in July 2017. On Jun. 28, 2017 he started Xtandi 160 mg PO daily and olaparib 200 mg PO daily. His life expectancy was less than 6 months.

Treatment: The treatment began on Sep. 6, 2017 with AS up to 19.2 g daily. The patient was also taking Casodex 160 mg PO daily, Zoladex 10.8 mg IM every 3 months, rapamycin 1 mg PO daily, Xtandi 160 mg PO daily, and PB 12 g PO daily. On November 8 dasatinib 50 mg PO daily was added to the treatment. On Jan. 11, 2018 Zoladex was replaced by degarelix 240 mg SQ every 4 weeks. The patient discontinued the disclosed services on Mar. 14, 2018 because of high cost of prescription medications.

Response to Treatment: Follow-up PET/CT of Jan. 8, 2018 and Mar. 13, 2018 compared to baseline of Nov. 6, 2017 showed resolution of the right upper lung metastatic nodule. The overall size of the prostate gland was improved, and metabolic activity decreased. Baseline PSA was normal at baseline but increased to 12.2 ng/mL on Mar. 19, 2018. The patient was symptom free most of the time. The genomic analysis of tumor tissue of Oct. 5, 2016 revealed the following abnormalities: ATM Q513, MYC amplification, FAM123B A850-F851Ins30, LRP1B R799, LYN amplification and PREX2 A1577V. Olaparib was selected based on ATM mutation and dasatinib based on LYN amplification. Guardant 360 blood genomic analysis of Oct. 5, 2016 showed amplifications of PIK3CA, MYC and CCNE1. AS treatment was selected based on MYC amplification. The patient did not repeat Guardant 360 for personal reasons. The response to treatment was determined as PR.

Conclusion: The patient had aggressive metastatic prostate cancer and accomplished CR of lung metastasis and objective response of prostate tumor. This was followed by an increase of the PSA indicating the beginning of progression of the disease.

Example 49

A 59-year-old African American male presented to Burzynski Clinic in November 2018 and was diagnosed with poorly differentiated adenocarcinoma of the prostate, Gleason's score 10 with metastases to the lymph nodes, bones and lungs, Stage IV. The patient had a short two-year history of his cancer. His diagnosis and treatment were done at MDACC in Houston. In December 2016 he developed hematuria and underwent TURP on Jan. 23, 2017. He also had an enlarged prostate and extensive metastases to the abdominal and pelvic lymph nodes. His initial pathology diagnosis was high grade metastatic urothelial carcinoma for which he received chemotherapy with cisplatin and gemcitabine starting Feb. 8, 2017. He developed substantial toxicity and had further evaluation of cancer tissue and tissue genomic testing based on recommendation. As the result, his diagnosis was changed to poorly differentiated adenocarcinoma of the prostate, Gleason's score 10 with BRACA2 mutation, high PDL1 expression and high TMB. His chemotherapy was discontinued, and he started degarelix on Apr. 26, 2017 and continued until August 2017. He did not respond and developed metastases to the bones and lungs. The lymph node biopsy confirmed adenocarcinoma of the prostate on Aug. 16, 2017. He was started on abiraterone and Lupron injection every 4 months. On Sep. 14, 2017 he was started on chemotherapy with cabazitaxel and carboplatin every 3 weeks×10 and denosumab monthly. He accomplished a decrease of his PSA and bony metastases. On Jul. 16, 2018 he was started on olaparib. His cancer progressed in September 2018 with development of the tumor extending from the prostate to the urinary bladder and an increase in the PSA. On Oct. 1, 2018 olaparib was discontinued and he was restarted on abiraterone. On Oct. 22, 2018 he began chemotherapy with carboplatin and paclitaxel for 6 cycles. His life expectancy was less than 3 months.

Treatment: His treatment began on Nov. 19, 2018 with AS up to 19.2 g daily. He also continued Lupron, abiraterone, carboplatin, paclitaxel and denosumab at MDACC. On Jan. 22, 2019 olaparib 600 mg PO daily was added to his treatment. He discontinued the disclosed services on Mar. 19, 2019 for personal reasons.

Response to Treatment: The follow-up bone scan on Dec. 27, 2018 compared to the baseline of Sep. 28, 2018 showed a decrease of all the bony metastases. The CT of Dec. 27, 2018 compared to baseline of Sep. 28, 2018 showed a decrease in the size of the pelvic mass. The PSA was at a low level and stable during the treatment. The blood genomic analysis by Guardant 360 on Jan. 3, 2019 showed a decrease of TP53 H178_5183del, APCS 1971 F and ND of EGFR V742V and EGFR amplification.

Conclusion: This was a very aggressive case of metastatic prostate cancer which failed to respond to 3 different hormonal treatments, the newest type of chemotherapy and targeted therapy. He accomplished PR of extensive bone involvement (without confirmation by the second scan), improvement in his condition, elimination of EGFR mutation and amplification, and a decrease of concentration of mutated TP53 and APC. He responded to the combination of AS, hormonal and targeted therapy, and the modified chemotherapy regimen to which he did not respond to previously.

Example 50

A 69-year-old Chinese male presented to Burzynski Clinic in July 2019 and was diagnosed in February 2017 with adenocarcinoma of the prostate, Gleason score 9, with metastases to the bones, Stage IV. The patient had a 2-year history of his cancer. In February 2017, he had an elevation of PSA of 9.1 ng/mL. After establishing the diagnosis on Apr. 3, 2017, he underwent a radical prostatectomy. The resection margins were negative for cancer but lymphovascular invasion and perineural invasion were extensively present. He was started on Lupron thereafter but discontinued on Jun. 7, 2019. In January 2019 he began enzalutamide which was discontinued on Jun. 7, 2019. Bone scan and CT of May 23, 2019 revealed progression of bone metastases. At that time, he was given 5 radiation treatments to the right ribs and scapula. His life expectancy was less than 6 months.

Treatment: The treatment began on Jul. 8, 2019 with AS up to 19.2 g daily. He also took abiraterone, 500 mg PO daily and prednisone 5 mg PO daily. On Jul. 9, 2019 rucaparib 300 mg daily was added to the treatment. On Jul. 18, 2019 he started pembrolizumab 200 mg IV every 2 weeks under the care of his local oncologist. He discontinued rucaparib and pembrolizumab on Sep. 16, 2019. On Sep. 23, 2019 A10 infusions were added to the treatment up to 144 g daily. He decided to discontinue the treatment on Nov. 4, 2019.

Response to Treatment: The follow-up bone scan of Sep. 11, 2019 showed progression of the disease. The treatment plan was changed but the patient discontinued the treatment before the evaluation of his response. His blood genomic analysis of Sep. 5, 2019 showed ND of NF1 T1295S compared to baseline of Jul. 1, 2019.

Conclusion: This patient had very aggressive and advanced prostate cancer which failed radical prostatectomy, radiation therapy and three modalities of hormonal therapy. His treatment plan at Burzynski Clinic was prepared based on the genomic analysis by Guardant 360 and Foundation Medicine, but apparently did not cover a sufficient number of mutated genes. The mutation of NF1 was eliminated.

Example 51

A 37-year-old Caucasian male presented to Burzynski Clinic in November 2017 and was diagnosed with adenoid cystic carcinoma of the lung with metastases to the liver and peritoneum, Stage IV. The patient had a 5-year history of his disease. He was diagnosed in February 2012 and underwent pneumonectomy followed by radiation therapy in May 2012. He was also treated with chemotherapy: carboplatin and paclitaxel for 6 cycles from May 2, 2012 to Jun. 15, 2012. In Spring of 2016 he developed liver and peritoneal metastases confirmed by a biopsy on Apr. 29, 2016. He developed further progression documented by CT and MRI of Oct. 27, 2017. His life expectancy was determined as less than 6 months.

Treatment: The treatment began on Mar. 7, 2018 with AS up to 19.2 g daily and nivolumab 240 mg IV every 2 weeks and ipilimumab 60 mg IV every 6 weeks. He discontinued treatment for personal reasons on Oct. 10, 2018.

Response to Treatment: Follow-up CTs of May 29, 2018 and Jul. 10, 2018 compared to baseline of Apr. 17, 2018 showed stable liver and peritoneal metastases. Blood genomic analysis by Guardant 360 of May 16, 2016 and Nov. 7, 2017 was negative. The patient was in good condition during treatment.

Conclusion: The patient had extensive metastatic cancer to the liver and peritoneum which progressed after surgery, radiation and chemotherapy. His cancer stabilized during his 6 months of treatment at Burzynski Clinic.

Example 52

A 49-year-old Caucasian male presented to Burzynski Clinic in November 2016 and was diagnosed with anaplastic astrocytoma. The patient had a 13-year history of his disease. In 2003 he developed generalized epileptic seizures and was diagnosed with anaplastic astrocytoma after tumor resection on Jun. 24, 2003. Redo resection was performed on Jun. 27, 2003. He was given standard radiation therapy and received temozolomide from January to May 2017. The treatment was discontinued due to toxicity. He developed progression in January 2005. From November 2005 to December 2008 he was treated with PB and in 2007 erlotinib and lapatinib were added. He discontinued this regimen in December 2008. Instead he decided to have a dietary regimen. MRI's of January 2016, April 2016, Jul. 5, 2016 and Oct. 4, 2016 showed further progression. A biopsy on Apr. 25, 2016 revealed the features of anaplastic astrocytoma and grade II astrocytoma with IDH1 mutation. His life expectancy was less than 6 months.

Treatment: The treatment began on Nov. 1, 2016 with AS up to 19.2 g daily. In addition, he was prescribed pazopanib 200 mg PO daily, dasatinib 50 mg PO daily, everolimus 5 mg PO daily and bevacizumab 10 mg/kg IV every 2 weeks. On Jun. 5, 2017 vorinostat 100 mg PO daily was added to his treatment. The patient decided to discontinue the treatment on Nov. 13, 2017.

Results of Treatment: Baseline MRI of Oct. 4, 2016 compared with May 11, 2016 revealed a multifocal right frontal lobe enhancing lesion measuring 3.5×3.0 cm. Follow-up MM of Dec. 6, 2016 showed 30.7% decrease of the size of the lesion and the next MRIs of Jan. 17, 2017, Feb. 23, 2017, Apr. 26, 2017, Jun. 20, 2017, Aug. 29, 2017 and Oct. 24, 2017 did not reveal any measurable enhancing lesion indicating CR. Tissue genomic analysis of the specimen obtained on Apr. 26, 2016 showed IDH1 R132H, ATRXS850fs*2 and TP53 R273C. Blood genomic analysis by Guardant 360 on Oct. 11, 2016 was negative.

Conclusion: The patient obtained a rapid CR after failure of two surgical resections, chemotherapy and targeted therapy and a long 13-year history of his malignant brain tumor.

Example 53

A 34-year-old Caucasian female presented to Burzynski Clinic in October 2017 and was diagnosed with anaplastic astrocytoma. The patient had 4-year history of her disease. In October 2014 she developed a grand mal seizure and MRI revealed multiple left frontal lobe lesions. In October 2014 she underwent tumor resection with pathology diagnosis of astrocytoma, grade II. MRI's of Jan. 11, 2016 and Mar. 17, 2017 revealed progression. She underwent a second resection in March 2017 with pathology diagnosis of anaplastic astrocytoma. Her recovery was complicated by bone infection for which she was operated in May 2017. She developed progression and was give 5 weeks of radiation therapy. MRI of Oct. 14, 2017 showed further progression. Her life expectancy was less than 6 months.

Treatment: The treatment began on Oct. 29, 2017 with AS up to 19.2 g daily and everolimus 5 mg PO daily, dasatinib 50 mg PO daily, pazopanib 200 mg PO daily and bevacizumab 10/kg IV every 2 weeks. She discontinued the treatment on Jul. 18, 2017 for personal reasons.

Results of Treatment: Baseline MRI of Oct. 14, 2017 showed left frontal enhancing lesion, 4.8×3.6 cm and right frontal lesion of 2.7×2.5 cm; both of them contrast enhancing. The follow-up MRI's of Nov. 16, 2017 and January 9, March 27 and Jun. 22, 2018 did not show measurable lesion in left frontal lobe indicating 80% decrease of the sum of measurement of both lesions. After temporary increase of the size of the second lesion on Jan. 9, 2018 there was further decrease on the next two MRI's, so that the sum of the measurements of both lesions was 70.9%, 75.1% and 75.1% smaller on January, March and June, 2018 MRI's correspondingly indicating PR. Genomic analysis of the tissue specimen of Mar. 18, 2017 by Foundation Medicine showed IDH1 R132H, ARID2 N127fs*18, ATRX N179fs*26, NOTCH F357del, and TP53 R273H.

Conclusion: This patient had a long 4-year history of multifocal malignant brain tumor. She was operated 3 times and treated with radiation therapy. Her tumor responded rapidly to the treatment with disappearance of the larger tumor and stabilization of the smaller one. This indicates genomic heterogenicity of her tumors. She was in good condition during the treatment.

Example 54

A 10-year-old Caucasian girl presented to Burzynski Clinic in April 2017 and was diagnosed with anaplastic astrocytoma of the brainstem/DIPG. She had only 1-month history of her disease. On Mar. 27, 2017 she developed acute onset of headache, diplopia, blurring of the vision and left facial droop, nausea and vomiting and was found to have a pontine mass. MRI of the spine was negative. On Mar. 30, 2017 she underwent a craniotomy with resection of the lesion within the 4th ventricle. Pathology diagnosis was diffuse anaplastic astrocytoma, IDH1-R 132 wild type and H3me3 positive indicating that there was no histone 3 mutation. However, genomic analysis of tumor tissue of Jun. 22, 2017 revealed H3F3A K28M mutation. Therefore, it was not diffuse midline glioma, H3 K27 mutant, but anaplastic astrocytoma of the brainstem, mostly of the pontine location which would also be diagnosed as DIPG. Her tumor was very aggressive, but she did not start any treatment yet. Her life expectancy was estimated below 2 months.

Treatment: The treatment began on Apr. 20, 2017 with AS up to 16.3 g daily, pazopanib 200 mg PO daily, everolimus 5 mg PO daily, dasatinib 50 mg PO daily and bevacizumab 10 mg/kg IV every 2 weeks. She passed away on Jul. 19, 2017.

Response to Treatment: MRIs of May 30, 2017 and Jul. 17, 2017 showed tumor progression. Her response was classified as PD.

Conclusion: This patient had a very aggressive anaplastic astrocytoma/DIPG which progressed rapidly after surgical treatment.

Example 55

A 40-year-old Caucasian male presented to Burzynski Clinic in November 2016 and was diagnosed with anaplastic oligodendroglioma. The patient had a 3-year history of his disease. In January 2013 he suffered epileptic seizures and was found to have a mass in the left frontal lobe. He underwent total resection on Feb. 6, 2013 and was diagnosed with anaplastic oligodendroglioma, IDH1 negative. He developed recurrence in February 2016 and underwent a second resection with pathology diagnosis the same as before. He had further recurrence by MRI of Sep. 12, 2016 and increased frequency of epileptic seizures. His life expectancy was determined as less than 6 months.

Treatment: The treatment began on Nov. 10, 2016 with AS up to 38.4 g daily, bevacizumab 10 mg/kg IV every 2 weeks, pazopanib 200 mg PO daily, dasatinib 50 mg PO daily and everolimus 5 mg PO daily. He decided to discontinue the treatment on Mar. 18, 2017 for personal reasons.

Response to Treatment: Baseline MRI of Nov. 8, 2016 showed a large bifrontal enhancing tumor measuring 5×4.3 cm. It decreased in size by more than 20% on Dec. 9, 2016 and by 27.7% on Jan. 5, 2017 and Feb. 16, 2017, indicating objective response to treatment. His tissue specimen of Feb. 9, 2016 showed PIK3CA E453K, IDH1 R132H, NOTCH1

L1593*23, NOTCH1 T1159fs*25, NOTCH3 splice site 2144+1 G>A-subclonal, PIK3R1 S399-Y408del splice site 917-IG>A, TERT promoter-146C>T, TP53 splice site 37G-1G>A. He passed away on Aug. 15, 2017.

Conclusion: This patient had very complex and numerous genomic abnormalities in his tumor. He underwent a total resection with recurrence requiring a second resection followed by another recurrence with a large bifrontal tumor. His tumor shrank during the treatment, but he decided to prematurely discontinue for personal reasons.

Example 56

A 34-year-old Indian male presented to Burzynski Clinic in April 2016 and was diagnosed with anaplastic oligodendroglioma with 1p/19q deletion and leptomeningeal carcinomatosis. The patient had a 7-year history of his disease. In July 2009 he developed epileptic seizures and an MRI confirmed a non-enhancing left frontotemporal mass. The biopsy on Jul. 31, 2009 confirmed the above diagnosis and was followed by a total tumor resection on Aug. 6, 2009. He was treated at MDACC with 24 cycles of temozolomide which was completed in July 2011. He developed a recurrent enhanced tumor on Jan. 20, 2013. The tumor was resected on Jan. 25, 2013 and had the same pathology diagnosis. He was given standard radiation therapy with temozolomide which completed on Mar. 29, 2013. MRI on Apr. 1, 2014 showed tumor progression with leptomeningeal carcinomatosis. Temozolomide was discontinued after five cycles and he enrolled in a Phase 1 trial with IDH 305 on Apr. 29, 2015. This treatment was discontinued after two cycles due to toxicity. In November 2014 he was found to have further progression and was started on temozolomide up to 200 mg/m2 until April 2015. MRI on Jul. 17, 2015 revealed further progression with a new tumor in the posterior fossa requiring a VP shunt. On Aug. 6, 2015 he was given lomustine and on Aug. 13, 2015 procarbazine. On Oct. 1, 2015 he developed bilateral pulmonary emboli and was given Lovenox, lomustine, and dacarbazine. MRI on Apr. 13, 2016 showed progression after four cycles of chemotherapy. From April 2016 to Jun. 16, 2016 he was treated at Burzynski Clinic with PB, three oral targeted drugs at 2 to 4 times dose reduction: dasatinib, everolimus and pazopanib and bevacizumab 10 mg/kg IV every 2 weeks. His life expectancy was less than 2 months.

Treatment: The treatment under RTT at Burzynski Clinic started on Jun. 21, 2016 and included AS up to 19.2 g/d, three oral targeted drugs at 2 to 4 times dose reduction: dasatinib, everolimus and pazopanib and bevacizumab 10 mg/kg IV every 2 weeks. On Sep. 15, 2016 A10 was added to the treatment up to 300 g/d. The treatment was discontinued on Oct. 17, 2016 when he developed grand mal seizures and intratumoral bleeding. He passed away on Dec. 3, 2016. He survived over 6 months from the treatment start.

Response to Treatment: Follow-up MRI of Oct. 19, 2016 showed more than 50% increase of the size of the large bifrontal tumor indicating PD.

Conclusion: This was a very advanced case of multicentric brain tumor with leptomeningeal carcinomatosis which failed two surgical resections, radiation therapy, five chemotherapy regimens, one targeted therapy combination and a clinical trial and developed PD on the current treatment.

Example 57

A 54-year-old Caucasian male presented to Burzynski Clinic on May 29, 2018 and was diagnosed with diffuse astrocytoma, grade 2. He had a short one-year history of his disease. At the end of 2016 he developed paresthesia in both lower extremities. MRI of Dec. 1, 2017 showed large left thalamic and small left parietal lesions. On Jan. 15, 2018 he had a left thalamic biopsy revealing diffuse astrocytoma, grade II, IDH1 negative. He received radiation therapy form Feb. 5, 2018 through Mar. 21, 2018 for a total of 59.4 Gy in 33 fractions. He also received temozolomide at 150 mg/m2 for 5 days every 28 days from Apr. 29, 2018 to May 3, 2018. The follow-up MRIs showed stable disease. His life expectancy was estimated for less than 6 months.

Treatment: The treatment began on Aug. 8, 2018 with AS up to 19.2 g daily and dasatinib 50 mg PO daily, everolimus 5 mg PO daily, pazopanib 200 mg PO daily and bevacizumab 10 mg/kg IV every 2 weeks. He decided to discontinue the treatment on Feb. 14, 2019.

Results of Treatment: The follow-up MRIs of Aug. 2, 2018, Oct. 25, 2018 and Jan. 17, 2019 revealed stable size of the tumor. MR spectroscopy of Jan. 24, 2018 did not show evidence of a viable tumor indicating CR; however, the baseline study of Oct. 25, 2018 was technically deficient. Genomic analysis of tissue specimen collected on Jan. 5, 2018 by Foundation Medicine revealed NF1 V2378fs*8, PTEN N323fs*23, and TERT promoter-124C>T. The patient was doing well during the treatment.

Conclusion: The patient was diagnosed with inoperable multicentric diffuse astrocytoma. He was a poor candidate for chemotherapy (/DH1 negative). His tumor size was stable during 6 months of treatment and posttreatment MR spectroscopy was negative for the presence of viable tumor; however, the baseline MR spectroscopy was technically deficient.

Example 58

A 51-year-old Caucasian female presented to Burzynski Clinic in June 2018 and was diagnosed with cholangiocarcinoma with multiple metastases to the lymph nodes, liver, brain and pleura and leptomeningeal carcinomatosis, Stage IV. The patient had a 3-year history of her disease. At the beginning of 2015 she developed abdominal pain and was found to have multiple liver lesions. A biopsy on Mar. 5, 2015 revealed poorly differentiated cholangiocarcinoma. She was given chemotherapy with cisplatin and gemcitabine on day 1 and 8 of a 21-day course. In October 2015 she was switched to maintenance gemcitabine every other week and discontinued chemotherapy in April 2016. She obtained a good partial response. In December 2016 she developed abdominal pain and in the following months there was an increase in the tumor marker CA19-9, and finally, reoccurrence of liver metastases. In August 2017 she was treated with insulin-potentiated low-dose chemotherapy and chemoembolization of liver metastases which resulted in a temporary decrease of CA19-9. In November 2017 MRI of the liver showed a slight increase in size of some metastases. On Feb. 17, 2018 she developed epileptic seizures and was found to have multiple brain metastases. She declined biopsy and recommended radiation therapy. The MRI of Mar. 19, 2018 showed progression of brain metastases with meningeal involvement. She was treated with pulsed electromagnetic field therapy but had further progression. She became bedbound and had paralysis of left upper and lower extremities and left facial nerve paralysis. On Mar. 31, 2018 she was admitted to hospice for terminal care. Her life expectancy was less than 1 month.

Treatment: The treatment began on Jun. 21, 2018 with AS up to 19.2 g daily, capecitabine 2000 mg PO daily in 2 weeks on and 1 week off cycles, bevacizumab 1000 mg IV every 2 weeks, sorafenib 200 mg PO daily, everolimus 5 mg PO daily and vorinostat 100 mg PO daily. The treatment was discontinued on Aug. 10, 2018 when she developed pneumonia and was hospitalized. On Aug. 17, 2018 she restarted AS, sorafenib, everolimus, capecitabine at a reduced dose to 500 mg, and bevacizumab. She discontinued the treatment on Oct. 15, 2018 and was hospitalized for sepsis due to an opportunistic infection. She passed away on Oct. 20, 2018.

Response to Treatment: The MRI of Sep. 19, 2018 compared to baseline of Jun. 22, 2018 showed 31% decrease in the size of metastatic lesions and leptomeningeal carcinomatosis as well as cerebral edema. CT/PET of Oct. 22, 2018 compared with baseline of Jun. 22, 2018 showed stable disease. There was improvement of tumor marker CA19-9 and the patient's condition. Baseline blood genomic analysis of Jun. 20, 2018 by Guardant 360 showed KRAS G12V and NF1 F710C. There was no follow-up analysis.

Conclusion: This was a case of very aggressive cancer previously treated with two chemotherapy regimens, chemoembolization and pulsed electromagnetic field therapy. She developed progression including leptomeningeal carcinomatosis which carries survival of less than 1 month and was admitted to terminal care at hospice. She accomplished objective response on the treatment at Burzynski Clinic and a 4-month survival but passed away from sepsis.

Example 59

A 72-year-old Caucasian male presented to Burzynski Clinic in February 2016 and was diagnosed with: 1) myelodysplastic syndrome, 2) chronic atypical myelogenous leukemia, 3) myelofibrosis, 4) refractory anemia, and 5) thrombocytopenia. The patient had a 3-year history of his disease. The initial diagnosis was based on bone marrow biopsy on Feb. 18, 2013. Extensive hematology evaluation was performed based on bone marrow biopsy and aspiration on Jan. 25, 2016. He also had serum JAK2 mutation but BCR-ABL was normal. The patient also had important coexisting diseases including chronic congestive heart failure, diabetes, essential hypertension, chronic kidney failure, glaucoma, hypothyroidism, hypercholesterolemia, history of recent pneumonia and bronchitis. He received only supportive treatment. His life expectancy was less than 6 months.

Treatment: The treatment began on Feb. 6, 2016 with AS up to 19.2 g daily. On Feb. 18, 2016 PB was added to the treatment up to 2.5 g PO 4 times daily. On Feb. 24, 2016 vorinostat up to 200 mg PO daily was also added. On Mar. 3, 2016 A10 was added up to 48 g IV ×6 daily. The treatment was temporarily discontinued on Mar. 24, 2016 because of hospitalization for acute myocardial infarction, pulmonary edema and pneumonia. He was intubated and placed on a ventilator. After discharge from the hospital he was placed again on his regimen and ruxolitinib 40 mg PO daily was added (Apr. 10, 2016). A10 was temporarily discontinued. On Mar. 23, 2017 the treatment was discontinued due to upper respiratory infection but AS and PB were restarted on Apr. 13, 2017. Vorinostat was restarted at 100 mg PO daily on May 1, 2017. Ruxolitinib was restarted at 30 mg daily on May 10, 2017. From Oct. 7, 2017 to Oct. 17, 2017 he was hospitalized for pneumonia and the treatment was temporarily discontinued during the admission. On Mar. 7, 2018 the treatment was discontinued, and the patient was hospitalized for meningitis and listeriosis. On Apr. 19, 2018 he developed a minor stroke and passed away on Apr. 25, 2018.

Response to Treatment: The patient's initial genomic analysis of bone marrow specimen of Feb. 18, 2013 showed MPL Y591D, RUNX1 R107C, ASXL1 R1273fs*7 and SRSF2 P95H. The repeated analysis on the specimen of Mar. 11, 2016 revealed an additional mutation of JAK2 V617, as well as BRACA2 12040V, HIST1H1D K185-A186>T, MAP3K6 P946L, NOTCH2 52379F, SPEN A2510V, STATSB R110H and TET2 C1875G. The treatment plan was prepared based on genomic abnormalities. The patient accomplished marked improvement in his condition. His baseline blood tests of Feb. 4, 2016 showed hemoglobin 9.7 g/dL (decreased), white blood cell count (WBC) 51.5/mL (very high) with approximately 50% of neutrophils and high platelets count of 646/mL. There was significant improvement on the follow-up tests. On Mar. 13, 2016 hemoglobin was 10.2, WBC 11.1 (normal) and platelets 185 (normal). The tests of Jul. 29, 2016, Sep. 20, 2017, Jan. 25, 2018 and Feb. 21, 2018 showed hemoglobin in the range of 9.6 to 10.5, and WBC and platelets were within normal range or slightly increased. The concentration in serum of driver mutated gene JAK2 was stable on Apr. 4, 2017. Initially the patient required a blood transfusion twice a week but in two months it was decreased to once every 2 weeks. Patient response was determined as PR.

Conclusion: This was a very complex case carrying a diagnosis of 5 malignancies and an additional 5 serious diseases. He accomplished marked objective improvement and survived 26 months versus the estimated less than 6 months. He died from opportunistic infection not related to the treatment.

Example 60

An 8-year-old Hispanic male reported to Burzynski Clinic in July 2020 and was diagnosed with DIPG, diffuse midline, high-grade glioma, H3F3A K27M mutant. The patient had a short 2-month history of his disease. On May 21, 2020 he was evaluated for progressive left side weakness, slurred speech, difficulty walking and swallowing. MRI showed a tumor located in the pons measuring 2.9×4.5 cm with areas of enhancement. The biopsy of May 22, 2020 established the above diagnosis. The tumor was inoperable. On May 27, 2020 the patient started intensity modulated radiation therapy (IMRT) and received the standard dose. His life expectancy was less than 6 months.

Treatment: The treatment began on Aug. 24, 2020 with AS up to 9.6 g daily and A10 up to 144 g daily. Starting from Sep. 29, 2020 bevacizumab 300 mg IV every 2 weeks, dasatinib 25 mg PO daily, pazopanib 200 mg PO daily and everolimus 3 mg PO daily were added to the treatment. The patient continues the treatment at present.

Response to Treatment: Follow-up MRI of Nov. 18, 2020 compared to Sep. 28, 2020 showed over 40% decrease of overall tumor size and 19% decrease of enhancing areas. Genomic analysis of tumor tissue by Foundation Medicine of Jul. 24, 2020 revealed MTOR E2419K subclonal, PTEN C136Y and H3F3A K28M. The results of genomic testing provided the rationale for the treatment plan. The patient accomplished good symptomatic improvement and became asymptomatic.

Conclusion: The patient was diagnosed with a uniformly deadly brain tumor but was showing initial response to treatment.

Example 61

A 61-year-old Saudi Arabic male presented to Burzynski Clinic in October 2016 and was diagnosed with adenocarcinoma of the esophagus with metastases to the liver, peritoneum and pleura, Stage IV. The patient had a 4-year history of his disease. His diagnosis was established in April 2012 when he underwent esophagectomy and gastric pull. From Sep. 11, 2012 to Nov. 14, 2012 he received adjuvant chemotherapy with oxaliplatin and capecitabine. On Oct. 15, 2016 the patient experienced an acute onset of hematuria and severe abdominal pain and was found to have a massive recurrence with multiple metastases to the lymph nodes, liver, peritoneum and pleura. On Oct. 10, 2016 he started PB 12 g PO daily, nivolumab 3 mg/kg IV every 3 weeks, ramucirumab 8 mg IV every 2 weeks, nab-paclitaxel 100 mg/m2, and carboplatin AUC=5 every 3 weeks. The CT of Dec. 6, 2016 showed resolution of right pleural effusion and stable for the other metastases but an increase of ascites. There was an embolus in the lung for which he was started on anticoagulant. His life expectancy was estimated at less than 2 months.

Treatment: The treatment began on Dec. 12, 2016 with AS up to 19.2 g daily. He also continued carboplatin/nab-paclitaxel and nivolumab every 3 weeks and ramucirumab every 2 weeks. On Dec. 15, 2016 he developed deep venous thrombosis in the left femoral vein. On Dec. 27, 2016 olaparib 200 mg PO daily was added to the treatment. The patient decided to discontinue carboplatin/nab-paclitaxel and ramucirumab on Apr. 5, 2017. The patient discontinued the treatment on May 30, 2017 and passed away a month later in Saudi Arabia.

Response to Treatment: PET/CT of Jan. 3, 2017 compared with PET/CT of Oct. 19, 2016 and CT of Dec. 6, 2016 revealed marked improvement. Instead of multiple metastases in the liver there was only one which decreased by 14%. There was resolution of pleural effusion and ascites and decreased peritoneal and pleural thickening. CT of Mar. 25, 2017 showed further decrease by 30% of liver metastasis. The last CT of May 30, 2017 did not show significant changes. Blood genomic analysis by Guardant 360 of Oct. 27, 2016 revealed TP53 O104 and P151H, KRAS G12D, BRAF E26A, NF1 11719T and ERRB2 C584G. There was no follow-up analysis. The patient had marked symptomatic improvement and he was free of pain.

Conclusion: This very advanced and rapidly progressing case of metastatic esophageal cancer was previously treated with surgery, chemotherapy, targeted therapy and immunotherapy. He accomplished a substantial decrease of tumor burden with only a single liver metastasis remaining which decreased 30%. The patient decided to return to Saudi Arabia before obtaining complete response and discontinued prematurely most of his medications which contributed to his death.

Example 62

An 11-year-old Caucasian boy presented to Burzynski Clinic in September 2017 and was diagnosed with ganglioglioma with leptomeningeal carcinomatosis. The patient had a short, less than a year history of his disease. On May 17, 2017 he developed confusion and symptoms of hydrocephalus. He was diagnosed with ganglioglioma with leptomeningeal carcinomatosis and had a VP shunt placement. He did not have any further treatment. His life expectancy was estimated for less than 4 months.

Treatment: The treatment began on Sep. 21, 2017 with AS up to 14.4 g daily, pazopanib 200 mg PO daily, dasatinib 20 mg PO daily, everolimus 2.5 mg daily and bevacizumab 10 mg/kg IV every 2 weeks. On Jun. 19, 2018, vorinostat 100 mg PO daily was added to the regimen. On Jan. 14, 2019 he started radiation therapy to the level of T1-T7 for 17 treatments and discontinued treatment under the disclosed care on Jan. 10, 2019.

Response to Treatment: The follow-up MRI of Jan. 12, 2018 compared to baseline of Aug. 25, 2017 showed more than 50% decrease of the enhancing lesions which include a decrease of leptomeningeal carcinomatosis and resolution of the lesions in the mid-thoracic region. The follow-up MRI of Jun. 2, 2018 revealed stable leptomeningeal involvement but a new tiny focus of enhancement at the T6-T7 level. The next MRI of Aug. 23, 2018 showed a minimal increase of the lesion at T6-T7. Blood genomic analyses by Guardant 360 of Sep. 18, 2017 and Sep. 6, 2018 were negative. Tissue genomic analysis by UPMC Presbyterian of Pittsburgh, PA revealed NF1 c.6655>T, p.D2219Y of uncertain significance. The patient had significant symptomatic improvement and reduction of pain.

Conclusion: The patient accomplished PR of difficult to treat and deadly leptomeningeal carcinomatosis and resolution of spinal nodules of ganglioglioma as well as improvement of the symptoms and quality of survival and extension of survival for over a year.

Example 63

A 64-year-old Caucasian male presented to Burzynski Clinic in November 2017 and was diagnosed with GIST with metastasis to the pelvis, Stage IV and adenocarcinoma of the prostate, Gleason score 7 with metastases to the bones, Stage IV. The patient had a 5-year history of his cancers. In December 2012, he underwent a TURP procedure and was diagnosed with adenocarcinoma of the prostate, Stage IV. His cancer metastasized to the bones and he was treated with Lupron injections from 2013 to May 2017. During the evaluation for prostate cancer he was found to have a rectal mass which was diagnosed as GIST in 2013. He underwent surgical resection and was treated with adjuvant therapy. In 2014 he developed recurrence and underwent a second resection. From April 2015 to Dec. 20, 2015 he was treated with imatinib 400 mg daily. While on imatinib he developed a next recurrence and underwent abdominal perineal resection in December 2015. Pathology diagnosis was consistent with high-grade GIST. He continued imatinib afterwards. In late 2016 he developed another recurrence in the ischiorectal space and was started on sunitinib on Dec. 21, 2016. CT of Sep. 24, 2017 revealed progression. Sunitinib was discontinued. His life expectancy was estimated as less than 6 months.

Treatment: The treatment began on Nov. 28, 2017 with AS up to 19.2 g daily. Sunitinib was restarted at 37.5 mg PO daily, 4 weeks on and 2 weeks off. On Mar. 1, 2018 he developed perforation of the tumor and passed away.

Response to Treatment: CT of Jan. 2, 2018, after 6 weeks of treatment, showed 39.7% decrease of the size of the pelvic mass. The patient was doing very well during the treatment. His baseline Guardant 360 blood genomic analysis of Nov. 15, 2017 revealed KIT M552del (Exon 11 deletion) and V654A mutation, NOTCH1 A465V and NF-1 A2617A, which provided rationale for the combination of AS and sunitinib. The patient did not have a follow-up Guardant 360. He had objective response to treatment.

Conclusion: This was a case of a very aggressive malignancy which failed to respond to multiple surgical resections, chemotherapy and targeted therapy. There was a rapid response to $AS^{+}$ sunitinib even though there was prior progression on sunitinib. The large necrotic tumor perforated during the treatment which caused the patient's death.

Example 64

A 57-year-old Caucasian female presented to Burzynski Clinic in April 2016 and was diagnosed with invasive, poorly differentiated, triple negative, adenocarcinoma of the breast with multiple metastases to the brain and leptomeninges. She had very aggressive and difficult to treat triple negative breast cancer. She complained of headaches, nausea and vomiting due to increased intracranial pressure from brain tumors. The history of her cancer began 6 years before. The initial diagnosis was based on lumpectomy of left breast nodule and lymph node dissection which was positive for cancer. She was followed with TAC chemotherapy from April to August 2010, and radiation therapy from September to October 2010. From December 2010 to October 2015 she was treated with hormonal therapy: Lupron and letrozole. In October 2015 she developed brain metastasis and underwent tumor resection followed with Gamma-Knife treatment and continued hormonal treatment for 3 months. In March 2016 she developed progression in the post-operative cavity and had 3 additional brain tumors. On Mar. 24, 2016 she had another Gamma-Knife procedure but due to increasing tumor size she received brain radiation.

Treatment: Her treatment at Burzynski Clinic started on Apr. 21, 2016 and included AS2-1, 19.2 g daily, bevacizumab 10 mg/kg every 2 weeks and capecitabine 1000 mg b.i.d., 2 weeks on and 1 week off. The patient decided to discontinue all treatments on Jun. 18, 2016 against medical advice. She passed away on Jul. 24, 2017.

Response to Treatment: The patient had resolution of her symptoms. Baseline MRI of the head of Apr. 20, 2016 had shown brain, leptomeningeal and dural metastases despite prior radiation therapy. Follow-up MRI of Jun. 22, 2016 did not show cancer involvement, indicating a Complete Response. The patient did not have confirmation by the next MRI because she decided to discontinue the treatment. At the time of her initial evaluation the genomic test on blood samples was not commercially available. Her treatment plan was based on tissue testing by Foundation Medicine, which revealed PTEN loss exons 4-7, NF1 splice site 480-11_4801del11, KDM6A loss, TP53 R196, LRP1B, MAP3K1 5398. The most important genes, PTEN, NF1, TP53 and MAPK, are affected by AS2-1.

Conclusion: The patient had a complete response of difficult-to-treat brain and meningeal metastases, which are typically treated with radiation therapy. Her prior treatment already included two different types of radiation therapy and two Gamma-Knife treatments. She was also treated with a combination of chemotherapy and hormonal therapy. There was no standard-of-care treatment available for her and her life expectancy was as short as one month, but she survived 15 months. She obtained a complete response of her brain and meningeal metastases after two months of treatment with the combination of AS2-1, a targeted agent and well-tolerated oral chemotherapy.

Example 65

A 63-year-old Caucasian male presented to Burzynski Clinic in January 2018 and was diagnosed with 1. myelodysplastic syndrome (MDS) with multilineage dysplasia and refractory recurrent thrombocytopenia, and 2. Non-Hodgkin's small cell, B-cell lymphoma (SLL). The patient had a 5-year history of his disease. In August 2013 he complained of declining energy and easy bruisability and in November 2013 he developed bleeding form the ears and acute onset of disorientation and was found with very low hemoglobin concentration and platelet count. Bone marrow aspiration and biopsy at that time established the above diagnosis. Since then he required weekly platelet transfusions. On Dec. 25, 2015 he had an acute onset of aphasia and quadriplegia due to intracerebral bleeding. He gradually recovered after rehabilitation. Since January 2016 he required HLA match platelet transfusion. The bone marrow biopsy at that time confirmed the same diagnosis with 3% blasts. He was placed on the stem cell transplant list, but it was not possible to match his type and he decided against transplantation. In March 2017 he was started on PB. The repeat bone marrow aspiration at that time (Apr. 19, 2017) confirmed MDS but also revealed features of Non-Hodgkin's small cell, B-cell lymphoma. He had SD as the result of treatment with PB. His life expectancy was estimated below 6 months.

Treatment: The treatment began on Jan. 6, 2018 with AS up to 19.2 g daily. On May 2, 2018 vorinostat 100 mg daily was added to the treatment and was discontinued on Oct. 24, 2018. On Feb. 16, 2019 he developed a fracture of the left femur and was hospitalized. AS was discontinued. AS was restarted on Jun. 7, 2019. On Jun. 8, 2019 he started weekly IV infusions of rituximab ×4 treatment at MDACC in Houston. He developed neurological toxicity from rituximab and discontinued after 4 treatments. He continues the treatment with AS at present and awaits the next evaluation.

Response to Treatment: The patient was diagnosed with complex malignancies: MDS and SLL which were expected to transform soon to acute leukemia. His bone marrow specimen was analyzed by Foundation Medicine on Apr. 19, 2017. The report has shown a number of genomic abnormalities including: CD796 Y196C-cubclonal, MYD88 L265P-subclonal, ARID1A Q1334-R1335insQ, BCOR E518, CXCR4 E338-subclonal, KLHL6 L65P-subclonal, RUNX1 R204Q. TMB was low. Based on genomic analysis the patient was advised to consider adding ibrutinib or acalabrutinib to target MYD88, CXCR4 and CD79B alterations and plerixafor to target CXCR4 but he did not have insurance coverage for such additional treatments and decided against it. He accomplished symptomatic and objective improvement. The frequency of platelet transfusions was decreased from twice a week to once a week. He survived over 2 years versus the expected less than 6 months. His response was determined as SD.

Conclusion: In this very complex case, a symptomatic and objective improvement was obtained as well as stabilization of the disease and life extension.

Example 66

A 2-year-and-10-month-old Caucasian male presented to Burzynski Clinic in November 2018 and was diagnosed with pilocytic astrocytoma transforming into high-grade glioma. The patient had a short 6-month history of his disease. In May 2018 he developed headaches, nausea and vomiting. MRI of May 30, 2018 showed a large tumor in the posterior fossa centered on the roof of the fourth ventricle with peripheral contrast enhancement and severe obstructive hydrocephalus. On Jun. 2, 2018 he underwent suboccipital craniotomy and C1 laminectomy for tumor resection. The diagnosis was pilocytic astrocytoma negative for BRAF mutation and rearrangement. There was a residual enhancing tumor in the vermis. His symptoms were aggravated and on Sep. 2, 2018 he had documented tumor recurrence. On the same date he had a placement of ventriculostomy catheter for hydrocephalus. The next day he had a placement of the second catheter terminating in the right lateral ventricle and on Sep. 4, 2018 he had a placement of a gastric tube for feeding. On Sep. 7, 2018 he had replacement of the right frontal catheter by Rickham reservoir. On Sep. 15, 2018 his Rickham catheter was removed due to staphylococcal infection and he started vancomycin. MRI of Oct. 3, 2018 showed rapidly expanding tumor which was treated by surgical resection on the same date. There was still a large residual tumor with the same pathology. On Oct. 11, 2018 he was treated for cerebrospinal fluid leak. His life expectancy was estimated as less than 6 months.

Treatment: The treatment began on Nov. 29, 2018 with AS up to 0.4 g daily. Starting from Dec. 4, 2018 the following medications have been added: bevacizumab 10 mg/kg IV every 2 weeks, dasatinib 20 mg PO daily, everolimus 2 mg PO daily and pazopanib 200 mg PO daily. The treatment wax discontinued on Nov. 15, 2019.

Response to Treatment: Baseline MRI of Nov. 29, 2018 showed two contrast enhancing nodules around the fourth ventricle. The follow-up MRI of Apr. 4, 2019 showed resolution of the nodules indicating the beginning of CR. The patient did not have confirmation of CR after 4 weeks and the next MRI of Oct. 17, 2019 showed reoccurrence of the nodules indicating progression after initial CR. The patient's genomic analysis of tumor tissue of Nov. 30, 2018 revealed P1K3CA Q546R and K567E. The patient had marked symptomatic improvement.

Conclusion: This was a case of an aggressive pilocytic astrocytoma transforming into a high-grade glioma. There were no standard of care curative treatments for this disease. He underwent three surgical procedures and had a number of complications. His tumor was recurring soon after the surgery, but it was gone after the treatment at Burzynski Clinic. The reason for the recurrence after the treatment was possibly poor compliance with treatment plan for personal reasons which caused interruptions in the treatment.

Example 67

A 50-year-old Caucasian female presented to Burzynski Clinic in February 2017 and was diagnosed with synovial sarcoma and pleomorphic sarcoma, high-grade, with metastases to the lymph nodes, lungs and bones, Stage IV. The patient had a 27-year history of sarcoma. In 1980 she developed a tumor in the left femur diagnosed as synovial sarcoma. She was treated with cobalt radiation and chemotherapy with methotrexate, cyclophosphamide, doxorubicin, ifosfamide and vincristine. In 2015 she developed a pathological fracture and in April 2015 she had an amputation of the left lower extremity including 14 cm of femur followed by the placement of a left leg prosthesis. From May 11, 2015 to Jun. 18, 2015 she was given two treatments of ifosfamide and doxorubicin. CT of December 2015 showed lung metastases. On Mar. 20, 2016 she underwent a video-assisted bronchoscopy/thoracoscopy in the left upper lobe with wedge resection and pathology confirming metastatic high-grade sarcoma. PET/CT on Apr. 1, 2016 showed a metastatic nodule in the left thigh. CT of Dec. 23, 2016 revealed multiple lung metastases and worsening of the involvement of the left thigh. There were metastases to the lymph nodes and T8 vertebra. Biopsy of the left thigh tumor confirmed metastasis from high-grade pleomorphic sarcoma. The patient came initially to the Burzynski clinic on Jan. 19, 2017 and was recommended gemcitabine and docetaxel and surgical consultation. The surgeon did not think that she would benefit from surgery. She was given the first cycle of recommended chemotherapy and returned to clinic for further treatment. Her life expectancy was estimated to be less than 3 months.

Treatment: The treatment began on Feb. 24, 2017 with AS up to 19.2 g daily. She also continued chemotherapy with gemcitabine and docetaxel. From Mar. 7, 2017 to Mar. 8, 2017 she was given palliative radiation to her left lower extremity. On Mar. 22, 2017 pembrolizumab 200 mg IV daily every 3 weeks was added under the care of her local oncologist. On Jul. 27, 2017 pazopanib 400 mg PO daily was added to her treatment and on Aug. 16, 2017 she started bevacizumab 10 mg/kg IV every 2 weeks under the care of her local oncologist. Bevacizumab, pazopanib and pembrolizumab were discontinued on Sep. 27, 2017. Pazopanib was restarted on Oct. 2, 2017 and bevacizumab on Oct. 10, 2017. On Nov. 30, 2017 the dose of pazopanib was decreased to 200 mg daily and dasatinib was added, 50 mg PO daily. On Dec. 28, 2017 everolimus 5 mg PO daily was added to the regimen. She discontinued treatment under the disclosed care on Feb. 20, 2018.

Response to Treatment: Baseline CT of Feb. 18, 2017 compared to Feb. 1, 2017 showed an increase of size of pulmonary nodules, metastatic inguinal lymph nodes, paraspinal mass at T8 and left upper thigh mass. There was new bilateral pleural effusion and pelvic ascites. CT of May 10, 2017 revealed a 46% decrease of the size of left upper thigh mass and multiple lymph nodes and resolution of pleural effusions and ascites. The largest pulmonary mass decreased by 30%. The other small nodules increased in size and there were a couple of small nodules not seen before. The next CT of Jul. 14, 2017 showed a decrease of size of some pulmonary nodules but an increase in the other. Left upper thigh mass decreased by 66% since baseline. The CT of Sep. 27, 2017 showed a further 82% decrease in the size of the upper thigh mass, a decrease of some pulmonary nodules, but an increase of the other and an increase in size of pelvic lymph nodes but decrease of inguinal lymph nodes. The last CT of Dec. 19, 2017 shows a decrease in the size of the pulmonary nodules and the lymph nodes which have increased before. The left upper thigh mass remained 82% smaller. The response was classified as PR. The patient had only one blood genomic test by Guardant 360 on Oct. 10, 2017 which showed TP53 R249T and c.97-28_99del (Splice Site Indel) and KIT amplification. Bone tumor genomic analysis by Foundation Medicine of Apr. 23, 2015 revealed TP53 R249T. The patient had marked symptomatic improvement including reduction of severe pain, swelling and tumor size in the left thigh.

Conclusion: The patient had a very aggressive and heterogenous malignant process. Prior to the treatment her metastases increased in less than 3 weeks. She accomplished reduction of her tumor load and marked physical improvement and survived 4 times longer than estimated.

Example 68

A 70-year-old Caucasian male presented to the clinic in February 2018 and was diagnosed with: 1. Squamous cell carcinoma with metastases to the skin, Stage IV; 2. Prostate cancer, diagnosed in 2011 status post radiation therapy and hormonal treatment; 3. Polycystic kidney disease status post renal transplant in 2006 on immune suppressive therapy. The patient had a short 1-year history of his skin cancer. In September 2017 he developed right shoulder pain. A few months prior to that he had a biopsy of a skin lesion in the right forearm which was confirmed as squamous cell carcinoma. On Dec. 26, 2017 he had a biopsy of the tumor in the right upper chest which confirmed squamous cell carcinoma of the skin origin. He underwent a surgical resection of the large tumor on Jan. 21, 2018 but developed a rapid regrowth of the tumor. He had a complication of hypercalcemia for which he was hospitalized. The evaluation at MDACC in Houston did not provide a reasonable treatment plan for him in view of the challenges of immunosuppression. His life expectancy was less than 3 months.

Treatment: The treatment began on Feb. 26, 2018 with ipilimumab 3 mg/kg IV every 3 weeks. On Mar. 5, 2018 rucaparib 300 mg PO daily and on Mar. 6, 2018 cetuximab 250 mg/m2 (512 mg) IV weekly were added to the treatment. On Mar. 28, 2018 AS was started up to 19.2 g daily. On Apr. 10, 2018 radiation therapy was started, 5 days a week for 6 weeks. On May 7, 2018 ipilimumab was discontinued after 4 treatments. On Oct. 27, 2018 A10 up to 150 g IV daily was added to the treatment. On Jan. 14, 2019 the patient developed acute aspiration pneumonia and was admitted to the hospital. The treatment for cancer was discontinued. He passed away on Jan. 27, 2019.

Response to Treatment: The patient had very aggressive and very large recurrent tumor originating in the right upper quadrant of the chest measuring 13×16 cm and satellite lesions. His evaluation at MDACC did not result in a treatment plan due to the challenges of immunosuppression necessary for his post-transplant condition. After 4 months of treatment he had dramatic improvement. PET/CT's of May 18, 2018 and Jun. 14, 2018 showed 60.6% decrease of tumor size. There was further decrease to 71.9% on Jul. 25, 2018 and Aug. 14, 2018 scans. His treatment was complicated by wound infection which was treated with antibiotics. He died from pneumonia which was difficult to treat due to immunosuppression. Blood genomic analysis by Guardant 360 of Jun. 4, 2018 compared to baseline of Feb. 13, 2018 revealed decrease of concentration of GNAS R 201H and ND of PDGFRA E 86A, APC E918E, TP53 H179Y, BRA CAI R1443*, ARID1A 51167F, METT7591, and NOTCH1 V220M. Patient's response was determined as PR.

Conclusion: Very challenging and advanced case of aggressive skin cancer which responded rapidly to the combination of AS, ipilimumab, cetuximab, rucaparib and radiation therapy. The patient survived approximately a year versus the estimated less than 3 months and had marked symptomatic and objective improvement.

Example 69

A 69-year-old male presented to Burzynski Clinic in December 2017 and was diagnosed with poorly differentiated diffuse adenocarcinoma of the stomach with metastases to the peritoneum, Stage IV. The patient has approximately a year history of his disease. His symptoms of epigastric pain and weight loss aggravated in February 2017. The biopsy of the stomach of Sep. 9, 2017 yielded the above diagnosis. ACT of Oct. 26, 2017 showed a soft tissue density mass lying between the greater curvature of the stomach, pancreas and duodenum causing a small bowel obstruction and soft tissue thickening of the gastric wall resulting with obstruction of the distal esophagus and narrowing of the splenic and mesenteric veins. Ascites was also present indicating development of carcinomatosis. The EGD and endoscopic ultrasonography and biopsy at MDACC in Houston confirmed peritoneal metastases, HER-2 negative. On Nov. 15, 2017 he was started on chemotherapy with oxaliplatin 175 mg and fluorouracil 4100 mg and he received the second cycle on Nov. 29, 2017 and the third on Dec. 13, 2017 with poor tolerance. His life expectancy was less than 6 months.

Treatment: The treatment began on Jan. 2, 2018 with AS up to 19.2 g daily and vorinostat 100 mg PO daily. He also continued his chemotherapy at 75% dose reduction. Vorinostat was discontinued on Mar. 11, 2018. He also discontinued chemotherapy on Feb. 17, 2018 due to neuropathy. The patient was advised to consider adding pembrolizumab and ramucirumab but instead he was enrolled in a clinical trial with pembrolizumab and discontinued the treatment under the disclosed care on Mar. 22, 2018.

Results of Treatment: CT's of Dec. 12, 2017, Jan. 10, 2017 and Mar. 27, 2018 showed stable thickening of the stomach wall. Baseline blood genomic analysis by Guardant 360 on Dec. 12, 2017 revealed EGFR V7421 mutation which was no longer present on Mar. 28, 2018 indicating molecular CR.

Conclusion: This was a case of very aggressive stomach cancer with biopsy confirmed peritoneal carcinomatosis. Patients CT could not determine response due to location of the primary tumor and metastases. However, genomic analysis of blood revealed elimination of the driving mutation of EGFR.

Example 70

A 45-year-old Caucasian male presented to Burzynski Clinic in June 2019 diagnosed with T-cell lymphoma with retroperitoneal and brain involvement, Stage IV. The patient had a 3-year history of his disease. In Spring of 2016 he developed abdominal pain and was found to have T cell lymphoma with retroperitoneal involvement. He underwent DA-EPOCH chemotherapy from March to July 2016, followed by autologous transplant in July 2016 at MDACC in Houston. In October 2017 he was admitted to clinical trial of pralatrexate and romidepsin at New York Columbia Medical Center. He developed sepsis, an airway abscess and progression of the disease. He was followed with immunotherapy with nivolumab but continued to progress. He then started on brentuximab/bendamustine and had a good response. This was followed with allogenic unrelated donor matched stem cell transplant in December 2018 at MDACC in Houston. He continued brentuximab until March 2019 when it was stopped due to severe neuropathy. In May 2019 he developed metastasis to the left parietal lobe of the brain which was confirmed by biopsy as T cell lymphoma. At that time, he was offered terminal care in hospice. His life expectancy was estimated as less than 2 months.

Treatment: The treatment began on Jun. 20, 2019 with AS up to 19.2 g daily. On Jul. 3, 2019 he received gamma radiation to his brain tumor. He decided to discontinue the treatment on Nov. 14, 2019.

Response to Treatment: Follow-up MRI of the head on Sep. 12, 2019 showed 87% decrease of the size of left parietal mass compared to baseline of May 20, 2019. There was contribution of gamma radiation to this response. PET/CT of Sep. 12, 2019 showed a number of small lymph nodes in the neck, chest and the abdomen not present on the baseline scan of Jun. 11, 2019. The patient became asymptomatic and on Jul. 25, 2019 he admitted that he was feeling great. Genomic analysis of the specimen of Jul. 1, 2016 by Foundation Medicine revealed CDKN1B K59fs*12, RB1 Y173fs*11, and TP53 K320*.

Conclusion: This patient exhausted standard of care treatments and clinical trials. He was treated with high dose chemotherapy, two different targeted therapies and immunotherapy and underwent two bone marrow transplants. He was advised to consider hospice care by the best cancer experts in the US and his expectancy was less than 2 months. He accomplished marked decrease of brain tumor size and survived over 5 months versus the estimated less than 2 months. He became completely asymptomatic and by his admission "feeling great." His deadly complication was the spread of his lymphoma to the brain for which no medications were available. AS has documented activity on brain tumors and its active ingredient, phenylacetate, increases the effect of radiation therapy by the factor of 2.5. The combination of AS and Gamma Knife accomplished 87% decrease of the size of the brain metastasis. The progression outside the brain could be treated with the addition of targeted medications to which he responded before or new drugs selected based on the blood genomic analysis.

Example 71

A 71-year-old Chinese male presented to Burzynski Clinic in April 2019 and was diagnosed with papillary carcinoma of the thyroid with metastases to the lymph nodes and lungs, Stage IV. The patient had an 11-year history of cancer. On Nov. 4, 2008 he underwent total thyroidectomy with dissection of multiple lymph nodes. The pathology diagnosis was papillary carcinoma. In December 2008 he underwent radiofrequency ablation with iodine-131, 150 mCi. PET/CT of Nov. 28, 2018 showed progressive increase in hypermetabolic activity in the lesions at the base of the neck and anterior thoracic inlet. There was hypermetabolic activity in mediastinal and bilateral hilar lymph nodes as well as multiple pulmonary nodules. His life expectancy was estimated as less than 6 months.

Treatment: The treatment began on Apr. 18, 2019 with AS up to 19.2 g daily and lenvatinib 10 mg PO daily. On Jan. 18, 2020 everolimus 2.5 mg PO daily was added to the treatment. On May 5, 2020 A10 was added up to 75 g IV daily. Everolimus was discontinued on Aug. 24, 2020 replaced by dasatinib 20 mg daily. The treatment with AS, A10 and dasatinib was discontinued on Nov. 6, 2020.

Response to Treatment: Baseline PET/CT of Nov. 28, 2018 showed hypermetabolic mass in the left thyroid/paratracheal region, multiple hypermetabolic lymph nodes in the hilar and subcarinal region and multiple pulmonary nodules. Follow-up PET/CT of Jul. 8, 2019 revealed decreased metabolism in the hilar lymph nodes and small right middle lobe pulmonary nodule and other pulmonary nodules resolved or not measurable. PET/CT of Sep. 5, 2019 showed improvement in the size and metabolic activity of the left paratracheal nodule and hilar and mediastinal lymph nodes. PET/CT of Aug. 13, 2020 showed further decrease of metabolic activity of paratracheal nodule and stable lung nodule. Blood genomic analysis of Apr. 17, 2019 was negative as well as the analysis of Jul. 25, 2019 and Dec. 9, 2019. On Jul. 14, 2020 there was an occurrence of DDR2 L749 L which became non-detectable on Nov. 2, 2020 as the result of the addition of dasatinib. Thyroglobulin blood levels were below normal during most of the treatment with an occasional fluctuation. The patient was on maintenance treatment with PB. His response was determined as PR.

Conclusion: The patient obtained PR of a difficult to control cancer after prior failure of surgery and radiofrequency ablation. He remained on a maintenance treatment.

Example 72

A 57-year-old Caucasian male presented to Burzynski Clinic in November 2019 and was diagnosed with high grade invasive urothelial carcinoma of the bladder with metastases to the lymph nodes, lungs, bones and brain, Stage IV. The patient had an 8-year history of his disease. His additional diagnosis of bladder cancer was established in April 2008 for which he underwent multiple resections. In April 2011 he was found to have regional lymph node involvement and had a radical cystectomy and placement of a neobladder. He was followed with 5 cycles of chemotherapy with cisplatin and gemcitabine from September 2010 to February 2011. He developed renal failure and chemotherapy was discontinued. In November 2014 he developed metastases to the abdomen and was started on nab-paclitaxel for 6 cycles which resulted in CR in March 2015. In 2017 he developed metastases to the lung and underwent a right lower lobe resection in March 2017. Genomic analysis of the tissue revealed BRACA1 mutation, EGFR amplification and PD-L1 expression greater than 50. He was given pembrolizumab from May 2017 to May 2018 when he progressed again. He then received trastuzumab/pertuzumab in clinical trial from September 2018 to September 2019. The PET/CT on Apr. 24, 2019 showed stable bone metastases. The PET/CT on Sep. 12, 2019 showed progression in the bones and in the right hilar lymph nodes. He was followed with 5 radiation treatments in November 2019 to T6-C7 to reduce pain. In September 2019 he was started on olaparib which was discontinued after 5 days due to alteration of his mental status. A CT showed multiple brain metastases. His life expectancy was estimated for less than 2 months.

Treatment: The treatment began on Nov. 5, 2019 with AS up to 19.2 g daily. On Dec. 3, 2019 he started radiation therapy to his brain which was completed on Dec. 11, 2019. On Jan. 8, 2020 he started ado-trastuzumab 3.6 mg/kg IV every 3 weeks under the care of his local oncologist. On Apr. 7, 2020 denosumab SC monthly was added under the care of his local oncologist. On Aug. 19, 2020 he was switched from ado-trastuzumab to trastuzumab 6 mg/kg IV every 3 weeks, capecitabine 1500 mg PO daily, and tucatinib 600 mg PO daily. He discontinued the treatment on Dec. 5, 2020 and passed away on Jan. 5, 2021.

Results of Treatment: MRI of the brain of Feb. 6, 2020 and Apr. 14, 2020 showed a 33% decrease of cerebral metastasis and the MRI of Jul. 16, 2020 showed a 13% decrease compared to baseline of Nov. 7, 2019. The PET/CT of Sep. 8, 2020 showed stable size of metastases compared to Apr. 6, 2020 indicating objective response. Blood genomic analysis by Guardant 360 of Apr. 16, 2020 compared to baseline of Nov. 5, 2019 showed ND of BRAF amplification and a decrease of TERT Promoter SNV, TP53 T253A and ERBB2 amplification (FIG. 10). There was marked improvement of survival from the estimated less than 2 months to the over a year which was recommended by the local oncologist of hospice.

Conclusion: This was a case of very advanced aggressive urothelial carcinoma which failed surgery, two different combinations of chemotherapy, targeted therapy and radiation therapy and was recommended terminal care in hospice. The patient improved markedly during his treatment at Burzynski Clinic and accomplished a reduction of the size of the metastatic tumor and a reduction of concentration of abnormal genes in the blood.

Example 73

A 73-year-old Caucasian female presented to the clinic in December 2019 and was diagnosed with invasive high-grade urothelial carcinoma with metastases to the lymph nodes and lungs, Stage IV. The patient had a short 6-month history of her cancer. In July 2019 she developed hematuria. A CT of Oct. 15, 2019 revealed a tumor of the left kidney. On the same date she had a placement of the ureteral stent and had ureteroscopy and left retrograde pyelogram and biopsy of the mass in the left upper calyx confirming the above diagnosis. CT urogram of Oct. 25, 2019 showed infiltrative mass of the left kidney extending to the left renal pelvis and retroperitoneal adenopathy and left renal vein thrombosis. PET/CT of Nov. 13, 2019 showed pulmonary and lymph node metastases. Her life expectancy was estimated for less than 6 months.

Treatment: The treatment began on Dec. 10, 2019 with AS up to 19.2 g daily. On Dec. 19, 2019 she was started on nivolumab 3 mg/kg IV and ipilimumab 1 mg IV every 3 weeks. She decided to discontinue the treatment on Mar. 18, 2020 for personal reasons.

Response to Treatment: Follow-up PET/CT of Feb. 24, 2020 showed resolution of pulmonary metastases and a decrease of metabolic activity in the renal tumor. Metabolic activity and size of small lymph nodes has increased. Patient's response was determined as PR, but it was not confirmed by follow up PET/CT. Blood genomic analysis by Guardant 360 compared to baseline of Dec. 5, 2019 revealed 55% decrease of the concentration of "driver" mutated gene KRAS G12D and increase of GNAS R201 C.

Conclusion: This patient had aggressive and advanced urothelial carcinoma which responded objectively by radiology and genomic criteria. She discontinued the treatment prematurely for non-medical reasons.

Example 74

An 11-year-old Caucasian female presented to Burzynski Clinic in May 2018 and was diagnosed with disseminated medulloblastoma with leptomeningeal carcinomatosis. The patient had less than 3 years history of her disease. In December 2015 she developed headaches, vomiting, diplopia and blurred vision. MRI revealed findings suggesting medulloblastoma with spinal cord metastases. She underwent a tumor resection and ventriculostomy in December 2015 with postoperative diagnosis of medulloblastoma. From January 2016 to February 2016 she underwent craniospinal radiation therapy of 54 Gy in 30 fractions. She was followed with cisplatin, vincristine, and lomustine from April 2016. She experienced hearing loss and cisplatin was replaced by carboplatin. Altogether she was given 4 cycles of each regimen until March 2017. MRI's of March 2018 and Apr. 18, 2018 revealed disseminated disease in the brain and spinal cord and leptomeningeal carcinomatosis. The patient's life expectancy was less than 2 months.

Treatment: The treatment at Burzynski Clinic started on May 14, 2018 and included AS up to 11.5 g/d, three oral targeted drugs at 2 to 4 times dose reduction: dasatinib, everolimus, and pazopanib and bevacizumab 10 mg/kg IV every 2 weeks. On Dec. 5, 2018 vorinostat 100 mg PO was added to the treatment. The treatment was discontinued by the patient's mother on Feb. 28, 2019.

Response to Treatment: Follow-up MRI of the brain and spine on Jun. 6, 2018 showed a decrease in size of the enhancing lesions in the spinal cord with the largest at T10-T11 level no longer seen. The follow-up MRI every 8 weeks up to Jan. 31, 2019 did not show significant changes, indicating PR. The patient survived over 9 months from the treatment start.

Conclusion: This case was a rapid PR of very advanced, recurrent, disseminated medulloblastoma with symptomatic improvement and increased survival.

Example 75

An 11-year-old Korean male presented to Burzynski Clinic in July 2019 diagnosed with medulloblastoma, classic type with dissemination through the brain and spinal cord. The patient had a 6-year history of his disease. On Aug. 1, 2013 he was evaluated for headaches and vomiting during the past 3 months and was found to have a brain tumor suspicious for medulloblastoma and hydrocephalus. On Aug. 2, 2013 he underwent a resection of the infratentorial tumor which established the above diagnosis. From Sep. 2, 2013 to Oct. 18, 2013 he received proton 3D therapy of 5580 cGy to the brain and 3600 cGy to the spine. On Nov. 13, 2013 he started 6 cycles of carboplatin, vincristine, Holocaust, EPS and cyclophosphamide, EPS, thiotepa completed on Jun. 4, 2014 and followed by an autologous bone marrow transplant. On Sep. 25, 2014 he started the second high-dose chemotherapy with cyclophosphamide and Alkeran and completed on Sep. 30, 2014, followed by an autologous bone transplant. MRI on Oct. 22, 2018 showed a diffuse infiltrative lesion in the pons and cerebellum and metastasis to the left frontal lobe. On Dec. 20, 2018 he started chemotherapy with carboplatin, ifosfamide, MESNA, etoposide, vincristinem, and methotrexate×6 through Dec. 28, 2018. MRI of Feb. 17, 2019 showed a spinal enhancing lesion in the dorsal spinal cord. On Feb. 26, 2019 he underwent the resection of the lesion in the left frontal lobe and on Apr. 23, 2019 he had a third craniotomy with resection of the cavernous angioma induced by radiation. In July 2019 he developed metastases to the spinal cord and was treated with IMRT×10 from Jul. 5, 2019 to Jul. 18, 2019. His life expectancy was less than 2 months.

Treatment: The treatment at Burzynski Clinic started on Jul. 30, 2019 and included AS up to 12 g/d, three oral targeted drugs at dose reduction from 2 to 4 times: dasatinib, everolimus and pazopanib and bevacizumab 10 mg/kg IV every 2 weeks. The treatment was discontinued on Jan. 23, 2020. The last contact with the patient's parents was on Feb. 19, 2020. At that time the patient switched to another physician. He survived over 6 months from treatment start.

Response to Treatment: Follow-up MRI of Aug. 26, 2019 showed a 23.3% decrease in the size of the brainstem mass indicating MR but the next MRI of Oct. 26, 2019 showed PD. MRI of the spine of Oct. 27, 2019 compared to Jun. 30, 2019 showed resolution of an 51 enhancing mass.

Conclusion: This was a very advanced case of recurrent disseminated medulloblastoma after 3 surgical resections, 2 radiation therapy regimens and 4 chemotherapy regimens, including 2 high-dose and 2 autologous bone marrow transplants. He accomplished resolution of the spinal cord lesion and temporary shrinkage of the brainstem lesion.

Example 76

Here, AS and A10 (ANP) and targeted, immunological, hormonal and/or chemotherapeutic agents were anti-cancer treatments administered to patients. In some cases, palliative RT and surgery were used in addition to anti-cancer drugs. ANPs were delivered via an ambulatory infusion pump and subclavian catheter every 4 hours. The dose of AS was gradually escalated from 0.1 g/kg/day to a maximum of 0.4 g/kg/day after 4 days and a flow rate from 50 mL/hr to 250 mL/hr by the personnel of BC. The dose of A10 was increased to the maximum of 12 g/kg/day. Most of the patients were continuing the treatment on the optimally tolerated dosage of AS of 0.2 to 0.4 g/kg/day and A10 of 5 g/kg/day and the flow rate of 200-250 mL/hr. Medications that were considered necessary for the patient's welfare, and did not interfere with the treatment, were prescribed at the discretion of the treating physician.

At baseline, history taking, physical examination, necessary laboratory, genomic and radiological evaluations were performed. Two largest perpendicular diameters of the radiologically significant lesions were measured including MRI contrast-enhanced lesions in the brain and spinal cord. The follow-up scans, usually at 4 to 8-week intervals, were used to determine the response.

Complete response (CR) required the disappearance of all enhancing lesions in the brain meninges and spinal cord, and stable or improved non-enhancing lesions, and disappearance of the lesions outside the brain by CT, or metabolically active lesions by PET. Partial response (PR) required a 50% or higher decrease of the sum of the products of the two largest perpendicular diameters of the lesions, and progressive disease (PD) was more than a 25% increase. Stable disease (SD) was the status between PR and PD, and minor response (MR) was more than a 25% decrease. Mixed response was determined when there was a CR or PR of some lesions and PD of the other lesions.

In clinical trials, the CR and PR were sustained for at least 4 weeks, and SD for 7 weeks. In private practice some patients did not agree to have a follow-up radiological evaluation because of exposure to radiation or the additional cost. Such responses were marked as CR* or PR*. Some patients with metastases in many organs accomplished CR or PR in one organ, for instance the liver, but not in the other sites. They were marked accordingly, for instance, CR (HEP) and SD (OSS), meaning CR in the liver and SD in the bones. Molecular response was determined by repeated Guardant 360 tests.

A treatment plan was formulated based on the patient's history and clinical evaluation including genomic data. All patients were treated with AS to cover 135 abnormal genes plus additional targeted drugs to act on genes not affected by AS. The genes affected by AS and A10 based on clinical genomic testing are listed in Table 51. In some cases, a mild form of chemotherapy was used at the beginning to accelerate the response and in some patients, A10 was added.

TABLE 51

Gene Abnormalities Affected by Antineoplastons Based on Genomic Testing in Patients.

| | |
|---|---|
| Mutations of ALK, I146IL - Esophageal Adenocarcinoma, N1544K - Ovarian Cancer | Mutations of GNAS, R201H* - Squamous Cell Carcinoma of the Skin |
| Mutations of AKT1, E17K - Breast Cancer, R346H - Prostate Cancer | Mutations of HIST1H1D, K185-A186 > T - Chronic Atypical, Myelogenous Leukemia |
| Mutations of APC, G29G - Breast Cancer, K445K - Breast Cancer, V2716L - Breast Cancer, E918E - Squamous Cell Carcinoma of the Skin, Q1378* - Colon Cancer, S457* - Colon Cancer, I1304fs - Colon CancerE888fs - Colorectal CancerR230C Colorectal CancerQ1090Q - Esophageal AdenocarcinomaS1360P - Esophageal Adenocarcinoma | Mutations of IDH1, R132H - Anaplastic Oligodendroglioma & Anaplastic Astrocytoma<br>Mutations of JAK2, V617 - MDS, Chronic Atypical Myelogenous Leukemia, Myelofibrosis, Refractory Anemia<br>Mutations of AR, A356E - Small Cell Carcinoma of the Lung, M887V - Ovarian Cancer, S510R - Colon Cancer |
| Mutations of ARAF, Y495Y - Breast Cancer<br>Mutations of MAP2K1, K57E - Breast Cancer | Mutations of KDMGA loss - Breast Cancer, Mutation of KIT - KIT Q 775 fs (Exon 16 deletion), Adenocarcinoma of uterine cervix |
| Mutations of ARID1A, S1798L - Breast Cancer, Salivary Gland Cancer, Head & Neck, S1167F - Squamous Cell Carcinoma of the Skin, G246V - Ovarian Cancer, R1889W - Ovarian Cancer, Q802fs - Colorectal Cancer | Mutations of KRAS, G12V - Cholangiocarcinoma & Colon, G12D - Urothelial Carcinoma & Esophagus, G12S - Colon Cancer, G13D - Colorectal Cancer, p.AG11GD - Colon Cancer |
| Mutations of ARID2, N127fs18 - Anaplastic Astrocytoma | Mutations and amplifications of CDK6 - Breast Cancer |
| Mutations of ASXL1, R1273f*s - Chronic Atypical Myelogenous Leukemia | Mutations of NOTCH2, S2379F - Chronic Atypical Myelogenous Leukemia |
| Mutations of ATRX, S850fs*2 -Anaplastic Astrocytoma, N179fs*26 - Anaplastic Astrocytoma | Mutations of NTRK1, Ovarian Cancer, P387L (possibly) - Lung Cancer, R766Q - Prostate Cancer |
| Mutations of BRCA1, H662Q - Breast Cancer, R1443* - Squamous Cell Carcinoma of the Skin | Mutations of MAP3K6, P646L - Chronic Atypical Myelogenous Leukemia |
| Mutations of BRCA2, D237N - Breast Cancer, 12040V - Chronic Atypical Myelogenous Leukemia | Mutations of MET, C385Y - Esophageal Adenocarcinoma, T895M - Breast Cancer, T7591 - Squamous Cell Carcinoma of the Skin, M391 - Breast Cancer |
| BRAF amplification - Urothelial Carcinoma & Ovarian Cancer, E264 - Esophagus, V600E - Colorectal Cancer | Mutations of MPL, Y591D - Chronic Atypical Myelogenous Leukemia |
| Mutations and amplifications of CCND1, Amplification - Breast Cancer, R291W - Ovarian Cancer, 296* - Breast Cancer | Mutations of NOTCH1, A465V - GIST, V220M - Squamous Cell Carcinoma of the Skin, D1681H - Breast Cancer, S223N - Ovarian Cancer |

TABLE 51-continued

| Gene Abnormalities Affected by Antineoplastons Based on Genomic Testing in Patients. | |
|---|---|
| CDK4 amplifications - Breast Cancer | Mutations of GNA11, N244S - Colon Cancer |
| Mutations of MAP2K4, Loss exon 2 - Breast Cancer | Mutations of MAP3K1, S398 - Breast Cancer |
| Mutations of CCNE1, P268P - Breast Cancer, R95Q - Breast Cancer | Mutations of NF1, Splice cite 480-11_4801del11 - Breast Cancer, Splice cite SNV - Lung Cancer, c.6655 > T - Ganglioglioma, p.D2219Y - Ganglioglioma, A2617A - GIST, F710C - Cholangiocarcinoma, V2378fs*8 - Diffuse Astrocytoma, I1719T - Esophagus, K583R - Ovarian Cancer |
| Mutations of PDGFRA, V299G - Breast Cancer, E86A - Squamous Cell Carcinoma of the Skin | Mutations and amplifications of MYC, Amplifications - Breast Cancer & Ovarian Cancer, S244S - Breast Cancer |
| Mutations of CDKN2A, D74N - Breast Cancer | Mutations of CDKN1B, K59fs* - T-Cell Lymphoma |
| Mutation of FGFR2, KCNH7 fusion - Cholangiocarcinoma | Mutations of GNAQ, Salivary Gland Cancer, Head & Neck |
| Mutation of FGFR3, H290Y - Colon Cancer | Mutations of H3F3A, K28N - DIPG, K27 - DIPG |
| Mutations of CTNNB1, S45-subclonal - Breast Cancer, T41A - Endometrial Adenocarcinoma<br>Mutations of PIK3R1, S399Y408del splice site 917-1G > A - Anaplastic Oligodendroglioma<br>Mutation of PTCH1, p.M17 Start loss-LOF - Breast Cancer<br>Mutations of DDR2, L749L - Thyroid Cancer<br>Mutations and amplifications of EGFR, Amplification - Breast Cancer & Prostate Cancer, P753L (possibly) - Lung Cancer, V524I - Breast Cancer, V7421 - Stomach Cancer, D321D - Colorectal Cancer | Mutations and amplifications of PIK3CA, Q546H - Breast Cancer, Q546K - Colon Cancer, Q546R - Pilocytic Astrocytoma, Q597H - Ovarian Cancer, Amplification - Breast & Ovarian Cancer, E542K - Breast, Colorectal & Prostate Cancer, E545K - Breast Cancer, E726K - Breast Cancer, E39K - Breast Cancer, E453K - Breast Cancer & Anaplastic Oligodendroglioma, R4-P18del - Breast Cancer, H1047L - Breast Cancer & Colon, H104R - Breast Cancer, K567E - Pilocytic Astrocytoma, I15431 - Colorectal Cancer, p.E545K - Colon Cancer, G1049R - Colon Cancer |
| Mutations of SMAD4, A406T - Lung Cancer, A451P - Colon Cancer, L495R - Colon Cancer, Q450H - Colon Cancer, D537V - Colorectal Cancer, P511L - Ovarian Cancer | Mutations of PTEN, C136Y - DIPG, Loss exons 4-7 - Breast Cancer, D252Y - Breast Cancer, R130* - Breast Cancer, Y27C - Breast Cancer, N323fs*23 - Diffuse Astrocytoma, R55fs - Colorectal Cancer, H196_1203DEL - Ovarian Cancer |
| Mutations of EWSR1, FLI1 fusion - Ewing Sarcoma, Lung Cancer, PNET & Neuroendocrine | Mutations of RAF1, P63P - Breast Cancer, Amplification - Ovarian Cancer |
| Mutations of FBXW7, Y545C - Lung Cancer, R658* - Colon Cancer | Mutations of RB1, Q217* - Breast Cancer, Y173fs* - T-Cell Lymphoma, H673fs - Prostate Cancer |
| Mutations and amplification of FGFR, Amplification - Breast Cancer, T320T - Breast Cancer, S726F - Breast Cancer, H791H - Breast Cancer, P47P - Breast Cancer, S430fs - Breast Cancer, R179H - Endometrial Adenocarcinoma | Mutations of GATA 3, P433fs43 - Breast Cancer, P409fs - Breast Cancer, PS405fs - Breast Cancer, D336fs - Breast Cancer, S430fs - Breast Cancer, c.1213_1214del - Breast Cancer, Multiplication - Head & Neck |
| Mutations and amplifications of FGFR1, Amplifications - Breast Cancer & Cholangiocarcinoma, S726F - Breast Cancer | ERBB2 amplification - Urothelial Carcinoma, C584G - Esophagus, V797del (Exon 20 deletion) - Prostate Cancer |
| Mutations of SRSF2, P95H - Chronic Atypical Myelogenous Leukemia | Mutations of SPEN, A2510V - Chronic Atypical Myelogenous Leukemia |
| Mutations of RUNX1, R107C - Chronic Atypical Myelogenous Leukemia | Mutations of STAT5B, R110H - Chronic Atypical Myelogenous Leukemia |
| Mutations of TET2, C1875G - Chronic Atypical Myelogenous Leukemia | Tert promoter, SNV - Lung Cancer and Urothelial Carcinoma, 124 C > T - Diffuse Astrocytoma, 146C > T - Anaplastic Oligodendroglioma |
| Mutations of TP53, V73fs - Breast Cancer, R175G - Breast Cancer, R196 - Breast Cancer, R249T - Pleomorphic Sarcoma, C176F - Breast Cancer, G187D - Breast Cancer, R282W - Breast Cancer & Colorectal Cancer, E287* - Breast Cancer, E285K - Breast Cancer, S241del - Breast Cancer, c.97-28_99del - Pleomorphic Sarcoma, Y126D - Lung Cancer, R273H - Lung Cancer & Anaplastic Astrocytoma & Colorectal Cancer, C176W - Small Cell Carcinoma of the Lung, K320* - T-Cell Lymphoma, T253A - Urothelial Carcinoma, Splice site 37G-1G > A - Anaplastic Oligodendroglioma, Q104 - Esophagus, P151H - Esophagus, H179Y - Squamous Cell Carcinoma of the Skin, R273C - Anaplastic Astrocytoma, R248W - Ovarian Cancer, R176H - Ovarian Cancer, R209fs - Ovarian Cancer, N235-Y236del - Ovarian Cancer, R248Q - Colon Cancer, R306* - Colon Cancer, C176Y - Colorectal Cancer, S241F - Colorectal Cancer, L252-1254del - | |

TABLE 51-continued

| Gene Abnormalities Affected by Antineoplastons Based on Genomic Testing in Patients. |
|---|
| Esophageal Adenocarcinoma, L145P - Endometrial Adenocarcinoma, R158H - Endometrial Adenocarcinoma, R213* - Endometrial Adenocarcinoma, Y220C - Endometrial Adenocarcinoma, R110P - Breast Cancer, V274G - Ovarian Cancer, c.376-4_384del - Prostate Cancer |

The goal of the treatment was to accomplish a CR and complete disappearance of abnormal genes from the patient's blood. At this point, the patient was advised to continue maintenance treatment for up to 8 months and monitor CR by radiological evaluations, preferably every 8 weeks, and blood genomic tests every 3 months.

Non-Evaluable Patients. For the purpose of this exemplary method (i.e., Example 76), the following patients were defined as non-evaluable: Patients with no pathology diagnosis (except for DIPG), no baseline and follow-up radiology or laboratory data (for hematologic malignancies), and less than 60 days on treatment (except for GBM). The patients who received the treatment only with antineoplastons were excluded from this report. These cases are evaluated in separate reports.

Results in Evaluable Patients

Radiological Responses and Survival. The total of 205 evaluable patients were treated by using a combination of AS, A10, and other treatments. The complete list of main diagnoses for the patients is provided in Table 52. and the list of secondary diagnoses in Table 53. The individual patient responses are provided in Table 54 and the tabulation of responses is in Tables 55-62. A key to the abbreviations used in Tables 52-62 is provided in Table 63. The patients were diagnosed with 39 different types of terminal malignancies. A group of 10 patients were diagnosed with more than one malignancy. This added 10 additional diagnostic groups increasing the number of cancer diagnoses 49. They included Ewing sarcoma, leptomeningeal carcinomatosis (3 patients), chronic atypical myelogenous leukemia, myelofibrosis, neuroendocrine carcinoma, pleomorphic sarcoma, PNET, refractory anemia, salivary gland cancer and synovial sarcoma (Table 53).

TABLE 52

Main Diagnoses for RTT Patients.

| Main Diagnoses | Evaluable Patients (N = 201) |
|---|---|
| 1 | Adenoid Cystic Carcinoma |
| 2 | Adenocarcinoma of the Appendix |
| 3 | Adenocarcinoma of the Uterine Cervix |
| 4 | Biliary tract- Cholangiocarcinoma |
| 5 | Brain Tumor - Anaplastic Astrocytoma |
| 6 | Brain Tumor - Diffuse Astrocytoma |
| 7 | Brain Tumor - Anaplastic Ependymoma |
| 8 | Brain Tumor - Anaplastic Oligodendroglioma |
| 9 | Brain Tumor - Brainstem Anaplastic Astrocytoma |
| 10 | Brain Tumor - Brainstem Glioma |
| 11 | Brain Tumor - DIPG H3K27 Mutation |
| 12 | Brain Tumor - DIPG No Pathology |
| 13 | Brain Tumor - Ganglioglioma |
| 14 | Brain Tumor - Glioblastoma Multiforme |
| 15 | Brain Tumor - Medulloblastoma |
| 16 | Brain Tumor - Pilocytic Astrocytoma |
| 17 | Breast Carcinoma |
| 18 | Carcinoma of Unknown Primary |
| 19 | Colorectal Carcinoma |
| 20 | Endometrial Carcinoma |
| 21 | Esophageal Carcinoma |

TABLE 52-continued

Main Diagnoses for RTT Patients.

| Main Diagnoses | Evaluable Patients (N = 201) |
|---|---|
| 22 | GIST |
| 23 | Head and Neck Carcinoma |
| 24 | Kidney Carcinoma |
| 25 | Lung Carcinoma - Non-Small Cell |
| 26 | Lung Carcinoma - Small Cell Carcinoma |
| 27 | Multiple Myeloma |
| 28 | Myelodysplastic Syndrome |
| 29 | Non-Hodgkin's Lymphoma |
| 30 | Osteosarcoma |
| 31 | Ovarian Carcinoma |
| 32 | Pancreatic Carcinoma |
| 33 | Prostate Carcinoma |
| 34 | Sarcoma |
| 35 | Skin Carcinoma |
| 36 | Stomach Carcinoma |
| 37 | Thyroid Carcinoma |
| 38 | Urothelial High-Grade Carcinoma |
| 39 | Uterine, Cervix, Vulvar, Endometrium Carcinoma |

TABLE 53

Secondary Diagnoses for RTT Patients.

| Secondary Diagnosis | Patient Number |
|---|---|
| Ewing Sarcoma | 025240 |
| Leptomeningeal Carcinomatosis | 025365 |
| Leptomeningeal Carcinomatosis | 025811 |
| Leptomeningeal Carcinomatosis | 026040 |
| Chronic Atypical Myelogenous Leukemia | 025300 |
| Myelofibrosis | 025300 |
| Neuroendocrine Carcinoma | 025240 |
| Pleomorphic Sarcoma | 025630 |
| Primitive Neuroectodermal Tumor - PNET | 025240 |
| Refractory Anemia | 025300 |
| Salivary Gland Cancer | 025228 |
| Synovial Sarcoma | 025630 |

TABLE 54

Individual Patient Responses.

| Breast Carcinoma | | | | | |
|---|---|---|---|---|---|
| 1. | 025365 | 1BE | | CR* | Dx |
| 2. | 025420 | 2BE | | CR | |
| 3. | 025879 | 3BE | | CR* | De |
| 4. | 025926 | 4BE | | CR | |
| 5. | 025931 | 5BE | BRA | PR | |
| 6. | 026169 | 6BE | HEP | PR | |
| 7. | 026196 | 7BE | HEP | CR* | Dx |
| 8. | 026322 | 8BE | CR | | |
| 9. | 026328 | 9BE | PR | | |
| 10. | 026330 | 10BE | | CR | |
| 11. | 025266 | 11BE | PUL | CR* | Dx |
| 12. | 026357 | 12BE | | CR* | |
| 13. | 026130 | 13BE | LYM | CR | De |
| 14. | 026170 | 14BE | | CR* | |
| 15. | 026284 | 15BE | BRA | PR | |

TABLE 54-continued

| Individual Patient Responses. | | | | | |
|---|---|---|---|---|---|
| 16. | 026182 | 16BE | BRA | PR* | Dd |
| 17. | 026205 | 17BE | | PR | |
| 18. | 026341 | 18BE | HEP | MR | |
| 19. | 026045 | 19BE | | CR* | |
| 20. | 026387 | 20BE | | PR | |
| 21. | 026412 | 21BE | | CR | |
| 22. | 026424 | 22BE | | SD | |
| 23. | 026435 | 23BE | | SD | |
| 24. | 026442 | 24BE | | PR | |
| 25. | 026448 | 25BE | | IM | |
| 26. | 026511 | 26BE | | CR | |
| 27. | 026555 | 27BE | | PD | |
| 28. | 026566 | 28BE | LYM | CR | |
| 29. | 026606 | 29BE | OSS | PD | |
| Colorectal Carcinoma | | | | | |
| 1. | 025672 | 1CL | CR | | |
| 2. | 025910 | 2CL | MR | Dx | |
| 3. | 026032 | 3CL | CR | Dd | |
| 4. | 026113 | 4CL | CR | Dx | |
| 5. | 026260 | 5CL | SD | | |
| 6. | 026254 | 6CL | SD | | |
| 7. | 026055 | 7CL | MR | | |
| 8. | 026264 | 8CL | MR | | |
| 9. | 026446 | 9CL | PD | | |
| 10. | 026411 | 10CL | CR | | |
| 11. | 026422 | 11CL | MR | | |
| 12. | 026487 | 12CL | PR | | |
| 13. | 026486 | 13CL | IM | | |
| 14. | 026528 | 14CL | CR | | |
| 15. | 026531 | 15CL | IM | | |
| 16. | 026549 | 16CL | PD | | |
| 17. | 025264 | 17CL | PD | | |
| Glioblastoma Multiforme | | | | | |
| 1. | 025231 | 1GB | CR | | |
| 2. | 025298 | 2GB | PD | | |
| 3. | 025344 | 3GB | PD | | |
| 4. | 025383 | 4GB | CR | | |
| 5. | 025402 | 5GB | CR | | |
| 6. | 025425 | 6GB | CR | | |
| 7. | 025547 | 7GB | PD | | |
| 8. | 025557 | 8GB | PR | | |
| 9. | 025612 | 9GB | CR | | |
| 10. | 025622 | 10GB | PD | | |
| 11. | 025642 | 11GB | CR | | |
| 12. | 025648 | 12GB | PR | | |
| 13. | 025690 | 13GB | PD | | |
| 14. | 025755 | 14GB | PD | | |
| 15. | 025766 | 15GB | PD | | |
| 16. | 025817 | 16GB | SD | | |
| 17. | 026061 | 17GB | PR | | |
| 18. | 012303 | 18GB | PD | | |
| 19. | 026119 | 19GB | CR | | |
| 20. | 026116 | 20GB | PD | | |
| 21. | 026133 | 21GB | CR | | |
| 22. | 026140 | 22GB | SD | | |
| 23. | 026131 | 23GB | PR | | |
| 24. | 026206 | 24GB | SD | | |
| 25. | 026228 | 25GB | PR | | |
| 26. | 026197 | 26GB | PD | | |
| 27. | 026236 | 27GB | PD | | |
| 28. | 026251 | 28GB | SD | | |
| 29. | 026276 | 29GB | CR | | |
| 30. | 026274 | 30GB | IM | | |
| 31. | 026291 | 31GB | IM | | |
| 32. | 026310 | 32GB | CR | | |
| 33. | 026326 | 33GB | PD | | |
| 34. | 026337 | 34GB | CR | | |
| 35. | 026346 | 35GB | PD | | |
| 36. | 026356 | 36GB | CR | | |
| 37. | 026362 | 37GB | SD | | |
| 38. | 025461 | 38GB | PR | | |
| 39. | 025450 | 39GB | PD | | |
| 40. | 026431 | 40GB | PD | | |
| 41. | 026432 | 41GB | PD | | |
| 42. | 026434 | 42GB | CR | | |
| 43. | 026436 | 43GB | CR | | |

TABLE 54-continued

| Individual Patient Responses. | | | | |
|---|---|---|---|---|
| 44. | 026469 | 44GB | PR | |
| 45. | 026458 | 45GB | MR | |
| 46. | 026547 | 46GB | OR | |
| 47. | 026496 | 47GB | CR | |
| 48. | 026512 | 48GB | OR | |
| 49. | 026525 | 49GB | IM | |
| 50. | 026539 | 50GB | CR | |
| 51. | 026570 | 51GB | CR | |
| 52. | 026595 | 52GB | IM | |
| 53. | 026611 | 53GB | PR | |
| Head and Neck Carcinoma | | | | |
| 1. | 025228 | 1HK | PR | |
| 2. | 025908 | 2HK | PD | |
| 3. | 025981 | 3HK | MR | |
| 4. | 025471 | 4HK | SD | |
| Kidney Carcinoma | | | | |
| 1. | 025883 | 1KI | PR | |
| 2. | 026283 | 2KI | CR | |
| Lung Carcinoma - Non-Small Cell | | | | |
| 1. | 025240 | 1LU | MR | Dx |
| 2. | 025840 | 2LU | MR | Dx |
| 3. | 026126 | 3LU | PR* | |
| 4. | 026143 | 4LU | CR | |
| 5. | 026183 | 5LU | PR | |
| 6. | 026246 | 6LU | MR | |
| 7. | 026354 | 7LU | PR | |
| 8. | 026372 | 8LU | SD | |
| Ovarian Carcinoma | | | | |
| 1. | 025889 | 1OA | MR | |
| 2. | 025905 | 2OA | PR* | |
| 3. | 026177 | 3OA | MR | |
| 4. | 026347 | 4OA | PR | |
| 5. | 026398 | 5OA | CR | |
| 6. | 026468 | 6OA | CR | |
| 7. | 026544 | 7OA | IM | |
| Pancreatic Carcinoma | | | | |
| 1. | 025544 | 1PT | PR | |
| 2. | 025734 | 2PT | PR | Dx |
| 3. | 026179 | 3PT | MR | |
| Prostate Carcinoma | | | | |
| 1. | 025671 | 1PS | CR | De |
| 2. | 025805 | 2PS | PR | Dx |
| 3. | 026101 | 3PS | PR | |
| 4. | 026200 | 4PS | PD | |
| 5. | 026384 | 5PS | CR | |
| 6. | 026445 | 6PS | CR | |
| 7. | 026553 | 7PS | IM | |
| II. Uncommon Cancers (Neoplastic Diseases) | | | | |
| Adenoid Cystic Carcinoma | | | | |
| 1. | 025869 | 1AC | SD | |
| 2. | 026576 | 2AC | IM | |
| Adenocarcinoma of Uterine Cervix | | | | |
| 1. | 025869 | 1UA | PR | |
| Anaplastic Astrocytoma | | | | |
| 1. | 025534 | 1AA | CR | |
| 2. | 025851 | 2AA | PR | Dx |
| 3. | 025674 | 3AA | PD | Dx |
| 4. | 026542 | 4AA | CR | |
| 5. | 026475 | 5AA | CR | |
| Anaplastic Oligodendroglioma | | | | |
| 1. | 025537 | 1AO | MR | Dx |
| 2. | 025411 | 2AO | PD | |
| 3. | 025825 | 3AO | SD | |
| Diffuse Astrocytoma | | | | |
| 1. | 026024 | 1AD | CR | |
| 2. | 026499 | 2AD | CR | |

TABLE 54-continued

| Individual Patient Responses. | | | | |
|---|---|---|---|---|
| 3. | 026591 | 3AD | SD | |
| Cholangiocarcinoma | | | | |
| 1. | 026040 | 1CC | MR | De |
| 2. | 026403 | 2CC | IM | |
| 3. | 026540 | 3CC | SD | |
| Chronic Atypical Myelogenous Leukemia | | | | |
| 1. | 025300 | 1MD | MR | Dx |
| DIPG (Diffuse Midline High Grade Glioma, H3F3A K27M Mutant) | | | | |
| 1. | 026367 | 1DI | MR | |
| 2. | 026450 | 2DI | PR | |
| 3. | 026466 | 3DI | SD | |
| 4. | 026474 | 4DI | IM | |
| 5. | 026519 | 5DI | SD | |
| 6. | 026546 | 6DI | PR | |
| 7. | 026557 | 7DI | MR | |
| Esophageal Carcinoma | | | | |
| 1. | 025524 | 1EC | MR | Dd |
| 2. | 026381 | 2EC | SD | |
| 3. | 026565 | 3EC | CR | |
| Ewing Sarcoma | | | | |
| 1. | 025240 | 1LU | PR | Dx |
| Ganglioglioma | | | | |
| 1. | 025811 | 1GG | PR | |
| Gastrointestinal Stromal Tumor (GIST) | | | | |
| 1. | 025881 | 1GI | MR | Dd |
| Leptomeningeal Carcinomatosis | | | | |
| 1. | 025365 | 1BE | CR | Dx |
| 2. | 025811 | 1GG | MR | |
| 3. | 026040 | 1CC | MR | De |
| Myelodysplastic Syndrome (MDS) | | | | |
| 1. | 025300 | 1MD | MR | Dx |
| 2. | 025914 | 2MD | MR | |
| Myelofibrosis | | | | |
| 1. | 025300 | 1MD | MR | Dx |
| Neuroendocrine Carcinoma | | | | |
| 1. | 025240 | 1LU | PR | Dx |
| Osteosarcoma | | | | |
| 1. | 025240 | 1OS | PD | |
| Pilocytic Astrocytoma | | | | |
| 1. | 026099 | 1PI | CR* | |
| 2. | 026583 | 2PI | SD | |
| Pleomorphic Sarcoma | | | | |
| 1. | 025630 | 1SR | MR | De |
| Primitive Neuroectodermal Tumor (PNET) | | | | |
| 1. | 025240 | 1LU | PR | Dx |
| Refractory Anemia | | | | |
| 1. | 025300 | 1MD | MR | Dx |
| Salivary Gland Carcinoma | | | | |
| 1. | 025228 | 1HK | PR | |
| Skin Carcinoma | | | | |
| 1. | 025989 | 1SK | PR | De |
| Stomach Carcinoma | | | | |
| 1. | 025901 | 1SM | CR | De |
| 2. | 026421 | 2SM | PD | |
| Synovial Sarcoma | | | | |
| 1. | 025630 | 1SR | MR | |

TABLE 54-continued

| Individual Patient Responses. | | | | |
|---|---|---|---|---|
| T-Cell Lymphoma | | | | |
| 1. | 026190 | 1LT | PR | |
| Thyroid Carcinoma | | | | |
| 1. | 026164 | 1TR | PR | |
| Urothelial Carcinoma | | | | |
| 1. | 026270 | 1UR | MR | Dd |
| 2. | 026288 | 2UR | MR | |
| Medulloblastoma | | | | |
| 1. | 026017 | 1MB | PR | |
| 2. | 026212 | 2MB | MR | |
| Anaplastic Ependymoma | | | | |
| 1. | 026444 | 1AE | PR | |
| 2. | 026522 | 2AE | IM | |
| Brainstem Anaplastic Astrocytoma | | | | |
| 1. | 026463 | 1BA | CR | |
| Endometrial Adenocarcinoma | | | | |
| 1. | 026378 | 1EN | MR | |
| Multiple Myeloma | | | | |
| 1. | 026414 | 1MM | MR | |
| Invasive Squamous Cell Carcinoma of the Cervix | | | | |
| 1. | 026554 | 1UT | CR | |
| Adenocarcinoma of the Appendix | | | | |
| 1. | 026480 | 1AP | CR | |
| Small Cell Carcinoma of the Lungs | | | | |
| 1. | 026580 | 1SL | CR | |
| Brainstem Glioma | | | | |
| 1. | 026201 | 1BSN | PR | |
| 2. | 025363 | 2BSN | SD | |
| 3. | 025765 | 3BSN | MR | |
| DIPG No Pathology | | | | |
| 1. | 025417 | 1DIN | PR | |
| 2. | 025456 | 2DIN | SD | |
| 3. | 025565 | 3DIN | SD | |
| 4. | 025682 | 4D1N | SD | |
| 5. | 025528 | 5DIN | SD | |
| 6. | 026282 | 6DIN | SD | |
| 7. | 025207 | 7DIN | SD | |
| 8. | 026425 | 8DIN | SD | |
| Adenocarcinoma of Unknown Primary | | | | |
| 1. | 025996 | 1UPP | PD | |

TABLE 55

Tabulation of Common Cancer Diagnoses.

| | Responses % | | | |
|---|---|---|---|---|
| Diagnosis | CR + PR | MR | SD | PD |
| Breast | 83 | 7 | 7 | 3 |
| Colorectal | 47 | 29 | 6 | 18 |
| Glioblastoma | 47 | 13 | 8 | 32 |
| Head & Neck | 25 | 25 | 25 | 25 |
| Kidney | 100 | 0 | 0 | 0 |
| Lung | 63 | 25 | 13 | 0 |
| Ovarian | 57 | 43 | 0 | 0 |
| Pancreatic | 67 | 33 | 0 | 0 |
| Prostate | 71 | 0 | 14 | 14 |

TABLE 56

| Tabulation of Uncommon Cancer Diagnoses. | | | | | | |
|---|---|---|---|---|---|---|
| | Patient Number | | | | | |
| Diagnosis | ALL | CR | PR | IM | SD | PD |
| Adenoid Cystic Carcinoma | 2 | | | 1 | 1 | |
| Adenocarcinoma of the Appendix | 1 | | | 1 | | |
| Biliary Tract - Cholangiocarcinoma | 3 | | 1 | 1 | 1 | |
| Brain Tumor - Anaplastic Astrocytoma | 5 | 3 | 1 | | | 1 |
| Brain Tumor - Diffuse Astrocytoma | 3 | 2 | | | 1 | |
| Brain Tumor - Anaplastic Ependymoma | 2 | | 1 | 1 | | |
| Brain Tumor - Anaplastic Oligodendroglioma | 3 | | | 1 | 1 | 1 |
| Brain Tumor - Brainstem Anaplastic Astrocytoma | 1 | 1 | | | | |
| Brain Tumor - Brainstem Glioma | 3 | | 1 | 1 | 1 | |
| Brain Tumor - DIPG H3K27 Mutation | 7 | 1 | 3 | 1 | 2 | |
| Brain Tumor - DIPG No Pathology | 8 | | 1 | | 7 | |
| Brain Tumor - Ganglioglioma | 1 | | 1 | | | |
| Brain Tumor - Medulloblastoma | 2 | | 1 | 1 | | |
| Brain Tumor - Pilocytic Astrocytoma | 2 | 1 | | | 1 | |
| Carcinoma of Unknown Primary | 1 | | | | | 1 |
| Endometrial Adenocarcinoma | 1 | | | 1 | | |
| Esophageal Carcinoma | 3 | 1 | | 1 | 1 | |
| Stomach Cancer, Adenocarcinoma - SM | 2 | 1 | | | | 1 |
| Gastrointestinal Stromal Tumor - GIST | 1 | | | 1 | | |
| Small Cell Carcinoma of the Lungs | 1 | 1 | | | | |
| Multiple Myeloma | 1 | | | 1 | | |
| Myelodysplastic Syndrome - MDS | 2 | | 1 | | 1 | |
| T-Cell Lymphoma - Non-Hodgkin's Lymphoma | 1 | | 1 | | | |
| Osteosarcoma | 1 | | | | | 1 |
| Sarcoma | 1 | | 1 | | | |
| Skin Carcinoma | 1 | | 1 | | | |
| Thyroid Carcinoma | 1 | | 1 | | | |
| Urothelial High-Grade Carcinoma | 2 | | 1 | 1 | | |
| Adenocarcinoma of the Cervix | 1 | | 1 | | | |
| Invasive Squamous Cell Carcinoma of the Cervix | 1 | 1 | | | | |

Tumors were gone or shrunk in 65.6% of the total cases and progressed in 7.8%.

TABLE 57

| Tabulation of Subgroups of Breast Carcinoma. | | | | |
|---|---|---|---|---|
| | Responses % | | | |
| Subgroup | CR + PR | MR | SD | PD |
| Breast Carcinoma - BE $-, -, ^{+}$ | 100 | 0 | 0 | 0 |
| Breast Carcinoma - BE $-, ^{+}, ^{+}$ | 100 | 0 | 0 | 0 |
| Breast Carcinoma - BE $^{+}, -, -$ | 67 | 0 | 33 | 0 |
| Breast Carcinoma - BE $^{+}, -, ^{+}$ | 100 | 0 | 0 | 0 |
| Breast Carcinoma - BE $^{+}, ^{+}, -$ | 77 | 15 | 0 | 8 |
| Breast Carcinoma - BE Tri (−) | 67 | 0 | 33 | 0 |
| Breast Carcinoma - BE Tri ($^{+}$) | 100 | 0 | 0 | 0 |

TABLE 58

| Tabulation of Subgroups of Glioblastoma. | | | | |
|---|---|---|---|---|
| | Responses % | | | |
| Subgroup | CR + PR | MR | SD | PD |
| Brain Tumor - RGB | 56 | 11 | 15 | 19 |
| Brain Tumor - RGB Short | 40 | 0 | 0 | 60 |
| Brain Tumor - GB No SOC | 38 | 21 | 0 | 42 |
| Brain Tumor - GB No SOC Short | 100 | 0 | 0 | 0 |
| Brain Tumor - RGB Spinal Cord | 0 | 0 | 50 | 50 |

SOC—standard-of-care, RGB—recurrent glioblastoma multiforme, 60 days or more, and RGB—recurrent glioblastoma multiforme, less than 60 days.

TABLE 59

| Tabulation of Subgroups of Brain Cancer, Metastatic. | | | | | |
|---|---|---|---|---|---|
| | Patient Number | | | | |
| Primary Tumor | All | CR + PR | MR | SD | PD |
| Breast Carcinoma | 11 | 9 | | 1 | 1 |
| Kidney Carcinoma | 2 | 2 | | | |
| Lung Carcinoma | 2 | 1 | 1 | | |
| Biliary Tract | 1 | | 1 | | |
| Prostate Carcinoma | 1 | | | 1 | |
| Urothelial, High-Grade | 1 | | 1 | | |
| | Responses % | | | | |
| ALL | 18 | 66.7 | 16.7 | 11.1 | 5.6 |

Tumors were gone or decreased in 83.3% of the total cases and progressed in 5.6%.

TABLE 60

| Tabulation of Subgroups of Liver Cancer, Metastatic. | | | | | |
|---|---|---|---|---|---|
| | Patient Number | | | | |
| Primary Tumor | All | CR + PR | MR | SD | PD |
| Adenoid Cystic Cancer | 2 | | | 1 | 1 |
| Breast Cancer | 9 | 4 | 1 | 2 | 2 |
| Colorectal Cancer | 12 | 7 | 1 | 2 | 2 |
| Endometrial Cancer | 1 | | 1 | | |
| Head & Neck Cancer | 1 | 1 | | | |
| Lung Cancer | 2 | 1 | 1 | | |
| Small Cell Carcinoma - Lung | 1 | 1 | | | |
| Ovarian Cancer | 5 | 4 | 1 | | |
| Pancreatic Cancer | 1 | 1 | | | |
| Biliary Tract Cancer | 3 | | 2 | 1 | |
| Esophageal Cancer | 1 | 1 | | | |
| | Responses % | | | | |
| ALL | 38 | 53 | 18 | 16 | 13 |

Tumors were gone or shrunk in 71% of the total cases and progressed in 13%.

TABLE 61

| Tabulation of Subgroups of Bone Cancer, Metastatic. | | | | | |
|---|---|---|---|---|---|
| | Patient Number | | | | |
| Primary Tumor | All | CR + PR | MR | SD | PD |
| Breast Cancer | 22 | 7 | 5 | 7 | 3 |
| Colorectal Cancer | 3 | | | 2 | 1 |
| Lung Cancer | 5 | 2 | 1 | 1 | 1 |
| Prostate Cancer | 4 | 2 | | 1 | 1 |
| Adenoid Cystic Carcinoma | 1 | | | | 1 |
| Esophageal | 1 | 1 | | | |
| Small Cell Carcinoma - Lung | 1 | 1 | | | |
| Multiple Myeloma | 1 | | | 1 | |
| Osteosarcoma | 1 | | 1 | | |
| Sarcoma | 1 | | 1 | | |
| Urothelial Cancer | 1 | | | 1 | |
| | Responses % | | | | |
| ALL | 41 | 32 | 20 | 32 | 17 |

Tumors were gone or shrunk in 51% of the total cases and progressed in 17%.

TABLE 62

| Tabulation of Subgroups of Lung Cancer, Metastatic. | | | | | |
|---|---|---|---|---|---|
| | Patient Number | | | | |
| Primary Tumor | All | CR + PR | MR | SD | PD |
| Breast Cancer | 10 | 3 | 1 | 4 | 2 |
| Colorectal Cancer | 7 | 2 | 1 | 2 | 2 |
| Endometrial Cancer | 1 | | 1 | | |
| Head & Neck Cancer | 3 | 1 | | 1 | 1 |
| Lung Cancer w/Metastases to Lung | 1 | 1 | | | |
| Ovarian Cancer | 2 | 2 | | | |
| Prostate Cancer | 2 | 2 | | | |
| Adenoid Cystic Carcinoma | 1 | | 1 | | |
| Osteosarcoma | 1 | 1 | | | |
| Adenocarcinoma of the Cervix | 1 | 1 | | | |
| Uterine, Cervix, Vulvar, Endometrium | 1 | 1 | | | |
| Sarcoma | 1 | | 1 | | |
| Thyroid Cancer | 1 | 1 | | | |
| Urothelial Cancer | 2 | 1 | | 1 | |
| | Responses % | | | | |
| ALL | 35 | 46 | 14 | 23 | 14 |

Tumors were gone or shrunk in 60% of the total cases and progressed in 14%.

TABLE 63

| Abbreviations for Tables 52-62 | | | |
|---|---|---|---|
| am | amplification | IM | improvement |
| AS | Antineoplaston AS2- | LMN | leptomeningeal metastases |
| BC | Burzynski Clinic | LYM | lymph node metastases |
| BRA | brain metastases | MR | minor response |
| CH | chemotherapy | ND | non detectable |
| CR | complete response | OR | objective response |
| CR* | complete response not confirmed by the follow-up scan | OS | overall survival from treatment start |
| DAMA | discontinued against medical advice | OSS | bone metastases |
| Dd | patient died from their malignancy while on treatment | PE | physical examination |
| De | patient died from something other than their malignancy while on treatment | PR | partial response |
| Dx | patient died while on treatment, cause not documented | PR+ | progesterone positive |
| DEPB | dasatinib, everolimus, pazopanib, bevacizumab | PUL | pulmonary metastases |
| DESB | dasatinib, everolimus, sorafenib, bevacizumab | RT | radiation therapy |
| ER+ | estrogen positive | RTT | Right to Try |
| GBM | glioblastoma, glioblastoma multiforme | SKI | skin metastases |
| H | hormonal treatment | SU | surgery, the number before indicates how many |
| HER-2$^-$ | HER-2 negative | TNBC | triple negative breast cancer |
| HER-2$^+$ | HER-2 positive | TT | targeted therapy, in parenthesis is target of TT |
| * | response not confirmed by second scan | | |

The largest number of patients carried the diagnosis of GBM followed by breast cancer, colorectal, lung, head and neck, ovarian and prostate cancers. In most cases, the additional medications were selected based on data from genomic analysis or data coming from medical literature. There were 6 pediatric cases and 131 adults, 61 male and 76 females in 137 patients in this group. Median age was 55. The objective response rate in common cancers, which included CR, PR and MR, was very high and equaled to 73.8%. Stable disease was determined in 7.4% and progressive disease in 18.9%.

The group of 61 patients with uncommon cancers was evaluated separately. The details are shown in Table 56. There were 22 pediatric cases and 42 adults, 40 males and 24 females in 64 patients in this group. CR, PR and IM were documented in 65.6% and PD in 8.19%. The total objective response rate was 65.7%.

The survival analysis of patients with common cancer (FIG. 11) is 65.2% at 1 year, 36.5% at 2 years and 10.9% at 4 years versus 0% estimated survival at those intervals. The survival of patients with uncommon cancer (FIG. 12) is 51.2% at 1 year, 31.2% at 2 years and 23.4% at 4 years versus 0% estimated survival at those intervals.

Molecular Responses

In addition to radiological response, the second goal of the treatment was to accomplish molecular response indicated by no longer detectable abnormal genes or marked decrease of the concentration of the DNA of these genes in blood tests such as Guardant 360, Foundation One or Tempus. Based on laboratory results the listing of the genes affected by ANP is provided in Table 64.

TABLE 64

| Genes Affected by Antineoplastons Based on Laboratory Data. | | | | |
|---|---|---|---|---|
| ACO2 | CDC2 | DUSP1 | MCM2 | PPM1A |
| AKT | CDC42 | DUSP6 | MCM3 | PTCH1 |
| AKT1 | CDC6 | E2F1 | MCM4 | PTEN |
| ALK | CDC7 | EGFR | MCM5 | PTPN11 |
| APC | CDC20 | ERBB2 | MCM6 | PTPRR |
| AR | CDC25A | ERK | MCM7 | PTTG1 |
| ASK | CDC25B | FGFR | MDH1 | PTTG2 |
| ASPM | CDC25C | FGFR2 | MDM2 | PTTG3 |

TABLE 64-continued

| Genes Affected by Antineoplastons Based on Laboratory Data. | | | | |
|---|---|---|---|---|
| ATF3 | CDCA8 | FH | MDM4 | RAS |
| BAD | CDK2 | GADD45A | MEF26 | RB1 |
| BAX | CDK3 | GATA3 | MET | RBL1 |
| BCL2 | CDK4 | HDAC1 | NF1 | SDHC |
| BDNF | CDK6 | HDAC5 | NFKB | SKP2 |
| BLM | CDKN1A | HIF1A | NGF | SMAD4 |
| BRAF | CDKN1B | IDH2 | NOTCH1 | SMC1A |
| BRCA1 | CDKN2A | IDH3A | OGDH | SMC1L1 |
| BUB1 | CDKN2B | IDH3B | ORC1 | STAT5 |
| CASP5 | CDKN2C | IL1 | ORC1L | SUCLG1 |
| CCL2 | CFS1 | IL1A | ORC6L | SUCLG2 |
| CCNA2 | CHK-1 | IL1B | ORCL | TBC1D8 |
| CCNB1 | CLDND1 | IL6 | PCNA | TERT |
| CCNB2 | CSF1 | IL8 | PDGFRA | TFDP1 |
| CCND1 | CSF3 | IL15 | PDHA1 | TP53 |
| CCND2 | CTNNB1 | JUN | PIK3CA | TRIB3 |
| CCND3 | CXCL2 | KRAS | PIK3R1 | TSC1 |
| CCNE1 | DLD | MAD2L1 | PKMYT1 | UNC5B |
| CCNE2 | DLST | MAPK | PLK1 | WEE1 |

Table 51 provides alphabetic listing of 203 specific genomic abnormalities including mutations and amplifications which were affected by ANP in different diagnostic groups based on clinical results. Contrary to prescription targeted drugs which typically affect a single mutation of the genes, ANP seems to have a broad spectrum of activity which covers numerous mutations and amplifications. This suggests the application of ANP in the treatment of cancer patients who have at least one abnormal gene from the list regardless of cancer diagnosis. Such "pan-tumor" potential has been claimed for other drugs. For instance, a novel monoclonal antibody seribantumab, which affects NRG1 fusion, is proposed as pan-tumor treatment for different types of cancers which harbor such abnormality including non-small lung, breast, pancreatic, ovarian, colorectal, biliary and genitourinary cancers.

Toxicity. There were 98 patients who did not have any adverse events that were possibly ANP related. The remaining patients had multiple adverse events but only a small percent were grade 3. The grade 1 and 2 adverse events (minor toxicity) possibly ANP related, occurred in a small percentage of patients as well. Grade 3 toxicity of adverse events that were possibly ANP related, were recorded in 7 patients, but in 2 categories only, fatigue and hypokalemia. All were transient and recoverable. The adverse events possibly related to the additional drugs were less common compared to the published data due to reduced dosages resulting from synergistic effects.

Summary. This example provides the results of treatment of 200 terminal cancer patients diagnosed with 47 different malignancies. The report was limited to evaluable cases. Some patients were close to death on admission and died from cancer or additional medical complications within the first 60 days before the treatment could take effect. The other group of patients discontinued the treatment for personal or financial reasons or was not willing to have radiology evaluation of the results. Such cases are not included in this report. In the glioblastoma group the patients who were on the treatment less than 30 days were also evaluated based on rapid responses in these patients. The treatment plans were formulated based on genomic analysis or genomic published data. The principle was to treat "cancer" genes and remove them from the patient's body. The reported results of this exemplary method were better than expected and the average number of patients who accomplished objective responses were approximately 70%.

Example 77

In another exemplary method, clinal trials were conducted to establish that the AS and A10 (ANP) therapeutic regimens described herein had effects on a surrogate endpoint ("Milestone") that was reasonably likely to predict clinical benefit. In most of the trials, the Milestones were radiographic evidence of tumor shrinkage by x-ray, computer aided tomography or magnetic resonance imaging. Where appropriate, tumor markers such as Prostate Specific Antigen, blood counts, or bone marrow biopsy were used in order to assess a tumor's growth.

Where tumor size was used as the Milestone, each clinical trial protocol described a "complete response" as a complete disappearance of all tumors with no recurrence of tumors for at least four weeks. A "partial response" was described as at least a 50% reduction in total tumor size, with such reduction lasting at least four weeks. An "objective response" was described as either a complete or partial response for protocols BT-06, BT-07, BT-08, BT-09, BT-10, BT-11, BT-12, BT-13, BT-15, BT-21, BT-22, and BT-23. "Stable disease" was described as less than 50% reduction in size but no more than 25% increase in size of the tumor mass lasting for at least twelve weeks and 50% increase in CAN-1 protocol.

The protocols of the clinical trials involved a two-stage design, wherein the first stage proceeded until 20 patients were admitted into the trial. After a specified time period, the trial was continued until forty patients had been accrued. The following conclusions according to protocols based on 40 patients were be made: If there were three or fewer responses, then there is less than desired activity. If there were four or more responses, then there was sufficient evidence to conclude that the Antineoplaston regimen used showed beneficial activity.

Protocols Reaching Milestones:

Protocol BT-06, involving the study of Antineoplastons A10 and AS2-1 in children with high grade glioma (study and special exception patients). Objective responses: 4 patients (2 patients with a complete response and 2 patients with a partial response); Stable disease: 3 patients. Protocol BT-07, involving the study of Antineoplastons A10 and AS2-1 in patients with glioblastoma multiforme, not treated with radiation therapy or chemotherapy (study and special exception patients). Objective responses: 5 patients (2 patients with a complete response and 3 patients with a partial response); Stable disease: 5 patients. Protocol BT-08, involving the study of Antineoplastons A10 and AS2-1 in patients with anaplastic astrocytoma. Objective responses: 4 patients (3 patients with a complete response and 1 patient with a partial response); Stable disease: 5 patients. Protocol BT-09, involving the study of Antineoplastons A10 and AS2-1 in patients with brain tumors. Objective responses: 9 patients (4 patients with a complete response and 5 patients with a partial response); Stable disease: 12 patients. Protocol BT-10, involving the study of Antineoplastons A10 and AS2-1 in children with brain tumors. Objective responses: 7 patients (2 patients with a complete response and 5 patients with a partial response); Stable disease: 5 patients. Protocol BT-11, involving the study of Antineoplastons A10 and AS2-1 in patients with brainstem glioma. Objective responses: 9 patients (5 patients with a complete response and 4 patients with a partial response); Stable disease: 8 patients.

Protocol BT-12, involving the study of Antineoplastons A10 and AS2-1 in children with primitive neuroectodermal tumors (PNET). Objective responses: 4 patients (3 patients with a complete response and 1 patient with a partial response); Stable disease: 1 patient. Protocol BT-13, involving the study of Antineoplastons A10 and AS2-1 in children with low grade astrocytoma. Objective responses: 5 patients (4 patients with a complete response and 1 patient with a partial response); Stable disease: 4 patients. Protocol BT-15, involving the study of Antineoplastons A10 and AS2-1 in adult patients with anaplastic astrocytoma. Objective responses: 5 patients (2 patients with a complete response and 3 patients with a partial response); Stable disease: 6 patients. Protocol BT-21, involving the study of Antineoplastons A10 and AS2-1 in adults with primary malignant brain tumors. Objective responses: 4 patients (2 patients with a complete response and 2 patients with a partial response); Stable disease: 4 patients. Protocol BT-22, involving a study of Antineoplastons A10 and AS2-1 in children with primary malignant brain tumors (study and special exception patients). Objective responses: 5 patients (1 patient with a complete response and 4 patients with a partial response); Stable disease: 7 patients. Protocol BT-23, involving a study of Antineoplastons A10 and AS2-1 in children with visual pathway glioma. Objective responses: 4 patients (2 patients with a complete response and 2 patients with a partial response); Stable disease: 3 patients. The results of Protocols BT-06, BT-07, BT-08, BT-09, BT-10, BT-11, BT-12, BT-13, BT-15, BT-21, BT-22, and BT-23 are provided in Table 65.

TABLE 65

Protocol Results.

| Protocol Number | Patients Accrued | Evaluable Patients | Number and Percentage of Patients Showing Complete Response** | | Number and Percentage of Patients Showing Partial Response** | | Number and Percentage of Patients Showing Stable Disease** | | Number and Percentage of Patients Showing Progressive Disease** | |
|---|---|---|---|---|---|---|---|---|---|---|
| BT-06* | 19 | 11 | 2 | 18.2% | 2 | 18.2% | 3 | 27.3% | 4 | 36.4% |
| BT-07* | 102 | 69 | 2 | 2.9% | 3 | 4.3% | 5 | 7.2% | 59 | 85.5% |
| BT-08 | 19 | 18 | 3 | 16.7% | 1 | 5.5% | 5 | 27.8% | 9 | 50.0% |
| BT-09 | 40 | 31 | 4 | 12.9% | 5 | 16.1% | 12 | 38.7% | 10 | 32.3% |
| BT-10 | 34 | 30 | 2 | 6.7% | 5 | 16.7% | 5 | 16.7% | 18 | 60.0% |
| BT-11 | 40 | 31 | 5 | 16.1% | 4 | 12.9% | 8 | 25.8% | 14 | 45.2% |
| BT-12 | 13 | 12 | 3 | 25.0% | 1 | 8.3% | 1 | 8.3% | 7 | 58.3% |
| BT-13 | 11 | 9 | 4 | 44.4% | 1 | 11.1% | 4 | 44.4% | 0 | 0.0% |
| BT-15 | 27 | 21 | 2 | 9.5% | 3 | 14.3% | 6 | 28.6% | 10 | 47.6% |
| BT-21 | 40 | 27 | 2 | 7.4% | 2 | 7.4% | 4 | 14.8% | 19 | 70.4% |
| BT-22* | 43 | 32 | 1 | 3.1% | 4 | 12.5% | 7 | 21.9% | 20 | 62.5% |
| BT-23 | 12 | 8 | 2 | 25.0% | 2 | 25.0% | 3 | 37.5% | 1 | 12.5% |

Protocol CAN-1, involving a study of Antineoplastons A-10 and AS2-1 in 35 evaluable brain tumor patients. Complete and partial responses were obtained in patients diagnosed with glioblastoma multiforme, astrocytoma, oligodendroglioma, mixed glioma, medulloblastoma, and malignant meningioma. Objective responses: 17 patients (12 patients with a complete response and 5 patients with a partial response); Stable disease: 11 patients.

The Phase II Study according to Protocol CAN-1 included 35 evaluable brain tumor patients. Complete and partial responses were obtained in patients diagnosed with glioblastoma multiforme, astrocytoma, oligodendroglioma, mixed glioma, medulloblastoma, and malignant meningioma. The treatment with Antineoplastons A10 and AS2-1 resulted in 17 (48.6%) cases of objective responses and 11 (31.4%) cases of stable disease defined as less than 50% reduction, or less than 50% increase in size of the tumor mass, lasting for at least 12 weeks. The largest group of evaluable patients involved in the study had glioblastoma multiforme. Six of the cases were classified as complete and partial responses, four obtained stabilization, and four developed progression of the disease.

Of the 2,297 patients who have received at least one dose of Antineoplastons, the serious adverse events (SAEs) that have been experienced are as follows: hemoglobin (grade 3: 3 patients; grade 4: 1 patient), extravasation (grade 3: 1 patient), pain related to the central venous catheter (grade 3: 1 patient), fatigue (grade 3: 2 patients; grade 4: 1 patient), fever (grade 3: 2 patients), injection site reaction (grade 3: 1 patient), vomiting (grade 3: 2 patients), hypernatremia (grade 3: 2 patients; grade 4: 28 patients; grade 5: 6 patients—not confirmed by autopsy), confusion (grade 3: 1 patient), seizure (grade 3: 1 patient), somnolence (grade 3: 8 patients; grade 4: 1 patient), pain: head/headache (grade 3: 2 patients) and pain: joint (grade 3: 1 patient). 491 out of 2,298 patients experienced hypernatremia that was possibly related to the study drug, regardless of severity.

TABLE 66

Gene Abnormalities Affected by Antineoplastons Based on Genomic Testing in Patients - Jul. 15, 2015-Dec. 31, 2021.

Mutations of ALK
I1461L - Esophageal Adenocarcinoma
N1544K - Ovarian Cancer
Mutations of AKT1
E17K - Breast Cancer
R346H - Prostate Cancer
Mutations of APC
G29G - Breast Cancer
K445K - Breast Cancer
V2716L - Breast Cancer
E918E - Squamous Cell Carcinoma
Q1378* - Colon Cancer
S457* - Colon Cancer
I1304fs - Colon Cancer
E888fs - Colorectal Cancer
R230C - Colorectal Cancer
Q1090Q - Esophageal Adenocarcinoma
S1360P - Esophageal Adenocarcinoma
Mutations of AR
A356E - Small Cell Carcinoma of the Lung
M887V - Ovarian Cancer
S510R - Colon Cancer
Mutations of ARAF
Y495Y - Breast Cancer
Mutations of ARID1A
S1798L - Breast, Salivary Gland, and Head & Neck Cancer
S1167F - Squamous Cell Carcinoma
G246V - Ovarian Cancer
R1889W - Ovarian Cancer
Q802fs - Colorectal Cancer
Mutations of ARID2
N127fs18 - Anaplastic Astrocytoma
Mutations of ASXL1
R1273f*s - Chronic Atypical Myelogenous Leukemia
Mutations of ATRX
S850fs*2 - Anaplastic Astrocytoma
N179fs*26 - Anaplastic Astrocytoma
Mutations of BRCA1
H662Q - Breast Cancer
R1443* - Squamous Cell Carcinoma
Mutations of BRCA2
D237N - Breast Cancer
12040V - Chronic Atypical Myelogenous Leukemia
Mutations and Amplifications of BRAF
Amplification - Urothelial Carcinoma & Ovarian Cancer
E264 - Esophagus
V600E - Colorectal Cancer
Mutations and Amplifications of CCND1
Amplification - Breast Cancer
R291W - Ovarian Cancer
296* - Breast Cancer
Mutations of CCNE1
P268P - Breast Cancer
R95Q - Breast Cancer
CDK4 amplifications - Breast Cancer
Mutations and Amplifications of CDK6 - Breast Cancer
Mutations of CDKN1B
K59fs* - T-Cell Lymphoma
Mutations of CDKN2A
D74N - Breast Cancer
Mutations of CTNNB1
S45-subclonal - Breast Cancer
T41A - Endometrial Adenocarcinoma
Mutations of DDR2
L749L - Thyroid Cancer
Mutations and amplifications of EGFR
Amplification - Breast Cancer & Prostate Cancer
P753L (possibly) - Lung Cancer
V524I - Breast Cancer
V7421 - Stomach Cancer
D321D - Colorectal Cancer
Mutations of MET
C385Y - Esophageal Adenocarcinoma
T895M - Breast Cancer
T7591 - Squamous Cell Carcinoma
M391 - Breast Cancer
Mutations of MPL
Y591D - Chronic Atypical Myelogenous Leukemia
Mutations and amplifications of MYC
Amplifications - Breast Cancer & Ovarian Cancer
S244S - Breast Cancer
Mutations of NF1
Splice cite 480-11_4801del11 - Breast Cancer
Splice cite SNV - Lung Cancer
c.6655 > T - Ganglioglioma
p.D2219Y - Ganglioglioma
A2617A - GIST
F710C - Cholangiocarcinoma
V2378fs*8 - Diffuse Astrocytoma
I1719T - Esophagus
K583R - Ovarian Cancer
Mutations of NOTCH1
A465V - GIST
V220M - Squamous Cell Carcinoma
D1681H - Breast Cancer
S223N - Ovarian Cancer
Mutations of NOTCH2
S2379F - Chronic Atypical Myelogenous Leukemia
Mutations of NTRK1
Ovarian Cancer
P387L (possibly) - Lung Cancer
R766Q - Prostate Cancer
Mutations of PDGFRA
V299G - Breast Cancer
E86A - Squamous Cell Carcinoma
Mutations and Amplifications of PIK3CA
Amplification - Breast & Ovarian Cancer
Q546H - Breast Cancer
Q546K - Colon Cancer
Q546R - Pilocytic Astrocytoma
Q597H - Ovarian Cancer
E542K - Breast, Colorectal & Prostate Cancer
E545K - Breast Cancer
E726K - Breast Cancer
E39K - Breast Cancer
E453K - Breast Cancer & Anaplastic Oligodendroglioma
R4-P18del - Breast Cancer
H1047L - Breast Cancer & Colon
H104R - Breast Cancer
K567E - Pilocytic Astrocytoma
I15431 - Colorectal Cancer
p.E545K - Colon Cancer
G1049R - Colon Cancer
Mutations of PIK3R1
S399Y408del splice site 917-1G > A - Anaplastic Oligodendroglioma
Mutation of PTCH1
p.M17 Start loss-LOF - Breast Cancer
Mutations of PTEN
C136Y - DIPG
Loss exons 4-7 - Breast Cancer
D252Y - Breast Cancer
R130* - Breast Cancer
Y27C - Breast Cancer
N323fs*23 - Diffuse Astrocytoma
R55fs - Colorectal Cancer
H196_1203DEL - Ovarian Cancer
Mutations of RAF1
P63P - Breast Cancer
Amplification - Ovarian Cancer
Mutations of RB1
Q217* - Breast Cancer
Y173fs* - T-Cell Lymphoma TABLE 66-continued Gene Abnormalities Affected by Antineoplastons Based on Genomic Testing in Patients - Jul. 15, 2015-Dec. 31, 2021.

Mutations and amplifications of ERBB2
Amplification - Urothelial Carcinoma
C584G - Esophagus
V797del (Exon 20 deletion) - Prostate Cancer
Mutations of EWSR1
FLI1 fusion - Ewing Sarcoma, Lung Cancer, PNET & Neuroendocrine
Mutations of FBXW7
Y545C - Lung Cancer
R658* - Colon Cancer
Mutations and amplification of FGFR
Amplification - Breast Cancer
T320T - Breast Cancer
S726F - Breast Cancer
H791H - Breast Cancer
P47P - Breast Cancer
S430fs - Breast Cancer
R179H - Endometrial Adenocarcinoma
Mutations and Amplifications of FGFR1
Amplifications - Breast Cancer & Cholangiocarcinoma
S726F - Breast Cancer
Mutation of FGFR2
KCNH7 fusion - Cholangiocarcinoma
Mutation of FGFR3
H290Y - Colon Cancer
Mutations of GATA 3
P433fs43 - Breast Cancer
P409fs - Breast Cancer
PS405fs - Breast Cancer
D336fs - Breast Cancer
S430fs - Breast Cancer
c.1213_1214del - Breast Cancer
Multiplication - Head & Neck
Mutations of GNA11
N244S - Colon Cancer
Mutations of GNAQ
Salivary Gland Cancer
Head & Neck
Mutations of GNAS
R201H* - Squamous Cell Carcinoma
Mutations of H3F3A
K28N - DIPG
K27 - DIPG
Mutations of HIST1H1D
K185-A186 > T - Chronic Atypical Myelogenous Leukemia
Mutations of IDH1
R132H - Anaplastic Oligodendroglioma & Anaplastic Astrocytoma
Mutations of JAK2
V617 - MDS, Chronic Atypical Myelogenous Leukemia, Myelofibrosis, Refractory Anemia
Mutations of KRAS
G12V - Cholangiocarcinoma & Colon
G12D - Urothelial Carcinoma & Esophagus
G12S - Colon Cancer
G13D - Colorectal Cancer
p.AG11GD - Colon Cancer
Mutations of KDMGA - Breast Cancer Mutation of KIT
Q775 fs (Exon 16 deletion) Adenocarcinoma of uterine cervix
Mutations of MAP2K1
K57E - Breast Cancer
Mutations of MAP2K4
Loss exon 2 - Breast Cancer
Mutations of MAP3K1
S398 - Breast Cancer
Total # = 204

H673fs - Prostate Cancer
Mutations of RUNX1

R107C - Chronic Atypical Myelogenous Leukemia
Mutations of SMAD4
A406T - Lung Cancer
A451P - Colon Cancer
L495R - Colon Cancer
Q450H - Colon Cancer
D537V - Colorectal Cancer
P511L - Ovarian Cancer
Mutations of SPEN
A2510V - Chronic Atypical Myelogenous Leukemia
Mutations of SRSF2
P95H - Chronic Atypical Myelogenous Leukemia
Mutations of STAT5B
R110H - Chronic Atypical Myelogenous Leukemia
Tert promoter
SNV - Lung Cancer and Urothelial Carcinoma
124 C > T - Diffuse Astrocytoma
146C > T - Anaplastic Oligodendroglioma
Mutations of TET2
C1875G - Chronic Atypical Myelogenous Leukemia
Mutations of TP53
V73fs - Breast Cancer
R175G - Breast Cancer
R196 - Breast Cancer
R249T - Pleomorphic Sarcoma
C176F - Breast Cancer
G187D - Breast Cancer
R282W - Breast & Colorectal Cancer
E287* - Breast Cancer
E285K - Breast Cancer
S241del - Breast Cancer
c.97-28_99del - Pleomorphic Sarcoma
Y126D - Lung Cancer
R273H - Lung & Colorectal Cancer & Anaplastic Astrocytoma
C176W - Small Cell Carcinoma of the Lung
K320* - T-Cell Lymphoma
T253A - Urothelial Carcinoma
Splice site 37G-1G > A - Anaplastic Oligodendroglioma
Q104 - Esophagus
P151H- Esophagus
H179Y - Squamous Cell Carcinoma
R273C - Anaplastic Astrocytoma
R248W - Ovarian Cancer
R176H - Ovarian Cancer R209fs - Ovarian Cancer
N235-Y236del - Ovarian Cancer
R248Q - Colon Cancer
R306* - Colon Cancer
C176Y - Colorectal Cancer
S241F - Colorectal Cancer
L252-1254del - Esophageal Adenocarcinoma
L145P - Endometrial Adenocarcinoma
R158H - Endometrial Adenocarcinoma
R213* - Endometrial Adenocarcinoma
Y220C - Endometrial Adenocarcinoma
R110P - Breast Cancer
V274G - Ovarian Cancer
c.376-4_384del - Prostate Cancer
Mutations of MAP3K6
P646L - Chronic Atypical Myelogenous Leukemia

What is claimed is:

1. A method for treating cancer, the method comprising: sequencing a biological sample obtained from a subject having metastatic and/or terminal pancreatic cancer; and if one or more genomic aberrations in a combination of cancer related genes in the biological sample are identified, then administering to the subject a therapeutically effective amount of A10 and AS2-1, wherein A10 comprises phenylacetylglutaminate sodium (PG) and phenylacetylisoglutaminate sodium (iso-PG) in a 4:1 ratio;

wherein AS2-1 comprises phenylacetate (PN) and PG in a 4:1 ratio;

wherein the combination of cancer related genes comprises ARID1A, KIT, KRAS, NF1, SMAD4, and TP53; and measuring the subject's tumor response and/or molecular response to the A10 and AS2-1, wherein treating the cancer comprises increasing the subject's survivability, increasing the length of time before metastasis, reducing the likelihood of surgical intervention, reducing the need for administration of one or more additional therapeutic agents or regiments, reducing the size of one or more tumors in the subject, eliminating one or more tumors in the subject, reducing or eliminating the prevalence of one or more genomic aberrations, restoring the normal metabolism of one or more organ systems in the subject, restoring one or more aspect of cellular homeostasis and/or cellular functionality and/or metabolic dysregulation, or any combination thereof.

2. The method of claim 1, wherein the dose of A10 comprises about 0.4 g/kg/day to about 16 g/kg/day PG and about 0.1 g/kg/day to about 4 g/kg/day iso-PG.

3. The method of claim 1, wherein the dose of AS2-1 comprises about 0.064 g/kg/day to about 0.48 g/kg/day PN and about 0.016 g/kg/day to about 0.12 g/kg/day PG.

4. The method of claim 1, further comprising administering to the subject one or more additional therapeutic agents.

5. The method of claim 4, wherein the one or more additional therapeutic agents comprise bevacizumab, pazopanib, sorafenib, dasatinib, everolimus, or any combination thereof.

6. The method of claim 1, further comprising repeating the administering to the subject of the A10 and AS2-1.

7. The method of claim 1, wherein the one or more genomic aberrations comprise mutations, insertions, deletions, chromosomal rearrangements, copy number aberrations, or any combination thereof.

8. The method of claim 1, wherein the presence of the one or more genomic aberrations in the combination of cancer related genes in the biological sample obtained from the subject indicates that the administration of A10 and AS2-1 is likely to achieve a tumor response and/or a molecular response.

9. The method of claim 1, further comprising obtaining one or more biological samples from the subject.

10. The method of claim 1, wherein (i) if the expression and/or amount of the one or more genomic aberrations in the biological sample obtained after administering the A10 and AS2-1 is lower than the expression and/or amount of the same one or more genomic aberrations in a pre-administration biological sample, then continuing to administer to the subject the A10 and AS2-1, or (ii) if the expression and/or amount of the one or more genomic aberrations in the biological sample obtained after administering the A10 and AS2-1 is lower than the expression and/or amount of the same one or more genomic aberrations in a prior sample obtained after administering the A10 and AS2-1, then continuing to administer to the subject the A10 and AS2-1.

11. The method of claim 4, wherein the one or more additional therapeutic agents comprise chemotherapeutic agents, monoclonal antibodies, small molecules, or any combination thereof.

12. The method of claim 11, wherein monoclonal antibodies comprise adotrastuzumab, alemtuzumab, atezolizumab, avelumab, bevacizumab, blinatumomab, brentuximab, cemiplimab, cetuximab, daratumumab, denosumab, dinutuximab, durvalumab, elotuzumab, gemtuzumab, ibritumomab, inotuzumab, ipilimumab, necitumumab, nivolumab, obinutuzumab, ofatumumab, olaratumab, panitumumab, pembrolizumab, pertuzumab, ramucirumab, rituximab, tositumomab, trastuzumab, or any combination.

13. The method of claim 11, wherein small molecules comprise abemaciclib, afatinib, alectinib, alpelisib, axitinib, binimetinib, bosutinib, brigatinib, cabozantinib, carfilzomib, ceritinib, cgilteritinib, cobimetinib, copanlisib, crizotinib, dabrafenib, dacomitinib, dasatinib, duvelisib, encorafenib, entrectinib, erdafitinib, erlotinib, gefitinib, ibrutinib, imatinib, ivosidenib, lapatinib, larotrectinib, lenvatinib, lorlatinib, marizomib, neratinib, nilotinib, niraparib, olaparib, osimertinib, palbociclib, pazopanib, ponatinib, regorafenib, ribociclib, rucaparib, sorafenib, sunitinib, talazoparib, trametinib, vandetanib, vemurafenib, or any combination thereof.

14. The method of claim 1, wherein (i) the subject has not received treatment prior to the administering of the A10 and AS2-1, or (ii) wherein the subject has received treatment prior to the administering of the A10 and AS2-1, and wherein the treatment comprises surgical treatment, antibody treatment, chemotherapy treatment, radiation treatment, immunotherapy treatment, or any combination thereof.

* * * * *